United States Patent
Sanière et al.

(10) Patent No.: US 9,062,051 B2
(45) Date of Patent: Jun. 23, 2015

(54) COMPOUNDS AND PHARMACEUTICAL COMPOSITIONS THEREOF FOR THE TREATMENT OF PROLIFERATIVE DISORDERS

(71) Applicant: GALAPAGOS NV, Mechelen (BE)

(72) Inventors: Laurent Raymond Maurice Sanière, Romainville (FR); Jacques Huck, Romainville (FR); Graeme James Dykes, Singapore (SG); Benoit Antoine Schmitt, Mechelen (BE); Javier Blanc, Mechelen (BE); Anna Sara Butler, Northumberland (GB); Florence Marie-Emilie Bonnaterre, Romainville (FR); Stéphane Nicolas Alain Beaumont, Romainville (FR)

(73) Assignee: GALAPAGOS NV, Mechelen (BE)

( * ) Notice: Subject to any disclaimer, the term of this patent is extended or adjusted under 35 U.S.C. 154(b) by 0 days.

(21) Appl. No.: 14/461,629

(22) Filed: Aug. 18, 2014

(65) Prior Publication Data
US 2015/0080391 A1    Mar. 19, 2015

(51) Int. Cl.
C07D 401/14    (2006.01)
A61K 31/437    (2006.01)
C07D 471/04    (2006.01)
A61K 31/5377   (2006.01)
A61K 45/06     (2006.01)

(52) U.S. Cl.
CPC ............ *C07D 471/04* (2013.01); *A61K 31/437* (2013.01); *A61K 31/5377* (2013.01); *A61K 45/06* (2013.01); *C07D 401/14* (2013.01)

(58) Field of Classification Search
CPC ............................ C07D 401/14; A61K 31/437
USPC ........................................... 546/119; 514/303
See application file for complete search history.

(56) References Cited

U.S. PATENT DOCUMENTS
2010/0113415 A1    5/2010    Rajapakse et al.

FOREIGN PATENT DOCUMENTS
WO            2013100672       7/2013

OTHER PUBLICATIONS

Brand et al., Collagen-induced arthritis, Nature Protocols, 2007, vol. 2 No. 5, 1269-1275.
Bendele et al., Animal models or rheumatiod arthritis. J Musculoskel Neuron Interact, 2001, 1(4), 377-375.
Zhuang et al., Elevation of receptor tyrosine kinase EphA2 mediates resistance to trastuzumab therapy. Cancer Res,2010; 7(1): 299-308.
Xi Hq et al., Eph receptors and ephrins as targets for cancer therapy. J Cell Mol Med, 2012; 16(12): 2894-909.
Pasquale, Eph-Ephrin Bidirectional Signaling in Physiology and Disease. Cell, 2008: 133(1): 38-52.
Murai et al., 'Eph'ective signaling: forward, reverse and crosstalk. J Cell Sci, 2003; 116(14) : 2823-2832.
Ivanov et al., Expression of Eph receptors and their ligands, ephrins, during lipopolysaccharide fever in rats. Physiol Genomics, 2005; 21: 152-160.
Kwan-Tat et al., Activation of the Receptor EphB4 by Its Specific Ligand Ephrin B2 in Human Osteoarthritic Subchondral Bone Osteoblasts. Arthritis & Rheumatism, 2008; 58, No. 12 : 3820-3830.
Kiewlich et al., Kiewlich, D, et al. Anti-EphA2 antibodies decrease EphA2 protein levels in murine CT26 colorectal and human MDA-231 breast tumors but do not inhibit tumor growth. Neoplasia, 2008; 8 No. 1: 18-30.
Adams et al., Roles of ephrinB ligands and EphB receptors in cardiovascular development: demarcation of arterial/venous domains, vascular morphogenesis, and sprouting angiogenesis. Genes Dev, 1999; 13(3) : 295-306.
Brantley-Sieders et al., Eph/ephrin profiling in human breast cancer reveals significant associations between expression level and clinical outcome. PLoS One, 2011; 6(9): e24426.
Carles-Kinch et al., Antibody targeting of the EphA2 tyrosine kinase inhibits malignant cell behavior. Cancer Res, 2002; 62(10): 2840-7.
Gerety et al., Cardiovascular ephrinB2 function is essential for embryonic angiogenesis. Development, 2002; 129 (6): 1397-410.
Tandon et al., Emerging strategies for EphA2 receptor targeting for cancer therapeutics. Expert Opin Ther Targets,2011; 15(1) : 31-51.

(Continued)

*Primary Examiner* — Niloofar Rahmani
(74) *Attorney, Agent, or Firm* — Klauber & Jackson LLC

(57) ABSTRACT

The present invention discloses compounds according to Formula I:

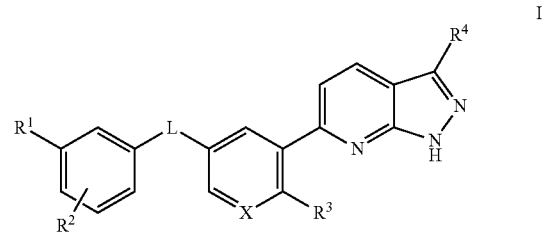

wherein $R^1$, $R^2$, $R^3$, $R^4$, L, and X are as defined herein.
The present invention relates to compounds, methods for their production, pharmaceutical compositions comprising the same, and their use in the prophylaxis and/or treatment of inflammatory conditions, type 2 diabetes, neurological and/or neurodegenerative diseases, autoimmune diseases, proliferative diseases (in particular metastatic diseases, and/or cancer), abnormal angiogenesis associated diseases, degradation of cartilage, and/or disruption of cartilage homeostasis, in particular in the prophylaxis and/or treatment of cancer. The present invention also discloses methods of treatment using the same compounds, for the prophylaxis and/or treatment of said diseases by administering the compound of the invention.

13 Claims, 1 Drawing Sheet

(56) References Cited

OTHER PUBLICATIONS

Beauchamp et al., Ephs and ephrins in cancer: Ephrin-A1 signalling. Seminars in Cell & Developmental Biology, 2012; 23, No. 1: 109-115.

Jensen et al., Asymmetric Organocatalytic Synthesis of Complex Cyclopenta[b]quinoline Derivatives. Organic Letters, 2001; 13, No. 14: 3678-3681.

Ogawa et al., The ephrin-A1 ligand and its receptor, EphA2, are expressed during tumor neovascularization.; Oncogene, 2000; 19, No. 52: 6043-6052.

Bolen et al., Systematic Review: Comparative Effectiveness and Safety of Oral Medications for Type 2 Diabetes Mellitus, Annals of Internal Medicine, 2007, vol. 147, No. 6, p. 386-399.

Kitamura et al., Enhancement of lymphocyte migration and cytokine production by ephrinB1 system in rheumatoid arthritis, Am J Physiol Cell Phusiol, 2008, 294: C189-C196.

Konstantinova et al., μEphA-Ephrin-A-Mediated [beta] Cell Communication Regulates Insulin Secretion from Pancreatic Islets, Cell, 2007, vol. 129, 359-370.

Zamora et al., Human leukocytes express ephrinB2 which activates microvascular endothelial cells, Cellular Immunology, 2006, 242, p. 99-109.

Zhao et al., Bidirectional ephrinB2-EphB4 signaling controls bone homeostasis, Cell Metabolism, 2006, 4, 111-121.

Janusz, MJ et al., Induction of osteoarthritis in the rat by surgical tear of the meniscus: Inhibition of joint damage by a matrix metalloproteinase inhibitor, 2002, Osteoarthritis Cartilage, 10, 785-91.

Prizker et al., Osteoarthritis cartilage histopathology: grading and staging, OsteoArthritis and Cartilage, 2006, vol. 14, p. 13-29.

Miescher et al., Production and characterization of a rat monoclonal antibody against the murine CD3 molecular complex, Immunology letters, 1989/1990, vol. 23, p. 113-118.

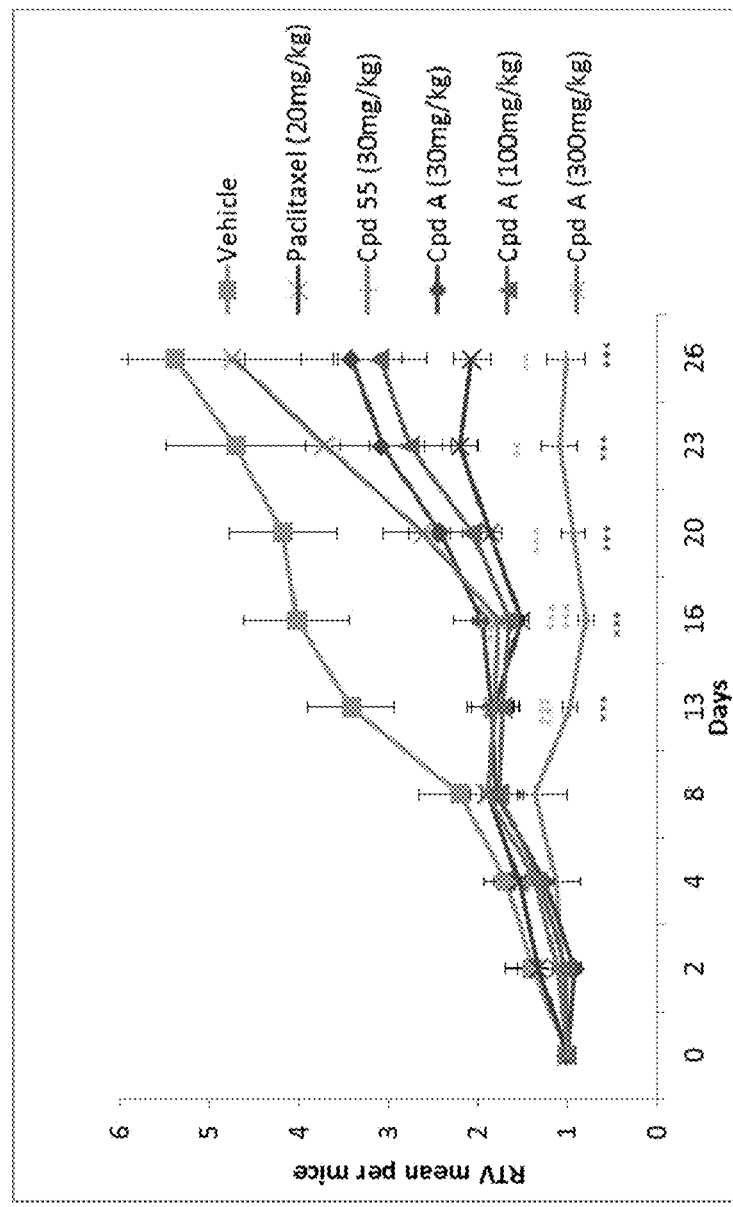

COMPOUNDS AND PHARMACEUTICAL COMPOSITIONS THEREOF FOR THE TREATMENT OF PROLIFERATIVE DISORDERS

RELATED APPLICATION

The present application claims the benefit under 35 U.S.C. §119 of G.B. Application No. 1315072.7, filed Aug. 23, 2013, the contents of which is hereby incorporated by reference in its entirety.

FIELD OF THE INVENTION

The present invention relates to compounds and their use in the prophylaxis and/or treatment of inflammatory conditions, type 2 diabetes, neurological and/or neurodegenerative diseases, autoimmune diseases, proliferative diseases (in particular metastatic diseases, and/or cancer), abnormal angiogenesis associated diseases, degradation of cartilage, and/or disruption of cartilage homeostasis.

In another particular aspect, the compounds of the invention are inhibitors of Ephrins (Eph) which are members of the largest known sub-family of receptor protein-tyrosine kinases (RTKs).

The present invention also provides methods for the production of the compound of the invention, pharmaceutical compositions comprising the compound of the invention, methods for the prophylaxis and/or treatment of diseases including inflammatory conditions, type 2 diabetes, neurological and/or neurodegenerative diseases, autoimmune diseases, proliferative diseases (in particular metastatic diseases), abnormal angiogenesis associated diseases, degradation of cartilage, and/or disruption of cartilage homeostasis by administering the compound of the invention.

BACKGROUND OF THE INVENTION

The ephrin receptors (Eph) super family shares 65-90% sequence homology in the kinase domain and 30-70% in the extracellular domain. At least 15 members of the Eph super family have been identified, from vertebrates, *Drosophila* and *C. elegans*, and it is the largest sub-family of receptor tyrosine kinases (RTKs), which itself is divided into two sub-groups. The first group is based on ligand-binding affinity whereas the second group is based on the structure of the extracellular domain.

The ephrin ligands are referred to hereafter as "Ephrin" and bind to the ephrin receptor referred to hereafter as "Eph".

The EphA (A1-A9) generally binds Ephrin A members that are linked to the plasma membrane through a glycosylphosphatidylinositol anchor, whereas the EphB (B1-B6) receptors generally bind Ephrin B members that transverse the cell membrane. Structurally, Eph receptors comprise an extracellular globular domain responsible for ligand binding, a cysteine-rich region, two fibronectin type III repeats, a region spanning the cell membrane, and a tyrosine kinase domain. (Tandon et al., 2011)

Within the Eph family, receptor-ligand binding occurs without discrimination between each subclass of the family, for example EphA4 binds Ephrin B with high affinity (Murai and Pasquale, 2003). Moreover, the Ephrins, which are membrane bound proteins, mediate bi-directional signals between adjacent cells. Interactions between Eph and Ephrin on adjacent cells promote the clustering of these molecules, which leads to the initiation of the signal, involving tyrosine phosphorylation mediated by Eph RTKs, and in turn results in the activation of various intracellular signaling pathways.

The role of Ephrin-Eph signaling is known in CNS, controlling development of neuronal networks, axon guidance and nervous system repair (Pasquale, 2008). Moreover, the cell-cell contact-dependent functioning of Eph and Ephrin is tightly regulated during normal embryonic development and maintenance of homeostasis. However during oncogenesis due to loss of cell contacts, the normal EphA2-Ephrin A1 signaling is disrupted, leading to overexpression of EphA2 and oncogenic signal transduction. This deregulated signaling leads to cytoskeleton modulation, cell adhesion, migration, metastasis, proliferation and angiogenesis, all being hallmarks of oncogenesis (Tandon et al., 2011; Xi et al., 2012).

EphA2 is overexpressed in several cancers including breast, ovarian, prostatic, pancreatic, lung, melanoma and colorectal cancer, as well as glioblastoma multiformes. In a large proportion of cases, EphA2 overexpression is correlated to advanced-stage disease or metastatic stage disease.

In breast cancer, EphA2 protein levels are increased in aggressive breast cancer cell lines versus non-transformed mammary epithelial cells, whereas EphA2 overexpression in breast cancer cells is negatively correlated with epidermal growth factor receptor (ER) expression. Interestingly, constitutive expression of EphA2 confers intrinsic resistance to trastuzumab in human epidermal growth factor receptor-2 (HER2) overexpressing cells, and therefore decreases the therapeutic effect of trastuzumab. These findings are further supported by clinical observations correlating high EphA2 expression levels with reduced overall and recurrence-free survival rates (Brantley-Sieders et al., 2011) on the one hand, and correlating EphA2 mRNA levels increase with overall survival of HER2-positive breast cancer patients, on the other hand (Zhuang et al., 2010). Consequently, inhibition of EphA2 expression may represent a promising avenue to reverse tratuzumab resistance.

In addition, it was also reported that EphA2 antisense oligonucleotides reduced the growth of the triple negative breast cancer cell lines MDA-MB-231 (Carles-Kinch et al., 2002).

Beyond EphA2, which plays a key role in breast cancer, several other Eph have been reported for their tumor promoter role and/or their expression has been correlated to poor prognosis like EphA4, EphB4, and EphB6.

In addition to the roles on neuronal and angiogenic patterning, EphB family members have a role in inflammation (Ivanov et al., 2005; Kitamura et al., 2008; Zamora et al., 2006), bone metabolism (Zhao et al., 2006) and in osteoarthritic bone remodeling. (Kwan Tat et al., 2008)

Finally, EphA and Ephrin A have been ascribed a role in the regulation of glucose, more specifically in the pancreatic beta cells. EphA were reported to negatively regulate insulin production, while reverse signaling through the Ephrin ligands would upregulate insuline production. Increased glucose levels trigger dephosphorylation and therefore inactivation of the receptor kinase and cause ephrin reverse signaling. Thus the insulin steady state level is dependent on the interaction between the ligand and the receptor, and by the active state of the receptor (Konstantinova et al., 2007).

Although currently a number of treatments for type 2 diabetes exist, they are accompanied by more or less serious side effects (Bolen et al., 2007). Therefore, there remains a need for an effective treatment for diabetes.

There is therefore a need to identify further compounds which may be effective in the treatment and/or prophylaxis of these diseases.

US 2010/0113415 (Rajapakse et al., 2010) discloses 1H-pyrazolo[3,4-b]pyridin-3-yl compounds, all of which must have an amino group in position 3.

The present invention provides compounds, methods for their manufacture and pharmaceutical compositions comprising a compound of the invention together with a suitable pharmaceutical carrier, which compounds and compositions may be used in the treatment and/or prophylaxis of these diseases. The present invention also provides for the use of a compound of the invention in the preparation of a medicine for the treatment of for the prophylaxis and/or treatment of diseases including inflammatory conditions, type 2 diabetes, neurological and/or neurodegenerative diseases, autoimmune diseases, proliferative diseases (in particular metastatic diseases, and/or cancer), abnormal angiogenesis associated diseases, degradation of cartilage, and/or disruption of cartilage homeostasis.

SUMMARY OF THE INVENTION

The present invention relates to compounds and their use in the prophylaxis and/or treatment of inflammatory conditions, type 2 diabetes, neurological and/or neurodegenerative diseases, autoimmune diseases, proliferative diseases (in particular metastatic diseases, and/or cancer), abnormal angiogenesis associated diseases, degradation of cartilage, and/or disruption of cartilage homeostasis. In particular, the compounds of the invention are inhibitors of EphA2.

The present invention also provides methods for the production of these compounds, pharmaceutical compositions comprising these compounds and methods for prophylaxis and/or treatment of inflammatory conditions, type 2 diabetes, neurological and/or neurodegenerative diseases, autoimmune diseases, proliferative diseases (in particular metastatic diseases, and/or cancer), abnormal angiogenesis associated diseases, degradation of cartilage, and/or disruption of cartilage homeostasis by administering the compounds of the invention.

Accordingly, in a first aspect of the invention, compounds of the invention are provided having a Formula (I):

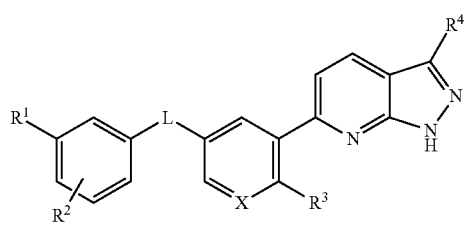

wherein
X is N, or CH;
L is —NH(C=O)—, or —C(=O)NH—;
$R^1$ is
  —CN,
  halo,
  $C_{1-4}$ alkyl optionally substituted with one or more independently selected $R^{6a}$ groups,
  $C_{1-4}$ alkoxy optionally substituted with one or more independently selected $R^{6b}$ groups,
  $C_{3-4}$ cycloalkyl,
  phenyl,
  —$SO_2C_{1-4}$ alkyl, or
  $NR^{7a}R^{7b}$;

$R^2$ is H, cyclopropyl, $C_{1-4}$ alkyl (optionally substituted with one or more halo), or $C_{1-4}$ alkoxy;
$R^3$ is —$CH_3$, —$CH_2CH_3$, or Cl;
$R^4$ is
  $C_{1-2}$ alkyl optionally substituted with one OH,
  $C_{1-2}$ alkyl substituted with one OH and one 5-6 membered heterocycloalkyl comprising one or two heteroatoms independently selected from N, O, and S,
  $C_{3-6}$ cycloalkyl optionally substituted with one OH;
each $R^{6a}$ is
  OH,
  halo, or
  $C_{1-4}$ alkoxy
each $R^{6b}$ is
  OH,
  halo,
  $C_{1-4}$ alkoxy,
  —$NR^{8a}R^{8b}$, or
  5-6 membered heterocycloalkyl comprising one or two heteroatoms independently selected from N, O, and S, optionally substituted with one $C_{1-4}$ alkyl;
each $R^{7a}$, $R^{7b}$ is independently selected from H, and $C_{1-4}$ alkyl; and
each $R^{8a}$ or $R^{8b}$ is independently selected from H, and $C_{1-4}$ alkyl.

In a particular embodiment, the compounds of the invention are inhibitors of EphA or Eph B. In a particular embodiment, the compounds of the invention are inhibitors of EphA2.

The compounds of the invention according to Formula I, surprisingly, exhibit an improved exposure in vivo as compared to structurally similar compounds described in the prior art. A higher exposure may allow for lowering the dose level of the compound, and consequently using a low dose level may be beneficial in reducing drug-drug interactions, side effects, and/or toxicity. The compounds of the invention also show activity in vivo, in particular in the reduction/blocking of tumorous growth, and in particular, may be useful in the prophylaxis and/or treatment of cancer.

The compounds of the invention are provided for use in the prophylaxis and/or treatment of inflammatory conditions, type 2 diabetes, neurological and/or neurodegenerative diseases, autoimmune diseases, proliferative diseases (in particular metastatic diseases, and/or cancer), abnormal angiogenesis associated diseases, degradation of cartilage, and/or disruption of cartilage homeostasis.

In a further aspect, the present invention provides pharmaceutical compositions comprising a compound of the invention, and a pharmaceutical carrier, excipient or diluent. In a particular aspect, the pharmaceutical composition may additionally comprise further therapeutically active ingredients suitable for use in combination with the compounds of the invention. In a more particular aspect, the further therapeutically active ingredient is an agent for the prophylaxis and/or treatment of inflammatory conditions, type 2 diabetes, neurological and/or neurodegenerative diseases, autoimmune diseases, proliferative diseases (in particular metastatic diseases, and/or cancer), abnormal angiogenesis associated diseases, degradation of cartilage, and/or disruption of cartilage homeostasis.

Moreover, the compounds of the invention, useful in the pharmaceutical compositions and treatment methods disclosed herein, are pharmaceutically acceptable as prepared and used.

In a further aspect of the invention, this invention provides a method of treating a mammal, in particular humans, with a condition selected from a condition selected from among those listed herein, and particularly inflammatory conditions, type 2 diabetes, neurological and/or neurodegenerative diseases, autoimmune diseases, proliferative diseases (in particular metastatic diseases, and/or cancer), abnormal angiogenesis associated diseases, degradation of cartilage, and/or disruption of cartilage homeostasis, which method comprises administering an effective amount of the pharmaceutical composition or compounds of the invention as described herein.

The present invention also provides pharmaceutical compositions comprising a compound of the invention, and a suitable pharmaceutical carrier, excipient or diluent for use in medicine. In a particular aspect, the pharmaceutical composition is for use in the prophylaxis and/or treatment of inflammatory conditions, type 2 diabetes, neurological and/or neurodegenerative diseases, autoimmune diseases, proliferative diseases (in particular metastatic diseases, and/or cancer), abnormal angiogenesis associated diseases, degradation of cartilage, and/or disruption of cartilage homeostasis.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description which proceeds with reference to the following illustrative drawing.

It will be appreciated that compounds of the invention may be metabolized to yield biologically active metabolites.

BRIEF DESCRIPTION OF THE FIGURE

FIG. 1: FIG. 1 shows the tumorous growth evolution in vivo for the comparative compound A, paclitaxel and a compound of the invention (Compound 55).

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Alkyl' means straight or branched aliphatic hydrocarbon with the number of carbon atoms specified. Particular alkyl groups have 1 to 8 carbon atoms. More particular is lower alkyl which has 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and isoamyl.

'Alkoxy' refers to the group —OR$^{26}$ where R$^{26}$ is alkyl with the number of carbon atoms specified. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Alkylene' refers to divalent alkene radical groups having the number of carbon atoms specified, in particular having 1 to 6 carbon atoms and more particularly 1 to 4 carbon atoms which can be straight-chained or branched. This term is exemplified by groups such as methylene (—CH$_2$—), ethylene (—CH$_2$—CH$_2$—), or —CH(CH$_3$)— and the like.

'Alkenyl' refers to monovalent olefinically (unsaturated) hydrocarbon groups with the number of carbon atoms specified. Particular alkenyl has 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$) and the like.

'Amino' refers to the radical —NH$_2$.

'Aryl' refers to a monovalent aromatic hydrocarbon group derived by the removal of one hydrogen atom from a single carbon atom of a parent aromatic ring system. In particular aryl refers to an aromatic ring structure, monocyclic or polycyclic, with the number of ring atoms specified. Specifically, the term includes groups that include from 6 to 10 ring members. Where the aryl group is a monocyclic ring system it preferentially contains 6 carbon atoms. Particularly aryl groups include phenyl, naphthyl, indenyl, and tetrahydronaphthyl.

'Cycloalkyl' refers to a non-aromatic hydrocarbyl ring structure, monocyclic or polycyclic, with the number of ring atoms specified. A cycloalkyl may have from 3 to 10 carbon atoms, and in particular from 3 to 7 carbon atoms. Such cycloalkyl groups include, by way of example, single ring structures such as cyclopropyl, cyclobutyl, cyclopentyl, cyclohexyl, and cycloheptyl.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, and the like having from 1 to 4, and particularly from 1 to 3 heteroatoms, more typically 1 or 2 heteroatoms, for example a single heteroatom.

'Heteroaryl' means an aromatic ring structure, monocyclic or polycyclic, that includes one or more heteroatoms independently selected from O, N and S and the number of ring atoms specified. In particular, the aromatic ring structure may have from 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g. adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

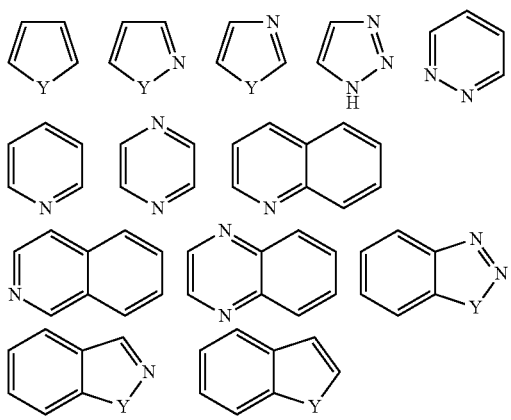

wherein each Y is selected from >C(=O), NH, O and S.

A fused heteroaryl ring system may also include carbocyclic rings and need only to include one heteroaryl ring. Examples of heteroaryl rings include, but are not limited to, dihydrobenzofuran, dihydroindole, dihydrobenzothiophene, dihydropyridinofuran, dihydropyrrolopyridine, dihydrothienopyridine, dihydrobenzodioxine, dihydrobenzooxathiine, dihydrobenzooxazine, dihydrobenzothiazine, dihydrodioxinopyridine, dihydrodioxaazaindene.

Examples of such representative heteroaryls include the following:

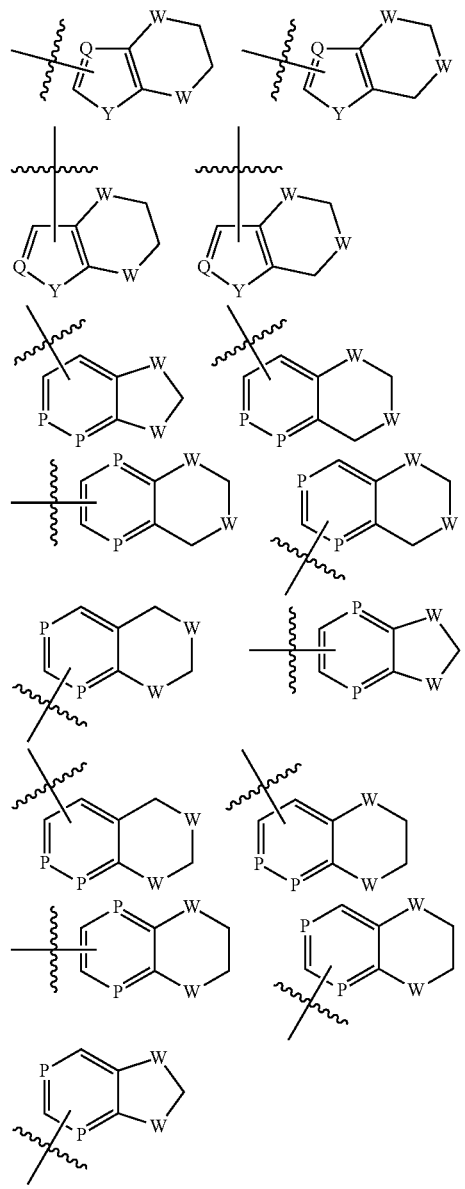

wherein each P is selected from N and CH; Y is selected from NH, O and S; and W is selected from $CH_2$, NH, O and S.

As used herein, the term 'heterocycloalkyl' means a stable non-aromatic ring structure, mono-cyclic or polycyclic, that includes one or more heteroatoms independently selected from O, N and S and the number of ring atoms specified. The non-aromatic ring structure may have from 4 to 10 ring members, and in particular from 4 to 7 ring members. A fused heterocyclic ring system may include carbocyclic rings and need only to include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

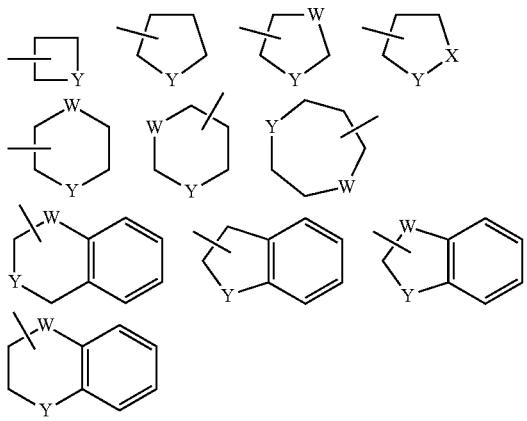

wherein each W is selected from $CH_2$, NH, O and S; and each Y is selected from NH, O, C(=O), $SO_2$, and S.

As used herein, the term 'heterocycloalkenyl' means a 'heterocycloalkyl, wherein one bond of the ring is reduced, thus the ring comprises a double bond. Particular examples of heterocycloalkenyl groups are shown in the following illustrative examples:

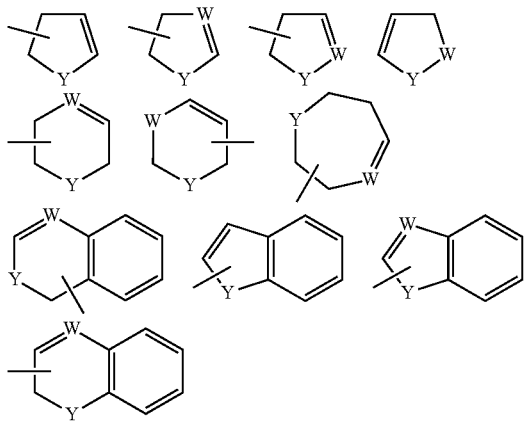

wherein each W is selected from $CH_2$, NH, O and S; and each Y is selected from NH, O, C(=O), $SO_2$, and S.

'Hydroxyl' refers to the radical —OH.

'Oxo' refers to the radical =O.

'Substituted' refers to a group in which one or more hydrogen atoms are each independently replaced with the same or different substituent(s).

'Sulfo' or 'sulfonic acid' refers to a radical such as —$SO_3H$.

'Thiol' refers to the group —SH.

As used herein, term 'substituted with one or more' refers to one to four substituents. In one embodiment it refers to one to three substituents. In further embodiments it refers to one or two substituents. In a yet further embodiment it refers to one substituent.

'Thioalkoxy' refers to the group —$SR^{26}$ where $R^{26}$ has the number of carbon atoms specified and particularly $C_1$-$C_8$ alkyl. Particular thioalkoxy groups are thiomethoxy, thioethoxy, n-thiopropoxy, isothiopropoxy, n-thiobutoxy, tert-thiobutoxy, sec-thiobutoxy, n-thiopentoxy, n-thiohexoxy, and 1,2-dimethylthiobutoxy. Particular thioalkoxy groups are lower thioalkoxy, i.e. with between 1 and 6 carbon atoms. Further particular alkoxy groups have between 1 and 4 carbon atoms.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term 'pharmaceutically acceptable cation' refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The "effective amount" can vary depending on the compound, the disease and its severity, and the age, weight, etc., of the subject to be treated.

'Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g. stabilization of a discernible symptom), physiologically, (e.g. stabilization of a physical parameter), or both. In a further embodiment, "treating" or "treatment" relates to slowing the progression of the disease.

As used herein the term 'inflammatory condition(s)' refers to the group of conditions including, rheumatoid arthritis, osteoarthritis, juvenile idiopathic arthritis, psoriasis, inflammatory bowel diseases (e.g. Crohn's disease, Whipple, chronic ulcerative colitis, or colitis), ankylosing spondylitis, and related diseases involving directly or indirectly cartilage in a short term or long term, such as that of the joints. Particularly the term refers to rheumatoid arthritis, primary and secondary osteoarthritis, and inflammatory bowel diseases.

As used herein the term 'neurological and/or neurodegenerative disease(s)' refers to the group of conditions including, stroke (including ischemic stroke), spinal cord injury (including paralysis) traumatic brain injury, Alzheimer's diseases, Parkinson's disease, amyotrophic lateral sclerosis, Huntington's diseases, and multiple sclerosis.

As used herein the term 'autoimmune disease(s)' refers to the group of diseases including obstructive airways disease, including conditions such as COPD, asthma (e.g intrinsic asthma, extrinsic asthma, dust asthma, infantile asthma) particularly chronic or inveterate asthma (for example late asthma and airway hyperreponsiveness), bronchitis, including bronchial asthma, systemic lupus erythematosus (SLE), cutaneous lupus erythrematosis, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease and ulcerative colitis), atherosclerosis and amyotrophic lateral sclerosis. Particularly the term refers to COPD, asthma, systemic lupus erythematosis, type I diabetes mellitus and inflammatory bowel disease.

As used herein the term 'proliferative disease(s)' refers to conditions such as cancer (e.g. uterine leiomyosarcoma, breast cancer or prostate cancer), myeloproliferative disorders (e.g. polycythemia vera, essential thrombocytosis and myelofibrosis), leukemia (e.g. acute myeloid leukaemia, acute and chronic lymphoblastic leukemia), metastatic diseases, multiple myeloma, psoriasis, restenosis, scleroderma or fibrosis. In particular the term refers to cancer, leukemia, metastatic diseases, multiple myeloma and/or psoriasis.

As used herein, the term 'cancer' refers to a malignant or benign growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types (such as but not limited to, melanoma, lymphoma, leukaemia, fibrosarcoma, rhabdomyosarcoma, and mastocytoma) and types of tissue carcinoma (such as but not limited to, colorectal cancer, small cell lung cancer and non-small cell lung cancer, breast cancer, pancreatic cancer, bladder cancer, renal cancer, gastric cancer, glioblastoma, primary liver cancer, ovarian cancer, prostate cancer, urinary tract cancer, thyroid cancer, oesophagus cancer, and uterine leiomyosarcoma). In particular, the term "cancer" refers to acute lymphoblastic leukemia, acute myeloidleukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, asopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor.

As used herein the term 'leukemia' refers to neoplastic diseases of the blood and blood forming organs. Such diseases can cause bone marrow and immune system dysfunction, which renders the host highly susceptible to infection and bleeding. In particular the term leukemia refers to acute myeloid leukaemia (AML), and acute lymphoblastic leukemia (ALL) and chronic lymphoblastic leukaemia (CLL).

As used herein the term "metastatic diseases" refers to diseases involving the transmission of pathogenic microorganisms or cancerous cells from an original site to one or more sites elsewhere in the body, usually by way of the blood vessels or lymphatics. In particular, metastatic disease disease refers to bile duct cancer, colon cancer, gallbladder cancer, malignant melanoma, myxoma, neuroendocrine tumors, Paget's disease of the breast, rectal cancer, superior vena cava syndrome, vulvar cancer.

As used herein the term "abnormal angiogenesis associated diseases" refers to diseases caused by the dysregulation of the processes mediating angiogenesis. In particular, abnormal angiogenesis associated disease refers to atherosclerosis, hypertension, tumor growth, inflammation, rheumatoid arthritis, wet-form macular degeneration, choroidal neovascularization, retinal neovascularization, and diabetic retinopathy.

As used herein the term 'diseases involving degradation and/or disruption of cartilage homeostasis' includes conditions such as osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis.

'Compound(s) of the invention', and equivalent expressions, are meant to embrace compounds of the Formula(e) as herein described, which expression includes the pharmaceutically acceptable salts, and the solvates, e.g. hydrates, and the solvates of the pharmaceutically acceptable salts where the context so permits. Similarly, reference to intermediates, whether or not they themselves are claimed, is meant to embrace their salts, and solvates, where the context so permits.

When ranges are referred to herein, for example but without limitation, $C_{1-8}$ alkyl, the citation of a range should be considered a representation of each member of said range.

Other derivatives of the compounds of this invention have activity in both their acid and acid derivative forms, but the acid sensitive form often offers advantages of solubility, tissue compatibility, or delayed release in the mammalian organism (Bundgaard, 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_{1-8}$ alkyl, $C_{2-8}$ alkenyl, $C_{6-10}$ optionally substituted aryl, and ($C_{6-10}$ aryl)-($C_{1-4}$ alkyl) esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be 2H/D, any carbon may be $^{13}C$, or any nitrogen may be 15N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$, and $^{13}N$, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e. as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated that compounds of the invention may be metabolized to yield biologically active metabolites.

THE INVENTION

The present invention relates to compounds and their use in the prophylaxis and/or treatment of inflammatory conditions, type 2 diabetes, neurological and/or neurodegenerative diseases, autoimmune diseases, proliferative diseases (in particular metastatic diseases, and/or cancer), abnormal angiogenesis associated diseases, degradation of cartilage, and/or disruption of cartilage homeostasis. In particular, the compounds of the invention are inhibitors of EphA2.

The present invention also provides methods for the production of these compounds, pharmaceutical compositions comprising these compounds and methods for prophylaxis and/or treatment of inflammatory conditions, type 2 diabetes, neurological and/or neurodegenerative diseases, autoimmune diseases, proliferative diseases (in particular metastatic diseases, and/or cancer), abnormal angiogenesis associated diseases, degradation of cartilage, and/or disruption of cartilage homeostasis by administering the compounds of the invention.

Accordingly, in a first aspect of the invention, compounds of the invention are provided having a Formula (I):

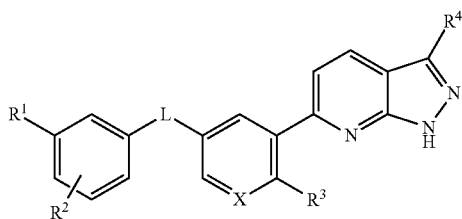

wherein
X is N, or CH;
L is —NH(C=O)—, or —C(=O)NH—;

$R^1$ is
—CN,
halo,
$C_{1-4}$ alkyl optionally substituted with one or more independently selected $R^{6a}$ groups,
$C_{1-4}$ alkoxy optionally substituted with one or more independently selected $R^{6b}$ groups,
$C_{3-4}$ cycloalkyl,
phenyl,
—$SO_2C_{1-4}$ alkyl, or
—$NR^{7a}R^{7b}$;
$R^2$ is H, cyclopropyl, $C_{1-4}$ alkyl (optionally substituted with one or more halo), or $C_{1-4}$ alkoxy;
$R^3$ is —$CH_3$, —$CH_2CH_3$, or Cl;
$R^4$ is
$C_{1-2}$ alkyl optionally substituted with one OH,
$C_{1-2}$ alkyl substituted with one OH and one 5-6 membered heterocycloalkyl comprising one or two heteroatoms independently selected from N, O, and S, or
$C_{3-6}$ cycloalkyl optionally substituted with one OH;
each $R^{6a}$ is
OH,
halo, or
$C_{1-4}$ alkoxy
each $R^{6b}$ is
OH,
halo,
$C_{1-4}$ alkoxy,
—$NR^{8a}R^{8b}$, or
5-6 membered heterocycloalkyl comprising one or two heteroatoms independently selected from N, O, and S, optionally substituted with one $C_{1-4}$ alkyl;
each $R^{7a}$, $R^{7b}$ is independently selected from H, and $C_{1-4}$ alkyl; and
each $R^{8a}$ or $R^{8b}$ is independently selected from H, and $C_{1-4}$ alkyl.

In one embodiment, a compound of the invention is according to Formula II:

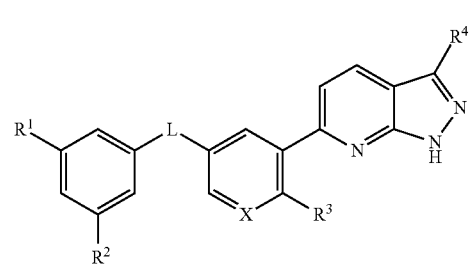

wherein $R^1$, $R^2$, $R^3$, $R^4$ and L are as defined above.

In one embodiment a compound of the invention is according to Formula I or II, wherein $R^1$ is CN, F, or Cl.

In one embodiment a compound of the invention is according to Formula I or II, wherein $R^1$ is $C_{1-4}$ alkyl. In a particular embodiment, $R^1$ is —$CH_3$, —$CH_2CH_3$, —$CH(CH_3)_2$, or —$C(CH_3)_3$. In a more particular embodiment, $R^1$ is —$CH_3$, or —$CH_2CH_3$. In a more particular embodiment, $R^1$ is —$CH_3$.

In one embodiment a compound of the invention is according to Formula I or II, wherein $R^1$ is $C_{1-4}$ alkyl substituted with one or more independently selected $R^{6a}$ groups. In another embodiment, $R^1$ is —$CH_3$, —$CH_2CH_3$, —$CH(CH_3)_2$, or —$C(CH_3)_3$, each of which is substituted with one or more independently selected $R^{6a}$ groups. In a particular embodiment, R¹ is C₁₋₄ alkyl substituted with one, two, or three independently selected R⁶ᵃ groups. In another particular embodiment, R¹ is —CH₃, —CH₂CH₃, —CH(CH₃)₂, or —C(CH₃)₃, each of which is substituted with one, two, or three independently selected R⁶ᵃ groups. In a more particular embodiment, R¹ is C₁₋₄ alkyl substituted with one R⁶ᵃ group. In another more particular embodiment, R¹ is —CH₃, —CH₂CH₃, —CH(CH₃)₂, or —C(CH₃)₃, each of which is substituted with one R⁶ᵃ group.

In one embodiment a compound of the invention is according to Formula I or II, wherein R⁶ᵃ is OH, halo, or C₁₋₄ alkoxy. In a particular embodiment, R⁶ᵃ is OH, F, or Cl. In another particular embodiment, R⁶ᵃ is —OCH₃, —OCH₂CH₃, —OCH(CH₃)₂, or —OC(CH₃)₃. In a more particular embodiment, R⁶ᵃ is OH, F, Cl, —OCH₃, or —OCH₂CH₃.

In one embodiment a compound of the invention is according to Formula I or II, wherein R¹ is —CF₃, —CH₂CF₃, —CH₂OH, or —CH₂OCH₃.

In one embodiment a compound of the invention is according to Formula I or II, wherein R¹ is C₁₋₄ alkoxy. In a particular embodiment, R¹ is —OCH₃, —OCH₂CH₃, —OCH(CH₃)₂, or —OC(CH₃)₃. In a more particular embodiment, R¹ is —OCH₃, or —OCH₂CH₃. In a more particular embodiment, R¹ is —OCH₃.

In one embodiment a compound of the invention is according to Formula I or II, wherein R¹ is C₁₋₄ alkoxy substituted with one or more independently selected R⁶ᵇ groups. In another embodiment, R¹ is —OCH₃, —OCH₂CH₃, —OCH(CH₃)₂, or —OC(CH₃)₃, each of which is substituted with one or more independently selected R⁶ᵇ groups. In a particular embodiment, R¹ is C₁₋₄ alkoxy substituted with one, two, or three independently selected R⁶ᵇ groups. In another particular embodiment, R¹ is —OCH₃, —OCH₂CH₃, —OCH(CH₃)₂, or —OC(CH₃)₃, each of which is substituted with one, two, or three independently selected R⁶ᵇ groups. In a more particular embodiment, R¹ is C₁₋₄ alkoxy substituted with one R⁶ᵇ group. In another more particular embodiment, R¹ is —OCH₃, —OCH₂CH₃, —OCH(CH₃)₂, or —OC(CH₃)₃, each of which is substituted with one R⁶ᵇ group.

In one embodiment a compound of the invention is according to Formula I or II, wherein R⁶ᵇ is OH, halo, or C₁₋₄ alkoxy. In a particular embodiment, R⁶ᵇ is OH, F, or Cl.

In one embodiment a compound of the invention is according to Formula I or II, wherein R⁶ᵇ is C₁₋₄ alkoxy. In a particular embodiment, R⁶ᵇ is —OCH₃, —OCH₂CH₃, —OCH(CH₃)₂, or —OC(CH₃)₃. In a more particular embodiment, R⁶ᵇ is —OCH₃, or —OCH₂CH₃.

In one embodiment a compound of the invention is according to Formula I or II, wherein R⁶ᵇ is —NR⁸ᵃR⁸ᵇ, wherein R⁸ᵃ and R⁸ᵇ are as described above. In a particular embodiment, each of R⁸ᵃ and R⁸ᵇ is independently selected from H, —CH₃, and —CH₂CH₃. In a more particular embodiment, R⁶ᵇ is —N(CH₃)₂, or —N(CH₃)CH₂CH₃.

In one embodiment a compound of the invention is according to Formula I or II, wherein R⁶ᵇ is 5-6 membered heterocycloalkyl comprising one or two heteroatoms independently selected from N, O, and S, optionally substituted with one C₁₋₄ alkyl. In a particular embodiment, R⁶ᵇ is pyrrolidinyl, morpholinyl, piperidinyl, piperazinyl, each of which is optionally substituted with C₁₋₄ alkyl. In another particular embodiment, R⁶ᵇ is 5-6 membered heterocycloalkyl comprising one or two heteroatoms independently selected from N, O, and S, optionally substituted with —CH₃, —CH₂CH₃, —CH(CH₃)₂, or —C(CH₃)₃. In a more particular embodiment, R⁶ᵇ is pyrrolidinyl, morpholinyl, piperidinyl, or piperazinyl, each of which is optionally substituted with —CH₃, —CH₂CH₃, —CH(CH₃)₂, or —C(CH₃)₃.

In one embodiment a compound of the invention is according to Formula I or II, wherein R¹ is C₃₋₆ cycloalkyl. In a particular embodiment, R¹ is cyclopropyl, cyclobutyl, or cyclopentyl. In a more particular embodiment, R¹ is cyclopropyl.

In one embodiment a compound of the invention is according to Formula I or II, wherein R¹ is —SO₂C₁₋₄ alkyl. In a particular embodiment, R¹ is —SO₂CH₃, —SO₂CH₂CH₃, or —SO₂CH(CH₃)₂. In a more particular embodiment, R¹ is —SO₂CH₃, or —SO₂CH₂CH₃. In a most particular embodiment, R¹ is —SO₂CH₃.

In one embodiment a compound of the invention is according to Formula I or II, wherein R¹ is —NR⁷ᵃR⁷ᵇ, wherein each R⁷ᵃ and R⁷ᵇ is as described above. In a particular embodiment, each of R⁷ᵃ and R⁷ᵇ is independently selected from H, —CH₃, and —CH₂CH₃. In a more particular embodiment, R¹ is —N(CH₃)₂, or —N(CH₃)CH₂CH₃.

In one embodiment a compound of the invention is according to Formula I or II, wherein R² is H.

In one embodiment a compound of the invention is according to Formula I or II, wherein R² is cyclopropyl.

In one embodiment a compound of the invention is according to Formula I or II, wherein R² is C₁₋₄ alkyl. In a particular embodiment, R² is —CH₃, —CH₂CH₃, —CH(CH₃)₂, or —C(CH₃)₃. In a more particular embodiment, R² is —CH₃, or —CH₂CH₃. In a more particular embodiment, R² is —CH₃.

In one embodiment a compound of the invention is according to Formula I or II, wherein R² is C₁₋₄ alkyl substituted with one or more halo. In another embodiment, R² is —CH₃, —CH₂CH₃, —CH(CH₃)₂, or —C(CH₃)₃, each of which is substituted with one or more halo. In a particular embodiment, R² is C₁₋₄ alkyl substituted with one or more fluoro. In another particular embodiment, R² is —CH₃, —CH₂CH₃, —CH(CH₃)₂, or —C(CH₃)₃, each of which is substituted with one or more fluoro. In a more particular embodiment, R² is —CF₃.

In one embodiment a compound of the invention is according to Formula I or II, wherein R² is C₁₋₄ alkoxy. In a particular embodiment, R² is —OCH₃, —OCH₂CH₃, —OCH(CH₃)₂, or —OC(CH₃)₃. In a more particular embodiment, R² is —OCH₃, or —OCH₂CH₃. In a more particular embodiment, R² is —OCH₃.

In one embodiment a compound of the invention is according to Formula IIIa or IIIb:

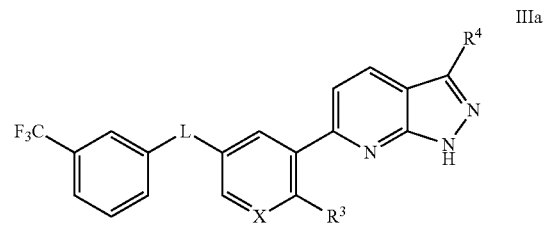

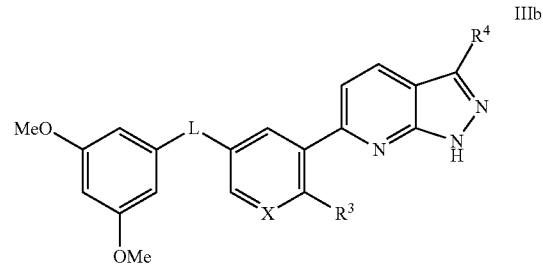

wherein X, L, R³, and R⁴ are as previously defined.

In one embodiment a compound of the invention is according to any one of Formulae I-IIIb, wherein L is —NH(C=O)—.

In one embodiment a compound of the invention is according to any one of Formulae I-IIIb, wherein L is —C(=O)NH—.

In one embodiment a compound of the invention is according to any one of Formulae I-IIIb, wherein $R^3$ is —CH$_3$.

In one embodiment a compound of the invention is according to any one of Formulae I-IIIb, wherein $R^3$ is Cl.

In one embodiment a compound of the invention is according to Formula IVa or IVb:

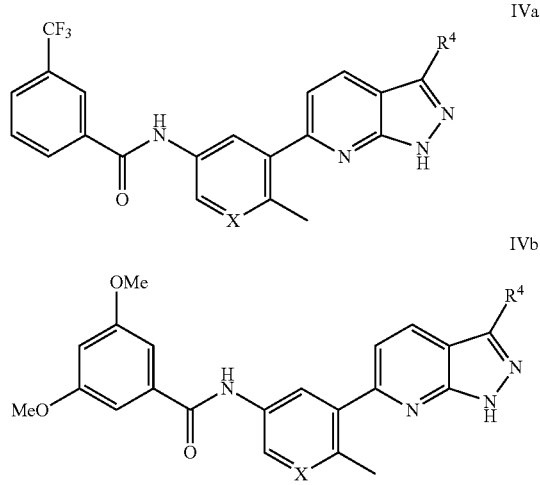

wherein X, and $R^4$ are as previously defined.

In one embodiment, a compound of the invention is according to any one of Formulae I-IVb, wherein $R^4$ is $C_{1-2}$ alkyl. In a particular embodiment, $R^4$ is —CH$_3$, or —CH$_2$CH$_3$.

In one embodiment a compound of the invention is according to any one of Formulae I-IVb, wherein $R^4$ is $C_{1-2}$ alkyl substituted with one OH. In another embodiment, $R^4$ is —CH$_3$, or —CH$_2$CH$_3$, each of which is substituted with one OH. In a particular embodiment, a compound of the invention is according to any one of Formulae I-IVb, wherein $R^4$ is —CH(OH)CH$_3$. In a more particular embodiment, $R^4$ is

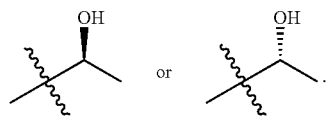

In one embodiment a compound of the invention is according to any one of Formulae I-IVb, wherein $R^4$ is $C_{1-2}$ alkyl substituted with one OH and one 5-6 membered heterocycloalkyl comprising one or two heteroatoms independently selected from N, O, and S. In another embodiment, $R^4$ is —CH$_3$, or —CH$_2$CH$_3$, each of which is substituted with one OH and one 5-6 membered heterocycloalkyl comprising one or two heteroatoms independently selected from N, O, and S. In a particular embodiment, $R^4$ is $C_{1-2}$ alkyl substituted with one OH and one heterocycloalkyl selected from pyrrolidinyl, piperidinyl, piperazinyl, and morpholinyl. In another particular embodiment, $R^4$ is —CH$_3$, or —CH$_2$CH$_3$, each of which is substituted with one OH and one heterocycloalkyl selected from pyrrolidinyl, piperidinyl, piperazinyl, and morpholinyl. In one embodiment a compound of the invention is according to any one of Formulae I-IVb, wherein $R^4$ is:

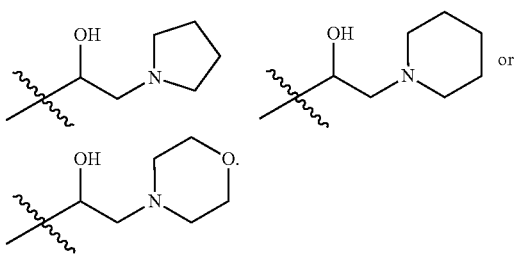

In one embodiment, a compound of the invention is according to any one of Formulae I-IVb, wherein $R^4$ is $C_{3-6}$ cycloalkyl. In a particular embodiment, $R^4$ is cyclopropyl, cyclobutyl, or cyclopentyl. In a more particular embodiment, $R^4$ is cyclopropyl.

In one embodiment a compound of the invention is according to any one of Formulae I-IVb, wherein $R^4$ is $C_{3-6}$ cycloalkyl substituted with one OH. In another embodiment, $R^4$ is cyclopropyl, cyclobutyl, or cyclopentyl, each of which is substituted with one OH. In one embodiment a compound of the invention is according to any one of Formulae I-IVb, wherein $R^4$ is

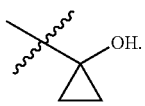

In one embodiment, a compound of the invention is according to anyone of Formulae I-IVb, wherein X is N.

In one embodiment, a compound of the invention is according to anyone of Formulae I-IVb, wherein X is CH.

In one embodiment, a compound of the invention is selected from:
N-(3-(3-(hydroxymethyl)-1H-pyrazolo[3,4-b]pyridin-6-yl)-4-methylphenyl)-3-(trifluoromethyl)benzamide,
N-(3-(3-(1-hydroxy-2-morpholinoethyl)-1H-pyrazolo[3,4-b]pyridin-6-yl)-4-methylphenyl)-3-(trifluoromethyl)benzamide,
N-(3-(3-(1-hydroxy-2-morpholinoethyl)-1H-pyrazolo[3,4-b]pyridin-6-yl)-4-methylphenyl)-3,5-dimethoxybenzamide,
3-(3-(1-hydroxy-2-morpholinoethyl)-1H-pyrazolo[3,4-b]pyridin-6-yl)-4-methyl-N-(3-(trifluoromethyl)phenyl)benzamide,
3-(dimethylamino)-N-(3-(3-(1-hydroxy-2-morpholinoethyl)-1H-pyrazolo[3,4-b]pyridin-6-yl)-4-methylphenyl)benzamide,
N-(3-(3-(1-hydroxy-2-morpholinoethyl)-1H-pyrazolo[3,4-b]pyridin-6-yl)-4-methylphenyl)-3,5-dimethylbenzamide,
N-(3-(3-ethyl-1H-pyrazolo[3,4-b]pyridin-6-yl)-4-methylphenyl)-3,5-dimethoxybenzamide,
N-(3-(3-(1-hydroxyethyl)-1H-pyrazolo[3,4-b]pyridin-6-yl)-4-methylphenyl)-3,5-dimethoxybenzamide,
N-(3-(3-(hydroxymethyl)-1H-pyrazolo[3,4-b]pyridin-6-yl)-4-methylphenyl)-3,5-dimethoxybenzamide,
3,5-dimethoxy-N-(4-methyl-3-(3-methyl-1H-pyrazolo[3,4-b]pyridin-6-yl)phenyl)benzamide,
N-(5-(3-ethyl-1H-pyrazolo[3,4-b]pyridin-6-yl)-6-methylpyridin-3-yl)-3,5-dimethoxybenzamide,
N-(3-(3-(hydroxymethyl)-1H-pyrazolo[3,4-b]pyridin-6-yl)-4-methylphenyl)-3,5-dimethylbenzamide, 3,5-dimethoxy-N-(6-methyl-5-(3-methyl-1H-pyrazolo[3,4-b]pyridin-6-yl)pyridin-3-yl)benzamide,
N-(3-(3-ethyl-1H-pyrazolo[3,4-b]pyridin-6-yl)-4-methylphenyl)-3-methoxy-5-methylbenzamide,
N-(3-(3-ethyl-1H-pyrazolo[3,4-b]pyridin-6-yl)-4-methylphenyl)-3-methyl-5-(2-morpholinoethoxyl)benzamide,
N-(3-(3-ethyl-1H-pyrazolo[3,4-b]pyridin-6-yl)-4-methylphenyl)-3-(2-methoxyethoxy)-5-methylbenzamide,
N-(4-chloro-3-(3-ethyl-1H-pyrazolo[3,4-b]pyridin-6-yl)phenyl)-3,5-dimethoxybenzamide,
N-(3-(3-ethyl-1H-pyrazolo[3,4-b]pyridin-6-yl)-4-methylphenyl)-3-(2-hydroxyethoxy)-5-methylbenzamide,
3-(2-(dimethylamino)ethoxy)-N-(3-(3-ethyl-1H-pyrazolo[3,4-b]pyridin-6-yl)-4-methylphenyl)-5-methylbenzamide,
N-(3-(3-ethyl-1H-pyrazolo[3,4-b]pyridin-6-yl)-4-methylphenyl)-3-methyl-5-(3-(4-methylpiperazin-1-yl)propoxy)benzamide,
N-(3-(3-(1-hydroxyethyl)-1H-pyrazolo[3,4-b]pyridin-6-yl)-4-methylphenyl)-3-methyl-5-(2-morpholinoethoxyl)benzamide,
N-(3-(3-(1-hydroxycyclopropyl)-1H-pyrazolo[3,4-b]pyridin-6-yl)-4-methylphenyl)-3,5-dimethoxybenzamide,
3-(2-aminoethoxy)-N-(3-(3-ethyl-1H-pyrazolo[3,4-b]pyridin-6-yl)-4-methylphenyl)-5-methylbenzamide,
3-(3-aminopropoxy)-N-(3-(3-ethyl-1H-pyrazolo[3,4-b]pyridin-6-yl)-4-methylphenyl)-5-methylbenzamide,
N-(4-ethyl-3-(3-ethyl-1H-pyrazolo[3,4-b]pyridin-6-yl)phenyl)-3,5-dimethoxybenzamide,
N-(3-(3-ethyl-1H-pyrazolo[3,4-b]pyridin-6-yl)-4-methylphenyl)-3-methoxy-5-(trifluoromethyl)benzamide,
N-(3-(3-(1-hydroxyethyl)-1H-pyrazolo[3,4-b]pyridin-6-yl)-4-methylphenyl)-3-(trifluoromethyl)benzamide,
3-cyclopropyl-N-(5-(3-ethyl-1H-pyrazolo[3,4-b]pyridin-6-yl)-6-methylpyridin-3-yl)-5-methoxybenzamide,
3-(2-aminoethoxy)-N-(3-(3-ethyl-1H-pyrazolo[3,4-b]pyridin-6-yl)-4-methylphenyl)-5-methoxybenzamide,
N-(3-(3-ethyl-1H-pyrazolo[3,4-b]pyridin-6-yl)-4-methylphenyl)-3-methoxy-5-(2-morpholinoethoxyl)benzamide,
N-(5-(3-ethyl-1H-pyrazolo[3,4-b]pyridin-6-yl)-6-methylpyridin-3-yl)-3-(trifluoromethyl)benzamide,
3-(2-aminoethoxy)-N-(5-(3-ethyl-1H-pyrazolo[3,4-b]pyridin-6-yl)-6-methylpyridin-3-yl)-5-methoxybenzamide,
3-(3-aminopropoxy)-N-(3-(3-ethyl-1H-pyrazolo[3,4-b]pyridin-6-yl)-4-methylphenyl)-5-methoxybenzamide,
3-(3-aminopropoxy)-N-(5-(3-ethyl-1H-pyrazolo[3,4-b]pyridin-6-yl)-6-methylpyridin-3-yl)-5-methoxybenzamide,
(S)—N-(3-(3-(1-hydroxyethyl)-1H-pyrazolo[3,4-b]pyridin-6-yl)-4-methylphenyl)-3,5-dimethoxybenzamide,
(R)—N-(3-(3-(1-hydroxyethyl)-1H-pyrazolo[3,4-b]pyridin-6-yl)-4-methylphenyl)-3,5-dimethoxybenzamide,
N-(5-(3-ethyl-1H-pyrazolo[3,4-b]pyridin-6-yl)-6-methylpyridin-3-yl)-3,5-dimethylbenzamide,
3-cyclopropyl-N-(3-(3-ethyl-1H-pyrazolo[3,4-b]pyridin-6-yl)-4-methylphenyl)-5-methoxybenzamide,
3,5-dimethyl-N-(6-methyl-5-(3-methyl-1H-pyrazolo[3,4-b]pyridin-6-yl)pyridin-3-yl)benzamide,
N-(6-methyl-5-(3-methyl-1H-pyrazolo[3,4-b]pyridin-6-yl)pyridin-3-yl)-3-(trifluoromethyl)benzamide,
N-(3-(3-(1-hydroxyethyl)-1H-pyrazolo[3,4-b]pyridin-6-yl)-4-methylphenyl)-3,5-dimethylbenzamide,
(S)—N-(3-(3-(1-hydroxyethyl)-1H-pyrazolo[3,4-b]pyridin-6-yl)-4-methylphenyl)-3-(trifluoromethyl)benzamide,
(R)—N-(3-(3-(1-hydroxyethyl)-1H-pyrazolo[3,4-b]pyridin-6-yl)-4-methylphenyl)-3-(trifluoromethyl)benzamide,
(N-(3-(3-(1-hydroxy-2-morpholinoethyl)-1H-pyrazolo[3,4-b]pyridin-6-yl)-4-methylphenyl)-3-methylbenzamide),
N-(3-(3-(1-hydroxy-2-(pyrrolidin-1-yl)ethyl)-1H-pyrazolo[3,4-b]pyridin-6-yl)-4-methylphenyl)-3,5-dimethylbenzamide,
N-(3-(3-cyclopropyl-1H-pyrazolo[3,4-b]pyridin-6-yl)-4-methylphenyl)-3,5-dimethoxybenzamide,
N-(3-(3-(2-hydroxyethyl)-1H-pyrazolo[3,4-b]pyridin-6-yl)-4-methylphenyl)-3-(trifluoromethyl)benzamide,
N-(5-(3-(hydroxymethyl)-1H-pyrazolo[3,4-b]pyridin-6-yl)-6-methylpyridin-3-yl)-3-(trifluoromethyl)benzamide,
N-(5-(3-(1-hydroxyethyl)-1H-pyrazolo[3,4-b]pyridin-6-yl)-6-methylpyridin-3-yl)-3,5-dimethoxybenzamide,
N-(5-(3-(hydroxymethyl)-1H-pyrazolo[3,4-b]pyridin-6-yl)-6-methylpyridin-3-yl)-3,5-dimethoxybenzamide,
N-(5-(3-cyclopropyl-1H-pyrazolo[3,4-b]pyridin-6-yl)-6-methylpyridin-3-yl)-3,5-dimethoxybenzamide,
N-(5-(3-ethyl-1H-pyrazolo[3,4-b]pyridin-6-yl)-6-methylpyridin-3-yl)-3-methoxy-5-(2-morpholinoethoxy)benzamide,
N-(5-(3-ethyl-1H-pyrazolo[3,4-b]pyridin-6-yl)-6-methylpyridin-3-yl)-3-methoxy-5-(trifluoromethyl)benzamide,
(3-(dimethylamino)-N-(3-(3-ethyl-1H-pyrazolo[3,4-b]pyridin-6-yl)-4-methylphenyl)-5-(trifluoromethyl)benzamide),
N-(3-(3-ethyl-1H-pyrazolo[3,4-b]pyridin-6-yl)-4-methylphenyl)-3-(2-morpholinoethoxy)-5-(trifluoromethyl)benzamide, and
3-cyclopropyl-N-(5-(3-ethyl-1H-pyrazolo[3,4-b]pyridin-6-yl)-6-methylpyridin-3-yl)-5-(2-morpholinoethoxyl)benzamide.

In one embodiment, the compound of the invention is N-{3-[3-((S)-1-Hydroxy-ethyl)-1H-pyrazolo[3,4-b]pyridin-6-yl]-4-methyl-phenyl}-3-trifluoromethyl-benzamide.

In another embodiment, the compound of the invention is not N-{3-[3-((S)-1-Hydroxy-ethyl)-1H-pyrazolo[3,4-b]pyridin-6-yl]-4-methyl-phenyl}-3-trifluoromethyl-benzamide.

In one embodiment a compound of the invention is not an isotopic variant.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound.

In one aspect a compound of the invention according to any one of the embodiments herein described is a solvate of a pharmaceutically acceptable salt of a compound.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

While specified groups for each embodiment have generally been listed above separately, a compound of the invention may be one for which one or more variables (for example, R groups) is selected from one or more embodiments according to any of the Formula(e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (Bundgaard, 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Particularly useful are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

CLAUSES

1) A compound according to Formula I:

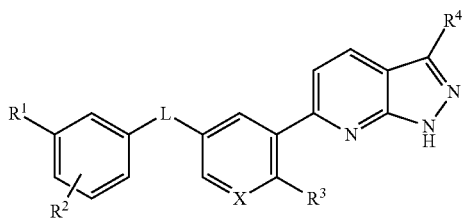

I wherein
X is N, or CH;
L is —NH(C=O)—, or —C(=O)NH—;
$R^1$ is
—CN,
halo,
$C_{1-4}$ alkyl optionally substituted with one or more independently selected $R^{6a}$ groups,
$C_{1-4}$ alkoxy optionally substituted with one or more independently selected $R^{6b}$ groups,
$C_{3-4}$ cycloalkyl,
phenyl,
—$SO_2C_{1-4}$ alkyl, or
—$NR^{7a}R^{7b}$;
$R^2$ is H, cyclopropyl, $C_{1-4}$ alkyl (optionally substituted with one or more halo), or $C_{1-4}$ alkoxy;
$R^3$ is —$CH_3$, —$CH_2CH_3$, or Cl;
$R^4$ is
$C_{1-2}$ alkyl optionally substituted with one OH,
$C_{1-2}$ alkyl substituted with one OH and one 5-6 membered heterocycloalkyl comprising one or two heteroatoms independently selected from N, O, and S,
$C_{3-6}$ cycloalkyl optionally substituted with one OH;

each $R^{6a}$ is
OH,
halo, or
$C_{1-4}$ alkoxy
each $R^{6b}$ is
OH,
halo,
$C_{1-4}$ alkoxy,
—$NR^{8a}R^{8b}$, or
5-6 membered heterocycloalkyl comprising one or two heteroatoms independently selected from N, O, and S, optionally substituted with one $C_{1-4}$ alkyl;
each $R^{7a}$, $R^{7b}$ is independently selected from H, and $C_{1-4}$ alkyl; and
each $R^{8a}$ or $R^{8b}$ is independently selected from H, and $C_{1-4}$ alkyl;
or pharmaceutically acceptable salt thereof.

2) A compound or pharmaceutically acceptable salt thereof, according to clause 1, wherein the compound is according to Formula II:

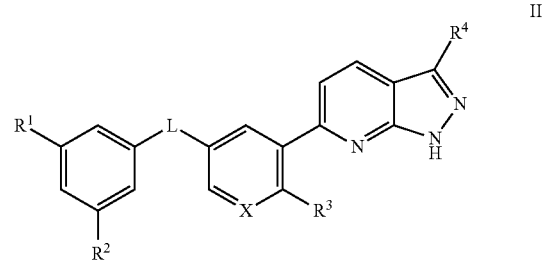

II wherein $R^1$, $R^2$, $R^3$, $R^4$ and L are as defined in clause 1.

3) A compound or pharmaceutically acceptable salt thereof, according to clause 1 or 2, wherein $R^1$ is CN, F, or Cl.
4) A compound or pharmaceutically acceptable salt thereof, according to clause 1 or 2, wherein $R^1$ is $C_{1-4}$ alkyl.
5) A compound or pharmaceutically acceptable salt thereof, according to clause 4, wherein $R^1$ is —$CH_3$, or —$CH_2CH_3$.
6) A compound or pharmaceutically acceptable salt thereof, according to clause 1 or 2, wherein $R^1$ is $C_{1-4}$ alkyl substituted with one or more independently selected $R^{6a}$ groups.
7) A compound or pharmaceutically acceptable salt thereof, according to clause 6, wherein each $R^{6a}$ is OH, F, Cl, —$OCH_3$, or —$OCH_2CH_3$.
8) A compound or pharmaceutically acceptable salt thereof, according to clause 1 or 2, wherein $R^1$ is —$CH_3$, or —$CH_2CH_3$, each of which is substituted with one or more independently selected OH, F, Cl, —$OCH_3$, or —$OCH_2CH_3$.
9) A compound or pharmaceutically acceptable salt thereof, according to clause 1 or 2, wherein $R^1$ is $C_{1-4}$ alkoxy.
10) A compound or pharmaceutically acceptable salt thereof, according to clause 5, wherein $R^1$ is —$OCH_3$, or —$OCH_2CH_3$.
11) A compound or pharmaceutically acceptable salt thereof, according to clause 1 or 2, wherein $R^1$ is $C_{1-4}$ alkoxy substituted with one or more independently selected $R^{6b}$ groups.
12) A compound or pharmaceutically acceptable salt thereof, according to clause 11, wherein each $R^{6b}$ is OH, F, Cl, —$OCH_3$, or —$OCH_2CH_3$.
13) A compound or pharmaceutically acceptable salt thereof, according to clause 11, wherein each $R^{6b}$ is —$NR^{8a}R^{8b}$.
14) A compound or pharmaceutically acceptable salt thereof, according to clause 13, wherein $R^{8a}$ and $R^{8b}$ are independently selected from —$CH_3$, and —$CH_2CH_3$.

15) A compound or pharmaceutically acceptable salt thereof, according to clause 11, wherein each $R^{6b}$ is pyrrolidinyl, morpholinyl, piperidinyl, piperazinyl, each of which is optionally substituted with $C_{1-4}$ alkyl.
16) A compound or pharmaceutically acceptable salt thereof, according to clause 1 or 2, wherein $R^1$ is —OCH$_3$, or —OCH$_2$CH$_3$, each of which is substituted with one or more independently selected OH, F, Cl, —OCH$_3$, —OCH$_2$CH$_3$, or —NMe$_2$.
17) A compound or pharmaceutically acceptable salt thereof, according to clause 1 or 2, wherein $R^1$ is cyclopropyl, cyclobutyl, or cyclopentyl.
18) A compound or pharmaceutically acceptable salt thereof, according to clause 1 or 2, wherein $R^1$ is —SO$_2$CH$_3$, or —SO$_2$CH$_2$CH$_3$.
19) A compound or pharmaceutically acceptable salt thereof, according to clause 1 or 2, wherein $R^1$ is $NR^{7a}R^{7b}$.
20) A compound or pharmaceutically acceptable salt thereof, according to clause 19, wherein $R^{7a}$ and $R^{7b}$ are independently selected from —CH$_3$, and —CH$_2$CH$_3$.
21) A compound or pharmaceutically acceptable salt thereof, according to any one of clauses 1-20, wherein $R^2$ is —CH$_3$, —CH$_2$CH$_3$, —OCH$_3$, or —OCH$_2$CH$_3$.
22) A compound or pharmaceutically acceptable salt thereof, according to any one of clauses 1-20, wherein $R^2$ is H
23) A compound or pharmaceutically acceptable salt thereof, according to any one of clauses 1 or 2, wherein the compound is according to Formula IIIa:

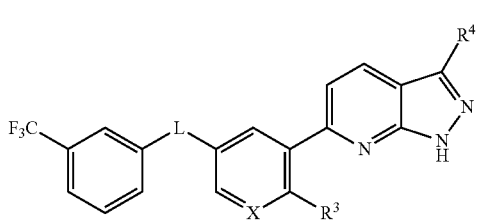

IIIa wherein X, L, $R^3$, and $R^4$ are as defined in clause 1.
24) A compound or pharmaceutically acceptable salt thereof, according to any one of clauses 1 or 2, wherein the compound is according to Formula IIIb:

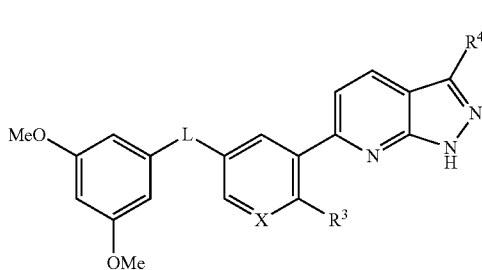

IIIb wherein X, L, $R^3$, and $R^4$ are as defined in clause 1.
25) A compound or pharmaceutically acceptable salt thereof, according to any one of clauses 1-24, wherein L is —NH(C=O)—.
26) A compound or pharmaceutically acceptable salt thereof, according to any one of clauses 1-24, wherein L is —C(=O)NH—.
27) A compound or pharmaceutically acceptable salt thereof, according to any one of clauses 1 or 2, wherein the compound is according to Formula IVa:

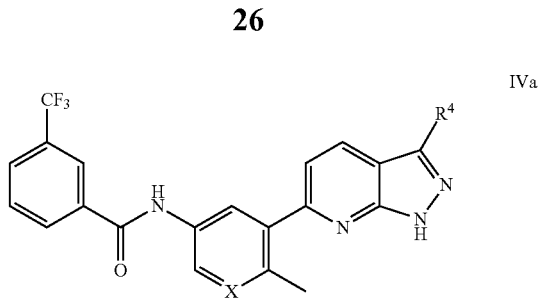

IVa wherein X, and $R^4$ is as described above.
28) A compound or pharmaceutically acceptable salt thereof, according to any one of clauses 1-27, wherein $R^4$ is $C_{1-2}$ alkyl.
29) A compound or pharmaceutically acceptable salt thereof, according to any one of clauses 1-27, wherein $R^4$ is —CH$_3$, or —CH$_2$CH$_3$.
30) A compound or pharmaceutically acceptable salt thereof, according to any one of clauses 1-27, wherein $R^4$ is $C_{1-2}$ alkyl substituted with one OH.
31) A compound or pharmaceutically acceptable salt thereof, according to any one of clauses 1-27, wherein $R^4$ is —CH(OH)CH$_3$.
32) A compound or pharmaceutically acceptable salt thereof, according to any one of clauses 1-27, wherein $R^4$ is:

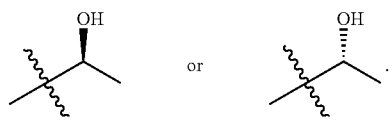

33) A compound or pharmaceutically acceptable salt thereof, according to any one of clauses 1-27, wherein $R^4$ is $C_{1-2}$ alkyl substituted with one OH and one 5-6 membered heterocycloalkyl comprising one or two heteroatoms independently selected from N, O, and S.
34) A compound or pharmaceutically acceptable salt thereof, according to any one of clauses 1-27, wherein In another particular embodiment, $R^4$ is —CH$_3$, or —CH$_2$CH$_3$, each of which is substituted with one OH and one heterocycle selected from pyrrolidinyl, piperidinyl, piperazinyl, and morpholinyl.
35) A compound or pharmaceutically acceptable salt thereof, according to any one of clauses 1-27, wherein In another particular embodiment, $R^4$ is:

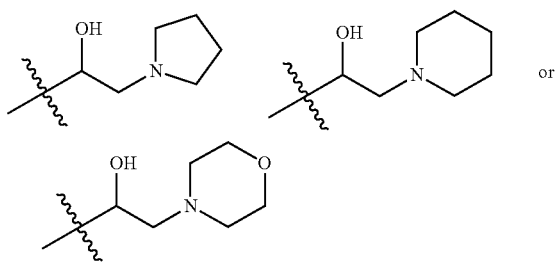

36) A compound or pharmaceutically acceptable salt thereof, according to any one of clauses 1-27, wherein $R^4$ is $C_{3-6}$ cycloalkyl.
37) A compound or pharmaceutically acceptable salt thereof, according to any one of clauses 1-27, wherein $R^4$ is cyclopropyl, cyclobutyl, or cyclopentyl.

38) A compound or pharmaceutically acceptable salt thereof, according to any one of clauses 1-27, wherein $R^4$ is $C_{3-6}$ cycloalkyl substituted with one OH.

39) A compound or pharmaceutically acceptable salt thereof, according to any one of clauses 1-27, wherein $R^4$ is cyclopropyl, cyclobutyl, or cyclopentyl, each of which is substituted with one OH.

40) A compound or pharmaceutically acceptable salt thereof, according to any one of clauses 1-27, wherein $R^4$ is

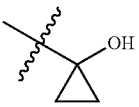

41) A compound or pharmaceutically acceptable salt thereof, according to any one of clauses 1-40, wherein X is CH.

42) A compound or pharmaceutically acceptable salt thereof, according to any one of clauses 1-40, wherein X is N.

43) A pharmaceutical composition comprising a pharmaceutically acceptable carrier and a pharmaceutically effective amount of the compound according to any one of clauses 1-42.

44) A pharmaceutical composition according to clause 43 comprising a further therapeutic agent.

45) A compound according to any one of clauses 1-42, or a pharmaceutical composition according to clause 43 or 44, for use in medicine.

46) A compound according to any one of clauses 1-42, or a pharmaceutical composition according to clause 43 or 44, for use in the prophylaxis, and/or treatment of proliferative diseases.

47) A method for the, prophylaxis and/or treatment of proliferative diseases (in particular metastatic diseases, and/or cancer), comprising administering an amount of the compound according to any one of clauses 1-42, or the pharmaceutical composition according to clause 43 or 44, sufficient to effect said treatment, or prophylaxis.

48) The method according to clause 8, wherein the compound according to any one of clause 1, or the pharmaceutical composition according to clause 2 or 3, is administered in combination with a further therapeutic agent.

49) The pharmaceutical composition according to clause 44, or the method according to clause 48, wherein the further therapeutic agent is an agent for the treatment proliferative diseases.

50) A compound or pharmaceutical composition for use according to clause 46, or the method according to clause 48, wherein the proliferative disease is breast cancer.

51) A compound or pharmaceutical composition for use according to clause 46, or the method according to clause 48, wherein the proliferative disease is melanoma.

52) A compound or pharmaceutical composition for use according to clause 46, or the method according to clause 48, wherein the proliferative disease is prostate cancer.

53) A compound or pharmaceutical composition for use according to clause 46, or the method according to clause 48, wherein the proliferative disease is renal cancer.

54) A compound or pharmaceutical composition for use according to clause 46, or the method according to clause 48, wherein the proliferative disease is sarcoma.

55) A compound or pharmaceutical composition for use according to clause 46, or the method according to clause 48, wherein the proliferative disease is uterine cancer.

56) A compound or pharmaceutical composition for use according to clause 46, or the method according to clause 48, wherein the proliferative disease is lung cancer.

57) A compound or pharmaceutical composition for use according to clause 46, or the method according to clause 48, wherein the proliferative disease is colon cancer.

58) A compound or pharmaceutical composition for use according to clause 46, or the method according to clause 48, wherein the proliferative disease is gastric cancer.

59) A compound or pharmaceutical composition for use according to clause 46, or the method according to clause 48, wherein the proliferative disease is liver cancer.

60) A compound or pharmaceutical composition for use according to clause 46, or the method according to clause 48, wherein the proliferative disease is ovarian cancer.

61) A compound or pharmaceutical composition for use according to clause 46, or the method according to clause 48, wherein the proliferative disease is pancreatic cancer.

Pharmaceutical Compositions

When employed as a pharmaceutical, a compound of the invention is typically administered in the form of a pharmaceutical composition. Such compositions can be prepared in a manner well known in the pharmaceutical art and comprise at least one active compound of the invention according to Formula I. Generally, a compound of the invention is administered in a pharmaceutically effective amount. The amount of compound of the invention actually administered will typically be determined by a physician, in the light of the relevant circumstances, including the condition to be treated, the chosen route of administration, the actual compound of the invention administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, a compound of the invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the compound of the invention according to Formula I is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compound of the inventions of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint or orange flavoring.

Injectable compositions are typically based upon injectable sterile saline or phosphate-buffered saline or other injectable carriers known in the art. As before, the active compound of the invention according to Formula I in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17$^{th}$ edition, 1985, Mack Publishing Company, Easton, Pa., which is incorporated herein by reference (Remington, 1985).

A compound of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1

Tablets

A compound of the invention according to Formula I may be admixed as a dry powder with a dry gelatin binder in an approximate 1:2 weight ratio. A minor amount of magnesium stearate may be added as a lubricant. The mixture may be formed into 240-270 mg tablets (80-90 mg of active compound of the invention according to Formula I per tablet) in a tablet press.

Formulation 2

Capsules

A compound of the invention according to Formula I may be admixed as a dry powder with a starch diluent in an approximate 1:1 weight ratio. The mixture may be filled into 250 mg capsules (125 mg of active compound of the invention according to Formula I per capsule).

Formulation 3

Liquid

A compound of the invention according to Formula I (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4

Tablets

A compound of the invention according to Formula I may be admixed as a dry powder with a dry gelatin binder in an approximate 1:2 weight ratio. A minor amount of magnesium stearate may be added as a lubricant. The mixture may be formed into 450-900 mg tablets (150-300 mg of active compound of the invention according to Formula I) in a tablet press.

Formulation 5

Injection

A compound of the invention according to Formula I may be dissolved or suspended in a buffered sterile saline injectable aqueous medium to a concentration of approximately 5 mg/mL.

Formulation 6

Topical

Stearyl alcohol (250 g) and a white petrolatum (250 g) may be melted at about 75° C. and then a mixture of A compound of the invention according to Formula I (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of inflammatory conditions, type 2 diabetes, neurological and/or neurodegenerative diseases, autoimmune diseases, proliferative diseases (in particular metastatic diseases, and/or cancer), abnormal angiogenesis associated diseases, degradation of cartilage, and/or disruption of cartilage homeostasis.

In another embodiment, the present invention provides compounds of the invention, or pharmaceutical compositions comprising a compound of the invention for use in the manufacture of a medicament for use in the prophylaxis and/or treatment of inflammatory conditions, type 2 diabetes, neurological and/or neurodegenerative diseases, autoimmune diseases, proliferative diseases (in particular metastatic diseases, and/or cancer), abnormal angiogenesis associated diseases, degradation of cartilage, and/or disruption of cartilage homeostasis.

In a particular embodiment, the present invention provides the use of a compound of the invention or pharmaceutical compositions comprising a compound of the invention, for use in the prophylaxis and/or treatment of inflammatory conditions, type 2 diabetes, neurological and/or neurodegenerative diseases, autoimmune diseases, proliferative diseases (in particular metastatic diseases, and/or cancer), abnormal angiogenesis associated diseases, degradation of cartilage, and/or disruption of cartilage homeostasis.

In additional method of treatment aspects, this invention provides methods of prophylaxis and/or treatment of a mammal with a condition selected from inflammatory conditions, type 2 diabetes, neurological and/or neurodegenerative diseases, autoimmune diseases, proliferative diseases (in particular metastatic diseases, and/or cancer), abnormal angiogenesis associated diseases, degradation of cartilage, and/or disruption of cartilage homeostasis, which methods comprise the administration of an effective amount of a compound of the invention or one or more of the pharmaceutical compositions herein described for the treatment or prophylaxis of said condition.

In one embodiment, the present invention provides pharmaceutical compositions comprising a compound of the invention, and another therapeutic agent. In a particular embodiment, the other therapeutic agent is for the treatment of inflammatory conditions, type 2 diabetes, neurological and/or neurodegenerative diseases, autoimmune diseases, proliferative diseases (in particular metastatic diseases, and/or cancer), abnormal angiogenesis associated diseases, degradation of cartilage, and/or disruption of cartilage homeostasis treatment agent.

In additional method of treatment aspects, this invention provides methods of prophylaxis and/or treatment of a mammal with a condition selected from inflammatory conditions, type 2 diabetes, neurological and/or neurodegenerative diseases, autoimmune diseases, proliferative diseases (in particular metastatic diseases, and/or cancer), abnormal angiogenesis associated diseases, degradation of cartilage, and/or disruption of cartilage homeostasis, which methods comprise the administration of an effective amount of a compound of the invention or one or more of the pharmaceutical compositions herein described for the treatment or prophylaxis of said condition.

In one embodiment, the present invention provides compounds of the invention or pharmaceutical compositions comprising a compound of the invention, for use in the prophylaxis and/or treatment of inflammatory conditions. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease and ulcerative colitis). More particularly, the inflammatory disease is selected from rheumatoid arthritis, and chronic obstructive pulmonary disease (COPD).

In one embodiment, the present invention provides the use of a compound of the invention or pharmaceutical compositions comprising a compound of the invention, in the prophylaxis and/or treatment of inflammatory conditions. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease and ulcerative colitis). More particularly, the inflammatory disease is selected from rheumatoid arthritis, and chronic obstructive pulmonary disease (COPD).

In one embodiment, the present invention provides the use of a compound of the invention or pharmaceutical compositions comprising a compound of the invention, in the manufacture of a medicine for the prophylaxis and/or treatment of inflammatory conditions. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease and ulcerative colitis). More particularly, the inflammatory disease is selected from rheumatoid arthritis, and chronic obstructive pulmonary disease (COPD).

In additional method of treatment aspects, this invention provides methods of prophylaxis and/or treatment of a mammal with a condition selected from inflammatory conditions, which methods comprise the administration of an effective amount of a compound of the invention or one or more of the pharmaceutical compositions herein described for the treatment or prophylaxis of said condition. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease and ulcerative colitis). More particularly, the inflammatory disease is selected from rheumatoid arthritis, and chronic obstructive pulmonary disease (COPD).

In one embodiment, the present invention provides compounds of the invention or pharmaceutical compositions comprising a compound of the invention, for use in the prophylaxis and/or treatment of type 2 diabetes.

In one embodiment, the present invention provides the use of a compound of the invention or pharmaceutical compositions comprising a compound of the invention, in the prophylaxis and/or treatment of type 2 diabetes.

In one embodiment, the present invention provides the use of a compound of the invention or pharmaceutical compositions comprising a compound of the invention, in the manufacture of a medicine for the prophylaxis and/or treatment of type 2 diabetes.

In additional method of treatment aspects, this invention provides methods of prophylaxis and/or treatment of a mammal with a condition selected from type 2 diabetes, which methods comprise the administration of an effective amount of a compound of the invention or one or more of the pharmaceutical compositions herein described for the treatment or prophylaxis of said condition.

In one embodiment, the present invention provides compounds of the invention or pharmaceutical compositions comprising a compound of the invention, for use in the prophylaxis and/or treatment of neurological and/or neurodegenerative diseases. In a particular embodiment, the neurological and/or neurodegenerative disease is selected from stroke, spinal cord injury, traumatic brain injury, Alzheimer's diseases, Parkinson's disease, amyotrophic lateral sclerosis, Huntington's diseases, and multiple sclerosis.

In one embodiment, the present invention provides the use of a compound of the invention or pharmaceutical compositions comprising a compound of the invention, in the prophylaxis and/or treatment of neurological and/or neurodegenerative diseases. In a particular embodiment, the neurological and/or neurodegenerative disease is selected from stroke, spinal cord injury, traumatic brain injury, Alzheimer's diseases, Parkinson's disease, amyotrophic lateral sclerosis, Huntington's diseases, and multiple sclerosis.

In one embodiment, the present invention provides the use of a compound of the invention or pharmaceutical compositions comprising a compound of the invention, in the manufacture of a medicine for the prophylaxis and/or treatment of neurological and/or neurodegenerative diseases. In a particular embodiment, the neurological and/or neurodegenerative disease is selected from stroke, spinal cord injury, traumatic brain injury, Alzheimer's diseases, Parkinson's disease, amyotrophic lateral sclerosis, Huntington's diseases, and multiple sclerosis.

In additional method of treatment aspects, this invention provides methods of prophylaxis and/or treatment of a mammal with a condition selected from neurological and/or neurodegenerative diseases, which methods comprise the administration of an effective amount of a compound of the invention or one or more of the pharmaceutical compositions herein described for the treatment or prophylaxis of said disease. In a particular embodiment, the neurological and/or neurodegenerative disease is selected from stroke, spinal cord injury, traumatic brain injury, Alzheimer's diseases, Parkinson's disease, amyotrophic lateral sclerosis, Huntington's diseases, and multiple sclerosis.

In one embodiment, the present invention provides compounds of the invention or pharmaceutical compositions comprising a compound of the invention, for use in the prophylaxis and/or treatment of autoimmune diseases. In a particular embodiment, the autoimmune disease is selected from COPD, asthma, systemic lupus erythematosis, type I diabetes mellitus and inflammatory bowel disease.

In one embodiment, the present invention provides the use of a compound of the invention or pharmaceutical compositions comprising a compound of the invention, in the prophylaxis and/or treatment of autoimmune diseases. In a particular embodiment, the autoimmune disease is selected from COPD, asthma, systemic lupus erythematosis, type I diabetes mellitus and inflammatory bowel disease.

In one embodiment, the present invention provides the use of a compound of the invention or pharmaceutical compositions comprising a compound of the invention, in the manufacture of a medicine for the prophylaxis and/or treatment of autoimmune diseases. In a particular embodiment, the autoimmune disease is selected from COPD, asthma, systemic lupus erythematosis, type I diabetes mellitus and inflammatory bowel disease.

In additional method of treatment aspects, this invention provides methods of prophylaxis and/or treatment of a mammal with a condition selected from autoimmune diseases, which methods comprise the administration of an effective amount of a compound of the invention or one or more of the pharmaceutical compositions herein described for the treatment or prophylaxis of said condition. In a particular embodiment, the autoimmune disease is selected from COPD, asthma, systemic lupus erythematosis, type I diabetes mellitus and inflammatory bowel disease.

In one embodiment, the present invention provides compounds of the invention or pharmaceutical compositions comprising a compound of the invention, for use in the prophylaxis and/or treatment of proliferative diseases. In a particular embodiment, the proliferative disease is cancer. In a more particular embodiment, the cancer is selected from melanoma, lymphoma, leukaemia, fibrosarcoma, rhabdomyosarcoma, mastocytoma, colorectal cancer, small cell lung cancer and non-small cell lung cancer, breast cancer, pancreatic cancer, bladder cancer, renal cancer, gastric cancer, glioblastoma, primary liver cancer, ovarian cancer, prostate cancer, urinary tract cancer, thyroid cancer, oesophagus cancer, malignant glioma and uterine leiomyosarcoma. In a more particular embodiment, the cancer is breast cancer. In another more particular embodiment, the cancer is melanoma, prostate cancer, renal cancer, sarcoma or uterine cancer. In yet another more particular embodiment, the cancer is lung cancer, colon cancer, gastric cancer, liver cancer, breast cancer, ovarian cancer, or pancreatic cancer.

In one embodiment, the present invention provides the use of a compound of the invention or pharmaceutical compositions comprising a compound of the invention, in the prophylaxis and/or treatment of proliferative diseases. In a particular embodiment, the proliferative disease is cancer. In a more particular embodiment, the cancer is selected from melanoma, lymphoma, leukaemia, fibrosarcoma, rhabdomyosarcoma, mastocytoma, colorectal cancer, small cell lung cancer and non-small cell lung cancer, breast cancer, pancreatic cancer, bladder cancer, renal cancer, gastric cancer, glioblastoma, primary liver cancer, ovarian cancer, prostate cancer, urinary tract cancer, thyroid cancer, oesophagus cancer, malignant glioma and uterine leiomyosarcoma. In a more particular embodiment, the cancer is breast cancer. In another more particular embodiment, the cancer is melanoma, prostate cancer, renal cancer, sarcoma or uterine cancer. In yet another more particular embodiment, the cancer is lung cancer, colon cancer, gastric cancer, liver cancer, breast cancer, ovarian cancer, or pancreatic cancer.

In one embodiment, the present invention provides the use of a compound of the invention or pharmaceutical compositions comprising a compound of the invention, in the manufacture of a medicine for the prophylaxis and/or treatment of proliferative diseases. In a particular embodiment, the proliferative disease is cancer. In a more particular embodiment, the cancer is selected from melanoma, lymphoma, leukaemia, fibrosarcoma, rhabdomyosarcoma, mastocytoma, colorectal cancer, small cell lung cancer and non-small cell lung cancer, breast cancer, pancreatic cancer, bladder cancer, renal cancer, gastric cancer, glioblastoma, primary liver cancer, ovarian cancer, prostate cancer, urinary tract cancer, thyroid cancer, oesophagus cancer, malignant glioma and uterine leiomyosarcoma. In a more particular embodiment, the cancer is breast cancer. In another more particular embodiment, the cancer is melanoma, prostate cancer, renal cancer, sarcoma or uterine cancer. In yet another more particular embodiment, the cancer is lung cancer, colon cancer, gastric cancer, liver cancer, breast cancer, ovarian cancer, or pancreatic cancer.

In additional method of treatment aspects, this invention provides methods of prophylaxis and/or treatment of a mammal with a condition selected from proliferative diseases (in particular metastatic diseases, and/or cancer), which methods comprise the administration of an effective amount of a compound of the invention or one or more of the pharmaceutical compositions herein described for the treatment or prophylaxis of said disease. In a particular embodiment, the proliferative disease is cancer. In a more particular embodiment, the cancer is selected from melanoma, lymphoma, leukaemia, fibrosarcoma, rhabdomyosarcoma, mastocytoma, colorectal cancer, small cell lung cancer and non-small cell lung cancer, breast cancer, pancreatic cancer, bladder cancer, renal cancer, gastric cancer, glioblastoma, primary liver cancer, ovarian cancer, prostate cancer and uterine leiomyosarcoma. In a more particular embodiment, the cancer is breast cancer. In another more particular embodiment, the cancer is melanoma, prostate cancer, renal cancer, sarcoma or uterine cancer. In yet another more particular embodiment, the cancer is lung cancer, colon cancer, gastric cancer, liver cancer, breast cancer, ovarian cancer, or pancreatic cancer.

In one embodiment, the present invention provides compounds of the invention or pharmaceutical compositions comprising a compound of the invention, for use in the prophylaxis and/or treatment of metastatic diseases. In a particular embodiment, the metastatic disease is bile duct cancer, colon cancer, gallbladder cancer, malignant melanoma, myxoma, neuroendocrine tumors, Paget's disease of the breast, rectal cancer, superior vena cava syndrome, vulvar cancer. In a more particular embodiment, the metastatic disease is breast cancer.

In one embodiment, the present invention provides the use of a compound of the invention or pharmaceutical compositions comprising a compound of the invention, in the prophylaxis and/or treatment of metastatic diseases. In a particular embodiment, the metastatic disease is bile duct cancer, colon cancer, gallbladder cancer, malignant melanoma, myxoma, neuroendocrine tumors, Paget's disease of the breast, rectal cancer, superior vena cava syndrome, vulvar cancer. In a more particular embodiment, the metastatic disease is breast cancer.

In one embodiment, the present invention provides the use of a compound of the invention or pharmaceutical compositions comprising a compound of the invention, in the manufacture of a medicine for the prophylaxis and/or treatment of metastatic diseases. In a particular embodiment, the metastatic disease is bile duct cancer, colon cancer, gallbladder cancer, malignant melanoma, myxoma, neuroendocrine tumors, Paget's disease of the breast, rectal cancer, superior vena cava syndrome, vulvar cancer. In a more particular embodiment, the metastatic disease is breast cancer.

In additional method of treatment aspects, this invention provides methods of prophylaxis and/or treatment of a mammal with a condition selected from metastatic disease, which methods comprise the administration of an effective amount of a compound of the invention or one or more of the pharmaceutical compositions herein described for the treatment or prophylaxis of said condition. In a particular embodiment, the metastatic disease is bile duct cancer, colon cancer, gallbladder cancer, malignant melanoma, myxoma, neuroendocrine tumors, Paget's disease of the breast, rectal cancer, superior vena cava syndrome, vulvar cancer. In a more particular embodiment, the metastatic disease is breast cancer.

In one embodiment, the present invention provides compounds of the invention or pharmaceutical compositions comprising a compound of the invention, for use in the prophylaxis and/or treatment of abnormal angiogenesis associated diseases. In a particular embodiment, the abnormal angiogenesis associated disease is selected from atherosclerosis, hypertension, tumor growth, inflammation, rheumatoid arthritis, wet-form macular degeneration, choroidal neovascularization, retinal neovascularization, diabetic retinopathy, and glioblastoma multiforma. In a more particular embodiment, the abnormal angiogenesis associated disease is tumor growth.

In one embodiment, the present invention provides the use of a compound of the invention or pharmaceutical compositions comprising a compound of the invention, in the prophylaxis and/or treatment of abnormal angiogenesis associated diseases. In a particular embodiment, the abnormal angiogenesis associated disease is selected from atherosclerosis, hypertension, tumor growth, inflammation, rheumatoid arthritis, wet-form macular degeneration, choroidal neovascularization, retinal neovascularization, diabetic retinopathy, and glioblastoma multiforma. In a more particular embodiment, the abnormal angiogenesis associated disease is tumor growth.

In another embodiment, the present invention provides compounds of the invention, or pharmaceutical compositions comprising a compound of the invention for use in the manufacture of a medicament for use in the prophylaxis and/or treatment of abnormal angiogenesis associated diseases. In a particular embodiment, the abnormal angiogenesis associated disease is selected from atherosclerosis, hypertension, tumor growth, inflammation, rheumatoid arthritis, wet-form macular degeneration, choroidal neovascularization, retinal neovascularization, diabetic retinopathy, and glioblastoma multiforma. In a more particular embodiment, the abnormal angiogenesis associated disease is tumor growth.

In additional method of treatment aspects, this invention provides methods of prophylaxis and/or treatment of a mammal with a condition selected from abnormal angiogenesis associated diseases, which methods comprise the administration of an effective amount of a compound of the invention or one or more of the pharmaceutical compositions herein described for the treatment or prophylaxis of said disease. In a particular embodiment, the abnormal angiogenesis associated disease is selected from atherosclerosis, hypertension, tumor growth, inflammation, rheumatoid arthritis, wet-form macular degeneration, choroidal neovascularization, retinal neovascularization, diabetic retinopathy, and glioblastoma multiforma. In a more particular embodiment, the abnormal angiogenesis associated disease is tumor growth.

In one embodiment, the present invention provides a compound of the invention or pharmaceutical compositions comprising a compound of the invention, for use in the prophylaxis and/or treatment of diseases involving degradation and/or disruption of cartilage homeostasis. In a particular embodiment, the disease involving degradation and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis.

In one embodiment, the present invention provides the use of a compound of the invention or pharmaceutical compositions comprising a compound of the invention, in the prophylaxis and/or treatment of diseases involving degradation and/or disruption of cartilage homeostasis. In a particular embodiment, the disease involving degradation and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis.

In one embodiment, the present invention provides the use of a compound of the invention or pharmaceutical compositions comprising a compound of the invention, in the manufacture of a medicine for the prophylaxis and/or treatment of diseases involving degradation and/or disruption of cartilage homeostasis. In a particular embodiment, the disease involving degradation and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis.

In additional method of treatment aspects, this invention provides methods of prophylaxis and/or treatment of a mammal with a condition selected from diseases involving degradation and/or disruption of cartilage homeostasis, which methods comprise the administration of an effective amount of a compound of the invention or one or more of the pharmaceutical compositions herein described for the treatment or prophylaxis of said disease. In a particular embodiment, the disease involving degradation and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis.

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prophylaxis and/or treatment of long-term conditions, such as degenerative conditions, the regimen for treatment usually stretches over many months or years so oral dosing is preferred for patient convenience and tolerance. With oral dosing, one to four (1-4) regular doses daily, especially one to three (1-3) regular doses daily, typically one to two (1-2) regular doses daily, and most typically one (1) regular dose daily are representative regimens. Alternatively for long lasting effect drugs, with oral dosing, once every other week, once weekly, and once a day are representative regimens. In particular, dosage regimen can be every 1-14 days, more particularly 1-10 days, even more particularly 1-7 days, and most particularly 1-3 days.

Using these dosing patterns, each dose provides from about 1 to about 1000 mg of a compound of the invention, with particular doses each providing from about 100 to about 500 mg and especially about 200 to about 300 mg.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compound of the inventions that demonstrate the same or a similar therapeutic activity and that are determined to be safe and efficacious for such combined administration. In a specific embodiment, co-administration of two (or more) agents allows for significantly lower doses of each to be used, thereby reducing the side effects seen.

In one embodiment, a compound of the invention or a pharmaceutical composition comprising a compound of the invention is administered as a medicament. In a specific embodiment, said pharmaceutical composition additionally comprises a further active ingredient.

In one embodiment, a compound of the invention is co-administered with another therapeutic agent for the treatment and/or prophylaxis of a disease involving inflammation, particular agents include, but are not limited to, immunoregulatory agents e.g. azathioprine, corticosteroids (e.g. prednisolone or dexamethasone), cyclophosphamide, cyclosporin A, tacrolimus, mycophenolate, mofetil, muromonab-CD3 (OKT3, e.g. Orthocolone®), ATG, aspirin, acetaminophen, ibuprofen, naproxen, and piroxicam.

In one embodiment, a compound of the invention is co-administered with another therapeutic agent for the treatment and/or prophylaxis of arthritis (e.g. rheumatoid arthritis), particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, tofacitinib, baricitinib, fostamatinib, and cyclosporin), and biological DMARDS (for example but without limitation infliximab, etanercept, adalimumab, rituximab, and abatacept).

In one embodiment, a compound of the invention is co-administered with another therapeutic agent for the treatment and/or prophylaxis of proliferative disorders, particular agents include but are not limited to: methotrexate, leukovorin, adriamycin, prednisone, bleomycin, cyclophosphamide, 5-fluorouracil, paclitaxel, docetaxel, gemcitabine, vincristine, vinblastine, vinorelbine, doxorubicin, tamoxifen, toremifene, megestrol acetate, anastrozole, goserelin, anti-HER2 monoclonal antibody (e.g. Herceptin™), capecitabine, raloxifene hydrochloride, EGFR inhibitors (e.g. Iressa®, Tarceva™, Erbitux™), VEGF inhibitors (e.g. Avastin™), proteasome inhibitors (e.g. Velcade™), Glivec® and hsp90 inhibitors (e.g. 17-AAG). Additionally, the compound of the invention according to Formula I may be administered in combination with other therapies including, but not limited to, radiotherapy or surgery. In a specific embodiment the proliferative disorder is selected from cancer, myeloproliferative disease and leukaemia.

In one embodiment, a compound of the invention is co-administered with another therapeutic agent for the treatment and/or prophylaxis of autoimmune diseases, particular agents include but are not limited to: glucocorticoids, cytostatic agents (e.g. purine analogs), alkylating agents, (e.g nitrogen mustards (cyclophosphamide), nitrosoureas, platinum compound of the inventions, and others), antimetabolites (e.g. methotrexate, azathioprine and mercaptopurine), cytotoxic antibiotics (e.g. dactinomycin anthracyclines, mitomycin C, bleomycin, and mithramycin), antibodies (e.g. anti-CD20, anti-CD25 or anti-CD3 (OTK3) monoclonal antibodies, Atgam® and Thymoglobuline®), cyclosporin, tacrolimus, rapamycin (sirolimus), interferons (e.g. IFN-β), TNF binding proteins (e.g. infliximab, etanercept, or adalimumab), mycophenolate, fingolimod and myriocin.

In one embodiment, a compound of the invention is co-administered with another therapeutic agent for the treatment and/or prophylaxis of asthma and/or rhinitis and/or COPD, particular agents include but are not limited to: beta2-adrenoceptor agonists (e.g. salbutamol, levalbuterol, terbutaline and bitolterol), epinephrine (inhaled or tablets), anticholinergics (e.g. ipratropium bromide), glucocorticoids (oral or inhaled). Long-acting β2-agonists (e.g. salmeterol, formoterol, bambuterol, and sustained-release oral albuterol), combinations of inhaled steroids and long-acting bronchodilators (e.g. fluticasone/salmeterol, budesonide/formoterol), leukotriene antagonists and synthesis inhibitors (e.g. montelukast, zafirlukast and zileuton), inhibitors of mediator release (e.g. cromoglycate and ketotifen), biological regulators of IgE response (e.g. omalizumab), antihistamines (e.g. ceterizine, cinnarizine, fexofenadine) and vasoconstrictors (e.g. oxymethazoline, xylomethazoline, nafazoline and tramazoline).

Additionally, a compound of the invention may be administered in combination with emergency therapies for asthma and/or COPD, such therapies include oxygen or heliox administration, nebulized salbutamol or terbutaline (optionally combined with an anticholinergic (e.g. ipratropium), systemic steroids (oral or intravenous, e.g. prednisone, prednisolone, methylprednisolone, dexamethasone, or hydrocortisone), intravenous salbutamol, non-specific beta-agonists, injected or inhaled (e.g. epinephrine, isoetharine, isoproterenol, metaproterenol), anticholinergics (IV or nebulized, e.g. glycopyrrolate, atropine, ipratropium), methylxanthines (theophylline, aminophylline, bamiphylline), inhalation anesthetics that have a bronchodilatory effect (e.g. isoflurane, halothane, enflurane), ketamine and intravenous magnesium sulfate.

In one embodiment, a compound of the invention is co-administered with another therapeutic agent for the treatment and/or prophylaxis of inflammatory bowel disease (IBD), particular agents include but are not limited to: glucocorticoids (e.g. prednisone, budesonide) synthetic disease modifying, immunomodulatory agents (e.g. methotrexate, leflunomide, sulfasalazine, mesalazine, azathioprine, 6-mercaptopurine and cyclosporin) and biological disease modifying, immunomodulatory agents (infliximab, adalimumab, rituximab, and abatacept).

In one embodiment, a compound of the invention is co-administered with another therapeutic agent for the treatment and/or prophylaxis of SLE, particular agents include but are not limited to human monoclonal antibodies (belimumab (Benlysta)), Disease-modifying antirheumatic drugs (DMARDs) such as antimalarials (e.g. plaquenil, hydroxychloroquine), immunosuppressants (e.g. methotrexate and azathioprine), cyclophosphamide and mycophenolic acid, immunosuppressive drugs and analgesics, such as nonsteroidal anti-inflammatory drugs, opiates (e.g. dextropropoxyphene and co-codamol), opioids (e.g. hydrocodone, oxycodone, MS Contin, or methadone) and the fentanyl duragesic transdermal patch.

In one embodiment, a compound of the invention is co-administered with another therapeutic agent for the treatment and/or prophylaxis of psoriasis, particular agents include but are not limited to: topical treatments such as bath solutions, moisturizers, medicated creams and ointments containing coal tar, dithranol (anthralin), corticosteroids like desoximetasone (Topicort™), fluocinonide, vitamin D3 analogues (for example, calcipotriol), argan oil and retinoids (etretinate, acitretin, tazarotene), systemic treatments such as methotrexate, cyclosporine, retinoids, tioguanine, hydroxyurea, sulfasalazine, mycophenolate mofetil, azathioprine, tacrolimus, fumaric acid esters or biologics such as Amevive™ Enbrel™, Humira™, Remicade™, Raptiva™ and ustekinumab (a IL-12 and IL-23 blocker). Additionally, a compound of the invention may be administered in combination with other therapies including, but not limited to phototherapy, or photochemotherapy (e.g. psoralen and ultraviolet A phototherapy (PUVA)).

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

Chemical Synthetic Procedures

General

The compound of the invention can be prepared from readily available starting materials using the following general methods and procedures. It will be appreciated that where typical or preferred process conditions (i.e. reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (Wuts and Greene, 2012).

The following methods are presented with details as to the preparation of a compound of the invention as defined hereinabove and the comparative examples. A compound of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 µm). Thin layer chromatography was carried out using pre-coated silica gel F-254 plates (thickness 0.25 mm) Analytical chiral column chromatography was performed on a Waters Alliance separation module 2690 and a PDA 2996 detector (254 nM). The chiral column was a Chiralpak AD-H (250×4.6 mm, 5 µm), flow rate of 1 mL/min a isocratic mode (50% Ethanol/50% Methanol). $^1$H NMR spectra were recorded on a Bruker DPX 400 NMR spectrometer (400 MHz or a Bruker Advance 300 NMR spectrometer (300 MHz). Chemical shifts (δ) for 1H NMR spectra are reported in parts per million (ppm) relative to tetramethylsilane (δ 0.00) or the appropriate residual solvent peak, i.e. $CHCl_3$ (δ 7.27), as internal reference. Multiplicities are given as singlet (s), doublet (d), triplet (t), quartet (q), quintuplet (quin), multiplet (m) and broad (br). Electrospray MS spectra were obtained on a Waters platform LC/MS spectrometer or with Waters Acquity UPLC with Waters Acquity PDA detector and SQD mass spectrometer. Columns used: UPLC BEH C18 1.7 µm 2.1×5 mm VanGuard Pre-column with Acquity UPLC BEH C18 1.7 µm 2.1×30 mm Column or Acquity UPLC BEH C18 1.7 µm 2.1×50 mm Column. All the methods are using $MeCN/H_2O$ gradients. MeCN and $H_2O$ contain either 0.1% Formic Acid or $NH_3$ (10 mM). Preparative LCMS: column used, Waters XBridge Prep C18 5 µm ODB 30 mm ID×100 mm L (preparative column) and Waters XBridge Prep C18 5 µm 4.6 mm ID×100 mm L (analytical column) All the methods are using either $MeOH/H_2O$ or $MeCN/H_2O$ gradients. MeOH, MeCN and $H_2O$ contain either 0.1% Formic Acid or 0.1% Diethylamine. Microwave heating was performed with a Biotage Initiator.

TABLE I

List of abbreviations used in the experimental section:

| Abbreviation | Definition |
| --- | --- |
| µL | microliter |
| app t | Apparent triplet |
| bd | Broad doublet |

TABLE I-continued

List of abbreviations used in the experimental section:

| Abbreviation | Definition |
|---|---|
| Boc | tert-Butyloxy-carbonyl |
| Boc$_2$O | Di-tert-butyl dicarbonate |
| bs | broad singlet |
| Cpd | Compound |
| d | doublet |
| Cial. prod | Commercial product |
| DAPI | 4',6-diamidino-2-phenylindole |
| DCM | Dichloromethane |
| dd | double doublet |
| dq | double quadruplet |
| DIPA | N,N-diisopropylethylamine |
| DMF | N,N-dimethylformamide |
| DMSO | Dimethylsulfoxide |
| EDCI•HCl | N-(3-Dimethylaminopropyl)-N'-ethylcarbodiimide hydrochloride |
| eq. | Equivalent |
| Et$_2$O | Diethyl ether |
| EtOAc | Ethyl acetate |
| EtOH | Ethanol |
| g | gram |
| h | hour |
| HATU | (O-(7-azabenzotriazol-1-yl)-N,N,N',N'-tetramethyluronium hexafluorophosphate) |
| HOBt | Hydroxybenzotriazole |
| HPLC | High pressure liquid chromatography |
| Int | Intermediate |
| IPE | Isopropyl ether |
| iPrOH | Isopropanol |
| L | liter |
| LC-MS | Liquid Chromatography-Mass Spectrometry |
| LDA | Lithium diisopropylamide |
| m | multiplet |
| MeOH | Methanol |
| mg | milligram |
| min | minute |
| mL | milliliter |
| mmol | millimoles |
| MS Ms'd | Mass measured by LC-MS |
| MW | Molecular weight |
| N.A. | Not available |
| nBuOH | n-Butanol |
| NMM | N-Methylmorpholine |
| Pd(PPh$_3$)$_4$ | Tetrakis(triphenylphosphine)palladium(0) |
| PdCl$_2$(dppf)•DCM | [1,1'-Bis(diphenylphosphino)ferrocene]dichloropalladium(II), complex with dichloromethane |
| Pinacolyl | Pinacol |
| PMB | Para methoxy benzyl |
| ppm | part-per-million |
| s | singlet |
| t | triplet |
| TEA | Triethylamine |
| TES | Triethylsilane |
| TBAF | Tetra-n-butylammonium fluoride |
| TBTU | O-(Benzotriazol-1-yl)-N,N,N',N'-tetramethyluronium tetrafluoroborate |
| THF | Tetrahydrofuran |
| IMDM | Iscove's Modified Dulbecco's Medium |
| RPMI | Roosevelt Park Memorial Institute |

Synthetic Preparation of the Compound of the Invention

Example 1

General Synthetic Methods 1.1. Preparation of the Compounds of the Invention.

1.1.1. Synthetic Methods Overview 1

General Method for the Synthesis of Intermediate Gen-5

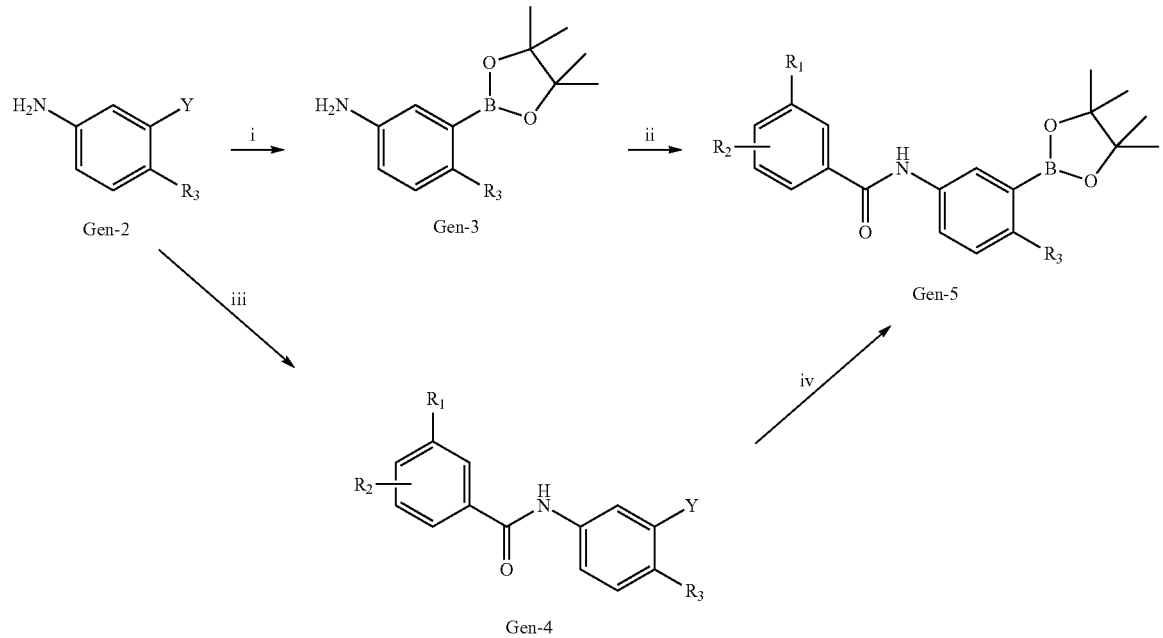

Wherein Y is I or Br
Step i: Method A
  A1: Formation of boronic ester
Step ii: Consists in One of the Following Methods
  B1: Amide bond forming reaction with an acid
  B2: Amide bond forming reaction with an acid chloride
  B3: Amide bond forming reaction with an acid transformed into an acid chloride
Step iii: Consists in One of the Following Methods
  B1: Amide bond forming reaction with an acid
  K. Amide bond forming by peptidic coupling with EDC/HOBt
Step iv: Consists in One of the Following Methods
  A2: Formation of boronic ester 1.1.2. Synthetic Methods Overview 2

General Method for the Synthesis of the Compounds of the Invention

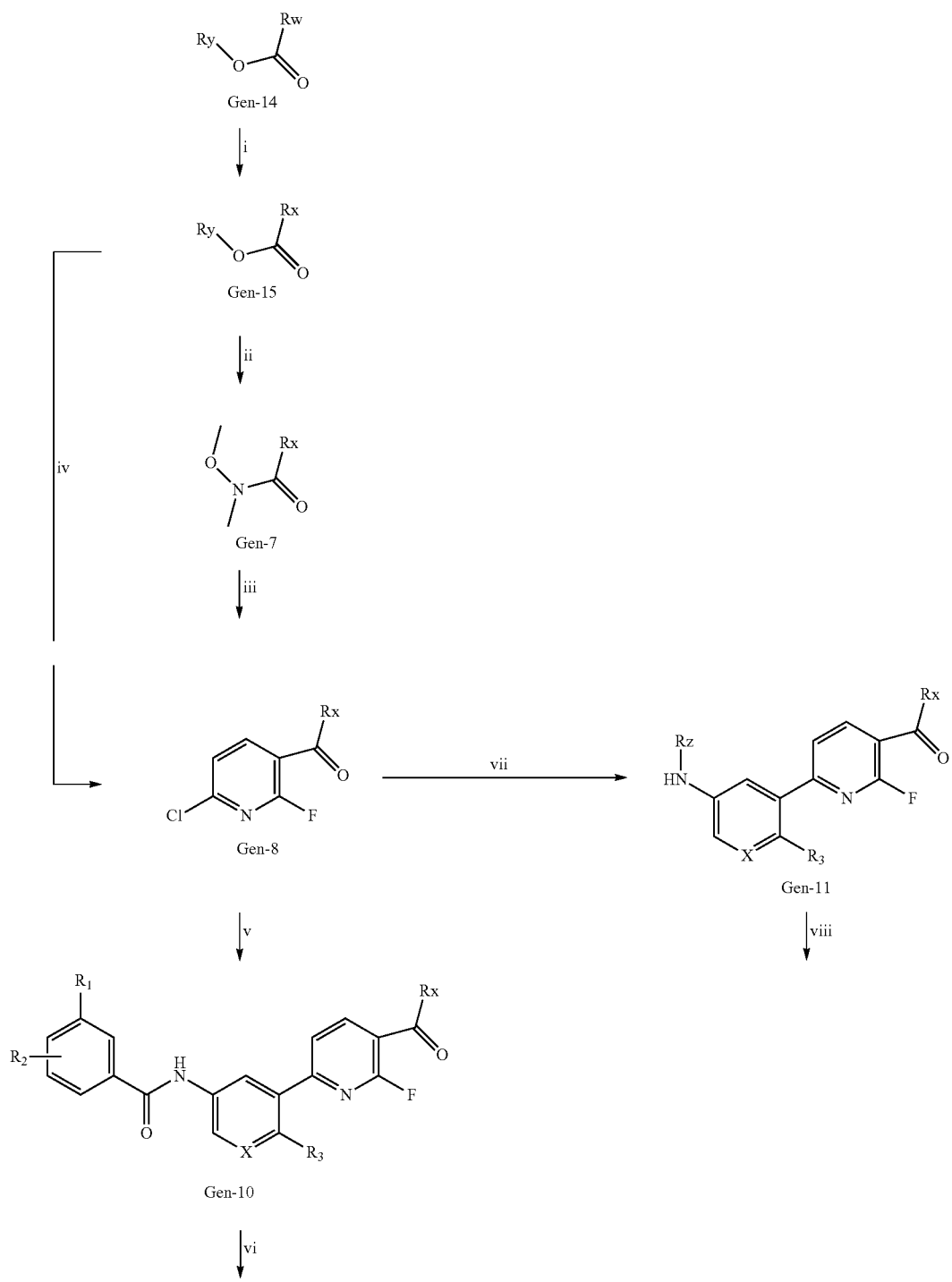

Wherein
- $R^y$ is H or Me or Et,
- $R^x$ is $R^4$ or $CH(OCH_3)_2$ or 2-(tert-Butyl-dimethyl-silanyloxy)-methyl or 1-(tert-Butyl-dimethyl-silanyloxy)-cyclopropane,
- $R^z$ is H or Boc, and
- $R^w$ is $R^4$ or $CH(OCH_3)_2$ Step i: Method C
  C. Sylil protection
Step ii: Method D
  D: Formation of Weinreb amide
Step iii: Method E
  E. Introduction of ketone
Step iv: Method E
  E. Introduction of ketone
Step v: Consists in One of the Following Methods
  F1: Suzuki coupling with Intermediate Gen-5
  F2: One pot formation of boronic and Suzuki with Intermediate Gen-4
Step vi: Consists in One or Several of the Following Methods
  G1: Cyclisation with hydrazine
  G2: Sylil deprotection
  G3: Boc deprotection
Step vii: Method F1
  F1: Suzuki coupling with Intermediate Gen-3 or Gen-27
Step viii: Method G1
  G1: Cyclisation with hydrazine
Step ix: Method B1
  B1: Amide bond forming reaction with an acid
  L: Aldehyde reduction into alcohol

1.1.3. Synthetic Methods Overview 3

General Method for the Synthesis of a Compound

Step i: Method H
  H. Suzuki coupling with Intermediate Gen-5
Step ii: Method I
  I1: PMB deprotection with TFA
  I2: PMB deprotection with $H_2SO_4$
Step iii:
  H. Suzuki coupling
Step iv:
  I1: PMB deprotection with TFA
  I2: PMB deprotection with $H_2SO_4$
Step v:
  B1: Amide bond forming reaction with an acid

1.1.4. Synthetic Methods Overview 4

General Method for the Synthesis of the Acid

1.2.1.2. Illustrative Synthesis of Intermediate Gen-3-a

4-Methyl-3-(4,4,5,5-tetramethyl-[1,3,2]dioxaborolan-2-yl)-phenylamine

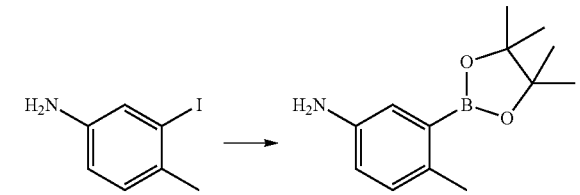

To a suspension, previously degazed with nitrogen bubbling for 1 h, of Intermediate Gen-2-b (300 g, 1.29 mol, 1 eq.), Intermediate Gen-9-a (343.2 g, 1.35 mol, 1.05 eq.) and potassium acetate (380 g, 3.9 mol, 3 eq.) in DMSO (2.65 L), previously degazed with nitrogen bubbling for 2 h, is added $PdCl_2$(dppf).DCM (52 g, 0.06 mol, 0.05 eq.). The reaction mixture is stirred at 80° C. under nitrogen overnight. The reaction is cooled to room temperature, then water (1.5 L) and EtOAc (3 L) are added. The biphasic solution is filtered through a plug of celite, and the cake is washed with EtOAc (2 L). The two layers of the filtrate are separated, the aqueous layer is extracted again with EtOAc (3 L) and the combined organic layers are washed with water (500 mL). The organic layer is dried over $Na_2SO_4$, filtered and evaporated to dryness. The residue is purified by chromatography on silica (elution cyclohexane/EtOAc: 95/5 to 70/30) to afford Intermediate Gen-3-a.

$^1$H NMR (300 MHz, $CDCl_3$-d) δ ppm 7.17 (1H, d), 6.99 (1H, d), 6.70 (1H, dd), 3.54 (2H, bs), 2.25 (3H, s), 1.36 (12H, s)

1.2.2. General Method B

Synthesis of Intermediate Gen-5

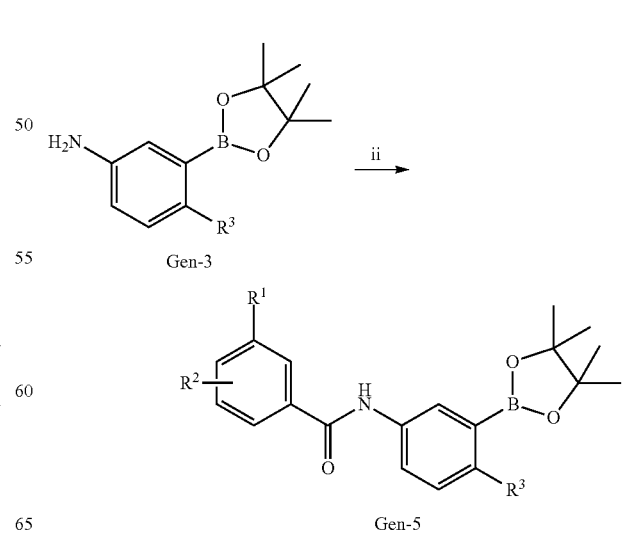

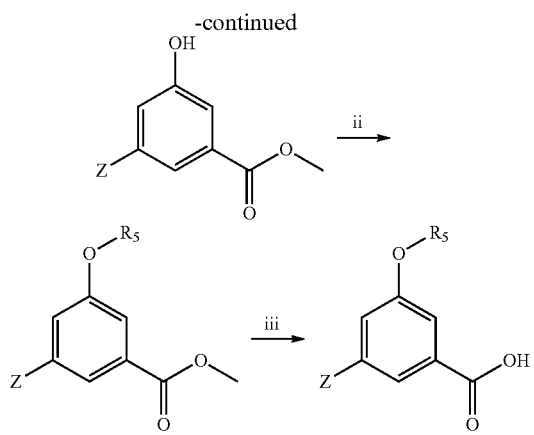

Wherein Z is Br or $R^2$

Step i: Method P

P: Formation of the ester

Step ii: Consists in One of the Following Methods

Q: O-alkylation

Step iii: Consists in One of the Following Methods $R^1$: Suzuki coupling with Gen-9-g $R^2$: Saponification

1.2. General Methods for the Synthesis of the Compounds of the Invention

1.2.1. General Method A

Synthesis of Intermediate Gen-3

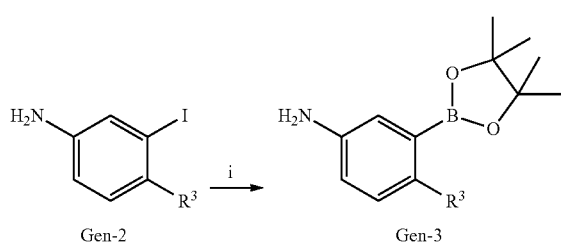

1.2.1.1. General Method A1

To a suspension, previously degazed with nitrogen bubbling, of Intermediate Gen-2 (1 eq.), Intermediate Gen-9-a (1.05 eq.) and potassium acetate (3 eq.) in DMSO, previously degazed with nitrogen bubbling, is added $PdCl_2$(dppf).DCM (0.05 eq.). The reaction mixture is heated at 80° C. under nitrogen overnight. The reaction is cooled to room temperature, then water and EtOAc are added. The biphasic solution is filtered through a plug of celite (slow), and the cake is washed with EtOAc. The two layers of the filtrate are separated, the aqueous layer is extracted again with EtOAc and the combined organic layers are washed with water. The organic layer is dried over $Na_2SO_4$, filtered and evaporated to dryness. The residue is purified by chromatography on silica gel to afford Intermediate Gen-3.

1.2.2.1. General Method B1

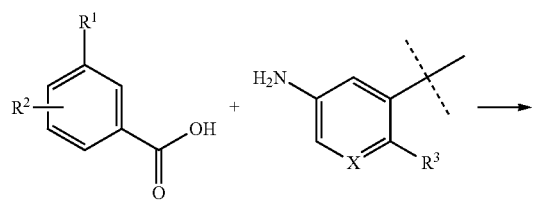

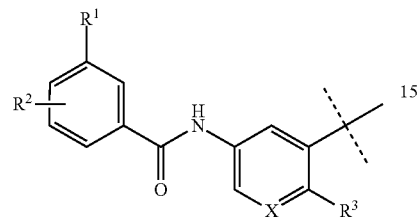

To a stirred solution of Intermediate Gen-1 (1 to 1.2 eq.), and amine derivative (1 eq.) in DCM or DMF are added TBTU or HATU (1 to 1.2 eq.) followed by TEA or NMM (2 to 3 eq.) at room temperature under argon, the reaction mixture is stirred at room temperature until completion. Then the reaction is quenched with water, the layers are separated. The organic layer is dried over $Na_2SO_4$, filtered and evaporated to dryness. Alternatively, the reaction is concentrated in vacuo, the residue is partionned between EtOAc or a mixture of EtOAc/nBuOH and a saturated aqueous $NH_4Cl$ solution or water. The layers are separated, the organic layer is dried over $Na_2SO_4$, filtered and evaporated to dryness. Then the residue is purified by chromatography on silica gel to afford the expected Intermediate.

1.2.2.2. Illustrative Synthesis of Intermediate Gen-5-a 3,5-Dimethoxy-N-[4-methyl-3-(4,4,5,5-tetramethyl-[1,3,2]dioxaborolan-2-yl)-phenyl]-benzamide

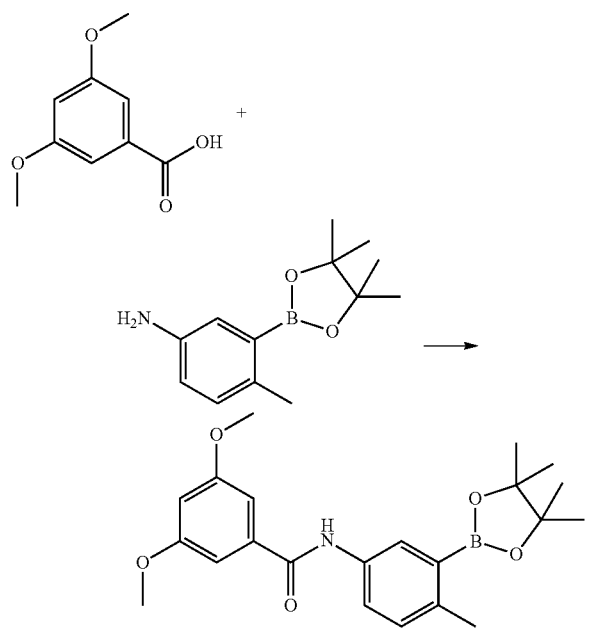

To a stirred solution of Intermediate Gen-1-a (602 mg, 3 mmol, 1 eq.), and Intermediate Gen-3-a (700 mg, 3 mmol, 1 eq.) in DCM (15 mL) are added TBTU (963 mg, 3 mmol, 1 eq.) followed by TEA (0.83 mL, 6 mmol, 2 eq.) at room temperature under argon, the reaction mixture is stirred at room temperature for 5 h. Then the reaction is quenched with water, the layers are separated. The organic layer is dried over $Na_2SO_4$, filtered and evaporated to dryness. The residue is purified by chromatography on silica gel (elution heptane/EtOAc: 80/20) to afford Intermediate Gen-5-a.

LCMS: MW (calcd): 397; m/z MW (obsd): 398 (M+H)

1.2.2.3. General Method B2

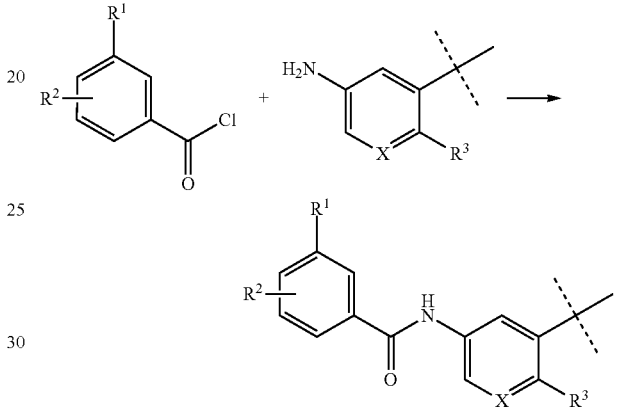

A solution of amine derivative (1 eq.) in DCM under nitrogen is cooled to 3° C., then TEA (1.1 eq.) followed by the corresponding benzoyl chloride (0.8 eq.) are added dropwise. Then the corresponding benzoyl chloride (0.05 eq.) is again added dropwise and the reaction is left to stir 10 min. The reaction mixture is quenched with water and diluted with DCM. The layers are separated and the organic layer is dried over $Na_2SO_4$, filtered and evaporated in vacuo. The majority of the solvent is removed and cyclohexane is added, the mixture is briefly stirred further at room temperature, the resulting solid is separated by filtration and washed with cyclohexane and dried to afford the expected Intermediate.

1.2.2.4. Illustrative Synthesis of Intermediate Gen-5-b

N-[4-Methyl-3-(4,4,5,5-tetramethyl-[1,3,2]dioxaborolan-2-yl)-phenyl]-3-trifluoromethyl-benzamide

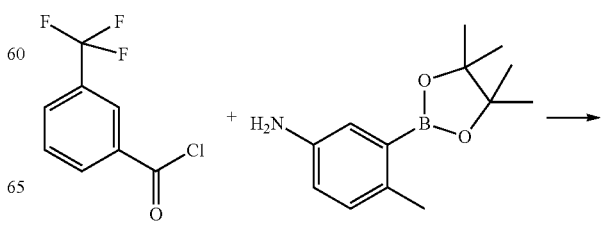

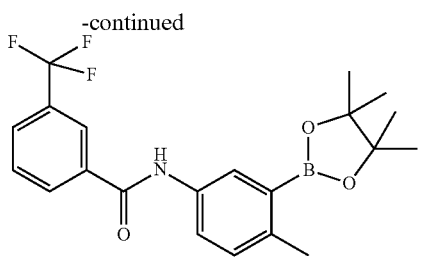

A solution of Intermediate Gen-3-a (293 g, 1.26 mol, 1.0 eq.) in DCM (3 L) under nitrogen is cooled to 3° C., then TEA (193 mL, 1.38 mol, 1.1 eq.) followed by Gen-1-e (150 mL, 1.0 mol, 0.8 eq.) are added dropwise. Then Gen-1-e (9.5 mL, 0.06 mol, 0.05 eq.) is added dropwise and the reaction is left to stir 10 min. The reaction mixture is quenched with water (1.5 L) and diluted with DCM (2 L). The layers are separated and the organic layer is dried over $Na_2SO_4$, filtered and evaporated in vacuo. The majority of the solvent is removed and cyclohexane (3.0 L) is added. The mixture is stirred at room temperature for few minutes, the resulting solid is separated by filtration and washed with cyclohexane and dried to afford Intermediate Gen-5-b.

LCMS: MW (calcd): 405; m/z MW (obsd): 406 (M+H).

1.2.2.5. General Method B3

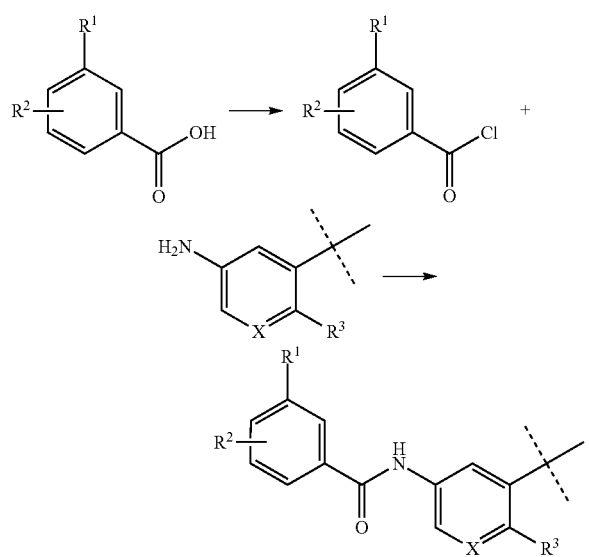

To a stirred solution of Gen-1 (1.1 eq.) at 0° C. is added oxalyl chloride (3 eq.). The reaction mixture is stirred for 5 min at this temperature and 1 drop of DMF is added. The reaction is stirred again at 0° C. and then at r.t until completion. The reaction mixture is concentrated in vacuo until dryness. The residue is dissolved in DCM. The solution is cooled to 0° C. and amine derivative (1 eq.) and TEA (5 eq.) were added. The reaction mixture is stirred 30 min at 0° C. and overnight at room temperature Then the reaction is quenched with water. DCM and $NH_4Cl$ were added. The two layers were separated. The organic layer is washed successively with a saturated solution of $NaHCO_3$ and Brine. The two layers are separated and the organic layer is extracted with DCM, then dried over $Na_2SO_4$, filtered and concentrated in vacuo until dryness. The solid obtained is recrystallized to give Intermediate Gen-5.

1.2.2.6. Illustrative Synthesis of Intermediate Gen-5-e

N-(3,5-Dimethyl-phenyl)-4-methyl-3-(4,4,5,5-tetramethyl-[1,3,2]dioxaborolan-2-yl)-benzamide

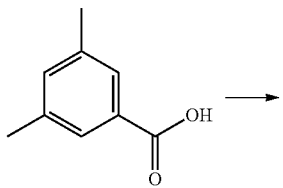

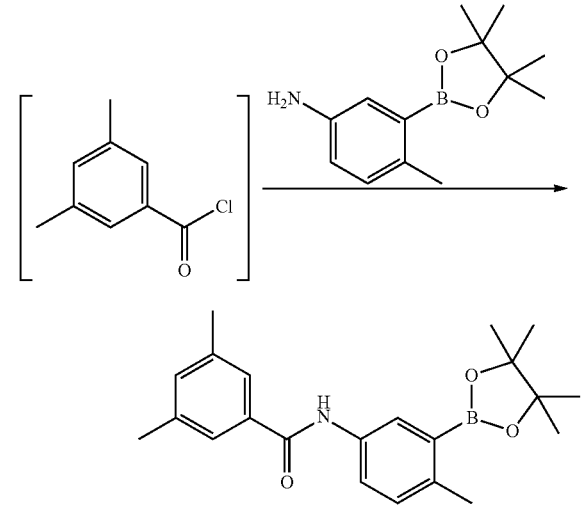

To a stirred solution of Gen-1-b (1.06 g, 7.08 mol, 1.1 eq.) at 0° C. in DCM (35 mL) is added oxalyl chloride (1.63 mL, 19.3 mol, 3 eq.). The reaction mixture is stirred 5 min at this temperature and 1 drop of DMF is added. The reaction is stirred again 45 min at 0° C. and 45 min at room temperature. The reaction mixture is concentrated in vacuo until dryness. The residue is dissolved in DCM (30 mL). The solution is cooled to 0° C. and amine derivative (1.5 g, 6.4 mol, 1 eq.) and TEA (3.26 g, 32.2 mol, 5 eq.) were added. The reaction mixture is stirred 30 min at 0° C. and overnight at room temperature. Then the reaction is quenched with water (20 mL). DCM (100 mL) and $NH_4Cl$ (100 mL) were added. The two layers were separated. The organic layer is washed successively with a saturated solution of $NaHCO_3$ (100 mL) and brine (100 mL). The two layers are separated and the aqueous layer is extracted with DCM (100 mL), then dried over $Na_2SO_4$, filtered and concentrated in vacuo until dryness. The solid obtained is recristallized in MeOH (50 mL) to give Intermediate Gen-5-e.

1.2.2.7. General Method A2

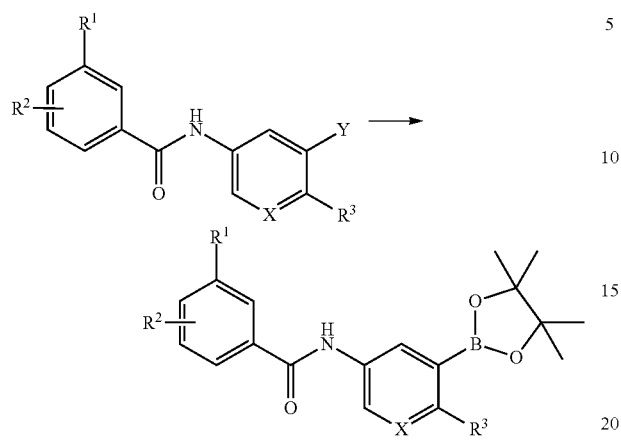

To a solution of Intermediate Gen 4 (1 eq.) in dioxane or DMF are added (BOpin)$_2$ (1.1 eq.), KOAc (3 eq.) and the mixture is stirred under nitrogen or argon at room temperature for 10 minutes. Then, Pd(dppf)Cl$_2$ (0.05 eq.) is added and the reaction mixture is irradiated at 120° C. with microwaves for 140 min or heated at 80° C. overnight. The mixture is used directly in the next step or concentrated in vacuo. The residue is taken with water and EtOAc. The organic layer is washed with water, brine, dried over Na$_2$SO$_4$, filtered and evaporated to dryness. The expected intermediate is purified by chromatography of silica gel (elution ether/EtOAc: 95/5 to 75/25).

1.2.2.8. Illustrative Synthesis of Intermediate Gen-5-f

N-[4-chloro-3-(4,4,5,5-tetramethyl-[1,3,2]dioxaborolan-2-yl)-phenyl]-3,5-dimethoxy-benzamide

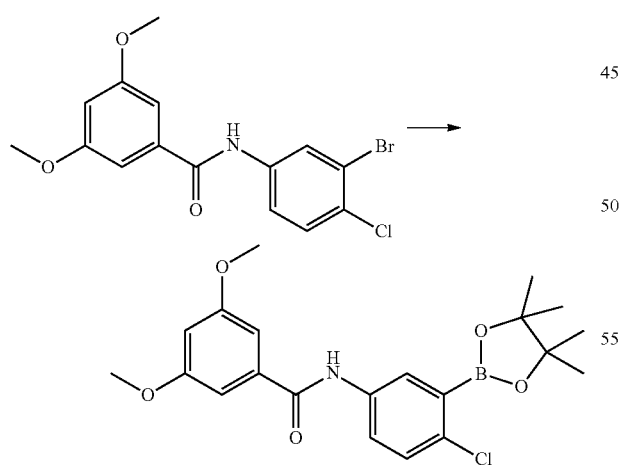

To a solution of Intermediate Gen-4-e (200 mg, 0.54 mmol, 1 eq.) in dioxane (9.0 mL) are added (BOPin)$_2$ (150 mg, 0.59 mmol, 1.1 eq.), KOAc (257 mg, 1.62 mmol, 3 eq.) and the mixture is stirred under nitrogen or argon at room temperature for 10 minutes. Then, Pd(dppf)Cl$_2$ (20 mg, 0.027 mmol, 0.05 eq.) is added and the reaction mixture is irradiate to micro-wave at 120° C. for 140 minutes to give intermediate Gen-5-f. The mixture is used directly in the next step.
LCMS: MW (calcd): 417; MW (obsd): 418 (M+H).

1.2.3. General Method C

Synthesis of Intermediate Gen-15

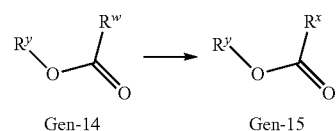

1.2.3.1. General Method C

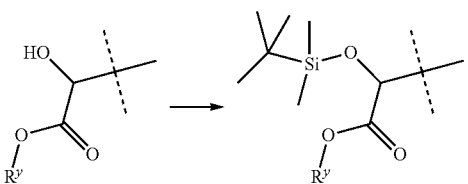

To a solution of hydroxy derivative (1 eq.) in DCM or DMF under stirring and nitrogen, are added 1H-imidazole (1.1 to 2.4 eq.) and Intermediate Gen-9-b (1.02 to 1.2 eq.). The reaction mixture is cooled during the addition, then stirred at room temperature until completion under nitrogen. The reaction mixture is diluted in IPE or DCM, the organic layer is washed once with an aqueous 1 M HCl solution or an aqueous 10% citric acid, if needed an another washing with a mixture of an aqueous 1 M HCl solution and brine (1/1) and once with brine, dried over Na$_2$SO$_4$, filtered and evaporated to dryness to give the expect Intermediate.

1.2.3.2. Illustrative Synthesis of Intermediate Gen-15-b (S)-2-(tert-Butyl-dimethyl-silanyloxy)-propionic acid methyl ester

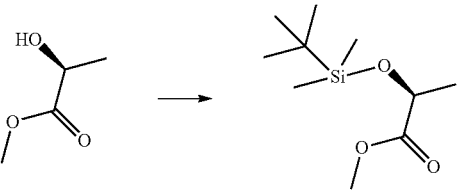

To a solution of Intermediate Gen-14-b (694 g, 6.67 mol, 1 eq.) in DCM (7 L) under stirring and nitrogen, are added 1H-imidazole (500 g, 7.34 mol, 1.1 eq.) and Intermediate Gen-9-b (1055 g, 7.00 mol, 1.05 eq.). The reaction mixture is cooled during the addition, then stirred at room temperature overnight under nitrogen. The reaction mixture is diluted in IPE (5.5 L), the organic layer is washed once with an aqueous 1 M HCl solution (2.8 L), once with a mixture of an aqueous 1 M HCl solution and brine (1/1) (1.4 L/1.4 L) and once with brine (2.8 L), dried over Na$_2$SO$_4$, filtered and evaporated to dryness to give Intermediate Gen-15-b.
$^1$H NMR (300 MHz, CDCl$_3$-d) δ ppm 4.34 (1H, q), 3.73 (3H, s), 1.40 (3H, d), 0.91 (9H, s), 0.90 (6H, d).

1.3. General Method D

Synthesis of Intermediate Gen-7

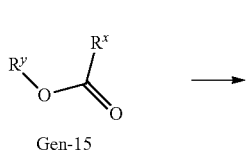 → 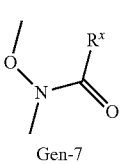

Gen-15      Gen-7

1.3.1. General Method D

To a suspension of Intermediate Gen-9-c (1.56 eq.) in THF under stirring and nitrogen is slowly added a 2.5 M butyllithium solution in hexane (3.55 eq.) at a temperature comprised between −15° C. and −10° C. over 1 h. After 50 min of stirring at −15° C., a solution of Intermediate Gen-15 (1 eq.) in THF is added dropwise to the amide solution below −60° C. over 30 min. Then the reaction mixture is stirred under nitrogen at −70° C. for 2 h. The reaction is quenched by slowly adding an aqueous 2 M HCl solution at −50° C., EtOAc is added to the reaction and the mixture is allowed to warm up to room temperature. The layers are separated and the aqueous layer (pH ~8-9) is extracted again with EtOAc. The combined organic layers are dried over Na$_2$SO$_4$, filtered and evaporated to dryness to afford Intermediate Gen-7.

1.3.2. Illustrative Synthesis of Intermediate Gen-7-d (S)-2-(tert-Butyl-dimethyl-silanyloxy)-N-methoxy-N-methyl-propionamide

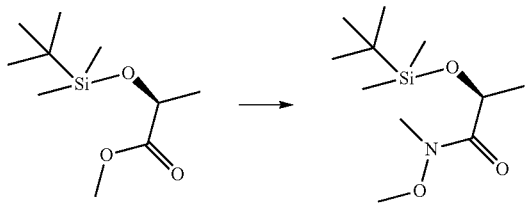 [SMILES: COC(=O)[C@H](C)O[Si](C)(C)C(C)(C)C ; CON(C)C(=O)[C@H](C)O[Si](C)(C)C(C)(C)C]

To a suspension of Intermediate Gen-9-c (139 g, 1.42 mol, 1.56 eq.) in THF (720 mL) under stirring and nitrogen is slowly added a 2.5 M butyllithium solution in hexane (1.3 L, 3.25 mol, 3.55 eq.) at a temperature between −15° C. and −10° C. over 1 h. After 50 min of stirring at −15° C., a solution of Intermediate Gen-15-b (200 g, 0.92 mol, 1 eq.) in THF (600 mL) is added dropwise to the amide solution below −60° C. over 30 min. Then the reaction mixture is stirred under nitrogen at −70° C. for 2 h. The reaction is quenched by slowly adding an aqueous 2 M HCl solution (600 mL) at −50° C., EtOAc (1 L) is added to the reaction and the mixture is allowed to warm up to room temperature. The layers are separated and the aqueous layer (pH ~8-9) is extracted again with EtOAc (500 mL). The combined organic layers are dried over Na$_2$SO$_4$, filtered and evaporated to dryness to afford Intermediate Gen-7-d.

$^1$H NMR (300 MHz, CDCl$_3$-d) δ ppm 4.78-4.63 (1H, m), 3.71 (3H, s), 3.23 (3H, bs), 1.37 (3H, d), 0.92 (9H, s), 0.11 (6H, d).

1.4. General Method E

Synthesis of Intermediate Gen-8

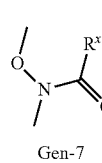 → 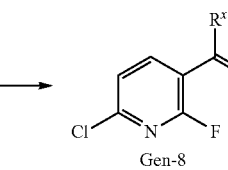 ← 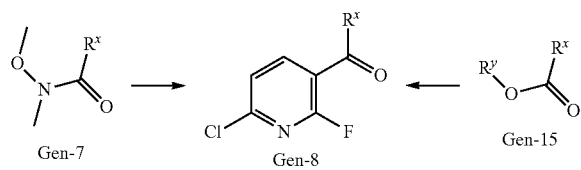

Gen-7           Gen-8           Gen-15

1.4.1. General Method E1

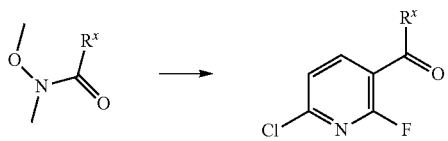

A solution of LDA is prepared by adding dropwise a 2.5 M butyllithium solution in hexane (1.1 to 1.2 eq.) to a solution of DIPA (1.07 to 1.2 eq.) in THF under nitrogen at a temperature comprised between −78° C. and −5° C. The reaction mixture is stirred 15 min to 30 min at the same temperature. Then Intermediate Gen-6-a (1 to 1.2 eq.) in THF is added dropwise between −78° C. and −60° C., and the reaction is stirred under nitrogen at −78° C. for 1 h to 1.33 h. Then Intermediate Gen-7 (1.1 to 1.2 eq.) is added dropwise or portionwise by monitoring the temperature. The mixture is stirred 1.5 h to 3 h between −78° C. and −70° C. and quenched with a saturated aqueous NH$_4$Cl solution. EtOAc is added, then the organic layer is separated, dried over Na$_2$SO$_4$, filtered and evaporated to dryness. The residue is purified by chromatography of silica gel to give Intermediate Gen-8.

1.4.2. Illustrative Synthesis of Intermediate Gen-8-d (S)-2-(tert-Butyl-dimethyl-silanyloxy)-1-(6-chloro-2-fluoro-pyridin-3-yl)-propan-1-one

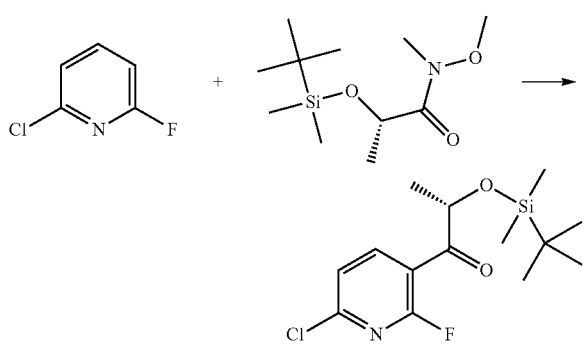

A solution of LDA is prepared by adding dropwise a 2.5 M butyllithium solution in hexane (308 mL, 0.77 mol, 1.167 eq.) to a solution of DIPA (100 g, 0.98 mol, 1.07 eq.) in THF (540 mL) under nitrogen at −5° C. The reaction mixture is stirred 30 min at −5° C. Then Intermediate Gen-6-a (86.8 g, 0.66 mol, 1 eq.) in THF (650 mL) is added dropwise below −60° C., and the reaction is stirred under nitrogen at −78° C. for 1.33 h. Then Intermediate Gen-7-d (180 g, 0.73 mol, 1.1 eq.) is added dropwise whilst monitoring the temperature. The mixture is stirred 3 h at −70° C. and quenched with a saturated aqueous NH$_4$Cl solution (400 mL). EtOAc (1 L) is added, then the organic layer is separated, dried over Na$_2$SO$_4$, filtered and evaporated to dryness. The residue is purified by cake of silica gel (elution cyclohexane/EtOAc: 100/0 to 95/5) to give Intermediate Gen-8-d.

$^1$H NMR (300 MHz, CDCl$_3$-d) δ ppm 8.18 (1H, dd), 7.34 (1H, dd), 4.88 (1H, dq), 1.43 (3.H, dd), 0.82 (9H s), 0.65 (6H, d).

1.4.3. General Method E2

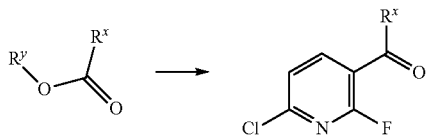

A solution of LDA is prepared by adding dropwise a 2.5 M butyllithium solution in hexane (1.1 eq.) to a solution of DIPA (1.1 eq.) in THF under nitrogen at −78°. The reaction mixture is stirred 15 min to 30 min at −78° C. Then Intermediate Gen-6-a (1 eq.) in THF is added dropwise, and the reaction is stirred under nitrogen at −78° C. for 1 h. Then Intermediate Gen-15 (1.1 to 1.2 eq.) is added, the mixture is stirred 1 h to 2 h at −78° C., then the reaction mixture is quenched with a saturated aqueous NH$_4$Cl solution. EtOAc is added, the organic layer is separated, dried over Na$_2$SO$_4$, filtered and evaporated to dryness. The residue is purified by chromatography of silica gel to give Intermediate Gen-8.

1.4.4. Illustrative Synthesis of Intermediate Gen-8-c 2-(tert-Butyl-dimethyl-silanyloxy)-1-(6-chloro-2-fluoro-pyridin-3-yl)-propan-1-one

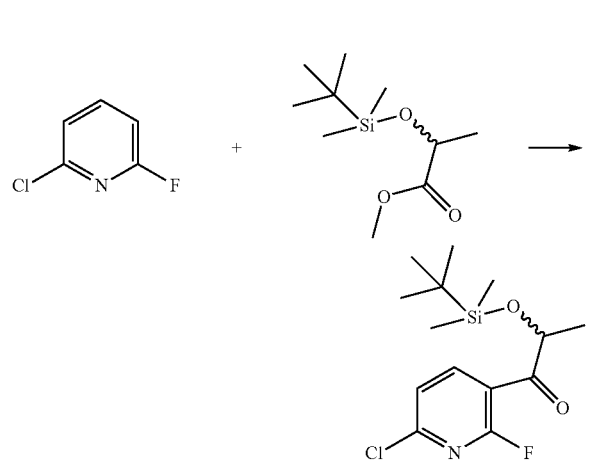

A solution of LDA is prepared by adding dropwise a 2.5 M butyllithium solution in hexane (8.8 mL, 22 mmol, 1.1 eq.) to a solution of DIPA (7.1 mL, 22 mmol, 1.1 eq.) in THF (40 mL) under nitrogen at −78° C. The reaction mixture is stirred 20 min at −78° C. Then Intermediate Gen-6-a (2.63 g, 20 mmol, 1 eq.) in THF (20 mL) is added dropwise, and the reaction is stirred under nitrogen at −78° C. for 1 h. Then Intermediate Gen-15-a (4.8 g, 22 mmol, 1.2 eq.) is added in one portion. The mixture is stirred 2 h at −78° C., then the reaction mixture is quenched with a saturated aqueous NH$_4$Cl solution. EtOAc is added, the organic layer is separated, dried over Na$_2$SO$_4$, filtered and evaporated to dryness. The residue is purified by chromatography of silica gel (elution heptanes/EtOAc: 95/5) to give Intermediate Gen-8-c.

LCMS: MW (calcd): 317 ($^{35}$Cl), 319 ($^{37}$Cl); m/z MW (obsd): 318 ($^{35}$Cl M+H), 320 ($^{37}$Cl M+H).

1.5. General Method F

Synthesis of Intermediate Gen-10

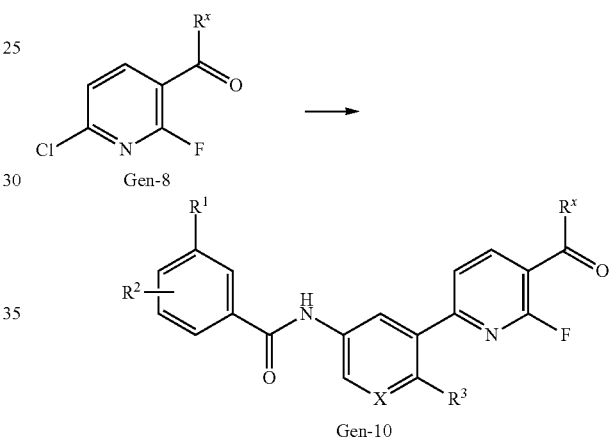

1.5.1. General Method F1

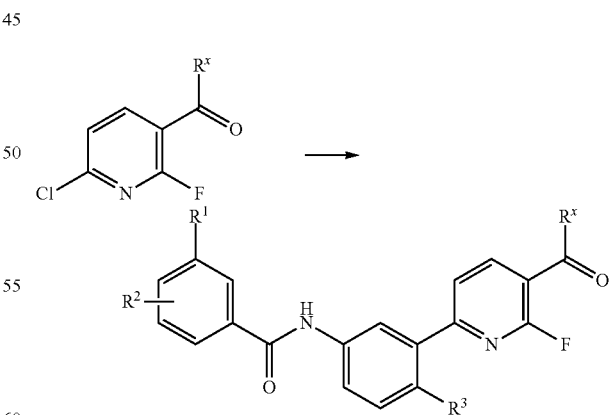

Intermediate Gen-8 (1 eq.), Intermediate Gen-5 (1 to 1.1 eq.), and cesium carbonate (1.5 to 2 eq.) or sodium carbonate (4 eq.) are dissolved in a mixture of 1,4-dioxane/water (4/1) at room temperature, the solution is degassed with nitrogen. Then PdCl$_2$(dppf).DCM or Pd(PPh$_3$)$_4$ (0.05 to 0.07 eq.) is added. The reaction mixture is heated 1 h to 2 h at 80° C., then cooled to room temperature. EtOAc and water are added to the reaction mixture, the layers are separated, and the aqueous layer is extracted once with EtOAc. The combined organic layers are washed with brine, dried over Na$_2$SO$_4$, filtered and evaporated to dryness. The crude is purified by chromatography of silica gel to afford Intermediate Gen-10.

1.5.2. Illustrative Synthesis of Intermediate Gen-10-d

N-(3-{5-[2-(S)(tert-Butyl-dimethyl-silanyloxy)-propionyl]-6-fluoro-pyridin-2-yl}-4-methyl-phenyl)-3-trifluoromethyl-benzamide

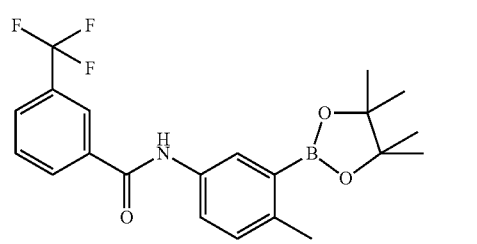

+

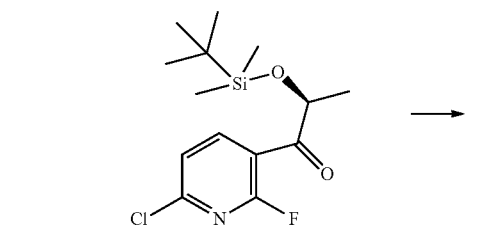

→

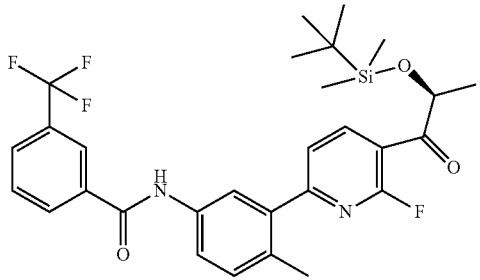

Intermediate Gen-8-d (60 g, 0.189 mol, 1 eq.), Intermediate Gen-5-b (76.52 g, 0.19 mol, 1 eq.), and cesium carbonate (120 g, 0.38 mol, 2 eq.) are dissolved in a mixture of 1,4-dioxane (1.15 L) and water (285 mL) at room temperature, the solution is degassed with nitrogen. Then PdCl$_2$(dppf).DCM (7.7 g, 0.009 mol, 0.05 eq.) is added. The reaction mixture is heated 1 h at 80° C., then cooled to room temperature with an ice bath. EtOAc (1.15 L) is added to the reaction mixture, the layers are separated, and the aqueous layer is extracted once with EtOAc (300 mL). The combined organic layers are washed with brine (800 mL), dried over Na$_2$SO$_4$, filtered and evaporated to dryness. The crude is purified by cake of silica gel (elution cyclohexane/EtOAc: 100/0 to 90/10) to afford Intermediate Gen-10-d.

$^1$H NMR (300 MHz, CDCl$_3$-d) δ ppm 8.28 (1H, dd), 8.17 (2H, d), 8.07 (1H, bd), 7.80 (1H, bd), 7.75 (1H, d), 7.70-7.60 (2H, m), 7.47 (1H, dd), 7.29 (1H, d), 5.00 (1H, dq), 2.41 (3H, s), 1.50 (3H, dd), 0.87 (9H, s), 0.11 (6H, d).

1.6. General Method F2

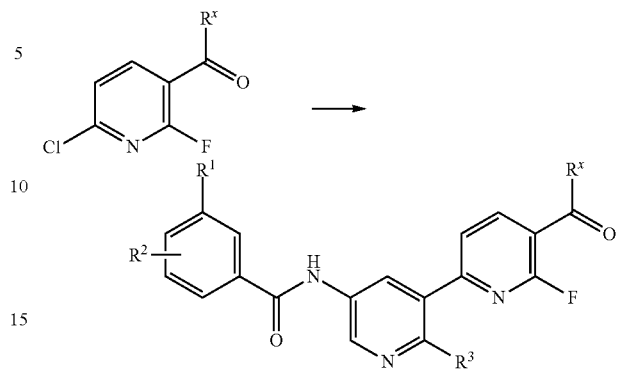

Intermediate Gen-4 (1 eq.), Intermediate Gen-9-a (1.1 eq.), and potassium acetate (3 eq.) are dissolved in 1,4-Dioxane at room temperature, the solution is degassed with nitrogen. Then PdCl$_2$(dppf) (0.07 eq.) is added, and the reaction mixture is refluxed for 3.25 h to 3.5 h. Then to the reaction mixture under nitrogen are added Intermediate Gen-8 (1 eq.), cesium carbonate (3 eq.), PdCl$_2$(dppf) (0.07 eq.) and water, and the mixture is refluxed for 0.66 h to 1.5 h. After cooling to room temperature, an aqueous NH$_4$Cl solution and EtOAc are added, the layers are separated, and the aqueous layer is extracted four times with EtOAc. The combined organic layers are washed with brine, dried over Na$_2$SO$_4$, filtered over a pad of silica gel and the filtrate is evaporated to dryness. The crude is purified by chromatography of silica gel to afford Intermediate Gen-10.

1.7. Illustrative Synthesis of Intermediate Gen-10-b

N-(5-Acetyl-6-fluoro-2'-methyl-[2,3']bipyridinyl-5'-yl)-3,5-dimethoxy-benzamide

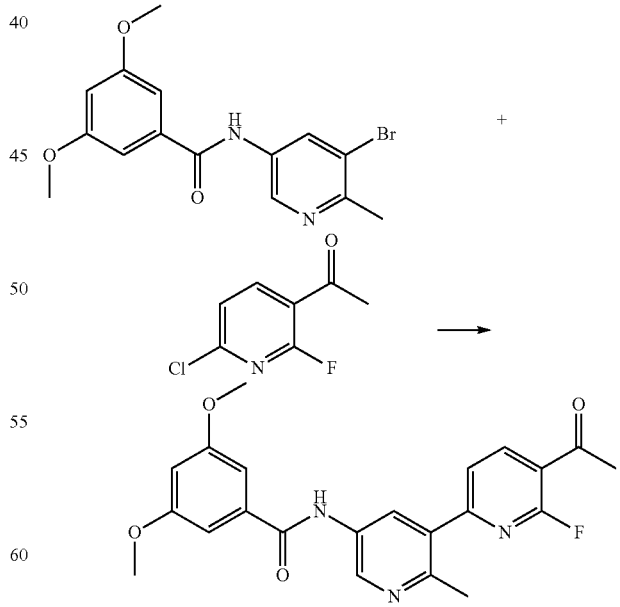

Intermediate Gen-4-a (15.07 g, 43 mmol, 1 eq.), Intermediate Gen-9-a (12 g, 47 mmol, 1.1 eq.), and potassium acetate (12.64 g, 13 mmol, 3 eq.) are dissolved in 1,4-Dioxane (400 mL) at room temperature, the solution is degassed with nitrogen. Then PdCl$_2$(dppf) (2.2 g, 3 mmol, 0.07 eq.) is added, and the reaction mixture is refluxed for 3.5 h. Then to the reaction mixture under nitrogen are added Intermediate Gen-8-b (7.45 g, 43 mmol, 1 eq.), cesium carbonate (41.95 g, 13 mmol, 3 eq.), PdCl₂(dppf) (2.20 g, 3 mmol, 0.07 eq.) and water (100 mL), and the mixture is refluxed for 1.5 h. After cooling to room temperature, an aqueous NH₄Cl solution and EtOAc are added, the layers are separated, and the aqueous layer is extracted four times with EtOAc. The combined organic layers are washed with brine, dried over Na₂SO₄, filtered over a pad of silica gel and the filtrate is evaporated to dryness. The crude is purified by chromatography of silica gel (elution heptane/EtOAc: 70/30 to 0/100) to afford Intermediate Gen-10-b.

LCMS: MW (calcd): 409; m/z MW (obsd): 410 (M+H).

1.8. General Method F1

Synthesis of Intermediate Gen-11

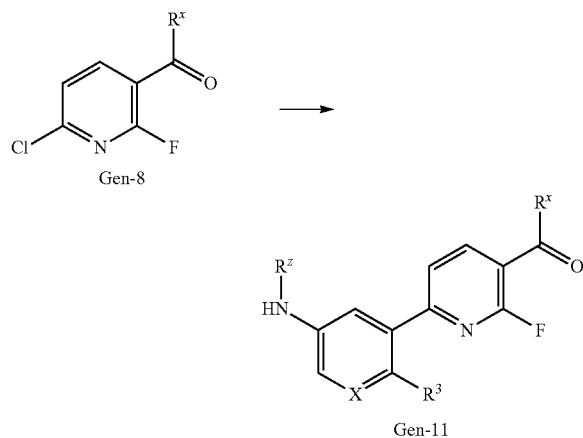

Intermediates Gen-11 are prepared from intermediates Gen-8 and Gen-3 or Gen-27 according to general method F1 described previously.

1.9. General Method G 1.9.1. General Method G1

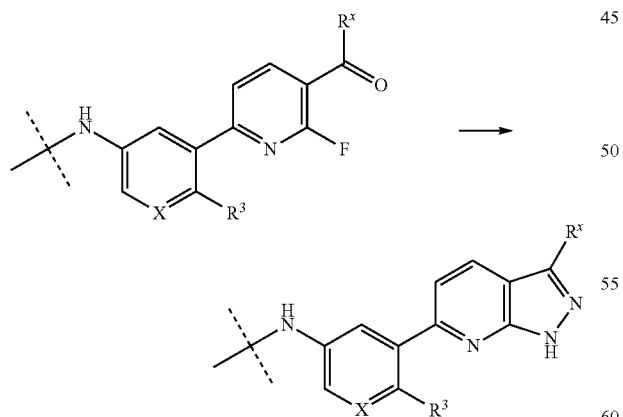

To a solution of (2-fluoro-3-ceto-pyridin-6-yl) derivative (1 eq.) in iPrOH or EtOH, is added hydrazine monohydrate (5 to 12 eq.), the reaction mixture is heated at reflux or at a temperature comprised between 120° C. and 130° C. under microwave irradiation for 45 min to 3 h. Then the reaction mixture is quenched with water, then iPrOH or EtOH is evaporated in vacuo. The residue is diluted in EtOAc and the organic layer is washed with water, brine, dried over Na₂SO₄, filtered and evaporated to dryness. Alternatively the reaction mixture is concentrated in vacuo. The expected intermediate is obtained by chromatography of silica gel or crystallization.

1.9.2. Illustrative Synthesis of Intermediate Gen-13-b 3-(3-Dimethoxymethyl-1H-pyrazolo[3,4-b]pyridin-6-yl)-4-methyl-phenylamine

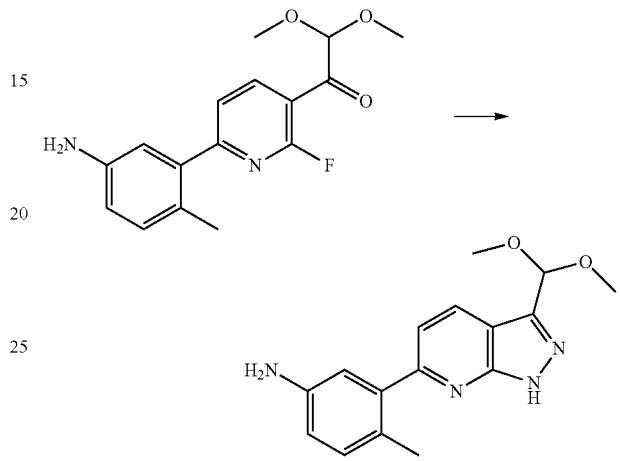

To a solution of Gen-11-b (758 mg, 2.5 mmol, 1 eq.) in EtOH (30 mL), is added hydrazine monohydrate (1.25 mL, 14.9 mmol, 6 eq.), the reaction mixture is heated at reflux for 2 h. Then the reaction mixture is concentrated in vacuo. The crude is purified by chromatography of silica gel (elution heptane/EtOAc: 100/0 to 35/65) to afford Intermediate Gen-13-b.

LCMS: MW (calcd): 298; m/z MW (obsd): 299 (M+H).

1.9.3. General Method G2

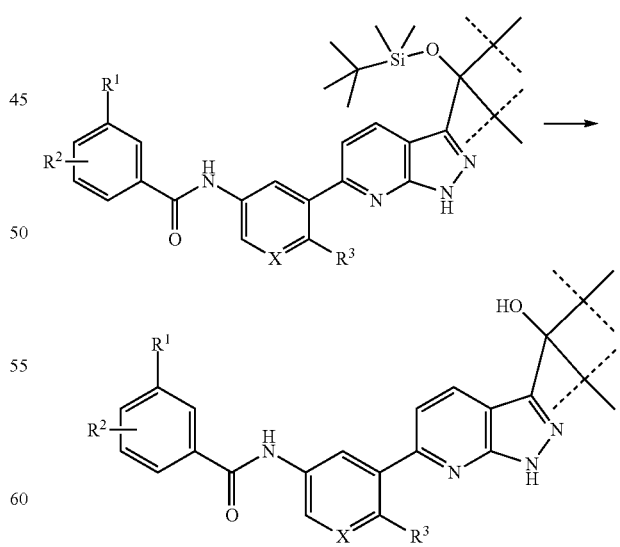

To a solution of protected hydroxy derivative (1 eq.) in THF is added a 1 M TBAF solution in THF (1.5 to 2 eq.), the reaction mixture is heated at 50° C. for 1.5 h to 3.5 h. Then the reaction mixture is concentrated in vacuo. The residue is purified by chromatography on silica gel then by a precipitation to afford the expected compound.

1.9.4. Illustrative Synthesis of Compound 29

N-{3-[3-(1-Hydroxy-cyclopropyl)-1H-pyrazolo[3,4-b]pyridin-6-yl]-4-methyl-phenyl}-3,5-dimethoxy-benzamide

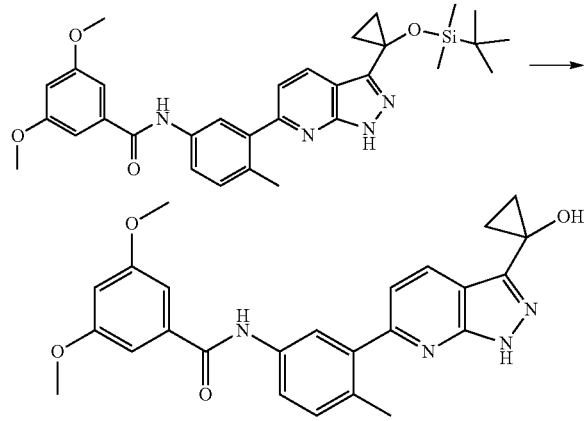

To a solution of Intermediate Gen-16-d (5.3 g, 9.5 mmol, 1 eq.) in THF (40 mL) is added a 1 M TBAF solution in THF (14.2 mL, 14.2 mmol, 1.5 eq.), the reaction mixture is heated at 50° C. for 1.5 h. Then the reaction mixture is concentrated in vacuo. The residue is purified by chromatography on silica gel (elution DCM/MeOH: 97/3 to 95/5) then the crude is dissolved in a minimum of DCM and the solution is added to a stirred solution of pentane. The resulting solid is separated by filtration and dried to afford Compound 29.

LCMS: MW (calcd): 444; m/z MW (obsd): 445 (M+H).

1.9.5. General Method G3

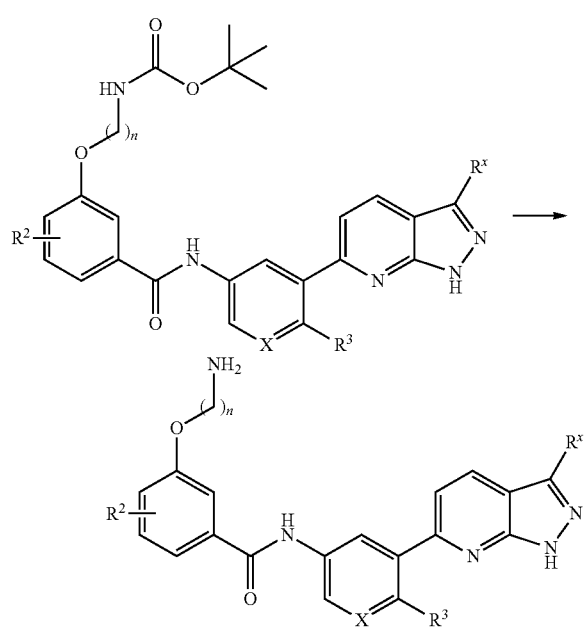

To a solution of protected amine derivative (1 eq.) in DCM is added TFA (0.7 mL), the reaction mixture is stirred at room temperature for 1.5 h to 7 h. Then, the reaction mixture is concentrated in vacuo. The mixture is quenched with an aqueous NaHCO$_3$ solution and extracted with EtOAc. The organic layers are combined, dried over Na$_2$SO$_4$, filtered and evaporated to dryness. The expected intermediate is purified by chromatography of silica gel (elution DCM/MeOH/Et$_3$N: 90:10:2 or DCM/MeOH: 80/20) or preparative LCMS.

1.9.6. Illustrative Synthesis of Compound 39

3-(2-amino-ethoxy)-N-[3-(3-ethyl-1H-pyrazolo[3,4-b]pyrin-6-yl)-4-methylphenyl]-5-methoxybenzamide

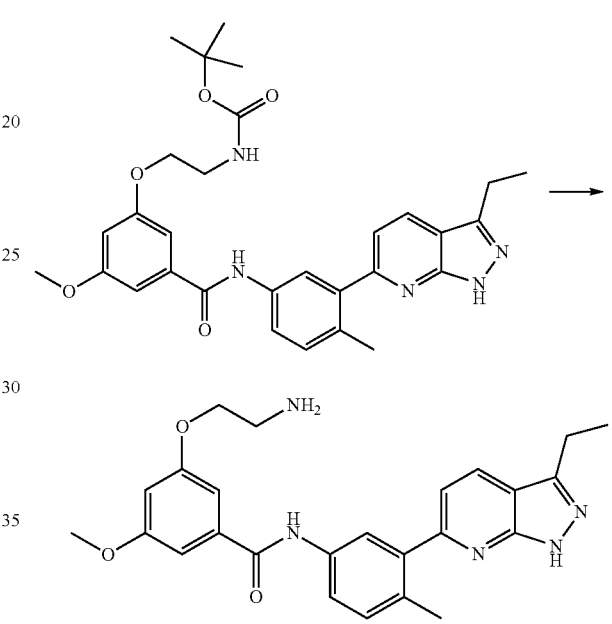

To a solution of Intermediate Gen-47-d (41 mg, 0.075 mmol, 1 eq.) in DCM (3.0 mL) is added TFA (0.7 mL), the reaction mixture is stirred at room temperature for 2.5 h. Then, the reaction mixture is concentrated in vacuo. The mixture is quenched with an aqueous NaHCO$_3$ solution and extracted with EtOAc. The organic layers are combined, dried over Na$_2$SO$_4$, filtered and evaporated to dryness. The crude is purified by chromatography of silica gel (elution DCM/MeOH/Et3N: 90:10:2) to give compound 39.

1H NMR (300 MHz, MeOD-d$_4$): δ ppm 8.33 (1H, d), 7.82 (1H, d), 7.72 (1H, dd), 7.36 (1H, d), 7.35 (1H, d), 7.19-7.14 (2H, m), 6.79-6.75 (1H, m), 4.19 (2H, t), 3.88 (3H, s), 3.80 (2H, t), 3.07 (2H, q), 2.37 (3H, s), 1.45 (3H, t).

1.9.7. General Method B1

Compounds 50, 19, 20, 21, 25, 27 or Intermediates Gen-17 are prepared from intermediates Gen-13-a, Gen-13-b, Gen-35-a, Gen-41-b, Gen-1-b, Gen-1-c, Gen-54-c, Gen-54-d, Gen-63-a, Gen-61-a and Gen-57-a according to general method B1 described previously.

1.9.8. General Method L

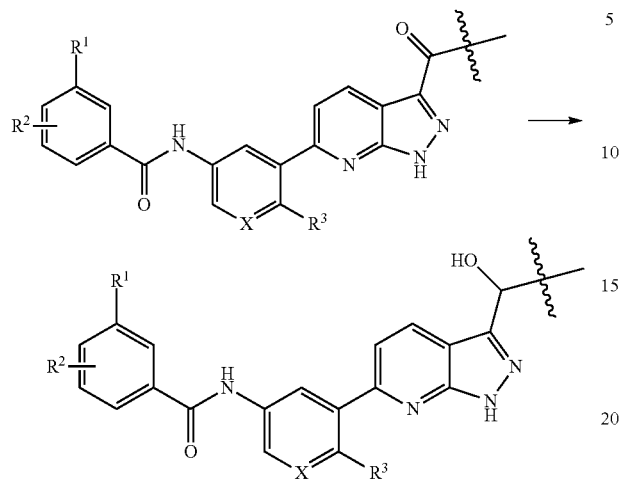

To a solution of carbonyl derivative (1 eq.) in THF under nitrogen at 0° C. is added dropwise a 1.4M MeMgBr solution in toluene/THF (7 eq.). The reaction mixture is allowed to warm up to room temperature and stirred at room temperature for 4.5 h. The reaction mixture is quenched with an aqueous NH$_4$Cl solution of and extracted with EtOAc. The organic layers are combined, dried over Na$_2$SO$_4$, filtered and evaporated to dryness. The expected intermediate is purified by chromatography of silica gel (elution DCM/MeOH: 100/0 to 95/5).

1.9.9. Illustrative Synthesis of Compound 35

N-{3-[3-(1-Hydroxy-ethyl)-1H-pyrazolo[3,4-b]pyridin-6-yl]-4-methyl-phenyl}-3-trifluoromethyl-benzamide

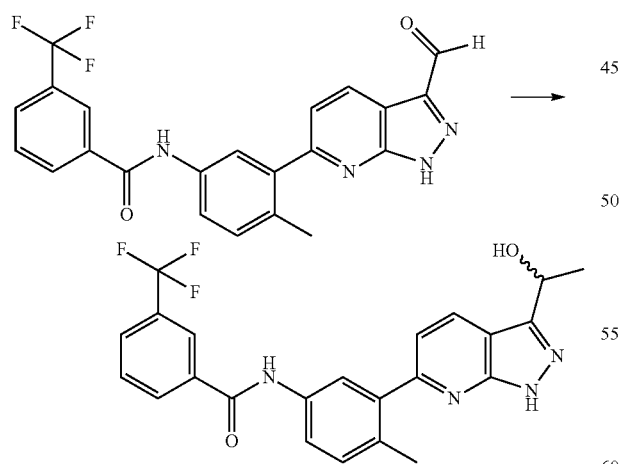

To a solution of Intermediate Gen-18-a (25 mg, 0.06 mmol, 1 eq.) in THF (6 mL) under nitrogen at 0° C. is added dropwise a 1.4 M MeMgBr solution in toluene/THF (295 µL, 0.41 mmol, 7 eq.). The reaction mixture is allowed to warm up to room temperature and stirred at room temperature for 4.5 h. Then the reaction is quenched with an aqueous NH$_4$Cl solution, and diluted with EtOAc, the two layers are separated, and the aqueous layer is extracted again with EtOAc. The combined organic layers are dried over Na$_2$SO$_4$, filtered and evaporated to dryness. The residue is purified by chromatography on silica gel (elution DCM/MeOH: 100/0 to 96/4) to afford Compound 35.

$^1$H NMR (300 MHz, MeOD-d$_4$) δ ppm 8.48 (1H, d), 8.27 (1H, bs), 8.20 (1H, bd), 7.89 (1H, bd), 7.83 (1H, d), 7.77-7.67 (2H, m), 7.35 (2H, d), 5.25 (1H, q), 2.36 (3H, s), 1.70 (3H, d).

LCMS: MW (calcd): 440; m/z MW (obsd): 441 (M+H).

1.9.10. General Method H

Synthesis of Intermediate Gen-25

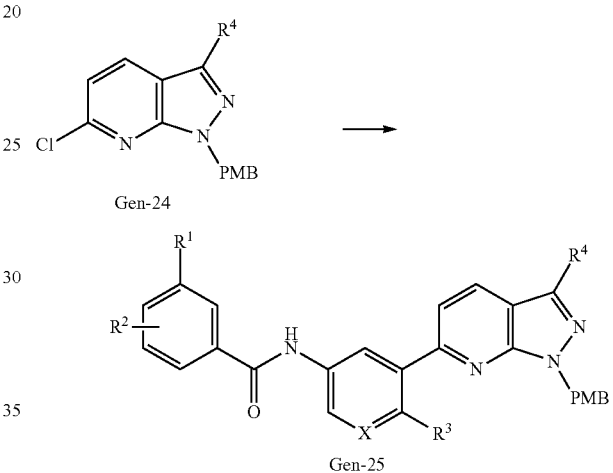

1.9.11. General Method

To a solution of Intermediate Gen-24 (1 eq.), Intermediate Gen-5 (1.2 eq.) and sodium carbonate (4 eq.) in 1,4-Dioxane/water (4/1), is added Pd(PPh$_3$)$_4$ (0.05 eq.) or PdCl$_2$dppf (0.05 eq.). The reaction mixture is purged with argon, then heated at 90° C. overnight. Then the reaction mixture is diluted with DCM, washed with brine, the organic layer is dried over Na$_2$SO$_4$ and concentrated. The residue is purified by chromatography on silica gel to afford intermediate Gen-25.

1.9.12. Illustrative Synthesis of Intermediate Gen-25-a:

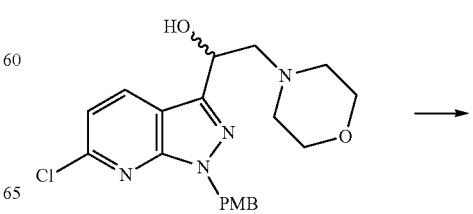

1.10.2. Illustrative Synthesis of Compound 6:

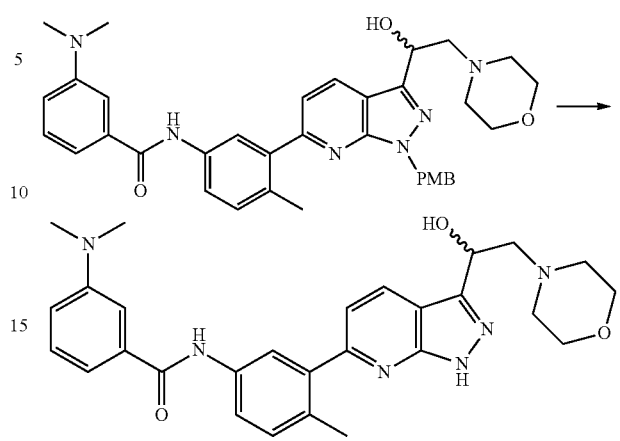

To a solution of Intermediate Gen-25-a (143 mg, 0.230 mmol, 1 eq.) in TFA (1 mL, 13 mmol, 56 eq) are added TES (50 µL, 0.313 mmol, 1.5 eq.), toluene (100 µL) and water (50 µL). The reaction is heated at 110° C. under microwaves for 2 h. The reaction mixture is concentrated, then diluted with DCM (25 mL) and a Na$_2$CO$_3$ solution (10 mL) is added. The two layers are separated, and the aqueous layer is extracted three times with DCM/MeOH 95:5. The combined organic layers are dried over Na$_2$SO$_4$, filtered and concentrated to dryness. The residue is purified by chromatography on silica gel (elution with DCM/MeOH 100:0 to 90:10) to afford Compound 6.

LCMS: MW (calcd): 500; m/z MW (obsd): 501 (M+H).

$^1$H NMR (400 MHz, CDCl3) δ ppm 13.36 (1H, s), 10.18 (1H, s), 8.39 (1H, d), 7.91 (1H, s), 7.77 (1H, d), 7.33-7.22 (5H, m), 6.92 (1H, d), 5.11 (1H, d), 3.57-3.55 (4H, m), 2.96 (6H, s), 2.83-2.79 (2H, m), 2.60-2.54 (4H, m), 2.33 (3H, s).

1.10.3. General Method 12

To Intermediate Gen-25 (1 eq.) cooled at 0° C. was added concentrated H2SO4. The reaction flask was allowed to stir at 0° C. for 1 h. The reaction mixture was then poured over crushed ice-water, basified with saturated Aqueous K$_2$CO$_3$ solution to a pH of 10, and then extracted with EtOAc. The organic layer was dried over Na$_2$SO$_4$, filtered and concentrated under vacuum. The residue is purified by chromatography on silica gel.

1.10.4. Illustrative Synthesis of compound 54

N-{3-[3-(1-Hydroxy-ethyl)-1H-pyrazolo[3,4-b]pyridin-6-yl]-4-methyl-phenyl}-3,5-dimethyl-benzamide

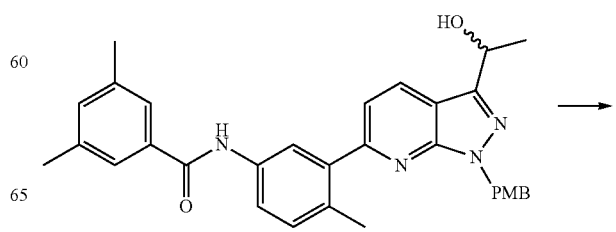

-continued

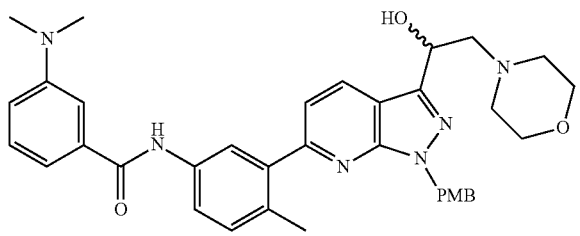

To a solution of Intermediate Gen-24-a (100 mg, 0.248 mmol, 1 eq.), Intermediate Gen-5-c (113 mg, 0.298 mmol, 1.2 eq.) and sodium carbonate (105 mg, 0.993 mmol, 4 eq.) in 1,4-Dioxane/water (4/1), is added Pd(PPh$_3$)$_4$ (14.3 mg, 0.0124 mmol, 0.05 eq). The reaction mixture is purged with argon then heated at 90° C. overnight. Then the reaction mixture is diluted with DCM (25 mL), washed with brine (10 mL), the organic layer is dried over Na$_2$SO$_4$ and concentrated. The residue is purified by chromatography on silica gel (elution DCM/MeOH: 100/0 to 96/4) to afford intermediate Gen-25-a.

1.10. General Method I

Synthesis of Compounds

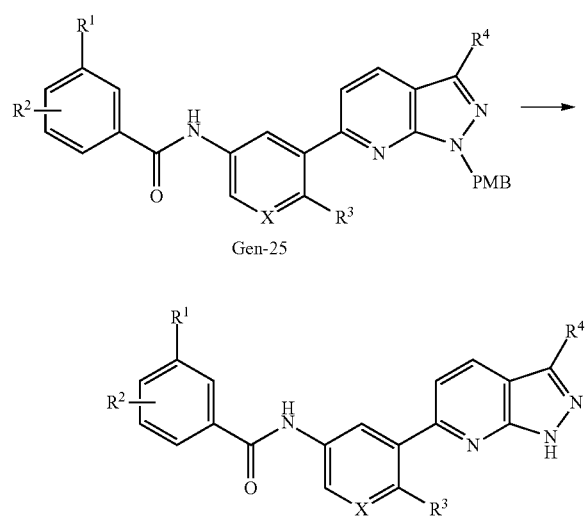

Gen-25

1.10.1. General Method II

To a solution of Intermediate Gen-25 (1 eq.) in TFA, are added TES, toluene and water. The reaction is heated at 110° C. under microwaves for 2 h. The reaction mixture is concentrated, then diluted with DCM and a Na$_2$CO$_3$ solution is added. The two layers are separated, and the aqueous layer is extracted 3 times with DCM/MeOH 95:5. The combined organic layers are dried over Na$_2$SO$_4$, filtered and concentrated to dryness. The residue is purified by chromatography on silica gel.

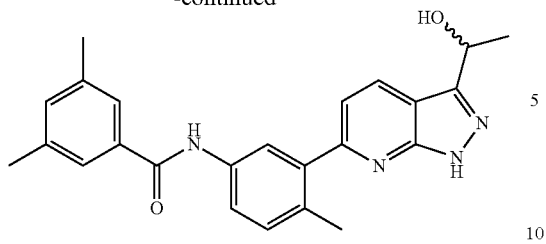

To Intermediate Gen-28-c (350 mg, 0.672 mmol, 1 eq.) cooled at 0° C. was added concentrated $H_2SO_4$ (4 mL). The reaction flask was allowed to stir at 0° C. for 1 h. The reaction mixture was then poured over crushed ice-water, basified with saturated aqueous $K_2CO_3$ solution until a pH of 10 is reached, and then extracted with EtOAc. The organic layer was dried over $Na_2SO_4$, filtered and concentrated under vacuum. The residue is purified by chromatography on silica gel (elution with EtOAc 100%) to afford Compound 54.

LCMS: MW (calcd): 400; m/z MW (obsd): 401 (M+H).

1.10.5. General Method K

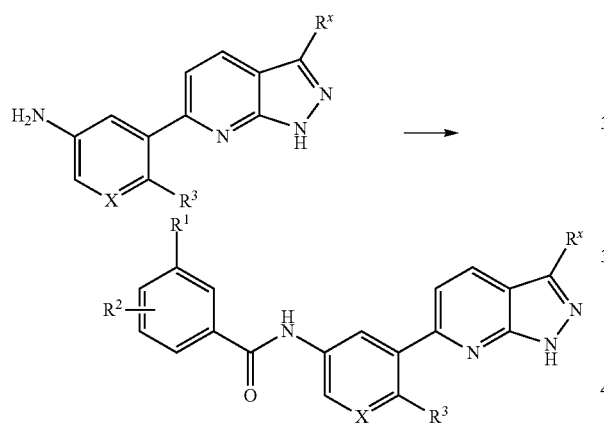

To a suspension of amine derivative (1 eq.), carboxylic acid (1.2 eq.), EDCI.HCl (1.3 eq.) and HOBt (1.3 eq.) in DMF is added $Et_3N$ (2.6 eq.). The reaction mixture is stirred overnight at room temperature. After 48 h, water was added and the mixture is extracted with EtOAc. The organic layers are combined, dried over $Na_2SO_4$, filtered and evaporated to dryness. The expected intermediate is purified by chromatography of silica gel (elution DCM/MeOH: 95/5 or 90/10) or preparative LCMS.

1.10.6. Illustrative Synthesis of Compound 42

N-[5-(3-Ethyl-1H-pyrazolo[3,4-b]pyridin-6-yl)-6-methyl-pyridin-3-yl]-3-trifluoromethyl-benzamide

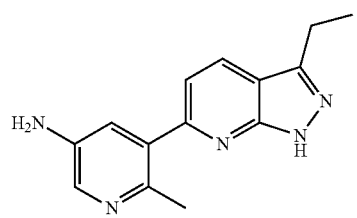

+

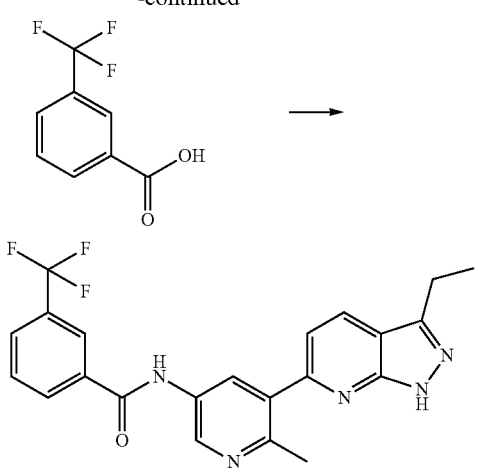

To a suspension of Intermediate Gen-13-a (63.3 mg, 0.25 mmol, 1 eq.), Gen-1-c (57 mg, 0.30 mmol, 1.2 eq.), EDCI-.HCl (62.3 mg, 0.325 mmol, 1.3 eq.) and HOBt (44 mg, 0.325 mmol, 1.3 eq.) in DMF (2.0 mL) is added $Et_3N$ (90 µL, 0.65 mmol, 2.6 eq.). The reaction mixture is stirred overnight at room temperature. After 48 h, water was added and the mixture is extracted with EtOAc. The organic layers are combined, dried over $Na_2SO_4$, filtered and evaporated to dryness. The crude is purified by chromatography of silica gel (elution DCM/MeOH: 95/5) to give Compound 42.

LCMS: MW (calcd): 245; MW (obsd): 426 (M+H).

$^1$H NMR (300 MHz, MeOD-$d_3$): δ ppm 8.92 (1H, d), 8.40 (1H, s), 8.38 (1H, d), 8.33 (1H, s), 8.27 (1H, d), 7.94 (1H, d), 7.80-7.74 (1H, m), 7.41 (1H, d), 3.08 (2H, q), 2.61 (3H, s), 1.46 (3H, t).

1.10.7. General Method M

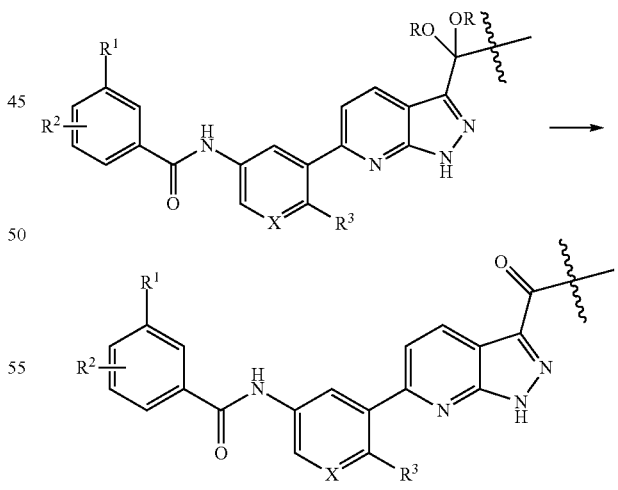

To a solution of acetal derived (1 eq.) in THF is added an aqueous 1 M HCl solution (15-20 eq.). The reaction mixture is stirred at 0° C. for 1.5 h to 2 h. Then the reaction mixture is quenched with a saturated $NaHCO_3$ solution and is extracted with EtOAc twice. The combined organic layers are dried over $Na_2SO_4$, filtered and concentrated in vacuo. The expected intermediate is purified by chromatography of silica gel (elution DCM/MeOH: 100/0 to 90/10).

1.10.8. Illustrative Synthesis of Intermediate Gen-18-a

N-[3-(3-Formyl-1H-pyrazolo[3,4-b]pyridin-6-yl)-4-methyl-phenyl]-3-trifluoromethyl-benzamide

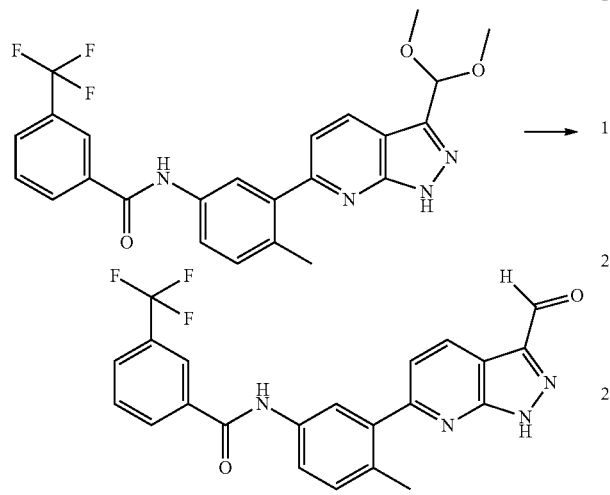

To a solution of Intermediate Gen-17-a (92 mg, 0.2 mmol, 1 eq.) in THF (10 mL) is added an aqueous 1 M HCl solution (2.9 mL, 2.93 mmol, 15 eq.). The reaction mixture is stirred at 0° C. for 2 h. Then the reaction mixture is quenched with a saturated NaHCO$_3$ solution and is extracted with EtOAc twice. The combined organic layers are dried over Na$_2$SO$_4$, filtered and concentrated in vacuo to afford Intermediate Gen-18-a. The crude is used directly in the next step without purification.

LCMS: MW (calcd): 424; m/z MW (obsd): 425 (M+H).

1.11. General Method O

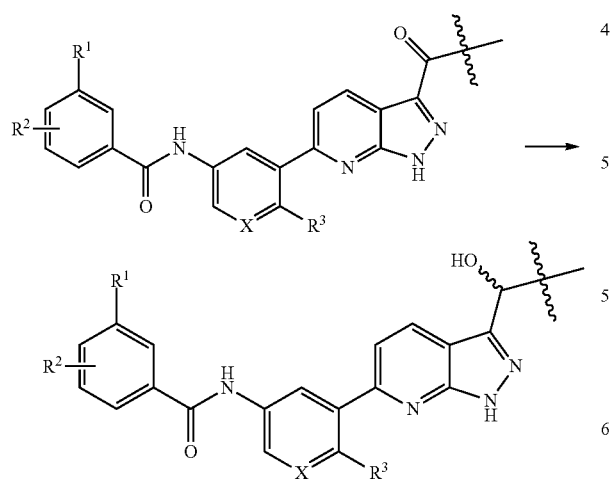

To a solution of carbonyl derivative (1 eq.) in EtOH/THF mixture is added NaBH$_4$ (1.2 eq). The reaction mixture is stirred at room temperature overnight. Then, reaction mixture is diluted with DCM and quenched with water. The two layers are separated, and the aqueous layer is extracted twice with DCM/MeOH 95:5. The combined layers are dried over Na$_2$SO$_4$ and concentrated to dryness to afford intermediate alcohol derivative.

1.12. Illustrative Synthesis of Intermediate Gen-28-a

N-[3-(3-Ethyl-1H-pyrazolo[3,4-b]pyridin-6-yl)-4-methyl-phenyl]-3,5-dimethoxy-benzamide

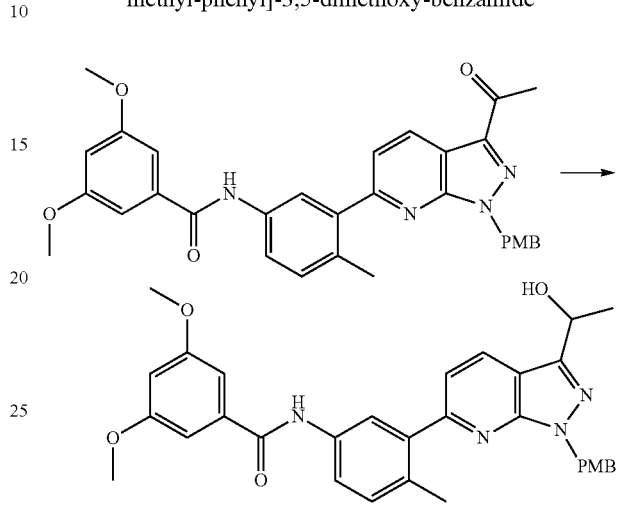

To a solution of intermediate Gen-27-a (143 mg, 259 mmol, 1 eq.) in EtOH/THF (1.5/0.5 mL) mixture, is added NaBH$_4$ (11.8 mg, 312 mol, 1.2 eq.). The reaction mixture is stirred at room temperature overnight. Then reaction mixture is diluted with DCM (20 mL) and quenched with water (5 mL). The two layers are separated, and the aqueous layer is extracted twice with 15 mL DCM/MeOH 95:5. The combined layers are dried over Na$_2$SO$_4$ and concentrated to dryness to afford intermediate Gen-28-a.

$^1$H NMR (400 MHz, CDCl3) δ ppm 8.15 (1H, d), 7.69 (2H, s), 7.48 (1H, d), 7.27 (4H, m), 6.92 (2H, s), 6.76 (2H, d), 6.55 (1H, s), 5.55 (2H, s), 5.20 (1H, m), 3.78 (6H, s), 3.69 (3H, s), 2.34 (3H, s), 1.66 (3H, s).

1.12.1. General Method P

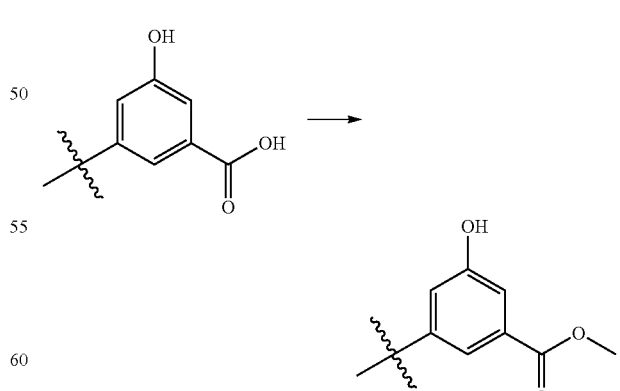

To a solution of acid derivative (1 eq.) in MeOH at r.t is added concentrated H$_2$SO$_4$. The reaction mixture is heated at 80° C. overnight. Then, a part of MeOH is evaporated, a saturated solution of NH$_4$Cl and EtOAc are added. The organic layer is separated, washed with NH₄Cl and brine, dried over Na₂SO₄, filtered and concentrated to dryness to give ester derivative.

1.12.2. Illustrative Synthesis of Intermediate Gen-36-a

3-Bromo-5-hydroxy-benzoic acid methyl ester

1.13.1. Illustrative Synthesis of intermediate Gen-37-a

3-Bromo-5-methoxy-benzoic acid methyl ester

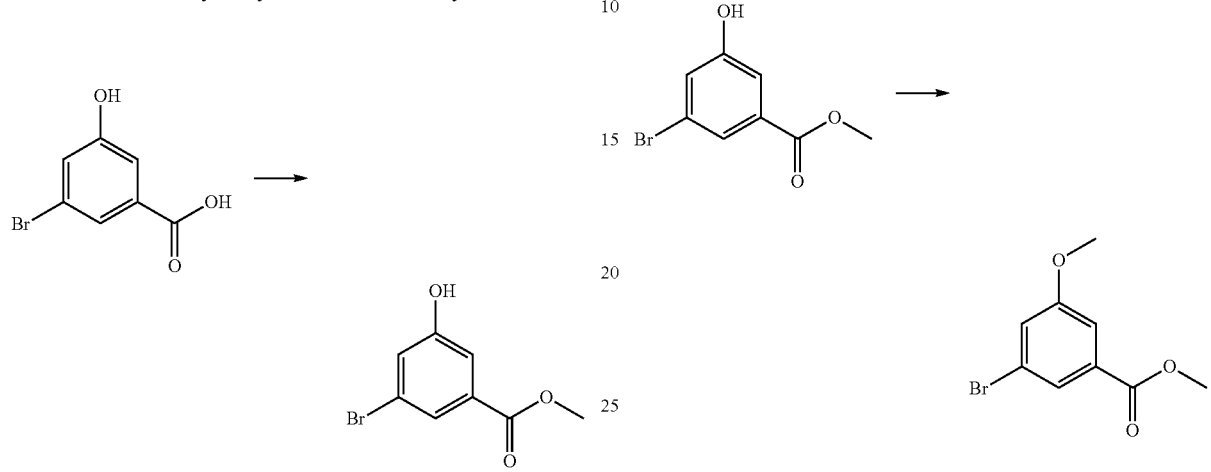

To a solution of Gen-1-g (1.74 g, 8 mmol, 1 eq.) in MeOH (50 mL) at r.t is added concentrated H₂SO₄ (6 drops). The reaction mixture is heated at 80° C. overnight. Then, a part of MeOH is evaporated, a saturated solution of NH₄Cl and EtOAc are added. The organic layer is separated, washed with NH₄Cl and brine, dried over Na₂SO₄, filtered and concentrated to dryness to give Gen-36-a.

To a solution of Gen-36-a (230 mg, 1 mmol, 1 eq.) in acetone (5 mL) are added K₂CO₃ (415 mg, 3 mmol, 3 eq.), MeI (185 µL, 3 mmol, 3 eq). The reaction mixture is stirred at r.t for 72 hrs. Then EtOAc and a saturated solution of NaHCO₃ are added. The organic layer is separated, washed with a saturated solution of NH₄Cl and brine, dried over Na₂SO₄, filtered and concentrated under vacuo to give Gen-37-a.

1.13. General Method Q

1.13.2. General Method R1

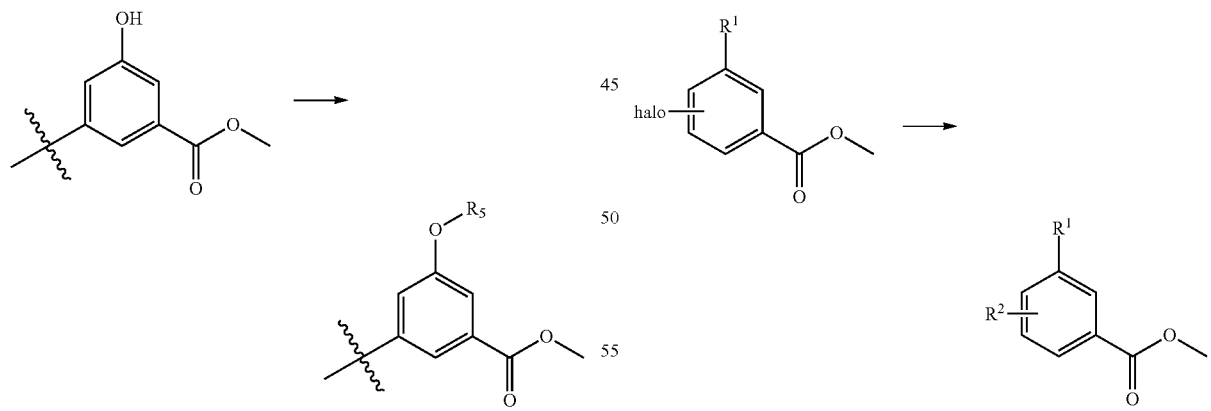

To a solution of phenol derivative (1 eq.) in acetone or toluene or DMF or ACN are added K₂CO₃ or Cs₂CO₃ (2 eq. to 4 eq.), RX (2 eq) and KI. The reaction mixture is stirred at r.t or reflux for 4 hrs to 72 hrs. Then EtOAc and a saturated solution of NaHCO₃ are added. The organic layer is separated, washed with a saturated solution of NH4Cl and brine, dried over Na₂SO₄, filtered and concentrated under vacuo to give the O-alkylated intermediate.

To a stirred solution of halogen derivative (1 eq.), boronate derivative (1.1 eq.) and Cs₂CO₃ (2.5 eq.) in degassed dioxane/H₂O is added Pd(dppf)Cl₂ (0.07 eq.). The reaction mixture is stirred 130° C. for 3 h under argon. Water and EtOAc are added and the layers are separated. The organic layer is combined, dried over Na₂SO₄, filtered and evaporated to dryness. The expected intermediate is purified by chromatography of silica gel (elution heptane/EtOAc: 100/0 to 25/75).

1.13.3. Illustrative Synthesis of Intermediate Gen-38-a

3-Cyclopropyl-5-methoxy-benzoic acid methyl ester

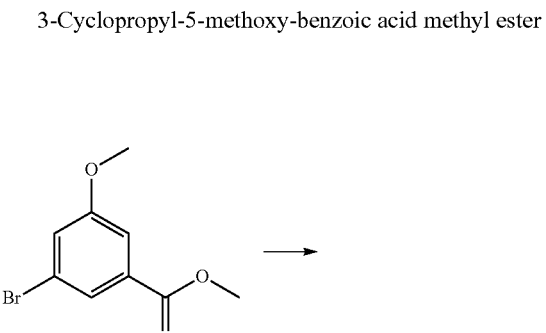

To a stirred solution of Intermediate Gen-37-a (230 mg, 0.94 mmol, 1 eq.), Gen-9-g (173.5 mg, 1.03 mmol, 1.1 eq.) and Cs$_2$CO$_3$ (766 mg, 2.35 mmol, 2.5 eq.) in degassed dioxane/H$_2$O (8 mL/2 mL) is added Pd(dppl)Cl$_2$ (48 mg, 0.066 mmol, 0.07 eq.). The reaction mixture is stirred 130° C. for 3 h under argon. Water and EtOAc are added and the layers are separated. The organic layer is combined, dried over Na$_2$SO$_4$, filtered and evaporated to dryness. The expected intermediate is purified by chromatography of silica gel (elution heptane/ EtOAc: 80/20).

LCMS: MW (calcd): 206; MW (obsd): 207 (M+H).

1.13.4. General Method R2

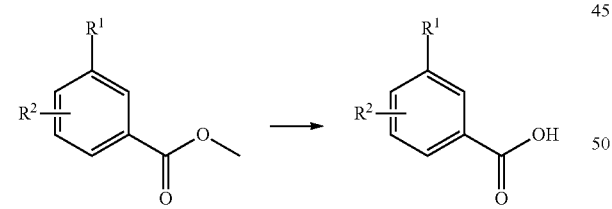

To a stirred solution of methyl ester derivative (1 eq.) in THF or THF/MeOH or THF/H$_2$O is added a solution of NaOH 1N (1-2 eq.) or LiOH. H$_2$O (1 eq.). The reaction mixture is stirred at room temperature overnight to 4 days. The solvent are evaporated to dryness to give the expected intermediate. Or the reaction mixture is evaporated to dryness and the residue is quenched with a saturated solution of NaHCO$_3$ and extracted with EtOAc. The aqueous layer is acidified with a saturated solution of NH$_4$Cl and HCl 1N, extracted with EtOAc. The organic layer is combined, dried over Na$_2$SO$_4$, filtered and evaporated to dryness to give the expected intermediate. (the intermediate is used directly in the next step without purification).

1.13.5. Illustrative Synthesis of Intermediate Gen-39-b

3-Cyclopropyl-5-(2-morpholin-4-yl-ethoxy) benzoic acid

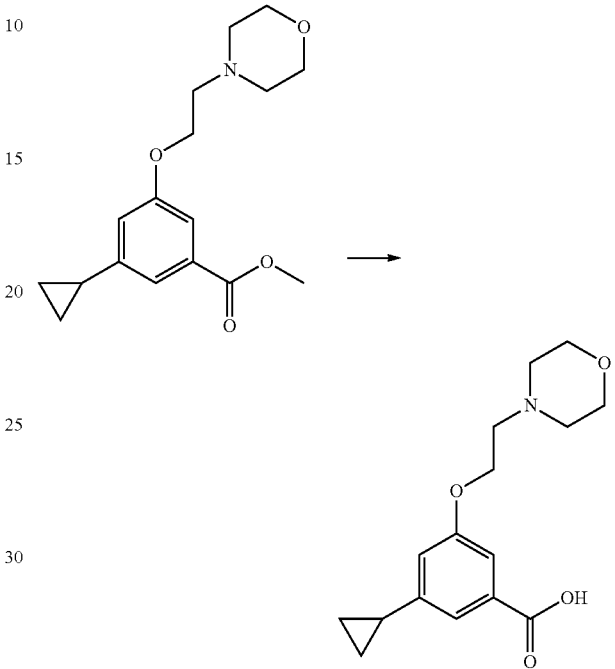

To a stirred solution of Intermediate Gen-38-b (255 mg, 0.835 mmol, 1 eq.) in THF (3.5 mL) is added a solution of NaOH 1N (0.84 mL, 0.835 mol, 1 eq.). The reaction mixture is stirred at room temperature overnight. The solvent are evaporated to dryness to give the expected intermediate Gen-39-b. (the intermediate is used directly in the next step without purification).

LCMS: MW (calcd): 290; MW (obsd): 291 (M+H).

Example 2

Preparation of the Intermediates

Intermediate Gen-4-a

N-(5-Bromo-6-methyl-pyridin-3-yl)-3,5-dimethoxy-benzamide

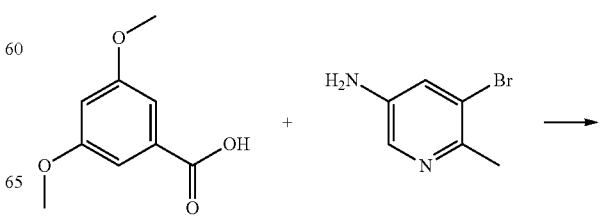

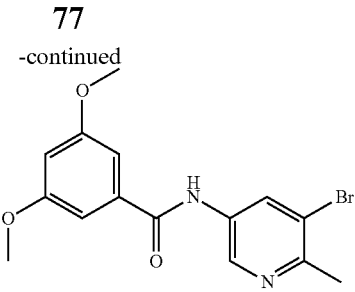

To a stirred solution of Intermediate Gen-1-a (1.87 g, 10 mmol, 1 eq.), and Intermediate Gen-2-a (1.82 g, 10 mmol, 1 eq.) in DMF (30 mL) are added HATU (3.75 g, 10 mmol, 1 eq.) followed by NMM (2.77 mL, 25 mmol, 2.5 eq.) at room temperature under argon, the reaction mixture is stirred at room temperature overnight. Then the reaction is concentrated in vacuo, the residue is partitioned between a mixture of EtOAc/nBuOH and water. The layers are separated, the organic layer is dried over $Na_2SO_4$, filtered and evaporated to dryness. Then the residue is purified by chromatography on silica gel (elution heptane/EtOAc: 100/0 to 0/100) to afford Intermediate Gen-4-a.

LCMS: MW (calcd): 350 ($^{79}$Br), 352 ($^{81}$Br); m/z MW (obsd): 351 ($^{79}$Br M+H), 353 ($^{81}$Br M+H).

Intermediate Gen-7-a

N-Methoxy-N-methyl-propionamide

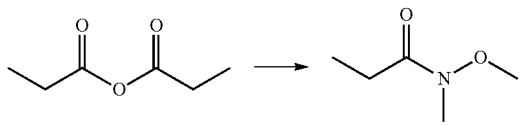

To a suspension of Intermediate Gen-9-c (9.53 g, 98 mmol, 1 eq.) in DCM (100 mL) at 0° C. under stirring and nitrogen are slowly added TEA (28.7 mL, 205 mol, 2.1 eq.) and. Intermediate Gen-15-g (12.5 mL, 98 mmol, 1 eq). Then the reaction mixture is allowed to warm up to room temperature and stirred at room temperature for 5 h. The reaction is quenched by slowly adding an aqueous $NH_4Cl$ solution, the layers are separated and the aqueous layer is extracted again with EtOAc. The combined organic layers are dried over $Na_2SO_4$, filtered and evaporated to dryness to afford Intermediate Gen-7-a. The crude product is used directly in the next step without purification.

$^1$H NMR (300 MHz, $CDCl_3$-d) δ ppm 3.69 (3H, s), 3.19 (3H, s), 2.46 (2H, d), 1.15 (3H, t).

Intermediate Gen-7-c

Cyclopropanecarboxylic acid methoxy-methyl-amide

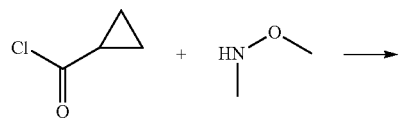

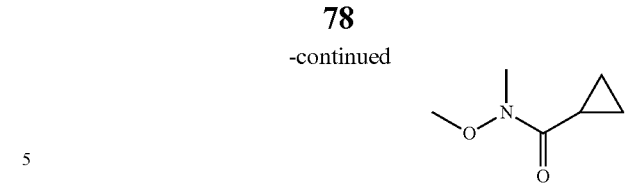

To a solution of intermediate Gen-9-c (933 mg, 9.56 mmol, 1 eq.) in DCM (10 mL) at 0° C., until N2 atmosphere is added TEA (2.8 mL, 20 mmol, 2.1 eq.) and Gen 15-h (870 μL, 9.54 mmol, 1 eq.). The reaction mixture is allowed to warm to r.t for 5 h. Then, the reaction mixture is quenched with a $NH_4Cl$ solution and extracted with EtOAc. The organic layer is dried over $Na_2SO_4$, filtered and concentrated to dryness to afford Gen-7-c Intermediate Gen-7-f 1-(tert-Butyl-dimethyl-silanyloxy)-cyclopropanecarboxylic acid methoxy-methyl-amide

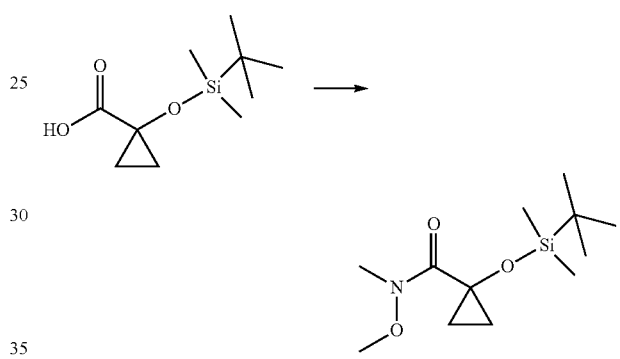

To a suspension of Intermediate Gen-9-c (2.38 g, 24.4 mmol, 1.2 eq.), Intermediate Gen-15-f (4.4 g, 20.3 mmol, 1 eq), EDCI.HCl (5.06 g, 26.4 mmol, 1.3 eq.) and HOBt (3.57 g, 26.4 mmol, 1.3 eq.) in DCM (200 mL) under stirring is added TEA (10.2 mL, 73.1 mol, 3.6 eq.). Then the reaction mixture is stirred at room temperature overnight, the reaction is quenched with an aqueous 1 M HCl solution, the layers are separated and the aqueous layer is extracted again with DCM. The combined organic layers are dried over $Na_2SO_4$, filtered and evaporated to dryness. The residue is purified by chromatography on silica gel (elution heptane/EtOAc: 95/5 to 90/10) to afford Intermediate Gen-7-f.

$^1$H NMR (300 MHz, $CDCl_3$-d) δ ppm 3.74 (3H, s), 3.41 (3H, s), 1.13 (2H, q), 0.90 (2H, q), 0.87 (9H, s), 0.13 (6H, s).

Intermediate Gen-13-a 5-(3-Ethyl-1H-pyrazolo[3,4-b]pyridin-6-yl)-6-methyl-pyridin-3-ylamine

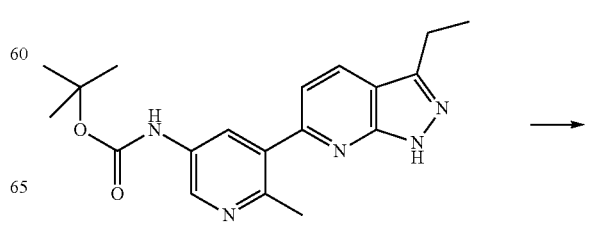

-continued

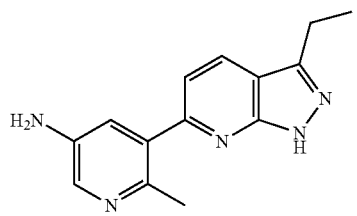

To a solution of Intermediate Gen-12-a (653 mg, 1.84 mmol, 1 eq.) in EtOH (9 mL) is added TFA (0.7 mL, 9.2 mmol, 10 eq.). The reaction mixture is stirred at room temperature for 4 h. Then the reaction mixture is quenched with a saturated NaHCO$_3$ solution and is extracted with DCM twice. The combined organic layers are dried over Na$_2$SO$_4$, filtered and concentrated in vacuo. The crude is purified by chromatography on silica gel (elution DCM/MeOH: 95/5 to 90/10) to afford Intermediate Gen-13-a.

LCMS: MW (calcd): 253; m/z MW (obsd): 254 (M+H).

Intermediate Gen-21-a

6-Chloro-3-iodo-1-(4-methoxy-benzyl)-1H-pyrazolo[3,4-b]pyridine

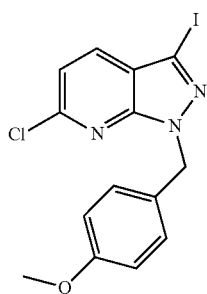 [SMILES: COc1ccc(Cn2nc(I)c3ccc(Cl)nc32)cc1]

Step i

6-Chloro-3-iodo-1H-pyrazolo[3,4-b]pyridine (Intermediate Gen-20-a)

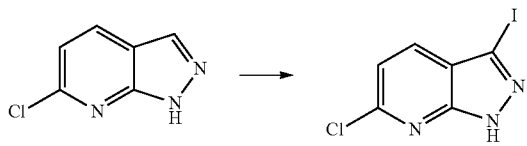 [SMILES: Clc1ccc2cn[nH]c2n1 ; Clc1ccc2c(I)n[nH]c2n1]

Intermediate Gen-19-a (5 g, 32.6 mmol, 1 eq) is dissolved in DMF (30 mL). I$_2$ (16.4 g, 64.6 mol, 2 eq) and KOH (6.8 g, 121 mmol, 3.7 eq) are added. The reaction mixture is stirred at rt for 3 h. Then the reaction is quenched with a 10% solution of Na$_2$S$_2$O$_3$. The aqueous layer is extracted four times with 50 mL Et$_2$O, three times with DCM and three times with DCM/MeOH 9:1. The combined organic layers are dried over Na$_2$SO$_4$, after washing with brine (50 mL), filtered and concentrated to afford Gen-20-a.

Step ii

6-Chloro-3-iodo-1-(4-methoxy-benzyl)-1H-pyrazolo-[3,4-b]pyridine (Intermediate Gen-21-a)

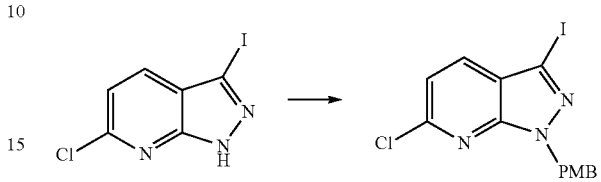

Intermediate Gen-20-a (8.5 g, 30.5 mmol, 1 eq) is dissolved in DMF (25 mL) at 0° C. NaH (1.47 g, 36.6 mmol, 1.2 eq) is added by portions. The reaction mixture is stirred at 0° C. for 30 min. PMBCl (5 mL, 37 mmol, 1.2 eq) in solution in DMF (5 mL) is added dropwise over 5 min. The mixture warmed up to rt and stirred at this temperature for 4 h. Then the reaction is quenched with NaHCO$_3$ and extracted three times with EtOAc (75 mL). The combined organic layers are dried over Na$_2$SO$_4$ after washing with brine (25 mL). After filtration and concentration, the crude is purified by chromatography on silica gel (elution with petrole ether/Et20 90:10 to 50:50) to afford Gen-21-a.

Intermediate Gen-22-b

6-Chloro-1-(4-methoxy-benzyl)-3-methyl-1H-pyrazolo[3,4-b]pyridine

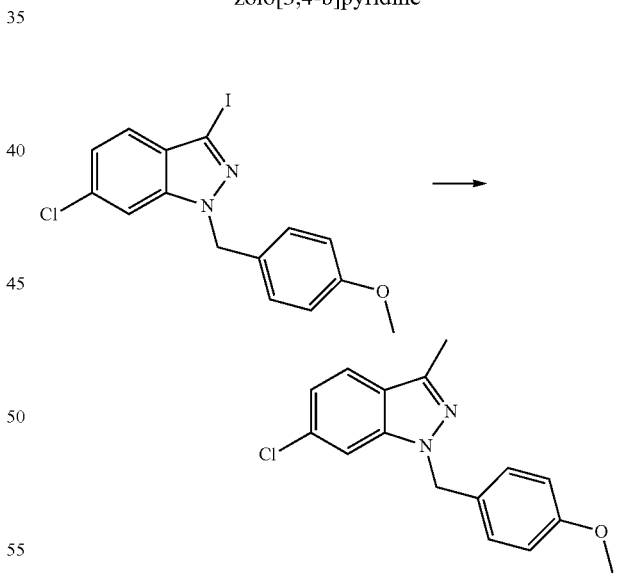

To a stirred solution of gen-21-a (400 mg, 1 mmol, 1 eq.), Pd(PPh$_3$)$_4$ (11.6 mg, 0.01 mmol, 0.01 eq.) and Cs$_2$CO$_3$ (652 mg, 2 mmol, 2 eq.) in degassed dioxane/H$_2$O mixture is added trimethylboroxine (0.1 mL, 0.7 mmol, 0.7 eq.) The reaction mixture is stirred overnight at 110° C. under argon. Then water and EtOAc are added and the organic phase is dried over Na$_2$SO$_4$, filtered and concentrated in vacuo. The crude is purified by chromatography on silica gel (elution with Heptane/EtOAc 80/20) to afforded Gen-22-b.

LCMS: MW (calcd): 287; m/z MW (obsd): 288 (M+H).

Intermediate Gen-23-b

6-Chloro-1-(4-methoxy-benzyl)-1H-pyrazolo[3,4-b]pyridine-3-carbaldehyde

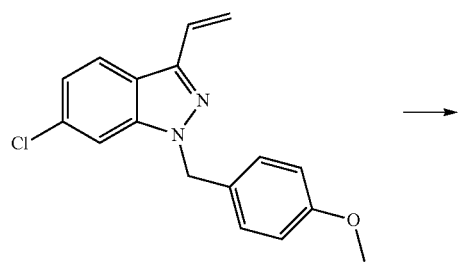

Intermediate Gen-22-a (4 g, 13.3 mmol, 1 eq.) is dissolved in DCM (400 mL). The reaction mixture is placed under $O_3$ atmosphere for 30 min. $Me_2S$ (5 mL, 60 mmol, 5 eq.) is added after nitrogen purge and the reaction mixture is stirred for 15 min at −78° C. before warming to r.t for 1 h. The reaction mixture is then concentrated under vacuo to dryness to afford Gen-23-b.

LCMS: MW (calcd): 300; m/z MW (obsd): 301 (M+H).

Intermediate Gen-24-a

1-[6-Chloro-1-(4-methoxy-benzyl)-1H-pyrazolo[3,4-b]pyridin-3-yl]-2-morpholin-4-yl-ethanol

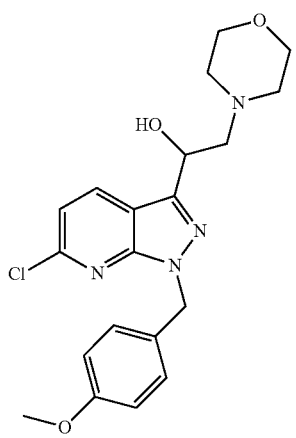 [SMILES: COc1ccc(Cn2nc(C(O)CN3CCOCC3)c3ccc(Cl)nc32)cc1]

Step i

6-Chloro-3-iodo-1-(4-methoxy-benzyl)-1H-pyrazolo[3,4-b]pyridine (Intermediate Gen-22-a)

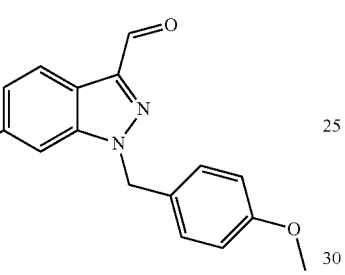

To a stirred solution of Gen-21-a (1 g, 2.50 mmol, 1 eq.) in dioxane (10 mL), was added Tributyl vinyl tin (873 mg, 2.75 mmol, 1.1 eq.) at room temperature The reaction mixture is degazed with argon. Then $PdCl_2(PPh_3)_2$ (88 mg, 0.125 mmol, 0.05 eq.) is added. The resulting mixture is heated at reflux for 3 h 30, then concentrated. The residue is diluted with EtOAc, washed twice with water and once with brine. The two layers are separated and the organic layer is dried over $Na_2SO_4$, filtered and concentrated. The crude is purified by chromatography on silica gel (elution Petroleum ether/EtOAc: 95/5 to 70/30) to afford Intermediate Gen-22-a.

LCMS: MW (calcd): 299 ($^{35}$Cl) 301 ($^{37}$Cl); m/z MW (obsd): 300 ($^{35}$Cl M+H) 302 ($^{37}$Cl M+H).

Step ii

2-Bromo-1-[6-chloro-1-(4-methoxy-benzyl)-1H-pyrazolo[3,4-b]pyridin-3-yl]-ethanol (Intermediate Gen-23-a)

Intermediate Gen-22-a (7.46 g, 24.89 mmol, 1 eq) is dissolved in a Dioxane/$H_2$O/DCM mixture (65/17/17). AcOH (1.42 mL, 24.89 mmol, 1 eq) is added and the reaction mixture is stirred at 0° C. for 15 min. NBS (6.64 g, 37.33 mmol, 1.5 eq) is added over 15 min at this temperature. Then the reaction mixture is stirred overnight at room temperature. The reaction is quenched with a saturated solution of $NaHCO_3$ (300 mL). The two layers are separated and the aqueous layer is extracted with DCM (300 mL). The combined organic layers are dried over $Na_2SO_4$, filtered and concentrated until dryness. The crude is purified by chromatography on silica gel (elution with DCM/EtOAc 95:5 to 75:25) to give Intermediate Gen-23-a.

LCMS: MW (calcd): 395 ($^{79}$Br$^{35}$Cl), 397 ($^{81}$Br$^{35}$Cl, $^{79}$Br$^{37}$Cl), 399 ($^{81}$Br$^{37}$Cl); m/z MW (obsd): 396 ($^{79}$Br$^{35}$Cl M+H), 398 ($^{81}$Br$^{35}$Cl, $^{79}$Br$^{37}$Cl M+H), 400 ($^{81}$Br$^{37}$Cl M+H).

Step iii

1-[6-Chloro-1-(4-methoxy-benzyl)-1H-pyrazolo[3,4-b]pyridin-3-yl]-2-morpholin-4-yl-ethanol (Intermediate Gen-24-a)

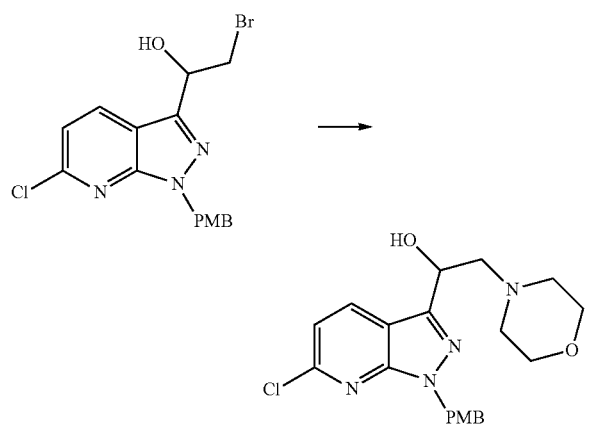

To a solution of Intermediate Gen-23-a (1.3 g, 3.28 mmol, 1 eq) was added morpholine (860 µL, 9.83 mmol, 3 eq). The reaction mixture is heated at reflux for 2 h 30. Then the reaction is diluted with DCM (50 mL). The organic layer is washed with a saturated solution of NH$_4$Cl. The aqueous layer is extracted three times with 15 mL of DCM. The combined organic layers are dried over Na$_2$SO$_4$, filtered and concentrated. The crude is purified on silica gel (elution with DCM/MeOH 100:0 to 98:2) to give gen-24-a.

Intermediate Gen-29-a (5-Bromo-6-methyl-pyridin-3-yl)-carbamic acid tert-butyl ester

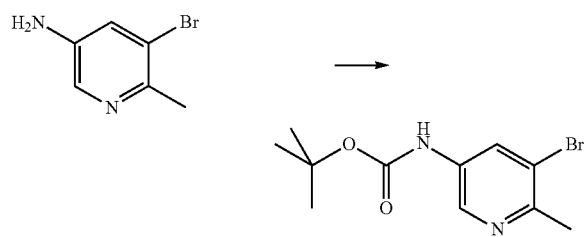

To a solution of Intermediate Gen-2-a (1.87 g, 10 mmol, 1 eq.) in DMF (20 mL) are added TEA (2.1 mL, 15 mmol, 1.5 eq.) then Boc$_2$O (3.27 g, 15 mmol, 1.5 eq.). The reaction mixture is heated at 90° C. overnight, then Boc$_2$O (1.09 g, 5 mmol, 0.5 eq.) is added and the reaction mixture is heated at 90° C. for 4 h. Then water is added and the mixture is extracted twice with EtOAc. The combined organic layers are dried over Na$_2$SO$_4$, filtered and concentrated in vacuo. The crude is purified by chromatography on silica gel (elution heptane/EtOH: 75/25) to afford Intermediate Gen-29-a.

LCMS: MW (calcd): 286 ($^{79}$Br), 288 ($^{81}$Br); m/z MW (obsd): 287 ($^{79}$Br M+H), 289 ($^{81}$Br M+H).

Intermediate Gen-30-a (5-Boronic-acid-6-methyl-pyridin-3-yl)-carbamic acid tert-butyl ester

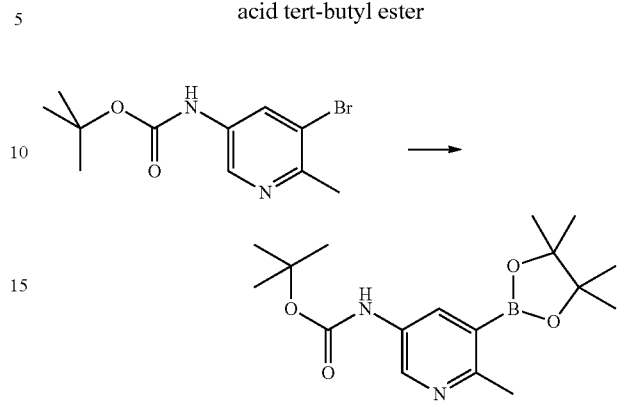

To a solution, previously degazed with nitrogen bubbling, of Intermediate Gen-29-a (850 mg, 2.96 mmol, 1 eq.) in 1,4 dioxane (15 mL) are added Intermediate Gen-9-a (827 mg, 3.26 mmol, 1.1 eq.) followed by potassium acetate (870 mg, 8.88 mmol, 3 eq.) and PdCl$_2$(dppf) (108 mg, 0.148 mmol, 0.05 eq.). The reaction mixture is refluxed under nitrogen overnight. The reaction is cooled to room temperature, then water and EtOAc are added. The two layers are separated, the aqueous layer is extracted again with EtOAc and the combined organic layers are dried over Na$_2$SO$_4$, filtered and evaporated to dryness to afford Intermediate Gen-30-a. The crude is used directly in the next step without purification.

LCMS: MW (calcd): 252; m/z MW (obsd): 253 (M+H).

Intermediate Gen-33-a

N-[3-(3-Ethyl-1H-pyrazolo[3,4-b]pyridin-6-yl)-4-methyl-phenyl]-3-(2-hydroxy-ethoxy)-5-methyl-benzamide

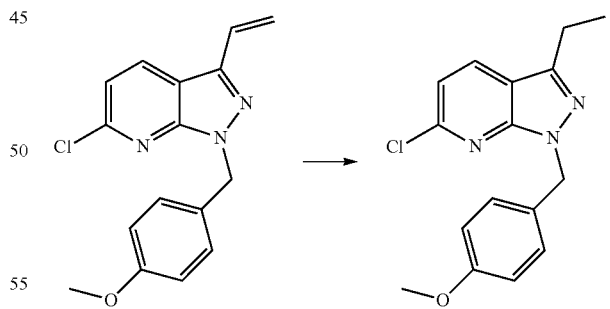

To a degazed suspension of intermediate Gen-22-a (5.6 g, 18.68 mmol, 1 eq.) in MeOH (100 mL) under nitrogen is added PtO$_2$ (560 mg, 0.1 eq.), purged with hydrogen. The reaction mixture is stirred at room temperature hydrogen (1 atm) overnight. The reaction mixture is filtered on celite, rinsed with EtOAc and evaporated to dryness to give intermediate Gen-33-a. The intermediate is used directly in the next step without purification.

LCMS: MW (calcd): 301; m/z MW (obsd): 302 (M+H).

Intermediate Gen-75-a

2-[6-Chloro-1-(4-methoxy-benzyl)-1H-pyrazolo[3,4-b]pyridin-3-yl]-ethanol

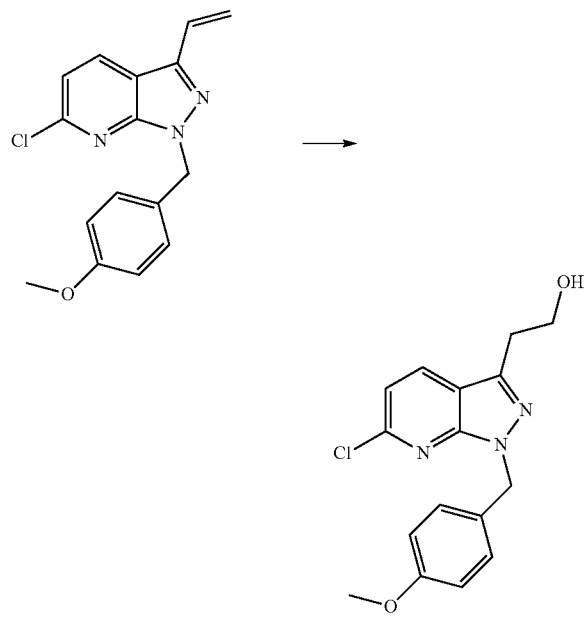

The intermediate Gen-75-a is synthesized using a classical procedure of hydroboration. (Jensen et al., 2011)

Intermediate Gen-44-a

3-Hydroxy-5-methoxy-benzoic acid methyl ester

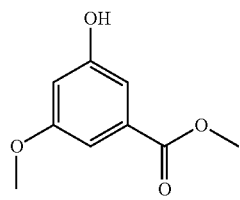

Step i

3-Acetoxy-5-hydroxy-benzoic acid (Intermediate Gen-41-a)

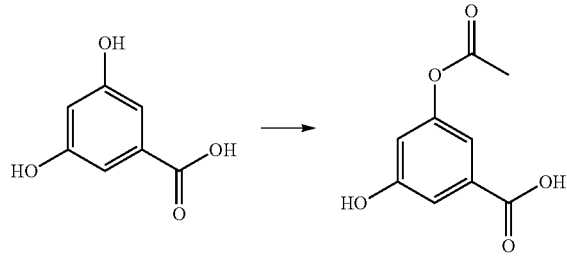

To a solution of Gen-40-a (4.12 g, 26.7 mmol, 1 eq.) in suspension in water (20 mL) is added NaOH (3.20 g, 80.2 mmol, 3 eq.). The reaction mixture is cooled down to 0° C. and acetic anhydride (2.50 mL, 26.7 mmol, 1 eq.) is added slowly. After 50 min, HCl 6N is added until pH 1. Then the mixture is extracted with EtOAc. The organic layer is washed with water, dried over $Na_2SO_4$, filtered, concentrated to dryness to give Gen-41-a which is used as such in the next step.

Step ii

3-Acetoxy-5-methoxy-benzoic acid methyl ester (Intermediate Gen-42-a)

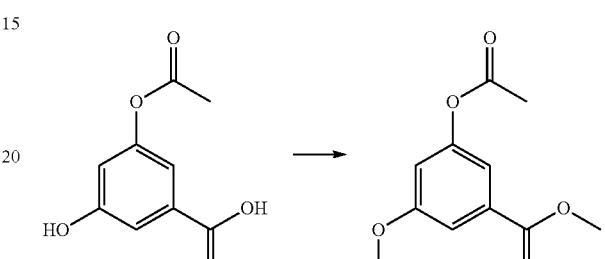

To a solution of Gen-41-a (4.97 g, 25 mmol, 1 eq.) in DMF (25 mL) at 0° C. is added $K_2CO_3$ (10.50 g, 76 mmol, 3 eq.) and MeI (3.95 mL, 63 mmol, 2.5 eq.). The reaction mixture is stirred at 0° C. for 1 h and allowed to warm to r.t for 1 h. Water and EtOAc are added. The organic layer is separated, washed with an aqueous 0.1 NaOH solution and brine, dried over $Na_2SO_4$, filtered and concentrated. The crude is purified by chromatography on silica gel (elution with Hept/EtOAc 100:0 to 80:20) to afford Gen-42-a.

LCMS: MW (calcd): 224; m/z MW (obsd): 225 (M+H).

Step iii

3-Hydroxy-5-methoxy-benzoic acid methyl ester (Intermediate Gen-44-a)

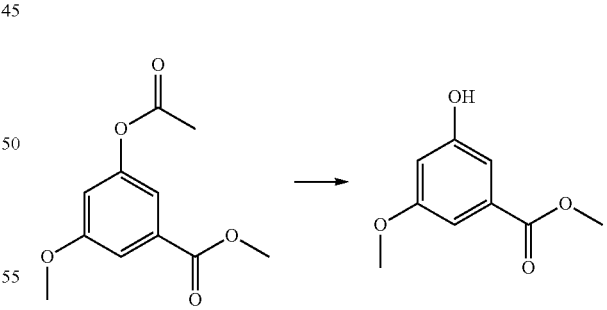

To a solution of Gen-42-a (3.77 g, 16.8 mmol, 1 eq.) in MeOH (60 mL) is added NaOMe 0.5M in MeOH (40.4 mL, 20.2 mmol, 1.2 eq.). The reaction mixture is stirred at r.t for 40 min. Then MeOH is evaporated. $Et_2O$ and water are added. The aqueous layer is acidified to pH 2 and extracted again with $Et_2O$. Organic layers are combined, dried over $Na_2SO_4$, filtered and concentrated. The crude is purified by chromatography on silica gel (elution with Hept/EtOAc 80:20) to afford Gen-44-a.

Intermediate Gen-50-a

3-Methoxy-5-trifluoromethyl-benzoic acid

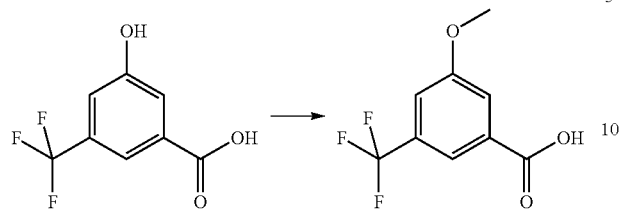

To a solution of Gen-40-b (503 mg, 2.4 mmol, 1 eq.) in acetone (15 mL) at r.t is added K₂CO₃ (1.01 g, 7.3 mmol, 3 eq.) and MeI (455 µL, 7.3 mmol, 3 eq.). The reaction mixture is heated at reflux for 2 hrs then at r.t overnight. 2N aqueous NaOH (12 mL, 24 mmol, 10 eq.) is added and the reaction mixture stirred for 2 hrs. Then acetone is evaporated. EtOAc is added. The aqueous layer is acidified until pH 1 and extracted with EtOAc. The organic layer is dried over Na₂SO₄, filtered and concentrated. The crude is purified by filtration on quaternary ammonium catch and release (SCE AX) column to afford Intermediate Gen-50-a.

LCMS: MW (calcd): 220; m/z MW (obsd): 219 (M−H).

Example 3

Preparation of the Compounds of the Invention

Compound 8

N-[3-(3-Ethyl-1H-pyrazolo[3,4-b]pyridin-6-yl)-4-methyl-phenyl]-3,5-dimethoxy-benzamide

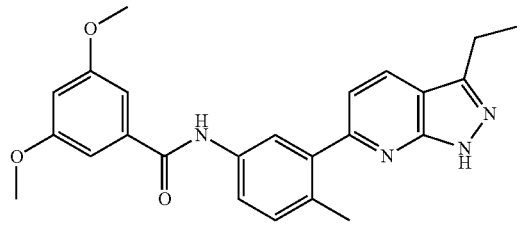 [SMILES: CCc1n[nH]c2nc(-c3cc(NC(=O)c4cc(OC)cc(OC)c4)ccc3C)ccc12]

Step i

1-[6-Chloro-1-(4-methoxy-benzyl)-1H-pyrazolo[3,4-b]pyridin-3-yl]-ethanone (Intermediate Gen-26-a)

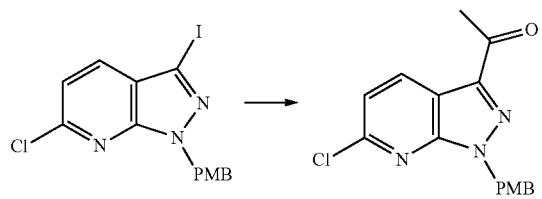

Intermediate Gen-21-a (3.03 g, 7.58 mmol, 1 eq.) is suspended in toluene (70 mL). Intermediate Gen-9-d (3.2 mL, 9.48 mmol, 1.25 eq.) is added. The reaction mixture is purged with argon and PdCl₂(PPh₃)₂ (0.27 g, 0.38 mmol, 0.05 eq.) is added. The reaction mixture is heated at 100° C. for 9 h. Then the reaction is diluted with MeOH (70 mL) and HCl 1M (70 mL) is added. The reaction mixture is stirred for further 4 h. DCM (90 mL) and a saturated solution of NaHCO₃ (90 mL) are added. The two layers are separated and the aqueous layer extracted with DCM (150 mL). The combined organic layers are dried over Na₂SO₄, filtered and concentrated. The solid obtained is recristallised in MeOH to give intermediate Gen-26-a.

Step ii

N-{3-[3-Acetyl-1-(4-methoxy-benzyl)-1H-pyrazolo[3,4-b]pyridin-6-yl]-4-methyl-phenyl}-3,5-dimethoxy-benzamide (Intermediate Gen-27-a)

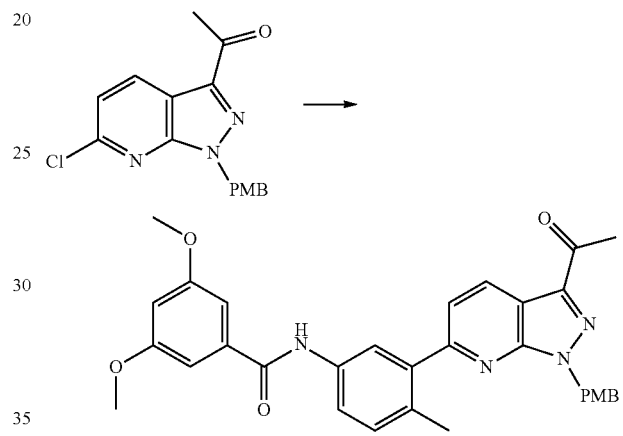

Suzuki coupling of Intermediate Gen-26-a and Intermediate Gen-5-a is performed according to general method H to afford Intermediate Gen-27-a.

¹H NMR (400 MHz, CDCl₃) δ ppm 8.65 (1H, d), 7.79 (2H, s), 7.64 (1H, d), 7.48 (1H, d), 7.41 (2H, d), 7.34 (1H, d), 7.70 (2H, d), 6.87 (2H, d), 6.63 (1H, s), 5.73 (2H, s), 3.86 (6H, s), 3.77 (3H, s), 2.73 (3H, s), 2.40 (3H, s).

Step iii

N-{3-[3-(1-Hydroxy-ethyl)-1-(4-methoxy-benzyl)-1H-pyrazolo[3,4-b]pyridin-6-yl]-4-methyl-phenyl}-3,5-dimethoxy-benzamide (Intermediate Gen-28-a)

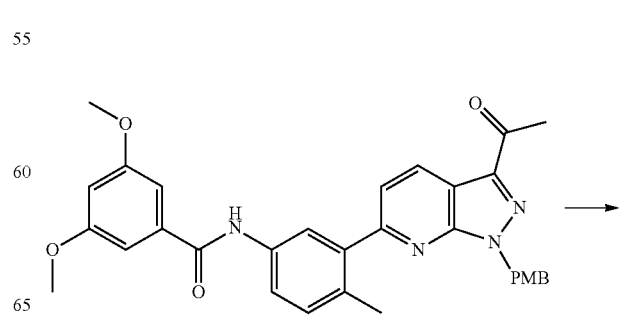

-continued

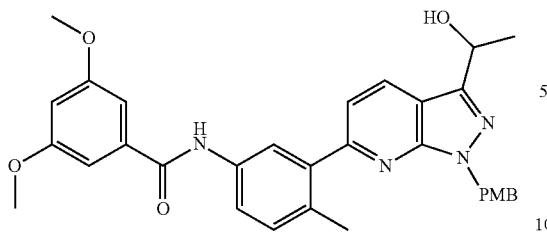

Intermediate Gen-27-a is reacted according to general method O to afford Gen-28-a.

¹H NMR (400 MHz, CDCl₃) δ ppm 8.15 (1H, d), 7.69 (2H, s), 7.48 (1H, d), 7.27 (4H, m), 6.92 (2H, s), 6.76 (2H, d), 6.55 (1H, s), 5.55 (2H, s), 5.20 (1H, m), 3.78 (6H, s), 3.69 (3H, s), 2.34 (3H, s), 1.66 (3H, s).

Step iv

N-[3-(3-Ethyl-1H-pyrazolo[3,4-d]pyridin-6-yl)-4-methyl-phenyl]-3,5-dimethoxy-benzamide (Compound 8)

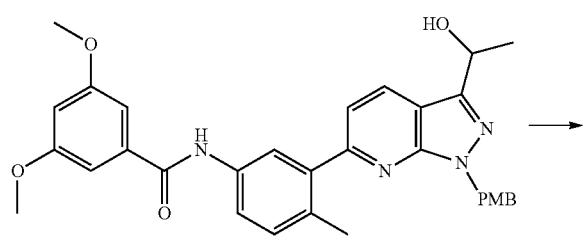

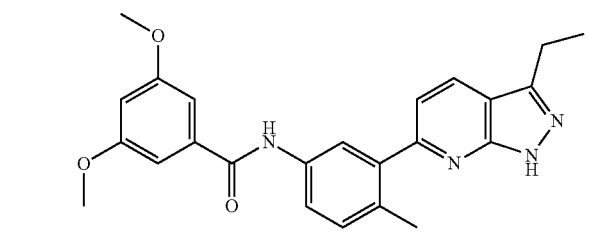

Intermediate Gen-28-a (25 mg, 45.3 mmol, 1 eq.), TFA (1 mL, 13 mmol, 3.5 eq.) and TES (100 μL, 0.626 mmol, 0.01 eq.) in water (100 μL) and toluene (1.0 mL) for 6.5 h at 110° in a sealed tube. The reaction mixture is concentrated, then diluted with DCM (15 mL) and a Na₂CO₃ solution (5 mL). The two layers are separated, and the aqueous layer is extracted 3 times with DCM/MeOH 95:5. The combined organic layers are dried over Na₂SO₄, filtered and concentrated to dryness. The residue is purified by chromatography on silica gel (elution DCM/MeOH: 100/0 to 96/4) to afford Compound 8.

LCMS: MW (calcd): 416; m/z MW (obsd): 417 (M+H).

¹H NMR (400 MHz, CDCl₃) δ ppm 13.20 (1H, s), 10.20 (1H, s), 8.30 (1H, d), 7.88 (1H, s), 7.77 (1H, d), 7.30 (2H, d), 7.27 (2H, d), 6.70 (1H, d), 3.82 (6H, s), 2.96 (2H, q), 2.31 (3H, s), 1.35 (3H, t).

Compound 23

N-[3-(3-Ethyl-1H-pyrazolo[3,4-b]pyridin-6-yl)-4-methyl-phenyl]-3-(2-hydroxy-ethoxy)-5-methyl-benzamide

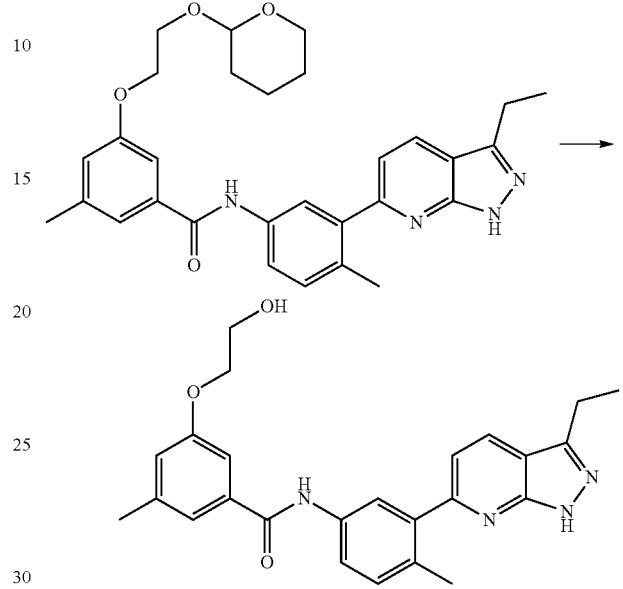

A solution of Intermediate Gen-64-b (40 mg, 0.078 mmol, 1 eq.) in MeOH (3.0 mL) and HCl 6N (1.0 mL) is stirred at room temperature for 2 h. The reaction mixture is concentrated in vacuo and the residue is taken with an aqueous NaHCO₃ solution and EtOAc. The layers are separated, the organic layer is washed with an aqueous NaHCO₃ solution. The aqueous layer is extracted with EtOAc, then the organic layers are combined, dried over Na₂SO₄, filtered and evaporated to dryness to give Compound 23.

LCMS: MW (calcd): 430; MW (obsd): 431 (M+H).

¹H NMR (400 MHz, CDCl₃): δ ppm 8.53 (1H, s), 8.14 (1H, d), 7.80 (1H, dd), 7.75 (1H, d), 7.34 (1H, d), 7.31 (1H, d), 7.27 (1H, m), 6.91 (1H, s), 4.12 (2H, t), 3.99 (2H, t), 2.99 (2H, q), 2.40 (3H, s), 2.38 (3H, s), 1.42 (3H, t).

Compound 35

N-{3-[3-(1-Hydroxy-ethyl)-1H-pyrazolo[3,4-b]pyridin-6-yl]-4-methyl-phenyl}-3-trifluoromethyl-benzamide

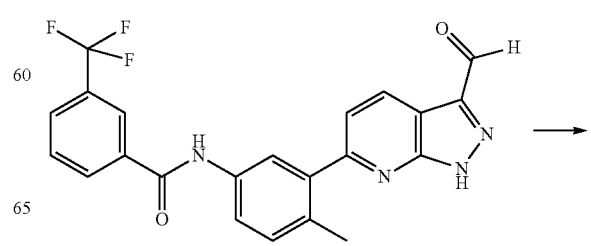

-continued

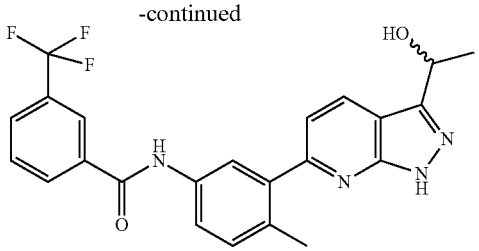

To a solution of Intermediate Gen-18-a (25 mg, 0.06 mmol, 1 eq.) in THF (6 mL) under nitrogen at 0° C. is added dropwise a 1.4 M MeMgBr solution in toluene/THF (295 μL, 0.41 mmol, 7 eq.). The reaction mixture is allowed to warm up to room temperature and stirred at room temperature for 4.5 h. Then the reaction is quenched with an aqueous NH$_4$Cl solution, and diluted with EtOAc, the two layers are separated, and the aqueous layer is extracted again with EtOAc. The combined organic layers are dried over Na$_2$SO$_4$, filtered and evaporated to dryness. The residue is purified by chromatography on silica gel (elution DCM/MeOH: 100/0 to 96/4) to afford Compound 35.

$^1$H NMR (300 MHz, MeOD-d$_4$) δ ppm 8.48 (1H, d), 8.27 (1H, bs), 8.20 (1H, bd), 7.89 (1H, bd), 7.83 (1H, d), 7.77-7.67 (2H, m), 7.35 (2H, d), 5.25 (1H, q), 2.36 (3H, s), 1.70 (3H, d).

LCMS: MW (calcd): 440; m/z MW (obsd): 441 (M+H).

Compound 55

N-{3-[3-((S)-1-Hydroxy-ethyl)-1H-pyrazolo[3,4-b]pyridin-6-yl]-4-methyl-phenyl}-3-trifluoromethyl-benzamide

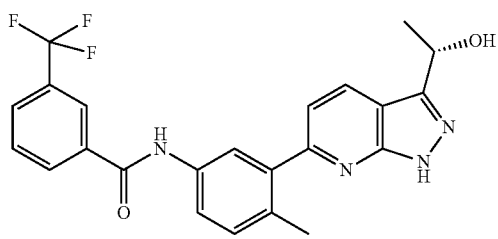 [SMILES: Cc1ccc(NC(=O)c2cccc(C(F)(F)F)c2)cc1-c1ccc2c([C@H](C)O)n[nH]c2n1]

Step i (S)-2-(tert-Butyl-dimethyl-silanyloxy)-propionic acid methyl ester (Intermediate Gen-15-b)

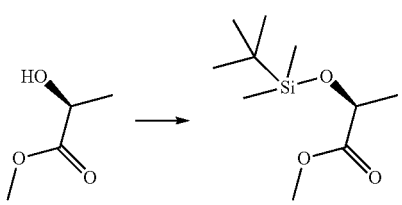

Under stirring and nitrogen, to a solution of Intermediate Gen-14-b (694 g, 6.67 mol, 1 eq.) in DCM (7 L), are added 1H-imidazole (500 g, 7.34 mol, 1.1 eq.) and Intermediate Gen-9-b (1055 g, 7.00 mol, 1.05 eq.). The reaction mixture is cooled during the addition, then stirred at room temperature overnight under nitrogen. The reaction mixture is diluted in IPE (5.5 L), the organic layer is washed once with an aqueous 1 M HCl solution (2.8 L), once with a mixture of an aqueous 1 M HCl solution and brine (1/1) (1.4 L/1.4 L) and once with brine (2.8 L), dried over Na$_2$SO$_4$, filtered and evaporated to dryness to give Intermediate Gen-15-b.

$^1$H NMR (300 MHz, CDCl$_3$-d) δ ppm 4.34 (1H, q), 3.73 (3H, s), 1.40 (3H, d), 0.91 (9H, s), 0.90 (6H, d).

Step ii (S)-2-(tert-Butyl-dimethyl-silanyloxy)-N-methoxy-N-methyl-propionamide (Intermediate Gen-7-d)

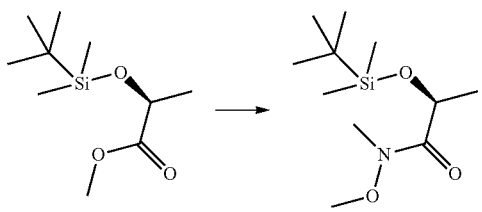 [SMILES: COC(=O)[C@H](C)O[Si](C)(C)C(C)(C)C ; CON(C)C(=O)[C@H](C)O[Si](C)(C)C(C)(C)C]

To a suspension of Intermediate Gen-9-c (139 g, 1.42 mol, 1.56 eq.) in THF (720 mL) under stirring and nitrogen is slowly added a 2.5 M butyllithium solution in hexane (1.3 L, 3.25 mol, 3.55 eq.) at a temperature comprised between −15° C. and −10° C. over 1 h. After 50 min of stirring at −15° C., a solution of Intermediate Gen-15-b (200 g, 0.91 mol, 1 eq.) in THF (600 mL) is added dropwise to the amide solution below −60° C. over 30 min. Then the reaction mixture is stirred under nitrogen at −70° C. for 2 h. The reaction is quenched by slowly adding an aqueous 2 M HCl solution (600 mL) at −50° C., EtOAc (1 L) is added to the reaction and the mixture is allowed to warm up to room temperature. The layers are separated and the aqueous layer (pH ~8-9) is extracted again with EtOAc (500 mL). The combined organic layers are dried over Na$_2$SO$_4$, filtered and evaporated to dryness to afford Intermediate Gen-7-d.

$^1$H NMR (300 MHz, CDCl$_3$-d) δ ppm 4.78-4.63 (1H, m), 3.71 (3H, s), 3.23 (3H, bs), 1.37 (3H, d), 0.92 (9H, s), 0.11 (6H, d).

Step iii (S)-2-(tert-Butyl-dimethyl-silanyloxy)-1-(6-chloro-2-fluoro-pyridin-3-yl)-propan-1-one (Intermediate Gen-8-d)

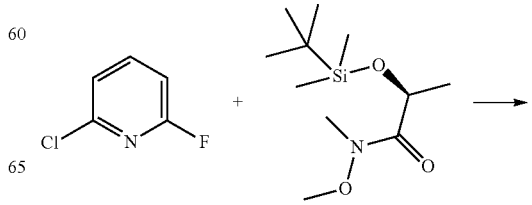

-continued

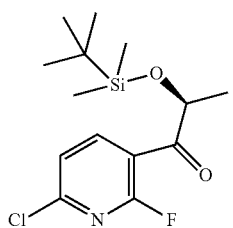

A solution of LDA is prepared by adding dropwise a 2.5 m butyllithium solution in hexane (308 mL, 0.77 mol, 1.167 eq.) to a solution of DIPA (100 g, 0.98 mol, 1.07 eq.) in THF (540 mL) under nitrogen at −5° C. The reaction mixture is stirred 30 min at −5° C. Then Intermediate Gen-6-a (86.8 g, 0.66 mol, 1 eq.) in THF (650 mL) is added dropwise below −60° C., and the reaction is stirred under nitrogen at −78° C. for 1.33 h. Then Intermediate Gen-7-d (180 g, 0.73 mol, 1.1 eq.) is added dropwise by monitoring the temperature. The mixture is stirred 3 h at −70° C. and quenched with a saturated aqueous NH$_4$Cl solution (400 mL). EtOAc (1 L) is added, then the organic layer is separated, dried over Na$_2$SO$_4$, filtered and evaporated to dryness. The residue is purified by cake of silica gel (elution cyclohexane/EtOAc: 100/0 to 95/5) to give Intermediate Gen-8-d.

$^1$H NMR (300 MHz, CDCl$_3$-d) δ ppm 8.18 (1H, dd), 7.34 (1H, dd), 4.88 (1H, dq), 1.43 (3.H, dd), 0.82 (9H s), 0.65 (6H, d)

Synthesis of Intermediate Gen-5-b

N-[4-Methyl-3-(4,4,5,5-tetramethyl-[7,3,2]dioxaborolan-2-yl)-phenyl]-3-trifluoromethyl-benzamide

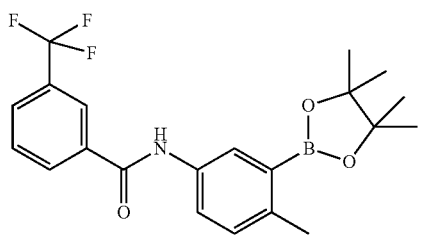 [SMILES: Cc1ccc(NC(=O)c2cccc(C(F)(F)F)c2)cc1B1OC(C)(C)C(C)(C)O1]

Step iv

4-Methyl-3-(4,4,5,5-tetramethyl-[1,3,2]dioxaborolan-2-yl)-phenylamine (Intermediate Gen-3-a)

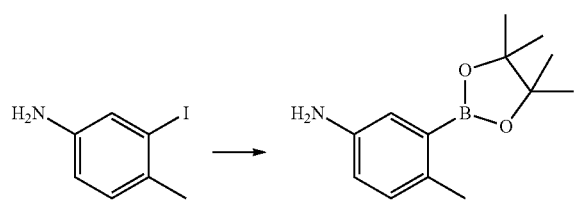

To a suspension, previously degazed with nitrogen bubbling for 1 h, of Intermediate Gen-2-b (300 g, 1.29 mol, 1 eq.), Intermediate Gen-9-a (343.2 g, 1.35 mol, 1.05 eq.) and potassium acetate (380 g, 3.9 mol, 3 eq.) in DMSO (2.65 L), previously degazed with nitrogen bubbling for 2 h, is added PdCl$_2$(dppf).DCM (52 g, 0.06 mol, 0.05 eq.). The reaction mixture is stirred at 80° C. under nitrogen overnight. The reaction is cooled to room temperature, then water (1.5 L) and EtOAc (3 L) were added. The biphasic solution is filtered through a plug of celite (slow), and the cake is washed with EtOAc (2 L). The two layers of the filtrate are separated, the aqueous layer is extracted again with EtOAc (3 L) and the combined organic layers are washed with water (500 mL). The organic layer is dried over Na$_2$SO$_4$, filtered and evaporated to dryness. The residue is purified by chromatography on silica (elution cyclohexane/EtOAc: 95/5 to 70/30) to afford Intermediate Gen-3-a.

$^1$H NMR (300 MHz, CDCl$_3$-d) δ ppm 7.17 (1H, d), 6.99 (1H, d), 6.70 (1H, dd), 3.54 (2H, bs), 2.25 (3H, s), 1.36 (12H, s).

Step v

N-[4-Methyl-3-(4,4,5,5-tetramethyl-[1,3,2]dioxaborolan-2-yl)-phenyl]-3-trifluoromethyl-benzamide (Intermediate Gen-5-b)

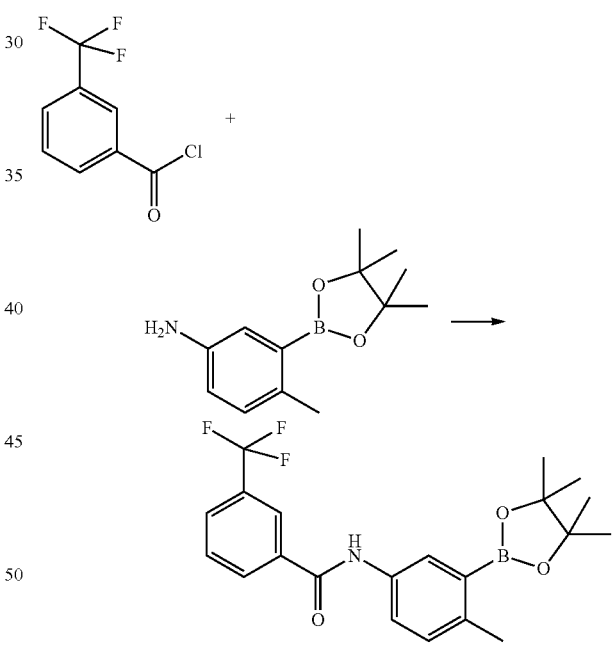

A solution of Intermediate Gen-3-a (293 g, 1.26 mol, 1.0 eq.) in DCM (3 L) under nitrogen is cooled to 3° C., then TEA (193 mL, 1.38 mol, 1.1 eq.) followed by Intermediate Gen-1-e (150 mL, 1.0 mol, 0.8 eq.) are added dropwise. Then Gen-1-e (9.5 mL, 0.06 mol, 0.05 eq.) is added dropwise and the reaction is left to stir 10 min. The reaction mixture is quenched with water (1.5 L) and diluted with DCM (2 L). The layers are separated and the organic layer is dried over Na$_2$SO$_4$, filtered and evaporated in vacuo. The majority of the solvent is removed and cyclohexane (3.0 L) is added. The mixture is stirred at room temperature for few minutes, the resulting solid is separated by filtration and washed with cyclohexane and dried to afford Intermediate Gen-5-b.

¹H NMR (300 MHz, CDCl₃-d) δ ppm 8.13 (1H, s), 8.05 (1H, bd), 8.00-7.9 (2H, m), 7.80 (1H, bd), 7.71 (1H, d), 7.61 (1H, t), 7.20 (1H, d), 2.54 (3H, s), 1.36 (12H, s).

Step vi (S)—N-(3-{5-[2-(tert-Butyl-dimethyl-silanyloxy)-propionyl]-6-fluoro-pyridin-2-yl}-4-methyl-phenyl)-3-trifluoromethyl-benzamide (Intermediate Gen-10-d)

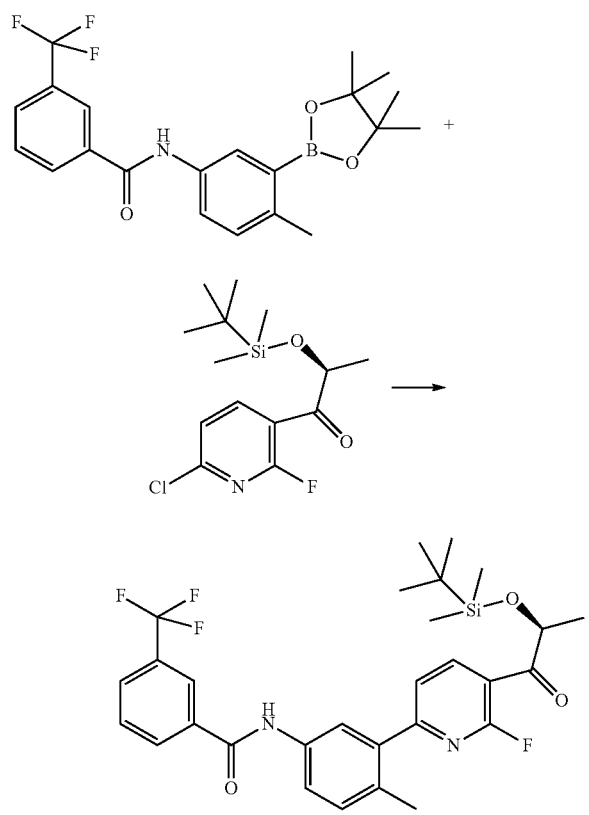

Intermediate Gen-8-d (60 g, 0.189 mol, 1 eq.), Intermediate Gen-5-b (76.52 g, 0.19 mol, 1 eq.), and cesium carbonate (120 g, 0.38 mol, 2 eq.) are dissolved in a mixture of 1,4-dioxane (1.15 L) and water (285 mL) at room temperature, the solution is degassed with nitrogen. Then PdCl₂(dppf).DCM (7.7 g, 0.009 mol, 0.05 eq.) is added. The reaction mixture is heated 1 h at 80° C., then cooled to room temperature with an ice bath. EtOAc (1.15 L) is added to the reaction mixture, the layers are separated, and the aqueous layer is extracted once with EtOAc (300 mL). The combined organic layers are washed with brine (800 mL), dried over Na₂SO₄, filtered and evaporated to dryness. The crude is purified by cake of silica gel (elution cyclohexane/EtOAc: 100/0 to 90/10) to afford Intermediate Gen-10-d.

¹H NMR (300 MHz, CDCl₃-d) δ ppm 8.28 (1H, dd), 8.17 (2H, d), 8.07 (1H, bd), 7.80 (1H, bd), 7.75 (1H, d), 7.70-7.60 (2H, m), 7.47 (1H, dd), 7.29 (1H, d), 5.00 (1H, dq), 2.41 (3H, s), 1.50 (3H, dd), 0.87 (9H, s), 0.11 (6H, d).

Step vii (S)—N-(3-{3-[1-(tert-Butyl-dimethyl-silanyloxy)-ethyl]-1H-pyrazolo[3,4-b]pyridin-6-yl}-4-methyl-phenyl)-3-trifluoromethyl-benzamide (Intermediate Gen-16-b)

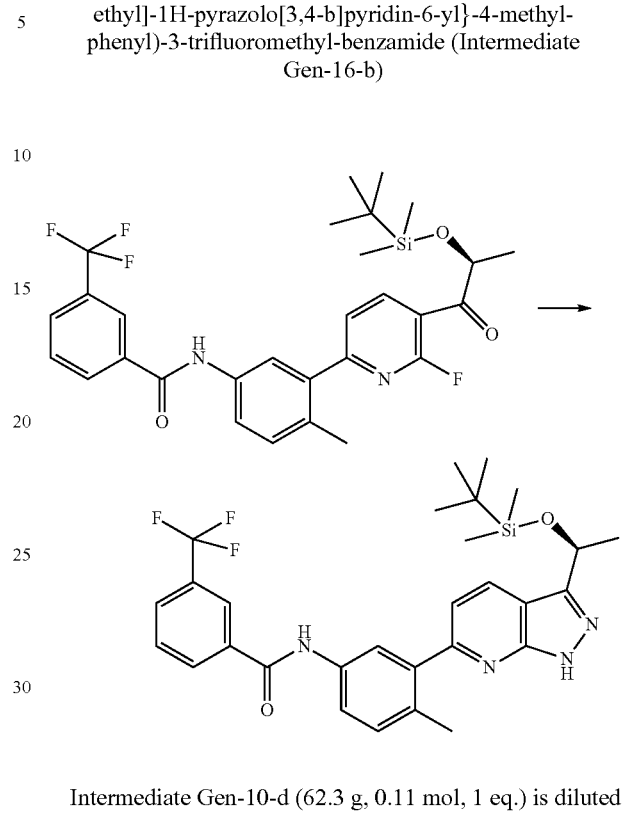

Intermediate Gen-10-d (62.3 g, 0.11 mol, 1 eq.) is diluted in iPrOH (340 mL). The reaction mixture is splitted in two equal parts (2×200 mL). hydrazine monohydrate (62.3 mL, 1.28 mol, 11.56 eq.) (2×31 mL) is added to the each part of the reaction just before heating the reaction mixture to 130° C. for 1 h. Both reaction mixtures are mixed and quenched with water (200 mL), then iPrOH is evaporated in vacuo. The residue is diluted in EtOAc (600 mL) and washed with brine (200 mL). The organic layer is dried over Na₂SO₄, filtered and evaporated to dryness to afford Intermediate Gen-16-b.

LCMS: MW (calcd): 554; m/z MW (obsd): 555 (M+H).

Step viii

N-{3-[3-((S)-1-Hydroxy-ethyl)-1H-pyrazolo[3,4-d]pyridin-6-yl]-4-methyl-phenyl}-3-trifluoromethyl-benzamide (Compound 55)

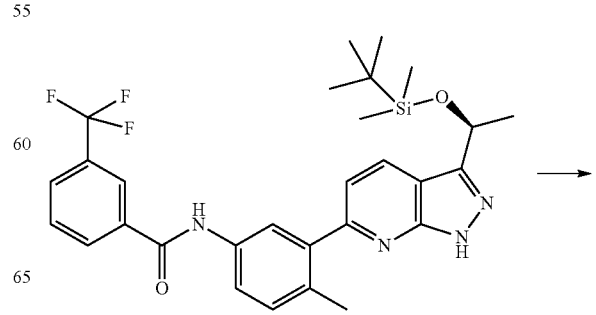

-continued

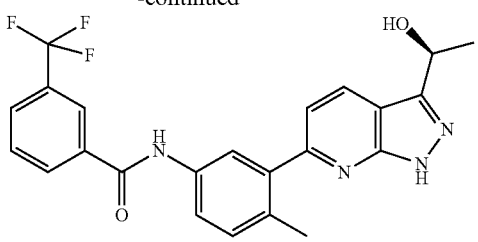

To a solution of Intermediate Gen-16-b (61 g, 0.11 mol, 1 eq.) in MeOH (280 mL), is added an aqueous 1 M HCl solution (220 mL). The suspension is heated for 1.5 h at 50° C. The reaction is quenched by the addition of a saturated $Na_2CO_3$ solution (200 mL) (pH ~8). MeOH is removed in vacuo and the mixture was extracted twice with EtOAc (200 mL). The combined organic layers are washed with brine (100 mL), dried over $Na_2SO_4$, filtered and evaporated to dryness. The residue is purified by chromatography on silica gel. The crude is dissolved in DCM (100 mL), this solution is added dropwise to a solution of heptane (500 mL) under stirring. The mixture is stirred vigorously at room temperature, the resulting solid is separated by filtration and dried to afford Compound 55.

$^1$H NMR (300 MHz, MeOD-$d_4$) δ ppm 8.45 (1H, d), 8.25 (1H, bs), 8.18 (1H, bd), 7.90-7.80 (2H, m), 7.75-7.63 (2H, m), 7.31 (2H, d), 5.26 (1H, q), 2.33 (3H, s), 1.69 (3H, d).

LCMS: MW (calcd): 440; m/z MW (obsd): 441 (M+H).

TABLE II

Intermediates for the synthesis of illustrative compounds of the invention

| Int | Structures | Name | Int - Mtd | MW | MS Ms'd |
|---|---|---|---|---|---|
| Gen-1-a | 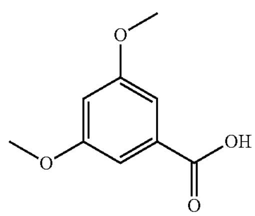 | 3,5-Dimethoxy-benzoic acid | Cial. prod | 182 | N.A. |
| Gen-1-b | 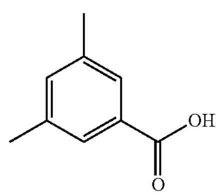 | 3,5-Dimethyl-benzoic acid | Cial. prod | 150 | N.A. |
| Gen-1-c | 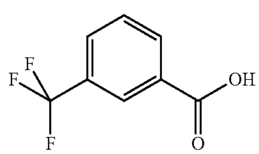 [SMILES: O=C(O)c1cccc(C(F)(F)F)c1] | 3-Trifluoromethyl-benzoic acid | Cial. prod | 190 | N.A. |
| Gen-1-d | 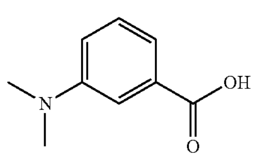 | 3-Dimethylamino-benzoic acid | Cial. prod | 165 | N.A. |
| Gen-1-e | 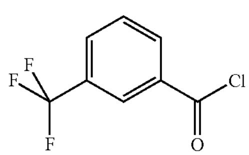 [SMILES: O=C(Cl)c1cccc(C(F)(F)F)c1] | 3-(Trifluoromethyl) benzoyl chloride | Cial. prod | 208 | N.A. |
| Gen-1-f | 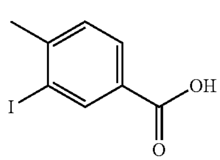 | 3-Iodo-4-methyl-benzoic acid | Cial. prod | 262 | N.A. |

TABLE II-continued

Intermediates for the synthesis of illustrative compounds of the invention

| Int | Structures | Name | Int - Mtd | MW | MS Ms'd |
|---|---|---|---|---|---|
| Gen-1-g | 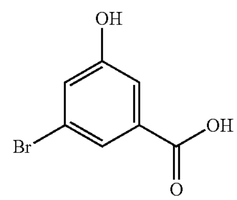 [SMILES: O=C(O)c1cc(O)cc(Br)c1] | 3-Bromo-5-hydroxy-benzoic acid | Cial. prod | 217 | N.A. |
| Gen-2-a | 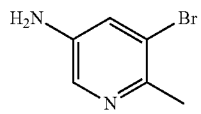 | 5-Bromo-6-methyl-pyridin-3-ylamine | Cial. prod | 186 ($^{79}$Br) 188 ($^{81}$Br) | N.A. |
| Gen-2-b | 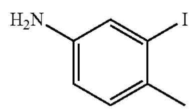 | 3-Iodo-4-methyl-phenylamine | Cial. prod | 233 | N.A. |
| Gen-2-c | 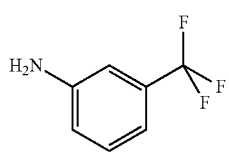 [SMILES: Nc1cccc(C(F)(F)F)c1] | 3-Trifluoromethyl-phenylamine | Cial. prod | 161 | N.A. |
| Gen-2-d | 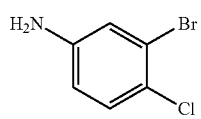 | 3-Bromo-4-chloro-phenylamine | Cial. prod | 206 | N.A. |
| Gen-2-e | 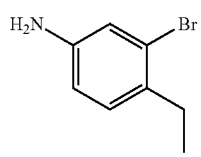 | 3-Bromo-4-ethyl phenylamine- | Cial. prod | 200 | N.A. |
| Gen-3-a | 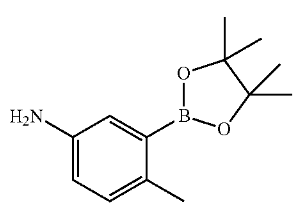 [SMILES: Cc1ccc(N)cc1B1OC(C)(C)C(C)(C)O1] | 4-Methyl-3-(4,4,5,5-tetramethyl-[1,3,2]dioxaborolan-2-yl)-phenylamine | Gen-2-b A | 233 | N.A. |
| Gen-4-a | 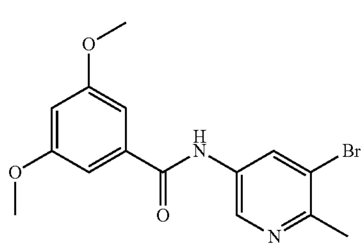 [SMILES: COc1cc(OC)cc(C(=O)Nc2cnc(C)c(Br)c2)c1] | N-(5-Bromo-6-methyl-pyridin-3-yl)-3,5-dimethoxy-benzamide | Gen-1-a + Gen-2-a See Int Gen-4-a B1 | 350 ($^{79}$Br) 352 ($^{81}$Br) | 351 ($^{79}$Br M + H) 353 ($^{81}$Br M + H) |

TABLE II-continued

Intermediates for the synthesis of illustrative compounds of the invention

| Int | Structures | Name | Int - Mtd | MW | MS Ms'd |
|---|---|---|---|---|---|
| Gen-4-b | 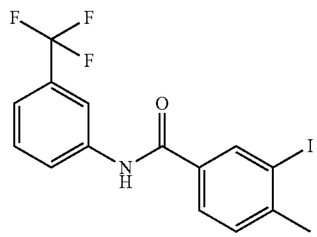 [SMILES: Cc1ccc(C(=O)Nc2cccc(C(F)(F)F)c2)cc1I] | 3-Iodo-4-methyl-N-(3-trifluoromethyl-phenyl)-benzamide | Gen-1-f + Gen-2-c K | 405 | N.A. |
| Gen-4-c | 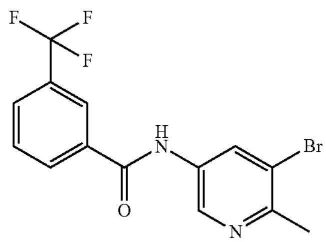 [SMILES: Cc1ncc(NC(=O)c2cccc(C(F)(F)F)c2)cc1Br] | N-(5-Bromo-6-methyl-pyridin-3-yl)-3-trifluoromethyl-benzamide | Gen-1-c + Gen-2-a B1 | 359 | 360 (M + H) |
| Gen-4-d | 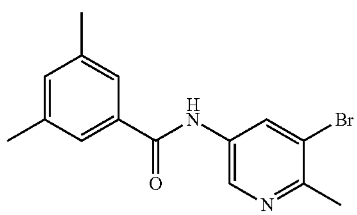 | N-(5-Bromo-6-methyl-pyridin-3-yl)-3,5-dimethyl-benzamide | Gen-1-b + Gen-2-a B1 | 319 | 320 (M + H) |
| Gen-4-e | 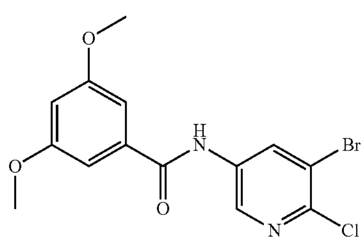 [SMILES: COc1cc(OC)cc(C(=O)Nc2cnc(Cl)c(Br)c2)c1] | N-(5-Bromo-6-chloro-pyridin-3-yl)-3,5-dimethoxy-benzamide | Gen-2-d + Gen-1-a B1 | 371 | 372 (M + H) |
| Gen-4-f | 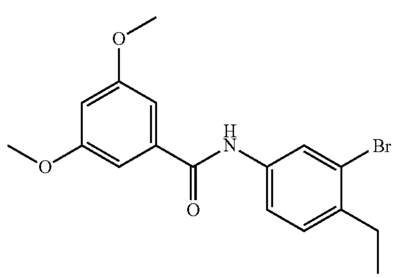 [SMILES: CCc1ccc(NC(=O)c2cc(OC)cc(OC)c2)cc1Br] | N-(3-Bromo-4-ethyl-phenyl)-3,5-dimethoxy-benzamide | Gen-1-a + Gen-2-e B1 | 364 | 365 (M + H) |
| Gen-5-a | 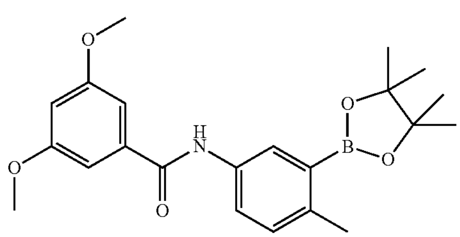 [SMILES: COc1cc(OC)cc(C(=O)Nc2ccc(C)c(B3OC(C)(C)C(C)(C)O3)c2)c1] | 3,5-Dimethoxy-N-[4-methyl-3-(4,4,5,5-tetramethyl-[1,3,2]dioxaborolan-2-yl)-phenyl]-benzamide | Gen-1-a + Gen-3-a B1 | 397 | 398 (M + H) |

TABLE II-continued

Intermediates for the synthesis of illustrative compounds of the invention

| Int | Structures | Name | Int - Mtd | MW | MS Ms'd |
|---|---|---|---|---|---|
| Gen-5-b | 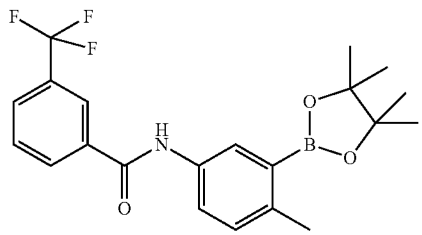 [SMILES: Cc1ccc(NC(=O)c2cccc(C(F)(F)F)c2)cc1B1OC(C)(C)C(C)(C)O1] | N-[4-Methyl-3-(4,4,5,5-tetramethyl-[1,3,2]dioxaborolan-2-yl)-phenyl]-3-trifluoromethyl-benzamide | Gen-1-e + Gen-3-a B2 | 405 | 406 (M + H) |
| Gen-5-c | 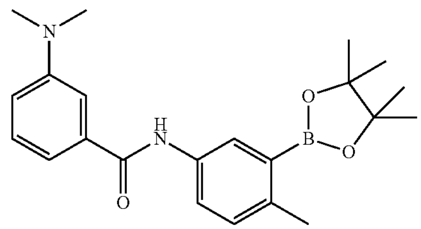 [SMILES: Cc1ccc(NC(=O)c2cccc(N(C)C)c2)cc1B1OC(C)(C)C(C)(C)O1] | 3-Dimethylamino-N-[4-methyl-3-(4,4,5,5-tetramethyl-[1,3,2]dioxaborolan-2-yl)-phenyl]-benzamide | Gen-1-d + Gen-3-a B1 or B2 | 380 | N.A. |
| Gen-5-d | 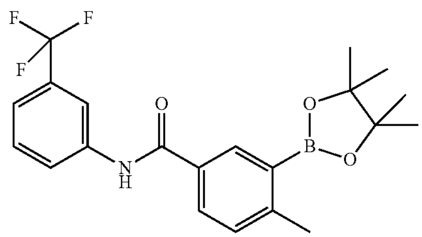 [SMILES: Cc1ccc(C(=O)Nc2cccc(C(F)(F)F)c2)cc1B1OC(C)(C)C(C)(C)O1] | 4-Methyl-3-(4,4,5,5-tetramethyl-[1,3,2]dioxaborolan-2-yl)-N-(3-trifluoromethyl-phenyl)-benzamide | Gen-4-b + Gen-9-a A2 | 405 | N.A. |
| Gen-5-e | 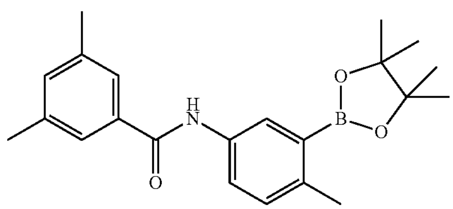 | 3,5-Dimethyl-N-[4-methyl-3-(4,4,5,5-tetramethyl-[1,3,2]dioxaborolan-2-yl)-phenyl]-benzamide | Gen-1-b + Gen-3-a B3 | 365 | N.A. |
| Gen-5-f | 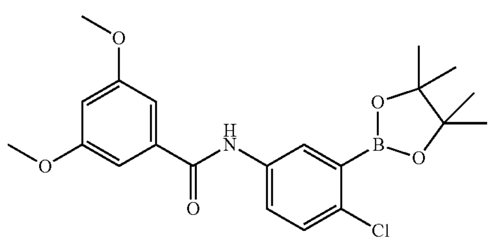 | N-[4-Chloro-3-(4,4,5,5-tetramethyl-[1,3,2]dioxaborolan-2-yl)-phenyl]-3,5-dimethoxy-benzamide | Gen-9-a + Gen-4-e A2 | 417 | 418 (M + H) |
| Gen-5-g | 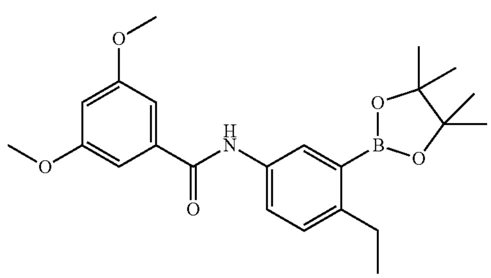 | N-[4-Ethyl-3-(4,4,5,5-tetramethyl-[1,3,2]dioxaborolan-2-yl)-phenyl]-3,5-dimethoxy-benzamide | Gen-9-a + Gen-4-f A2 | 411 | 412 (M + H) |
| Gen-6-a | 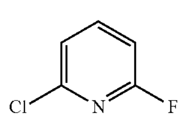 | 2-Chloro-6-fluoro-pyridine | Cial. prod | 131 ($^{35}$Cl) 133 ($^{37}$Cl) | N.A. |

TABLE II-continued

Intermediates for the synthesis of illustrative compounds of the invention

| Int | Structures | Name | Int - Mtd | MW | MS Ms'd |
|---|---|---|---|---|---|
| Gen-7-a | 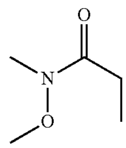 | N-Methoxy-N-methyl-propionamide | Gen-15-g See Int Gen-7-a | 117 | N.A. |
| Gen-7-b | 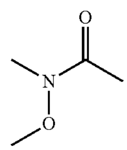 | N-Methoxy-N-methyl-acetamide | Cial. prod | 103 | N.A. |
| Gen-7-c | 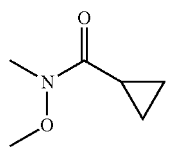 | Cyclopropanecarboxylic acid methoxy-methyl-amide | Gen-15-h + Gen-9-c See Int Gen-7-c | 129 | N.A. |
| Gen-7-d | 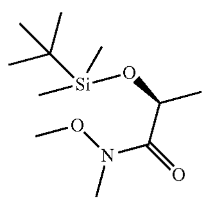 [SMILES: CON(C)C(=O)[C@H](C)O[Si](C)(C)C(C)(C)C] | (S)-2-(tert-Butyl-dimethyl-silanyloxy)-N-methoxy-N-methyl-propionamide | Gen-15-b D | 247 | N.A. |
| Gen-7-f | 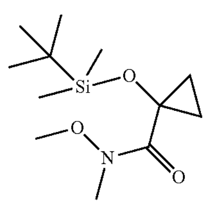 [SMILES: CON(C)C(=O)C1(O[Si](C)(C)C(C)(C)C)CC1] | 1-(tert-Butyl-dimethyl-silanyloxy)-cyclopropanecarboxylic acid methoxy-methyl-amide | Gen-15-f See Int Gen-7-f | 259 | N.A. |
| Gen-8-a | 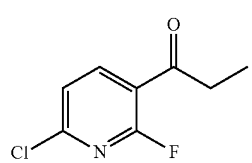 | 1-(6-Chloro-2-fluoro-pyridin-3-yl)-propan-1-one | Gen-6-a + Gen-7-a E1 | 187 ($^{35}$Cl) 188 ($^{37}$Cl) | N.A. |
| Gen-8-b | 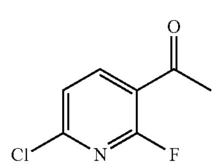 | 1-(6-Chloro-2-fluoro-pyridin-3-yl)-ethanone | Gen-6-a + Gen-7-b E1 | 173 ($^{35}$Cl) 175 ($^{37}$Cl) | 176 ($^{35}$Cl M + H) |
| Gen-8-c | 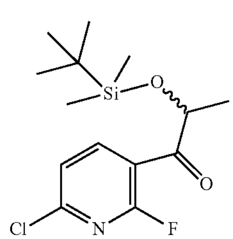 [SMILES: CC(O[Si](C)(C)C(C)(C)C)C(=O)c1ccc(Cl)nc1F] | 2-(tert-Butyl-dimethyl-silanyloxy)-1-(6-chloro-2-fluoro-pyridin-3-yl)-propan-1-one | Gen-6-a + Gen-15-a E2 | 317 ($^{35}$Cl) 319 ($^{37}$Cl) | 318 ($^{35}$Cl M + H) 320 ($^{37}$Cl M + H) |

TABLE II-continued

Intermediates for the synthesis of illustrative compounds of the invention

| Int | Structures | Name | Int - Mtd | MW | MS Ms'd |
|---|---|---|---|---|---|
| Gen-8-d | 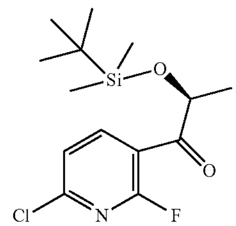 [SMILES: C[C@H](O[Si](C)(C)C(C)(C)C)C(=O)c1ccc(Cl)nc1F] | (S)-2-(tert-Butyl-dimethyl-silanyloxy)-1-(6-chloro-2-fluoro-pyridin-3-yl)-propan-1-one | Gen-6-a + Gen-7-d E1 | 317 ($^{35}$Cl) 319 ($^{37}$Cl) | 318 ($^{35}$Cl M + H) 320 ($^{37}$Cl M + H) |
| Gen-8-e | 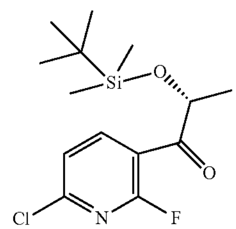 | (R)-2-(tert-Butyl-dimethyl-silanyloxy)-1-(6-chloro-2-fluoro-pyridin-3-yl)-propan-1-one | Gen-6-a + Gen-15-c E2 | 317 ($^{35}$Cl) 319 ($^{37}$Cl) | 318 ($^{35}$Cl M + H) 320 ($^{37}$Cl M + H) |
| Gen-8-f | 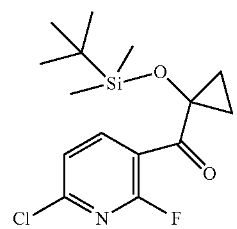 [SMILES: CC(C)(C)[Si](C)(C)OC1(C(=O)c2ccc(Cl)nc2F)CC1] | [1-(tert-Butyl-dimethyl-silanyloxy)-cyclopropyl]-(6-chloro-2-fluoro-pyridin-3-yl)-methanone | Gen-6-a + Gen-7-f E1 or Gen-6-a + Gen-15-d E2 | 329 ($^{35}$Cl) 331 ($^{37}$Cl) | 330 ($^{35}$Cl M + H) 332 ($^{37}$Cl M + H) |
| Gen-8-h | 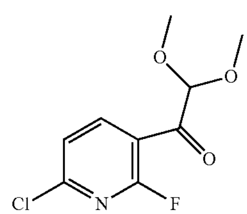 | 1-(6-Chloro-2-fluoro-pyridin-3-yl)-2,2-dimethoxy-ethanone | Gen-6-a + Gen-15-e E1 | 233 ($^{35}$Cl) 235 ($^{37}$Cl) | 234 ($^{35}$Cl M + H) 236 ($^{37}$Cl M + H) |
| Gen-8-i | 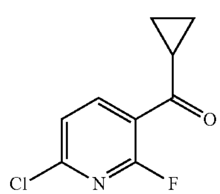 [SMILES: O=C(c1ccc(Cl)nc1F)C1CC1] | (6-Chloro-2-fluoro-pyridin-3-yl)-cyclopropyl-methanone | Gen-6-a + Gen-7-c E1 | 199 | N.A. |
| Gen-9-a | 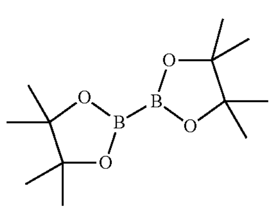 | 4,4,5,5,4',4',5',5'-Octamethyl-[2,2']bi[[1,3,2]dioxa-borolanyl] | Cial. prod | 254 | N.A. |
| Gen-9-b | 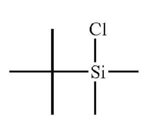 | tert-Butyldimethylsilyl chloride | Cial. prod | 150 | N.A. |
| Gen-9-c | 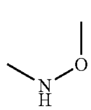 | N,O-dimethylhydroxylamine hydrochloride | Cial. prod | 97 | N.A. |

TABLE II-continued

Intermediates for the synthesis of illustrative compounds of the invention

| Int | Structures | Name | Int - Mtd | MW | MS Ms'd |
|---|---|---|---|---|---|
| Gen-9-d | 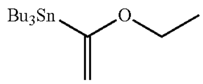 | Tributyl(1-ethoxyvinyl)tin | Cial. prod | 361 | N.A. |
| Gen-9-e | 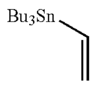 | Tributyl(vinyl)tin | Cial. prod | 317 | N.A. |
| Gen-9-f | 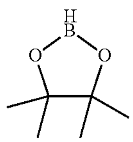 | 4,4,5,5-Tetramethyl-[1,3,2]dioxaborolane | Cial. prod | 127 | N.A. |
| Gen-9-g | 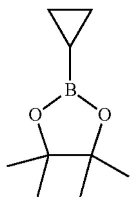 | 2-Cyclopropyl-4,4,5,5-tetramethyl-[1,3,2]dioxaborolane | Cial. prod | 168 | N.A. |
| Gen-9-h | 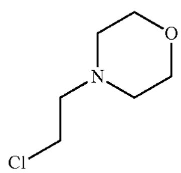 | 4-(2-Chloro-ethyl)-morpholine | Cial. prod | 149 | N.A. |
| Gen-9-i | 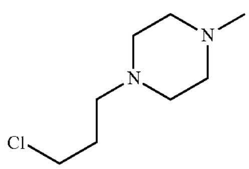 | 1-(3-Chloro-propyl)-4-methyl-piperazine | Cial. prod | 176 | N.A. |
| Gen-9-j | 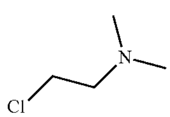 | (2-Chloro-ethyl)-dimethyl-amine | Cial. prod | 107 | N.A. |
| Gen-9-k | 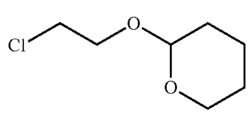 | 2-(2-Chloro-ethoxy)-tetrahydro-pyran | Cial. prod | 164 | N.A. |
| Gen-9-l | 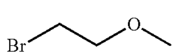 | 1-Bromo-2-methoxy-ethane | Cial. prod | 139 | N.A. |
| Gen-10-a | 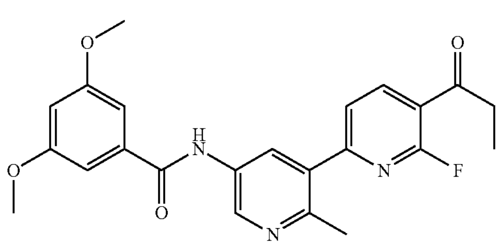 [SMILES: CCC(=O)c1ccc(-c2cc(NC(=O)c3cc(OC)cc(OC)c3)cnc2C)nc1F] | N-(6-Fluoro-2'-methyl-5-propionyl-[2,3']bipyridinyl-5'-yl)-3,5-dimethoxy-benzamide | Gen-4-a + Gen-8-a F2 | 423 | 424 (M + H) |

TABLE II-continued

Intermediates for the synthesis of illustrative compounds of the invention

| Int | Structures | Name | Int - Mtd | MW | MS Ms'd |
|---|---|---|---|---|---|
| Gen-10-b | 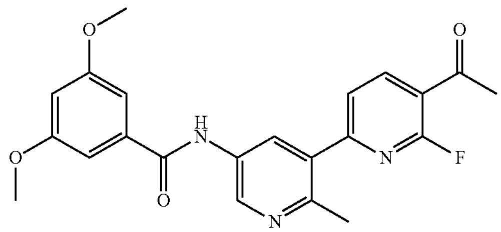 | N-(5-Acetyl-6-fluoro-2'-methyl-[2,3']bipyridinyl-5'-yl)-3,5-dimethoxy-benzamide | Gen-4-a + Gen-8-b F2 | 409 | 410 (M + H) |
| Gen-10-c | 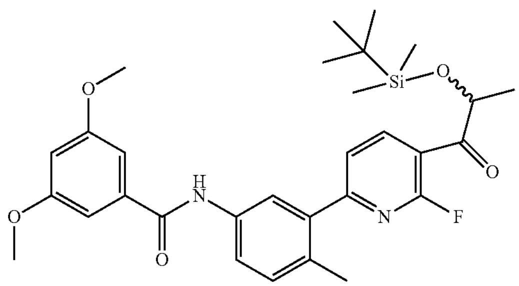 [SMILES: COc1cc(OC)cc(C(=O)Nc2ccc(C)c(-c3ccc(C(=O)C(C)O[Si](C)(C)C(C)(C)C)c(F)n3)c2)c1] | N-(3-{5-[2-(tert-Butyl-dimethyl-silanyloxy)-propionyl]-6-fluoro-pyridin-2-yl}-4-methyl-phenyl)-3,5-dimethoxy-benzamide | Gen-8-c + Gen-5-a F1 | 552 | 553 (M + H) |
| Gen-10-d | 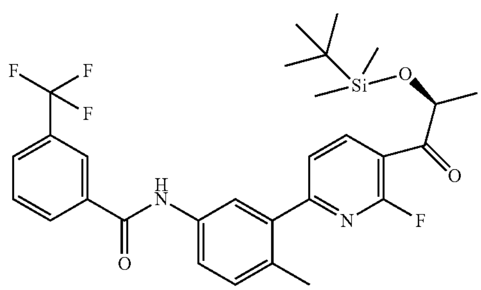 [SMILES: Cc1ccc(NC(=O)c2cccc(C(F)(F)F)c2)cc1-c1ccc(C(=O)[C@H](C)O[Si](C)(C)C(C)(C)C)c(F)n1] | N-(3-{5-[2-(S)(tert-Butyl-dimethyl-silanyloxy)-propionyl]-6-fluoro-pyridin-2-yl}-4-methyl-phenyl)-3-trifluoromethyl-benzamide | Gen-8-d + Gen-5-b F1 | 560 | 561 (M + H) |
| Gen-10-e | 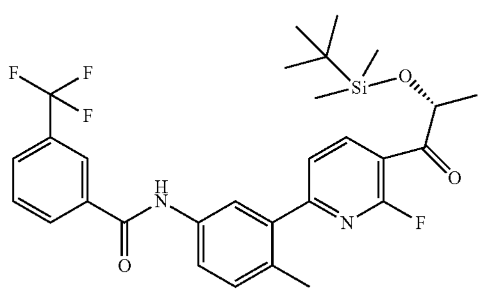 [SMILES: Cc1ccc(NC(=O)c2cccc(C(F)(F)F)c2)cc1-c1ccc(C(=O)[C@@H](C)O[Si](C)(C)C(C)(C)C)c(F)n1] | N-(3-{5-[2-(R)(tert-Butyl-dimethyl-silanyloxy)-propionyl]-6-fluoro-pyridin-2-yl}-4-methyl-phenyl)-3-trifluoromethyl-benzamide | Gen-8-e + Gen-5-b F1 | 560 | 561 (M + H) |
| Gen-10-f | 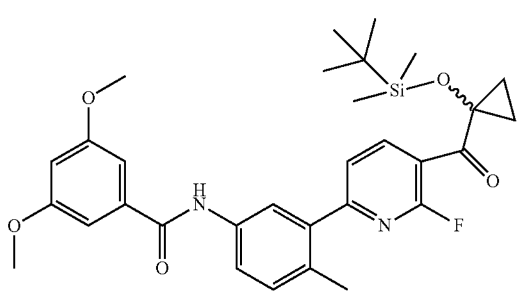 [SMILES: COc1cc(OC)cc(C(=O)Nc2ccc(C)c(-c3ccc(C(=O)C4(O[Si](C)(C)C(C)(C)C)CC4)c(F)n3)c2)c1] | N-(3-{5-[1-(tert-Butyl-dimethyl-silanyloxy)-cyclopropanecarbonyl]-6-fluoro-pyridin-2-yl}-4-methyl-phenyl)-3,5-dimethoxy-benzamide | Gen-8-f + Gen-5-a F1 | 564 | 565 (M + H) |

TABLE II-continued

Intermediates for the synthesis of illustrative compounds of the invention

| Int | Name | Int - Mtd | MW | MS Ms'd |
|---|---|---|---|---|
| Gen-10-g | N-(5-Acetyl-6-fluoro-2'-methyl-[2,3']bipyridinyl-5'-yl)-3-trifluoromethyl-benzamide | Gen-4-c + Gen-8-b F2 | 417 | 418 (M + H) |
| Gen-10-h | N-(5-Acetyl-6-fluoro-2'-methyl-[2,3']bipyridinyl-5'-yl)-3,5-dimethyl-benzamide | Gen-4-d + Gen-8-b F2 | 377 | 378 (M + H) |
| Gen-10-i | N-(3-{5-[(R)-2-(tert-Butyl-dimethyl-silanyloxy)-propionyl]-6-fluoro-pyridin-2-yl}-4-methyl-phenyl)-3,5-dimethoxy-benzamide | Gen-5-a + Gen-8-e F1 | 552 | 553 (M + H) |
| Gen-10-j | N-(3-{5-[(S)-2-(tert-Butyl-dimethyl-silanyloxy)-propionyl]-6-fluoro-pyridin-2-yl}-4-methyl-phenyl)-3,5-dimethoxy-benzamide | Gen-5-a + Gen-8-d F1 | 552 | 553 (M + H) |
| Gen 11-a | (6-Fluoro-2'-methyl-5-propionyl-[2,3']bipyridinyl-5'-yl)-carbamic acid tert-butyl ester | Gen-30-a + Gen-8-a F1 | 359 | 360 (M + H) |
| Gen-11-b | 1-[6-(5-Amino-2-methyl-phenyl)-2-fluoro-pyridin-3-yl]-2,2-dimethoxy-ethanone | Gen-3-a + Gen-8-h F1 | 304 | 305 (M + H) |

TABLE II-continued

Intermediates for the synthesis of illustrative compounds of the invention

| Int | Structures | Name | Int - Mtd | MW | MS Ms'd |
|---|---|---|---|---|---|
| Gen-12-a | 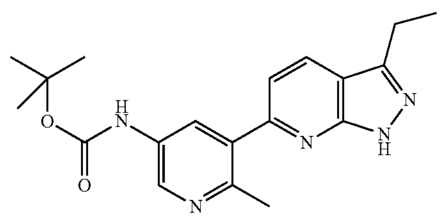 [SMILES: CCc1n[nH]c2nc(-c3cc(NC(=O)OC(C)(C)C)cnc3C)ccc12] | [5-(3-Ethyl-1H-pyrazolo[3,4-b]pyridin-6-yl)-6-methyl-pyridin-3-yl]-carbamic acid tert-butyl ester | Gen-11-a G1 | 353 | 354 (M + H) |
| Gen-13-a | 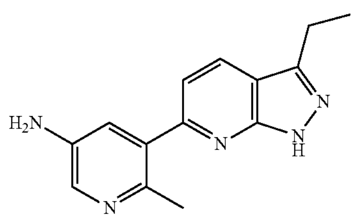 [SMILES: CCc1n[nH]c2nc(-c3cc(N)cnc3C)ccc12] | 5-(3-Ethyl-1H-pyrazolo[3,4-b]pyridin-6-yl)-6-methyl-pyridin-3-ylamine | Gen-12-a See Int Gen-13-a | 253 | 254 (M + H) |
| Gen-13-b | 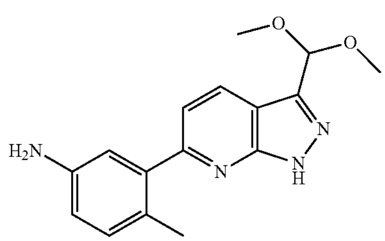 [SMILES: COC(OC)c1n[nH]c2nc(-c3cc(N)ccc3C)ccc12] | 3-(3-Dimethoxymethyl-1H-pyrazolo[3,4-b]pyridin-6-yl)-4-methyl-phenylamine | Gen-11-b G1 | 298 | 299 (M + H) |
| Gen-14-a | 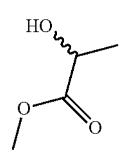 | 2-Hydroxy-propionic acid methyl ester | Cial. prod | 104 | N.A. |
| Gen-14-b | 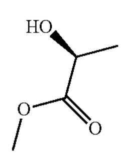 | (S)-2-Hydroxy propionic acid methyl ester | Cial. prod | 104 | N.A. |
| Gen-14-c | 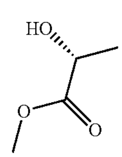 | (R)-2-Hydroxy-propionic acid methyl ester | Cial. prod | 104 | N.A. |
| Gen-14-d | 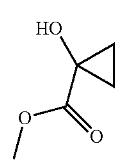 | 1-Hydroxy-cyclopropanecarboxylic acid methyl ester | Cial. prod | 116 | N.A. |
| Gen-14-e | 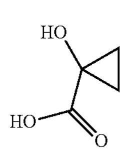 | 1-Hydroxy-cyclopropanecarboxylic acid | Cial. prod | 102 | N.A. |

TABLE II-continued

Intermediates for the synthesis of illustrative compounds of the invention

| Int | Structures | Name | Int - Mtd | MW | MS Ms'd |
|---|---|---|---|---|---|
| Gen-15-a | 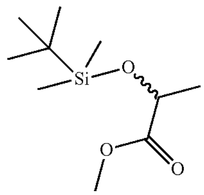 | 2-(tert-Butyl-dimethyl-silanyloxy)-propionic acid methyl ester | Gen-14-a C | 218 | N.A. |
| Gen-15-b | 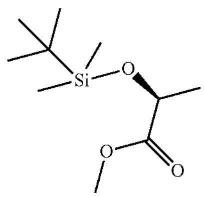 | (S)-2-(tert-Butyl-dimethyl-silanyloxy)-propionic acid methyl ester | Gen-14-b C | 218 | N.A. |
| Gen-15-c | 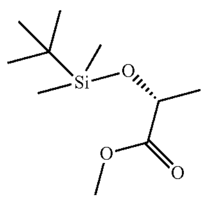 | (R)-2-(tert-Butyl-dimethyl-silanyloxy)-propionic acid methyl ester | Gen-14-c C | 218 | N.A. |
| Gen-15-d | 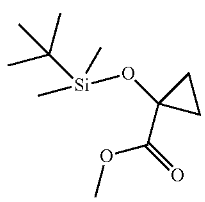 | 1-(tert-Butyl-dimethyl-silanyloxy)-cyclopropanecarboxylic acid methyl ester | Gen-14-d C | 230 | N.A. |
| Gen-15-e | 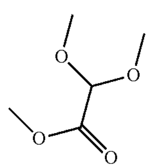 | Dimethoxy-acetic acid methyl ester | Cial. prod | 134 | N.A. |
| Gen-15-f | 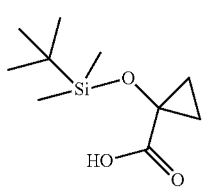 | 1-(tert-Butyl-dimethyl-silanyloxy)-cyclopropanecarboxylic acid | Gen-14-e C | 216 | N.A. |
| Gen-15-g | 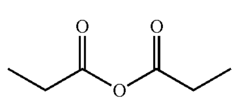 | Propionic anhydride | Cial. prod | 130 | N.A. |
| Gen-15-h | 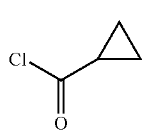 | Cyclopropanecarbonyl chloride | Cial. prod | 104 | N.A. |

TABLE II-continued

Intermediates for the synthesis of illustrative compounds of the invention

| Int | Name | Int - Mtd | MW | MS Ms'd |
|---|---|---|---|---|
| Gen-16-a | N-(3-{3-[1-(tert-Butyl-dimethyl-silanyloxy)-ethyl]-1H-pyrazolo[3,4-b]pyridin-6-yl}-4-methyl-phenyl)-3,5-dimethoxy-benzamide | Gen-10-c G1 | 546 | 547 (M + H) |
| Gen-16-b | N-(3-{3-[(S)-1-(tert-Butyl-dimethyl-silanyloxy)-ethyl]-1H-pyrazolo[3,4-b]pyridin-6-yl}-4-methyl-phenyl)-3-trifluoromethyl-benzamide | Gen-10-d G1 | 554 | 555 (M + H) |
| Gen-16-c | N-(3-{3-[(R)-1-(tert-Butyl-dimethyl-silanyloxy)-ethyl]-1H-pyrazolo[3,4-b]pyridin-6-yl}-4-methyl-phenyl)-3-trifluoromethyl-benzamide | Gen-10-e G1 | 554 | 555 (MH) |
| Gen-16-d | N-(3-{3-[1-(tert-Butyl-dimethyl-silanyloxy)-cyclopropyl]-1H-pyrazolo[3,4-b]pyridin-6-yl}-4-methyl-phenyl)-3,5-dimethoxy-benzamide | Gen-10-f G1 | 558 | 559 (M + H) |
| Gen-16-e | N-(3-{3-[(R)-1-(tert-Butyl-dimethyl-silanyloxy)-ethyl]-1H-pyrazolo[3,4-b]pyridin-6-yl}-4-methyl-phenyl)-3,5-dimethoxy-benzamide | Gen-10-i G1 | 546 | 547 (M + H) |

TABLE II-continued

Intermediates for the synthesis of illustrative compounds of the invention

| Int | Structures | Name | Int - Mtd | MW | MS Ms'd |
|---|---|---|---|---|---|
| Gen-16-f | 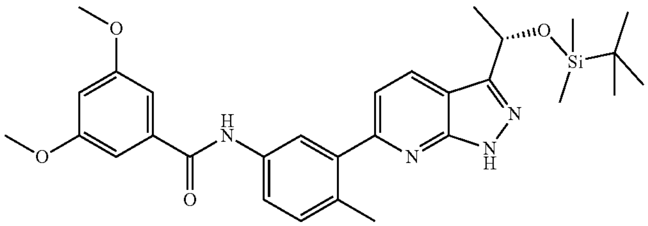 [SMILES: COc1cc(OC)cc(C(=O)Nc2ccc(C)c(-c3ccc4c([C@H](C)O[Si](C)(C)C(C)(C)C)n[nH]c4n3)c2)c1] | N-(3-{3-[(S)-1-(tert-Butyl-dimethyl-silanyloxy)-ethyl]-1H-pyrazolo[3,4-b]pyridin-6-yl}-4-methyl-phenyl)-3,5-dimethoxy-benzamide | Gen-10-j G1 | 546 | 547 (M + H) |
| Gen-17-a | 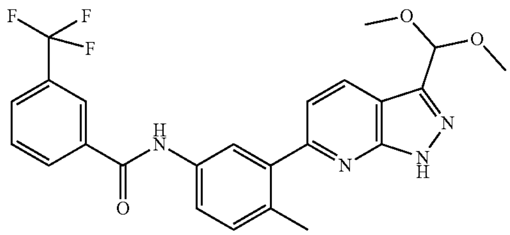 [SMILES: COC(OC)c1n[nH]c2nc(-c3cc(NC(=O)c4cccc(C(F)(F)F)c4)ccc3C)ccc12] | N-[3-(3-Dimethoxymethyl-1H-pyrazolo[3,4-b]pyridin-6-yl)-4-methyl-phenyl]-3-trifluoromethyl-benzamide | Gen-13-b + Gen-1-c B1 | 470 | 471 (M + H) |
| Gen-17-b | 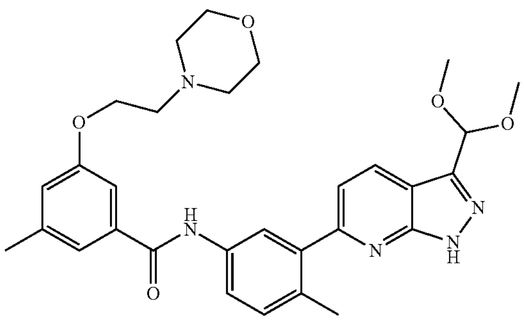 | N-[3-(3-Dimethoxymethyl-1H-pyrazolo[3,4-b]pyridin-6-yl)-4-methyl-phenyl]-3-methyl-5-(2-morpholin-4-yl-ethoxy)-benzamide | Gen-13-b + Gen-54-c B1 | 545 | 546 (M + H) |
| Gen-18-a | 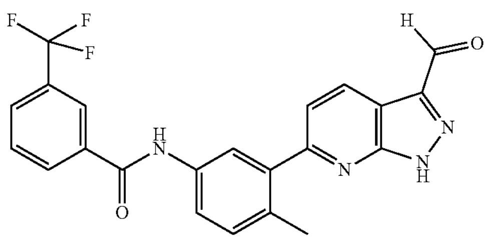 [SMILES: Cc1ccc(NC(=O)c2cccc(C(F)(F)F)c2)cc1-c1ccc2c(C=O)n[nH]c2n1] | N-[3-(3-Formyl-1H-pyrazolo[3,4-b]pyridin-6-yl)-4-methyl-phenyl]-3-trifluoromethyl-benzamide | Gen-17-a M | 424 | 425 (M + H) |
| Gen-18-b | 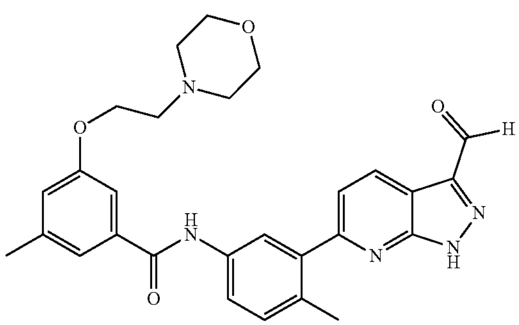 [SMILES: Cc1cc(OCCN2CCOCC2)cc(C(=O)Nc2ccc(C)c(-c3ccc4c(C=O)n[nH]c4n3)c2)c1] | N-[3-(3-Formyl-1H-pyrazolo[3,4-b]pyridin-6-yl)-4-methyl-phenyl]-3-methyl-5-(2-morpholin-4-yl-ethoxy)-benzamide | Gen-17-b M | 499 | 500 (M + H) |
| Gen-19-a | 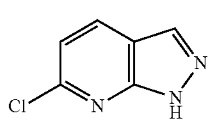 | 6-Chloro-1H-pyrazolo[3,4-b]pyridine | Cial. prod | 153 ($^{35}$Cl) 281 ($^{37}$Cl) | N.A. |

TABLE II-continued

Intermediates for the synthesis of illustrative compounds of the invention

| Int | Name | Int - Mtd | MW | MS Ms'd |
|---|---|---|---|---|
| Gen-20-a | 6-Chloro-3-iodo-1H-pyrazolo[3,4-b]pyridine | Gen-19-a See Int Gen-24-a | 279 ($^{35}$Cl) 281 ($^{37}$Cl) | N.A. |
| Gen-21-a | 6-Chloro-3-iodo-1-(4-methoxy-benzyl)-1H-pyrazolo[3,4-b]pyridine | Gen-20-a See Int Gen-24-a | 399 ($^{35}$Cl) 401 ($^{37}$Cl) | N.A. |
| Gen-22-a | 6-Chloro-1-(4-methoxy-benzyl)-3-vinyl-1H-pyrazolo[3,4-b]pyridine | Gen-21-a See Int Gen-24-a | 299 ($^{35}$Cl) 301 ($^{37}$Cl) | N.A. |
| Gen-22-b | 6-Chloro-1-(4-methoxy-benzyl)-3-methyl-1H-pyrazolo[3,4-b]pyridine | Gen-21-a See Int Gen-22-b | 287 ($^{35}$Cl) 288 ($^{37}$Cl) | 288 ($^{35}$Cl) 289 ($^{37}$Cl) |
| Gen-23-a | 2-Bromo-1-[6-chloro-1-(4-methoxy-benzyl)-1H-pyrazolo[3,4-b]pyridin-3-yl]-ethanol | Gen-22-a See Int Gen-24-a | 396 ($^{35}$Cl) 398 ($^{37}$Cl) | N.A. |

TABLE II-continued

Intermediates for the synthesis of illustrative compounds of the invention

| Int | Structures | Name | Int - Mtd | MW | MS Ms'd |
|---|---|---|---|---|---|
| Gen-23-b | 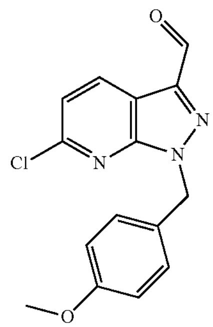 [SMILES: COc1ccc(Cn2nc(C=O)c3ccc(Cl)nc32)cc1] | 6-Chloro-1-(4-methoxy-benzyl)-1H-pyrazolo[3,4-b]pyridine-3-carbaldehyde | Gen-22-a See gen-23-b | 300 ($^{35}$Cl) 302 ($^{37}$Cl) | 301 ($^{35}$Cl) 303 ($^{37}$Cl) |
| Gen-24-a | 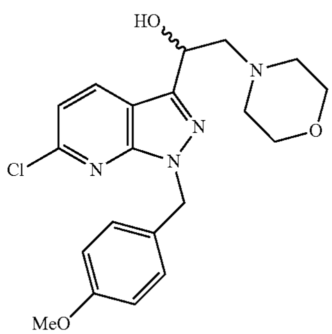 [SMILES: COc1ccc(Cn2nc(C(O)CN3CCOCC3)c3ccc(Cl)nc32)cc1] | 1-[6-Chloro-1-(4-methoxy-benzyl)-1H-pyrazolo[3,4-b]pyridin-3-yl]-2-morpholin-4-yl-ethanol | Gen-23-a See Int Gen-24-a | 402 ($^{35}$Cl) 404 ($^{37}$Cl) | N.A. |
| Gen-24-b | 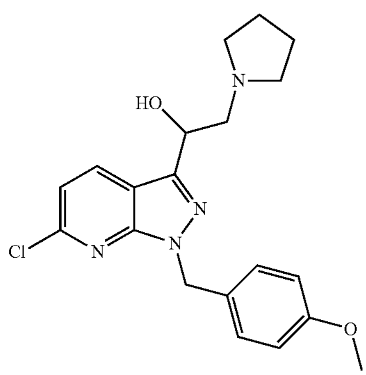 [SMILES: COc1ccc(Cn2nc(C(O)CN3CCCC3)c3ccc(Cl)nc32)cc1] | 1-[6-Chloro-1-(4-methoxy-benzyl)-1H-pyrazolo[3,4-b]pyridin-3-yl]-2-pyrrolidin-1-yl-ethanol | Gen-23-a + Gen-74-b See Int Gen-24-a | 386 | N.A. |
| Gen-25-a | 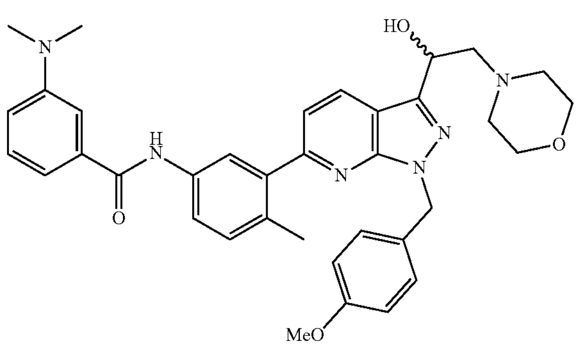 [SMILES: COc1ccc(Cn2nc(C(O)CN3CCOCC3)c3ccc(-c4cc(NC(=O)c5cccc(N(C)C)c5)ccc4C)nc32)cc1] | 3-Dimethylamino-N-{3-[3-(1-hydroxy-2-morpholin-4-yl-ethyl)-1-(4-methoxy-benzyl)-1H-pyrazolo[3,4-b]pyridin-6-yl]-4-methyl-phenyl}-benzamide | Gen-24-a + Gen-5-c H | 620 | N.A. |

… TABLE II-continued

Intermediates for the synthesis of illustrative compounds of the invention

| Int | Structures | Name | Int - Mtd | MW | MS Ms'd |
|---|---|---|---|---|---|
| Gen-25-b | 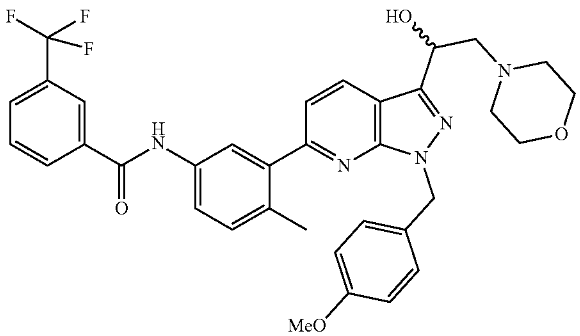 [SMILES: COc1ccc(Cn2nc(C(O)CN3CCOCC3)c3ccc(-c4cc(NC(=O)c5cccc(C(F)(F)F)c5)ccc4C)nc32)cc1] | 3-trifluoromethyl-N-{3-[3-(1-hydroxy-2-morpholin-4-yl-ethyl)-1-(4-methoxy-benzyl)-1H-pyrazolo[3,4-b]pyridin-6-yl]-4-methyl-phenyl}-benzamide | Gen-24-a + Gen-5-b H | 645 | N.A. |
| Gen-25-c | 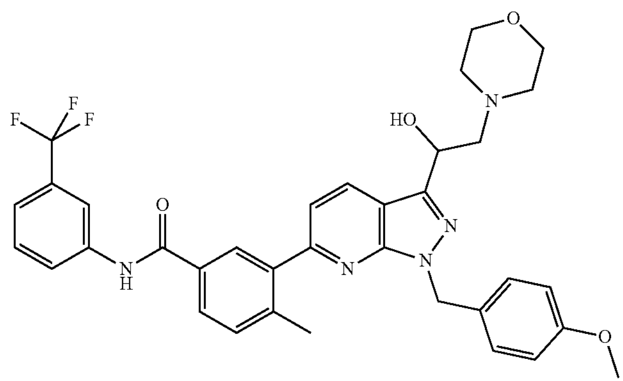 [SMILES: COc1ccc(Cn2nc(C(O)CN3CCOCC3)c3ccc(-c4cc(C(=O)Nc5cccc(C(F)(F)F)c5)ccc4C)nc32)cc1] | 3-[3-(1-Hydroxy-2-morpholin-4-yl-ethyl)-1-(4-methoxy-benzyl)-1H-pyrazolo[3,4-b]pyridin-6-yl]-4-methyl-N-(3-trifluoromethyl-phenyl)-benzamide | Gen-24-a + Gen-5-d H | 645 | N.A. |
| Gen-25-d | 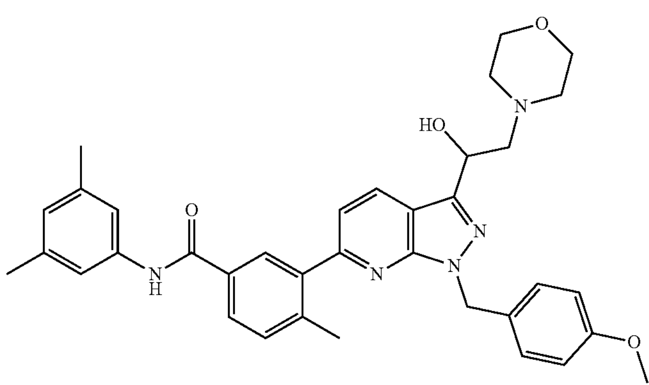 | N-(3,5-Dimethyl-phenyl)-3-[3-(1-hydroxy-2-morpholin-4-yl-ethyl)-1-(4-methoxy-benzyl)-1H-pyrazolo[3,4-b]pyridin-6-yl]-4-methyl-benzamide | Gen-24-a + Gen-5-e H | 605 | 606 (M + H) |
| Gen-25-g | 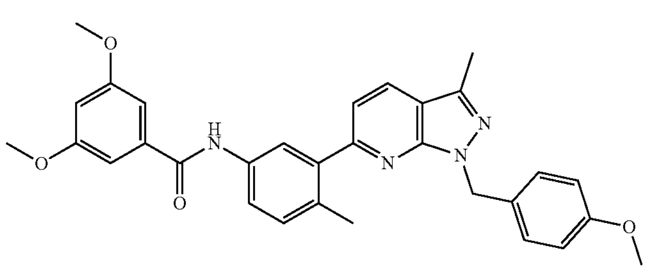 | 3,5-Dimethoxy-N-{3-[1-(4-methoxy-benzyl)-3-methyl-1H-pyrazolo[3,4-b]pyridin-6-yl]-4-methyl-phenyl}-benzamide | Gen-22-b + Gen-5-a H | 522 | 523 (M + H) |

TABLE II-continued

Intermediates for the synthesis of illustrative compounds of the invention

| Int | Structures | Name | Int - Mtd | MW | MS Ms'd |
|---|---|---|---|---|---|
| Gen-26-a | 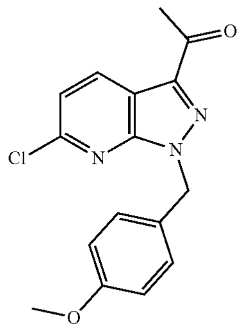 [SMILES: COc1ccc(Cn2nc(C(C)=O)c3ccc(Cl)nc32)cc1] | 1-[6-Chloro-1-(4-methoxy-benzyl)-1H-pyrazolo[3,4-b]pyridin-3-yl]-ethanone | Gen-21-a See Cpd 8 | 315 ($^{35}$Cl) 317 ($^{37}$Cl) | (M + H) |
| Gen-25-h | 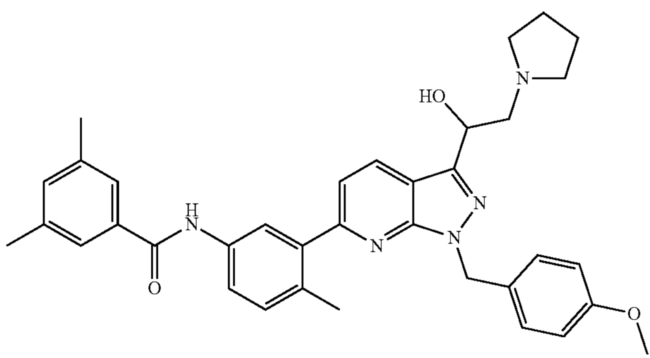 | N-{3-[3-(1-Hydroxy-2-pyrrolidin-1-yl-ethyl)-1-(4-methoxy-benzyl)-1H-pyrazolo[3,4-b]pyridin-6-yl]-4-methyl-phenyl}-3,5-dimethyl-benzamide | Gen-24-b + Gen-5-e H | 589 | N.A. |
| Gen-27-a | 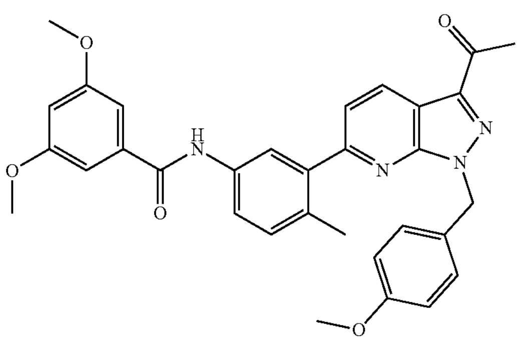 [SMILES: COc1ccc(Cn2nc(C(C)=O)c3ccc(-c4cc(NC(=O)c5cc(OC)cc(OC)c5)ccc4C)nc32)cc1] | N-{3-[3-Acetyl-1-(4-methoxy-benzyl)-1H-pyrazolo[3,4-b]pyridin-6-yl]-4-methyl-phenyl}-3,5-dimethoxy-benzamide | Gen-26-a + Gen-5-a H | 550 | N.A. |
| Gen-27-b | 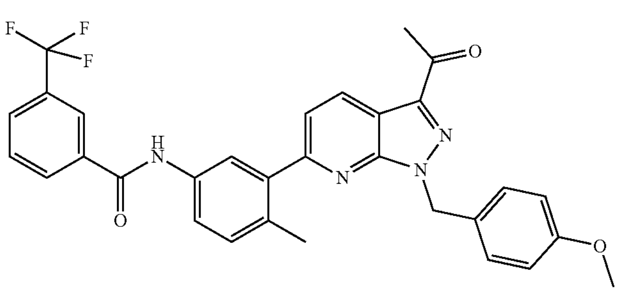 [SMILES: COc1ccc(Cn2nc(C(C)=O)c3ccc(-c4cc(NC(=O)c5cccc(C(F)(F)F)c5)ccc4C)nc32)cc1] | N-{3-[3-Acetyl-1-(4-methoxy-benzyl)-1H-pyrazolo[3,4-b]pyridin-6-yl]-4-methyl-phenyl}-3-trifluoromethyl-benzamide | Gen-26-a + Gen-5-d H | 558 | N.A. |

TABLE II-continued

Intermediates for the synthesis of illustrative compounds of the invention

| Int | Structures | Name | Int - Mtd | MW | MS Ms'd |
|---|---|---|---|---|---|
| Gen-27-c | 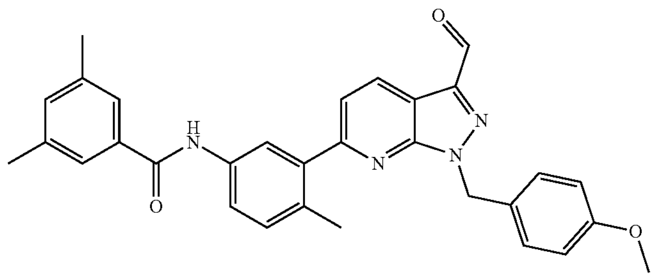 | N-{3-[3-Formyl-1-(4-methoxy-benzyl)-1H-pyrazolo[3,4-b]pyridin-6-yl]-4-methyl-phenyl}-3,5-dimethyl-benzamide | Gen-23-b + Gen-5-e H | 504 | N.A. |
| Gen-28-a | 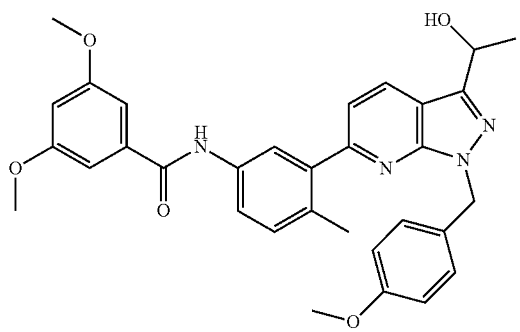 [SMILES: COc1ccc(Cn2nc(C(C)O)c3ccc(-c4cc(NC(=O)c5cc(OC)cc(OC)c5)ccc4C)nc32)cc1] | N-{3-[3-(1-Hydroxy-ethyl)-1-(4-methoxy-benzyl)-1H-pyrazolo[3,4-b]pyridin-6-yl]-4-methyl-phenyl}-3,5-dimethoxy-benzamide | Gen-27-a O | 552 | N.A. |
| Gen-28-b | 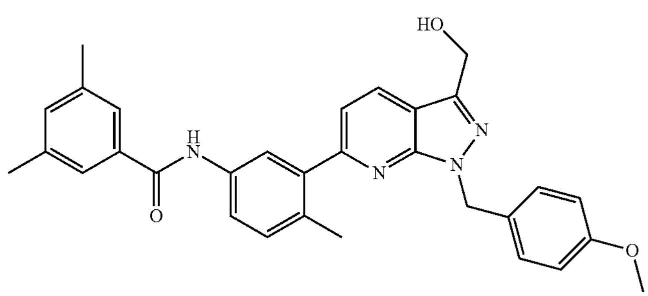 | N-{3-[3-Hydroxymethyl-1-(4-methoxy-benzyl)-1H-pyrazolo[3,4-b]pyridin-6-yl]-4-methyl-phenyl}-3,5-dimethyl-benzamide | Gen-27-c O | 506 | 507 (M + H) |
| Gen-28-c | 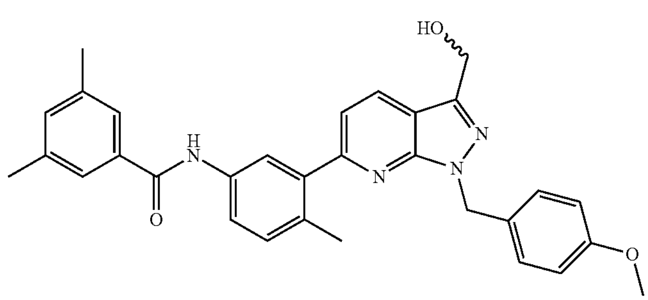 | N-{3-[3-(1-Hydroxy-ethyl)-1-(4-methoxy-benzyl)-1H-pyrazolo[3,4-b]pyridin-6-yl]-4-methyl-phenyl}-3,5-dimethyl-benzamide | Gen-27-c L | 520 | 521 (M + H) |
| Gen-29-a | 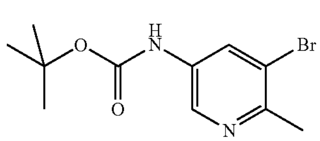 [SMILES: Cc1ncc(NC(=O)OC(C)(C)C)cc1Br] | (5-Bromo-6-methyl-pyridin-3-yl)-carbamic acid tert-butyl ester | Gen-2-a See Int Gen-29-a | 286 ($^{79}$Br) 288 ($^{81}$Br) | 287 $^{79}$Br M + H) 288 ($^{81}$Br M + H) |

TABLE II-continued

Intermediates for the synthesis of illustrative compounds of the invention

| Int | Structures | Name | Int - Mtd | MW | MS Ms'd |
|---|---|---|---|---|---|
| Gen-30-a | 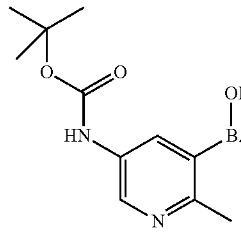 | (5-(Boronic acid)-6-methyl-pyridin-3-yl)-carbamic acid tert-butyl ester | Gen-29-a See Int Gen-30-a | 252 | 253 (M + H) |
| Gen-33-a | 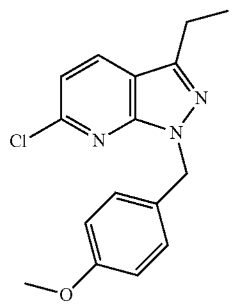 [SMILES: CCc1nn(Cc2ccc(OC)cc2)c2nc(Cl)ccc12] | 6-Chloro-3-ethyl-1-(4-methoxy-benzyl)-1H-pyrazolo[3,4-b]pyridine | Gen-22-a See Int Gen-33-a | 301 | 302 (M + H) |
| Gen-34-a | 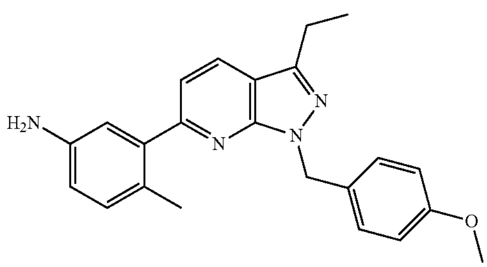 [SMILES: CCc1nn(Cc2ccc(OC)cc2)c2nc(-c3cc(N)ccc3C)ccc12] | 3-[3-Ethyl-1-(4-methoxy-benzyl)-1H-pyrazolo[3,4-b]pyridin-6-yl]-4-methyl-phenylamine | Gen-33-a + Gen-3-a H | 372 | 373 (M + H) |
| Gen-35-a | 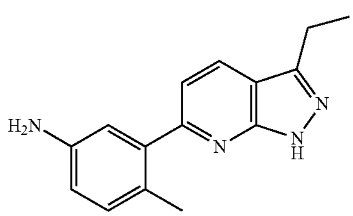 [SMILES: CCc1n[nH]c2nc(-c3cc(N)ccc3C)ccc12] | 3-(3-Ethyl-1H-pyrazolo[3,4-b]pyridin-6-yl)-4-methyl-phenylamine | Gen-34-a I2 | 252 | 253 (M + H) |
| Gen-36-a | 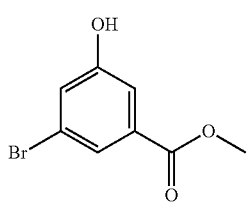 | 3-Bromo-5-hydroxy-benzoic acid methyl ester | Gen-1-g P | 231 | 232 (M + H) |
| Gen-37-a | 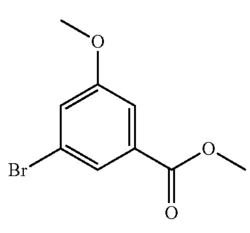 | 3-Bromo-5-methoxy-benzoic acid methyl ester | Gen-36-a Q | 245 | 246 (M + H) |

TABLE II-continued

Intermediates for the synthesis of illustrative compounds of the invention

| Int | Structures | Name | Int - Mtd | MW | MS Ms'd |
|---|---|---|---|---|---|
| Gen-37-b | 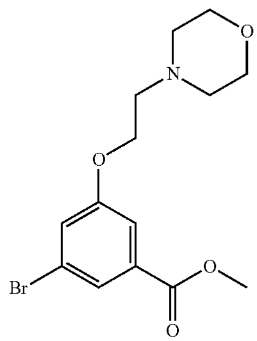 [SMILES: COC(=O)c1cc(Br)cc(OCCN2CCOCC2)c1] | 3-Bromo-5-(2-morpholin-4-yl-ethoxy)-benzoic acid methyl ester | Gen-36-a + Gen-9-h Q | 344 | 345 (M + H) |
| Gen-38-a | 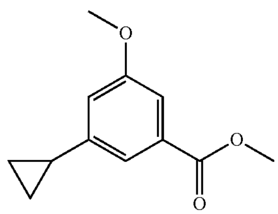 | 3-Cyclopropyl-5-methoxy-benzoic acid methyl ester | Gen-37-a R1 | 206 | 207 (M + H) |
| Gen-38-b | 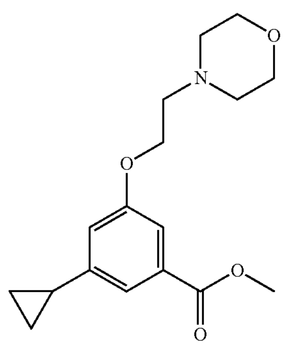 [SMILES: COC(=O)c1cc(OCCN2CCOCC2)cc(C2CC2)c1] | 3-Cyclopropyl-5-(2-morpholin-4-yl-ethoxy)-benzoic acid methyl ester | Gen-37-b + Gen-9-g R1 | 305 | N.A. |
| Gen-38-c | 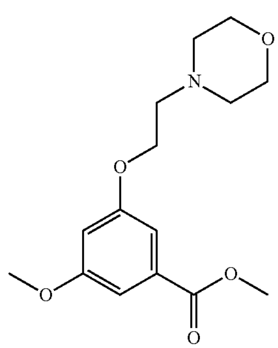 [SMILES: COC(=O)c1cc(OC)cc(OCCN2CCOCC2)c1] | 3-Methoxy-5-(2-morpholin-4-yl-ethoxy)-benzoic acid methyl ester | Gen-9-h + Gen-44-a Q | 295 | N.A. |
| Gen-39-a | 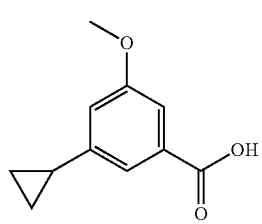 | 3-Cyclopropyl-5-methoxy-benzoic acid | Gen-38-a R2 | 191 | 190 (M − H) |

TABLE II-continued

Intermediates for the synthesis of illustrative compounds of the invention

| Int | Structures | Name | Int - Mtd | MW | MS Ms'd |
|---|---|---|---|---|---|
| Gen-39-b | 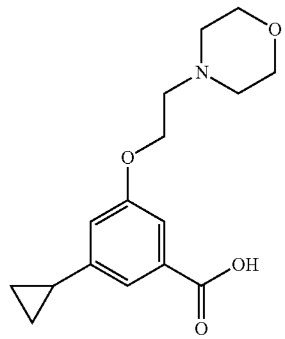 [SMILES: O=C(O)c1cc(OCCN2CCOCC2)cc(C2CC2)c1] | 3-Cyclopropyl-5-(2-morpholin-4-yl-ethoxy)-benzoic acid | Gen-38-b R2 | 290 | 289 (M − H) |
| Gen-39-c | 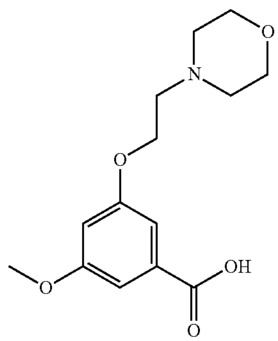 [SMILES: COc1cc(OCCN2CCOCC2)cc(C(=O)O)c1] | 3-Methoxy-5-(2-morpholin-4-yl-ethoxy)-benzoic acid | Gen-38-c R2 | 281 | 280 (M − H) |
| Gen-40-a | 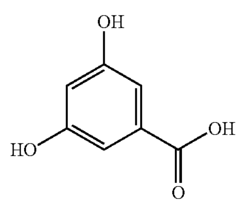 [SMILES: O=C(O)c1cc(O)cc(O)c1] | 3,5-Dihydroxy-benzoic acid | Cial. prod | 154 | N.A. |
| Gen-40-b | 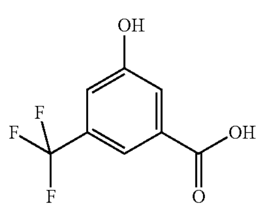 [SMILES: O=C(O)c1cc(O)cc(C(F)(F)F)c1] | 3-Hydroxy-5-trifluoromethyl-benzoicacid | Cial. prod | 206 | N.A. |
| Gen-40-c | 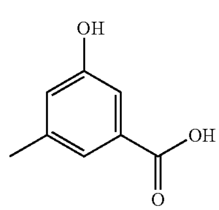 | 3-Hydroxy-5-methyl-benzoic acid | Cial. prod | 152 | N.A. |

TABLE II-continued

Intermediates for the synthesis of illustrative compounds of the invention

| Int | Structures | Name | Int - Mtd | MW | MS Ms'd |
|---|---|---|---|---|---|
| Gen-41-a | 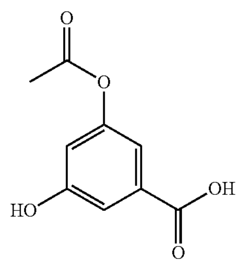 | 3-Acetoxy-5-hydroxy-benzoic acid | Gen-40-a See Int Gen-44-a | 196 | 195 (M − H) |
| Gen-41-b | 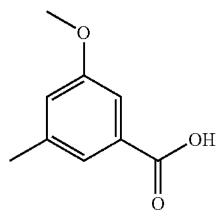 | 3-Methoxy-5-methyl-benzoic acid | Gen-40-c Q | 166 | 165 (M − H) |
| Gen-42-a | 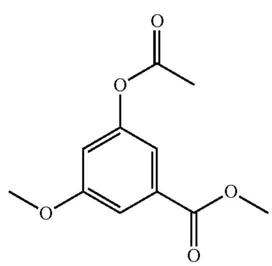 | 3-Acetoxy-5-methoxy-benzoic acid methyl ester | Gen-41-a Q | 224 | N.A. |
| Gen-43-a | 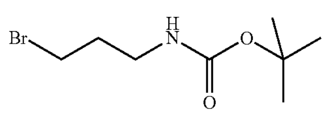 | (3-Bromo-propyl)-carbamic acid tert-butyl ester | Cial. prod | 238 | N.A. |
| Gen-43-b | 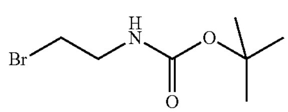 | (2-Bromo-ethyl)-carbamic acid tert-butyl ester | Cial. prod | 224 | N.A. |
| Gen-44-a | 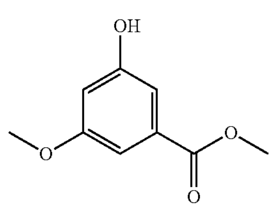 | 3-Hydroxy-5-methoxy-benzoic acid methyl ester | Gen-42-a See Int Gen-44-a | 182 | N.A. |
| Gen-44-b | 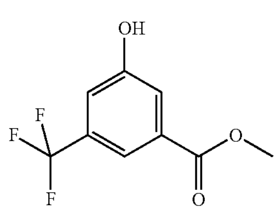 | 3-Hydroxy-5-trifluoromethyl-benzoic acid methyl ester | Gen-40-b P | 220 | 221 (M + H) |

TABLE II-continued

Intermediates for the synthesis of illustrative compounds of the invention

| Int | Structures | Name | Int - Mtd | MW | MS Ms'd |
|---|---|---|---|---|---|
| Gen-45-a | 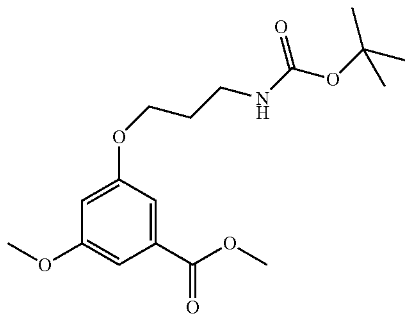 [SMILES: COC(=O)c1cc(OC)cc(OCCCNC(=O)OC(C)(C)C)c1] | 3-(3-tert-Butoxycarbonylamino-propoxy)-5-methoxy-benzoic acid methyl ester | Gen-44-a + Gen-43-a Q | 339 | 340 (M + H) |
| Gen-45-b | 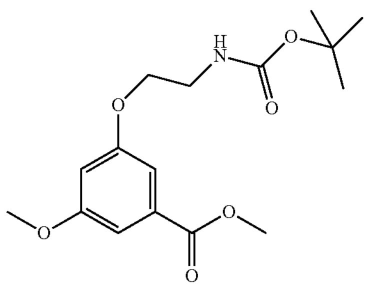 [SMILES: COC(=O)c1cc(OC)cc(OCCNC(=O)OC(C)(C)C)c1] | 3-(2-tert-Butoxycarbonylamino-ethoxy)-5-methoxy-benzoic acid methyl ester | Gen-44-a + Gen-43-b Q | 325 | 326 (M + H) |
| Gen-46-a | 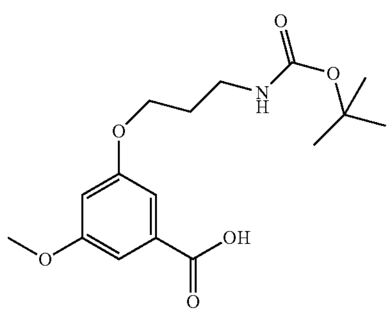 [SMILES: COc1cc(OCCCNC(=O)OC(C)(C)C)cc(C(=O)O)c1] | 3-(3-tert-Butoxycarbonylamino-propoxy)-5-methoxy-benzoic acid | Gen-45-a R2 | 325 | 324 (M − H) |
| Gen-46-b | 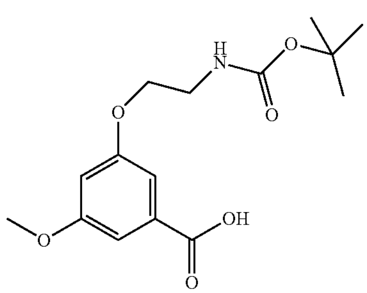 [SMILES: COc1cc(OCCNC(=O)OC(C)(C)C)cc(C(=O)O)c1] | 3-(2-tert-Butoxycarbonylamino-ethoxy)-5-methoxy-benzoic acid | Gen-45-b R2 | 311 | 310 (M − H) |
| Gen-47-a | 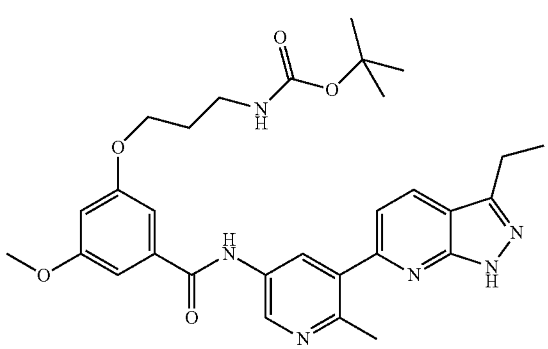 [SMILES: CCc1n[nH]c2nc(-c3cc(NC(=O)c4cc(OC)cc(OCCCNC(=O)OC(C)(C)C)c4)cnc3C)ccc12] | (3-{3-[5-(3-Ethyl-1H-pyrazolo[3,4-b]pyridin-6-yl)-6-methyl-pyridin-3-ylcarbamoyl]-5-methoxy-phenoxy}-propyl)-carbamic acid tert-butyl ester | Gen-46-a + Gen-13-a B1 | 560 | 561 (M + H) |

TABLE II-continued

Intermediates for the synthesis of illustrative compounds of the invention

| Int | Structures | Name | Int - Mtd | MW | MS Ms'd |
|---|---|---|---|---|---|
| Gen-47-b | 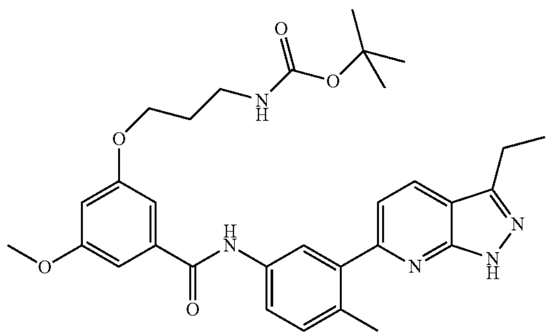 [SMILES: CCc1n[nH]c2nc(-c3cc(NC(=O)c4cc(OC)cc(OCCCNC(=O)OC(C)(C)C)c4)ccc3C)ccc12] | 3-{3-[3-(3-Ethyl-1H-pyrazolo[3,4-b]pyridin-6-yl)-4-methyl-phenylcarbamoyl]-5-methoxy-phenoxy}-propyl)-carbamic acid tert-butyl ester | Gen-46-a + Gen-35-a B1 | 559 | 560 (M + H) |
| Gen-47-c | 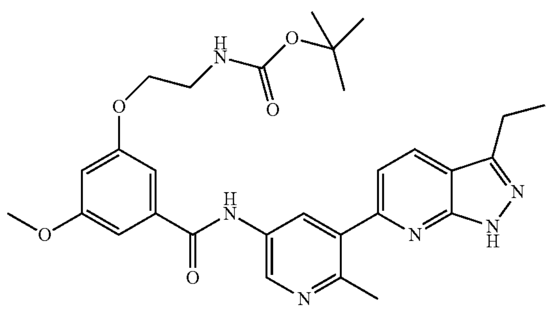 [SMILES: CCc1n[nH]c2nc(-c3cc(NC(=O)c4cc(OC)cc(OCCNC(=O)OC(C)(C)C)c4)cnc3C)ccc12] | (2-{3-[5-(3-Ethyl-1H-pyrazolo[3,4-b]pyridin-6-yl)-6-methyl-pyridin-3-ylcarbamoyl]-5-methoxy-phenoxy}-ethyl)-carbamic acid tert-butyl ester | Gen-13-a + Gen-46-b B1 | 546 | 547 (M + H) |
| Gen-47-d | 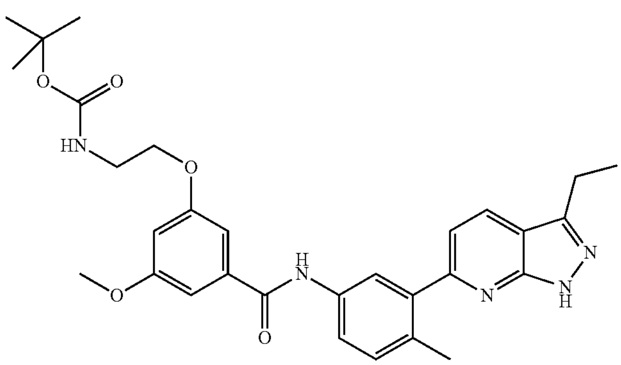 [SMILES: CCc1n[nH]c2nc(-c3cc(NC(=O)c4cc(OC)cc(OCCNC(=O)OC(C)(C)C)c4)ccc3C)ccc12] | (2-{3-[3-(3-Ethyl-1H-pyrazolo[3,4-b]pyridin-6-yl)-4-methyl-phenylcarbamoyl]-5-methoxy-phenoxy}-ethyl)-carbamic acid tert-butyl ester | Gen-35-a + Gen-46-b K | 545 | 546 (M + H) |
| Gen-48-a | 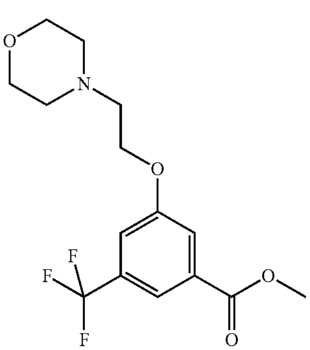 [SMILES: COC(=O)c1cc(OCCN2CCOCC2)cc(C(F)(F)F)c1] | 3-(2-Morpholin-4-yl-ethoxy)-5-trifluoromethyl-benzoic acid methyl ester | Gen-44-b + Gen-9-hQ | 333 | 334 (M + H) |

TABLE II-continued

Intermediates for the synthesis of illustrative compounds of the invention

| Int | Structures | Name | Int - Mtd | MW | MS Ms'd |
|---|---|---|---|---|---|
| Gen-49-a | 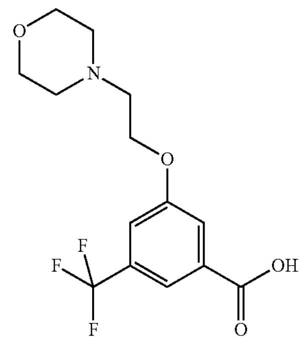 [SMILES: O=C(O)c1cc(OCCN2CCOCC2)cc(C(F)(F)F)c1] | 3-(2-Morpholin-4-yl-ethoxy)-5-trifluoromethyl-benzoic acid | Gen-48-a R2 | 319 | 318 (M − H) |
| Gen-50-a | 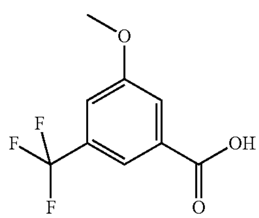 | 3-Methoxy-5-trifluoromethyl-benzoic acid | Gen-40-b See Int Gen-50-a | 220 | 219 (M − H) |
| Gen-51-a | 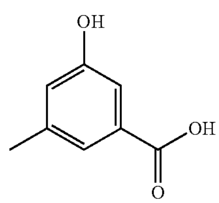 | 3-Hydroxy-5-methyl-benzoic acid | Cial. prod | 152 | N.A |
| Gen-52-a | 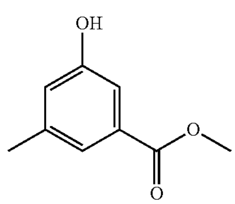 | 3-Hydroxy-5-methyl-benzoic acid methyl ester | Gen-51-a P | 166 | 167 (M + H) |
| Gen-53-a | 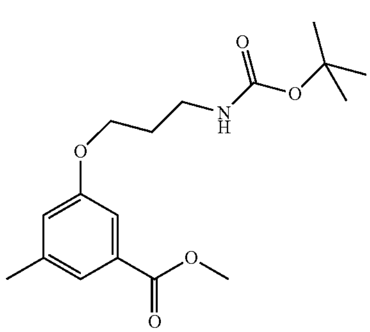 [SMILES: COC(=O)c1cc(C)cc(OCCCNC(=O)OC(C)(C)C)c1] | 3-(3-tert-Butoxycarbonylamino-propoxy)-5-methyl-benzoic acid methyl ester | Gen-52-a + Gen-43-aQ | 323 | 324 (M + H) |

TABLE II-continued

Intermediates for the synthesis of illustrative compounds of the invention

| Int | Structures | Name | Int - Mtd | MW | MS Ms'd |
|---|---|---|---|---|---|
| Gen-53-b | 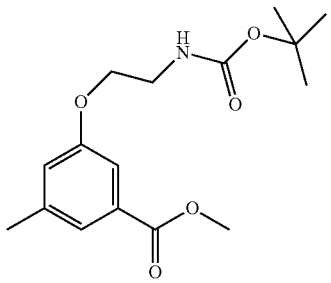 [SMILES: COC(=O)c1cc(C)cc(OCCNC(=O)OC(C)(C)C)c1] | 3-(2-tert-Butoxycarbonylamino-ethoxy)-5-methyl-benzoic acid methyl ester | Gen-52-a + Gen-43-b Q | 309 | 310 (M + H) |
| Gen-53-c | 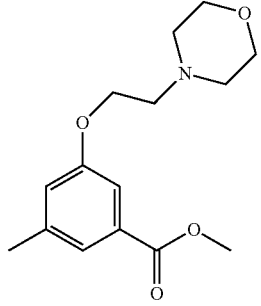 [SMILES: COC(=O)c1cc(C)cc(OCCN2CCOCC2)c1] | 3-Methyl-5-(2-morpholin-4-yl-ethoxy)-benzoic acid methyl ester | Gen-52-a + Gen-9-h Q | 279 | 280 (M + H) |
| Gen-53-d | 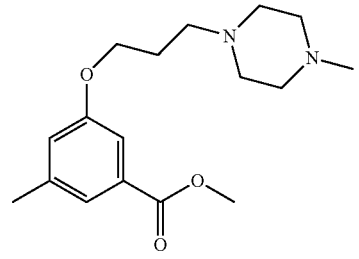 | 3-Methyl-5-[3-(4-methyl-piperazin-1-yl)-propoxy]-benzoic acid methyl ester | Gen-52-a + Gen-9-i Q | 306 | 307 (M + H) |
| Gen-54-a | 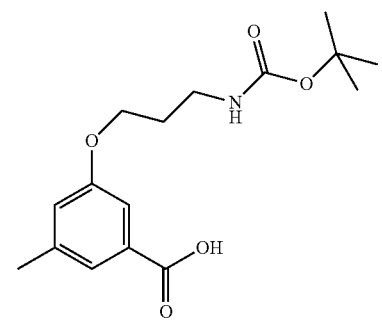 [SMILES: Cc1cc(OCCCNC(=O)OC(C)(C)C)cc(C(=O)O)c1] | 3-(3-tert-Butoxycarbonylamino-propoxy)-5-methyl-benzoic acid | Gen-53-a R2 | 309 | 308 (M − H) |
| Gen-54-b | 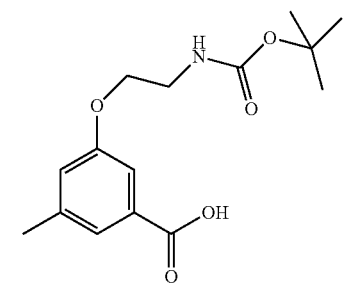 [SMILES: Cc1cc(OCCNC(=O)OC(C)(C)C)cc(C(=O)O)c1] | 3-(2-tert-Butoxycarbonylamino-ethoxy)-5-methyl-benzoic acid | Gen-53-b R2 | 295 | 294 (M − H) |

TABLE II-continued

Intermediates for the synthesis of illustrative compounds of the invention

| Int | Structures | Name | Int - Mtd | MW | MS Ms'd |
|---|---|---|---|---|---|
| Gen-54-c | 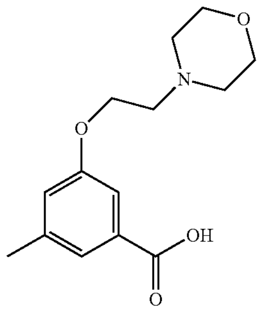 [SMILES: Cc1cc(OCCN2CCOCC2)cc(C(=O)O)c1] | 3-Methyl-5-(2-morpholin-4-yl-ethoxy)-benzoic acid | Gen-53-c R2 | 265 | 264 (M − H) |
| Gen-54-d | 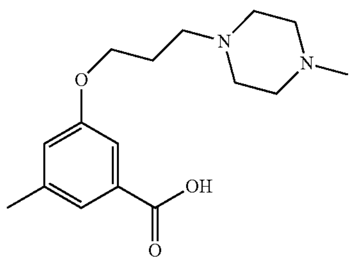 | 3-Methyl-5-[3-(4-methyl-piperazin-1-yl)-propoxy]-benzoic acid | Gen-53-d R2 | 292 | 291 (M − H) |
| Gen-55-a | 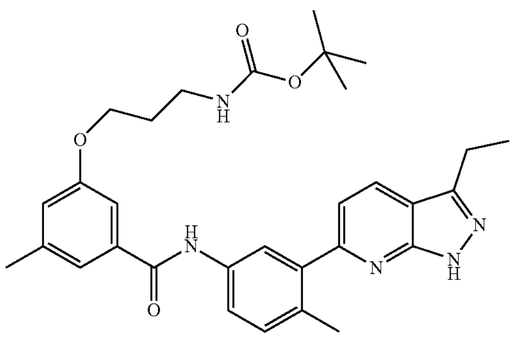 [SMILES: CCc1n[nH]c2nc(-c3cc(NC(=O)c4cc(C)cc(OCCCNC(=O)OC(C)(C)C)c4)ccc3C)ccc12] | (3-{3-[3-(3-Ethyl-1H-pyrazolo[3,4-b]pyridin-6-yl)-4-methyl-phenylcarbamoyl]-5-methyl-phenoxy}-propyl)-carbamic acid tert-butyl ester | Gen-35-a + Gen-54-a B1 | 543 | 544 (M + H) |
| Gen-55-b | 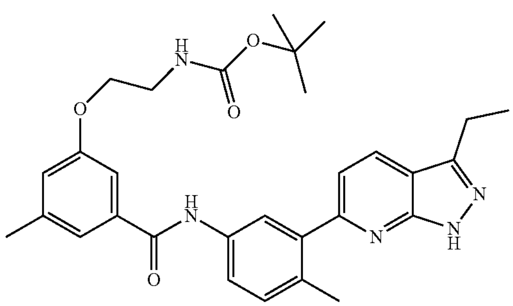 [SMILES: CCc1n[nH]c2nc(-c3cc(NC(=O)c4cc(C)cc(OCCNC(=O)OC(C)(C)C)c4)ccc3C)ccc12] | (2-{3-[3-(3-Ethyl-1H-pyrazolo[3,4-b]pyridin-6-yl)-4-methyl-phenylcarbamoyl]-5-methyl-phenoxy}-ethyl)-carbamic acid tert-butyl ester | Gen-35-a + Gen-54-b B1 | 529 | 530 (M + H) |
| Gen-56-a | 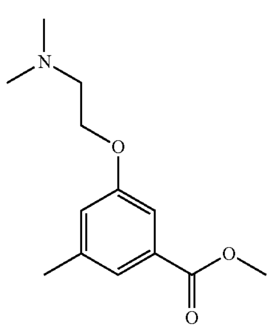 | 3-(2-Dimethylamino-ethoxy)-5-methyl-benzoic acid methyl ester | Gen-52-a + Gen-9-J Q | 237 | 238 (M + H) |

TABLE II-continued

Intermediates for the synthesis of illustrative compounds of the invention

| Int | Name | Int - Mtd | MW | MS Ms'd |
|---|---|---|---|---|
| Gen-57-a | 3-(2-Dimethylamino-ethoxy)-5-methyl-benzoic acid | Gen-56-a R2 | 223 | 222 (M − H) |
| Gen-58-a | 3-Methyl-5-[2-(tetrahydro-pyran-2-yloxy)-ethoxy]-benzoic acid methyl ester | Gen-52-a + Gen-9-k Q | 294 | 295 (M + H) |
| Gen-59-a | 3-Methyl-5-[2-(tetrahydro-pyran-2-yloxy)-ethoxy]-benzoic acid | Gen-58-a R2 | 280 | 279 (M − H) |
| Gen-60-a | 3-(2-Methoxy-ethoxy)-5-methyl-benzoic acid methyl ester | Gen-52-a + Gen-9-l Q | 224 | 225 (M + H) |

TABLE II-continued

Intermediates for the synthesis of illustrative compounds of the invention

| Int | Structures | Name | Int - Mtd | MW | MS Ms'd |
|---|---|---|---|---|---|
| Gen-61-a | 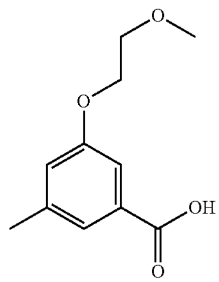 | 3-(2-Methoxy-ethoxy)-5-methyl-benzoic acid | Gen-60-a R2 | 210 | 209 (M − H) |
| Gen-62-a | 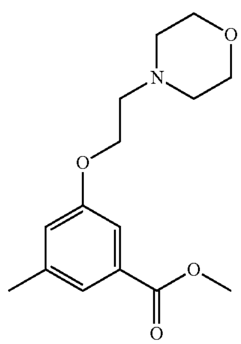 | 3-Methyl-5-(2-morpholin-4-yl-ethoxy)-benzoic acid methyl ester | Gen-9-h + Gen-52-a Q | 279 | 280 (M + H) |
| Gen-63-a | 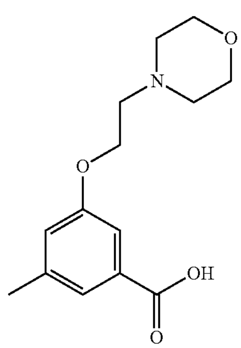 [SMILES: Cc1cc(OCCN2CCOCC2)cc(C(=O)O)c1] | 3-Methyl-5-(2-morpholin-4-yl-ethoxy)-benzoic acid | Gen-62-a R2 | 265 | 264 (M − H) |
| Gen-64-a | 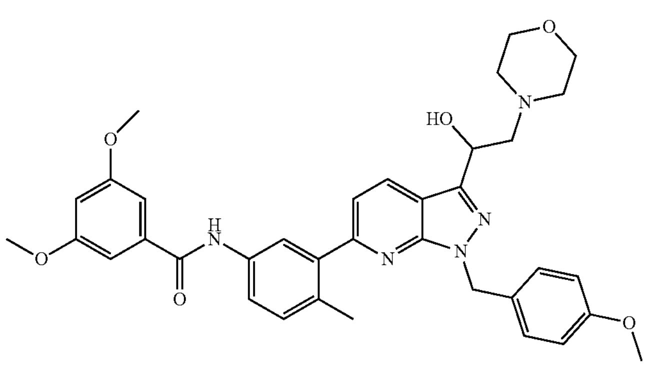 | N-{3-[3-(1-Hydroxy-2-morpholin-4-yl-ethyl)-1-(4-methoxy-benzyl)-1H-pyrazolo[3,4-b]pyridin-6-yl]-4-methyl-phenyl}-3,5-dimethoxy-benzamide | Gen-5-a + Gen-24-a F1 | 637 | 638 (M + H) |

TABLE II-continued

Intermediates for the synthesis of illustrative compounds of the invention

| Int | Structures | Name | Int - Mtd | MW | MS Ms'd |
|---|---|---|---|---|---|
| Gen-64-b | 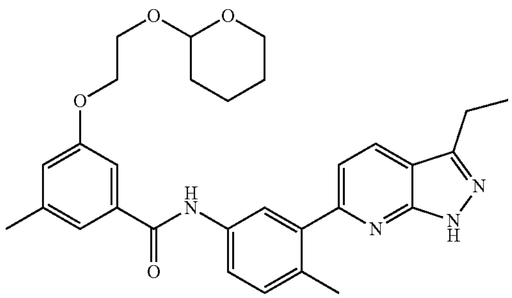 [SMILES: CCc1n[nH]c2nc(-c3cc(NC(=O)c4cc(C)cc(OCCOC5CCCCO5)c4)ccc3C)ccc12] | N-[3-(3-Ethyl-1H-pyrazolo[3,4-b]pyridin-6-yl)-4-methyl-phenyl]-3-methyl-5-[2-(tetrahydro-pyran-2-yloxy)-ethoxy]-benzamide | Gen-59-a + Gen-35-a B1 | 514 | 515 (M + H) |
| Gen-65-a | 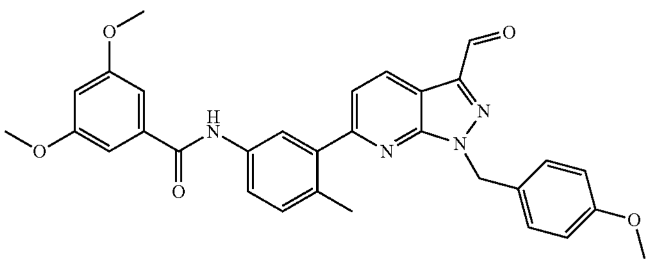 | N-{3-[3-Formyl-1-(4-methoxy-benzyl)-1H-pyrazolo[3,4-b]pyridin-6-yl]-4-methyl-phenyl}-3,5-dimethoxy-benzamide | Gen-5-a + Gen-23-a F1 | 536 | 537 (M + H) |
| Gen-66-a | 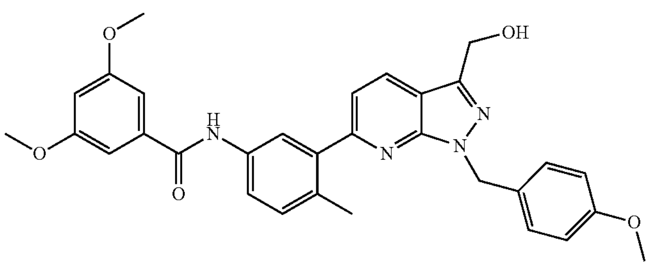 | N-{3-[3-Hydroxymethyl-1-(4-methoxy-benzyl)-1H-pyrazolo[3,4-b]pyridin-6-yl]-4-methyl-phenyl}-3,5-dimethoxy-benzamide | Gen-65-a O | 538 | N.A. |
| Gen-67-a | 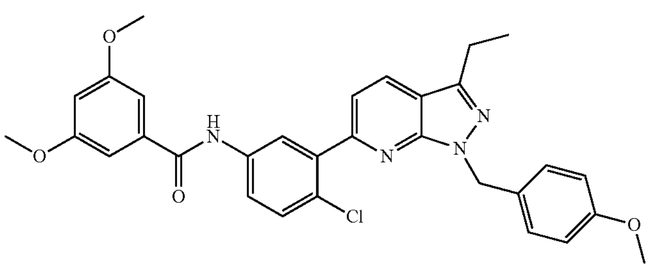 | N-{3-[3-Formyl-1-(4-methoxy-benzyl)-1H-pyrazolo[3,4-b]pyridin-6-yl]-4-methyl-phenyl}-3,5-dimethoxy-benzamide | Gen-5-f + Gen-33-a F1 | 556 | 557 (M + H) |
| Gen-67-b | 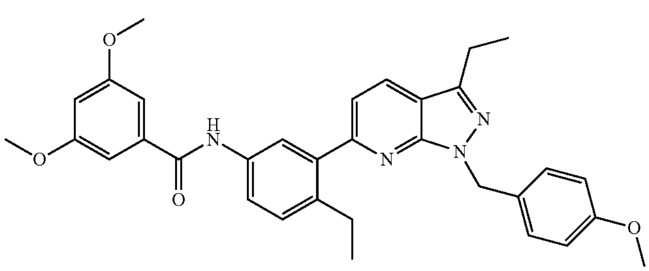 | N-{4-Ethyl-3-[3-ethyl-1-(4-methoxy-benzyl)-1H-pyrazolo[3,4-b]pyridin-6-yl]-phenyl}-3,5-dimethoxy-benzamide | Gen-5-g + Gen-33-a F1 | 550 | 551 (M + H) |

TABLE II-continued

Intermediates for the synthesis of illustrative compounds of the invention

| Int | Structures | Name | Int - Mtd | MW | MS Ms'd |
|---|---|---|---|---|---|
| Gen-68-a | 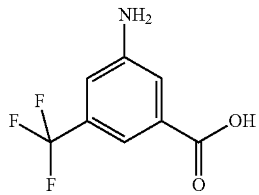 [SMILES: Nc1cc(C(=O)O)cc(C(F)(F)F)c1] | 3-Amino-5-trifluoromethyl-benzoic acid | Cial. prod | 205 | N.A |
| Gen-69-a | 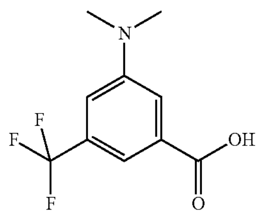 [SMILES: CN(C)c1cc(C(=O)O)cc(C(F)(F)F)c1] | 3-Dimethylamino-5-trifluoromethyl-benzoic acid | Gen-68-a Q | 233 | 232 (M − H) |
| Gen-70-a | 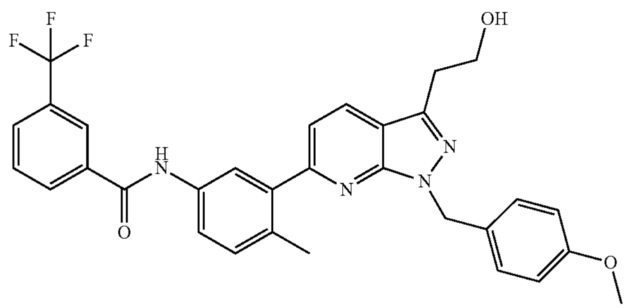 [SMILES: COc1ccc(Cn2nc(CCO)c3ccc(-c4cc(NC(=O)c5cccc(C(F)(F)F)c5)ccc4C)nc32)cc1] | N-{3-[3-(2-Hydroxy-ethyl)-1-(4-methoxy-benzyl)-1H-pyrazolo[3,4-b]pyridin-6-yl]-4-methyl-phenyl}-3-trifluoromethyl-benzamide | Gen-75-a F1 | 560 | N.A. |
| Gen-71-a | 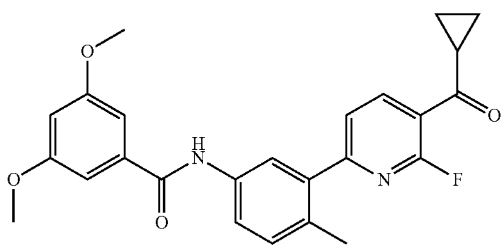 [SMILES: COc1cc(OC)cc(C(=O)Nc2ccc(C)c(-c3ccc(C(=O)C4CC4)c(F)n3)c2)c1] | N-[3-(5-Cyclopropanecarbonyl-6-fluoro-pyridin-2-yl)-4-methyl-phenyl]-3,5-dimethoxy-benzamide | Gen-5-a + Gen-8-i F1 | 434 | 435 (M + H) |
| Gen-72-a | 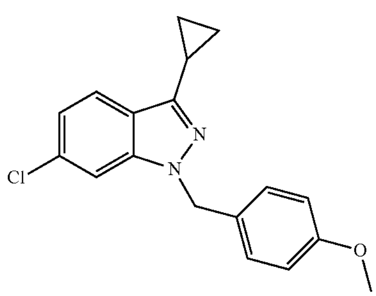 [SMILES: COc1ccc(Cn2nc(C3CC3)c3ccc(Cl)cc32)cc1] | 6-Chloro-3-cyclopropyl-1-(4-methoxy-benzyl)-1H-pyrazolo[3,4-b]pyridine | Gen-21-a + Gen-9-g F1 | 313 | 314 (M + H) |
| Gen-73-a | 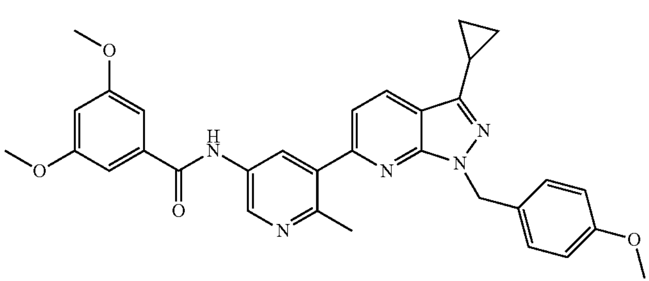 | N-{5-[3-Cyclopropyl-1-(4-methoxy-benzyl)-1H-pyrazolo[3,4-b]pyridin-6-yl]-6-methyl-pyridin-3-yl}-3,5-dimethoxy-benzamide | Gen-5-h + Gen-72-a F1 | 549 | 550 (M + H) |

TABLE II-continued

Intermediates for the synthesis of illustrative compounds of the invention

| Int | Structures | Name | Int - Mtd | MW | MS Ms'd |
|---|---|---|---|---|---|
| Gen-74-a | 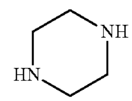 | Piperazine | Cial. prod | 86 | N.A. |
| Gen-74-b | 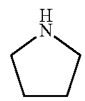 | Pyrrolidine | Cial. prod | 71 | N.A. |
| Gen-74-c | 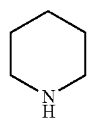 | Piperidine | Cial. prod | 85 | N.A. |
| Gen-74-d | 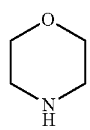 | Morpholine | Cial. prod | 87 | N.A. |
| Gen-75-a | 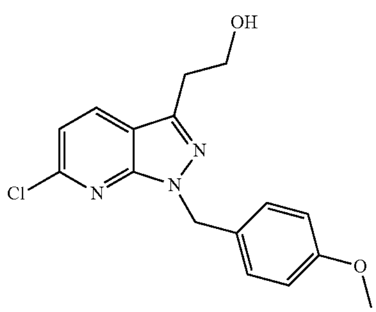 [SMILES: COc1ccc(Cn2nc(CCO)c3ccc(Cl)nc32)cc1] | 2-[6-Chloro-1-(4-methoxy-benzyl)-1H-pyrazolo[3,4-b]pyridin-3-yl]-ethanol | Gen-22-a | 317 | N.A. |

TABLE III

Illustrative compounds of the invention

| Cpd # | Structure | Name | Mtd (Int) | MW | MS Ms'd |
|---|---|---|---|---|---|
| 1 | 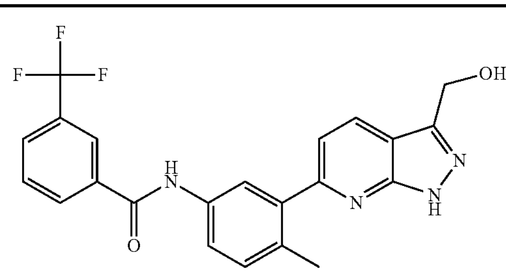 | N-(3-(3-(hydroxymethyl)-1H-pyrazolo[3,4-b]pyridin-6-yl)-4-methylphenyl)-3-(trifluoromethyl)benzamide | Cial. prod | 426 | N.A. |

TABLE III-continued

Illustrative compounds of the invention

| Cpd # | Structure | Name | Mtd (Int) | MW | MS Ms'd |
|---|---|---|---|---|---|
| 2 | 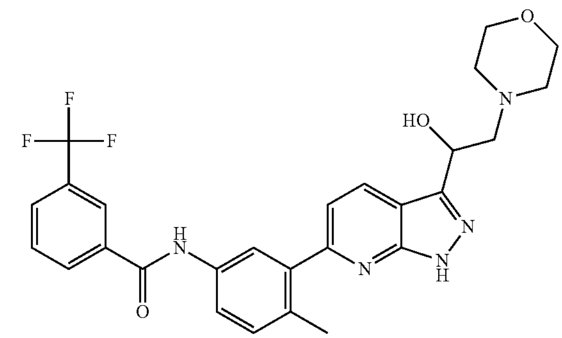 [SMILES: Cc1ccc(NC(=O)c2cccc(C(F)(F)F)c2)cc1-c1ccc2c(C(O)CN3CCOCC3)n[nH]c2n1] | N-{3-[3-(1-Hydroxy-2-morpholin-4-yl-ethyl)-1H-pyrazolo[3,4-b]pyridin-6-yl]-4-methyl-phenyl}-3-trifluoromethyl-benzamide | Gen-25-b I1 | 525 | 526 (M + H) |
| 3 | 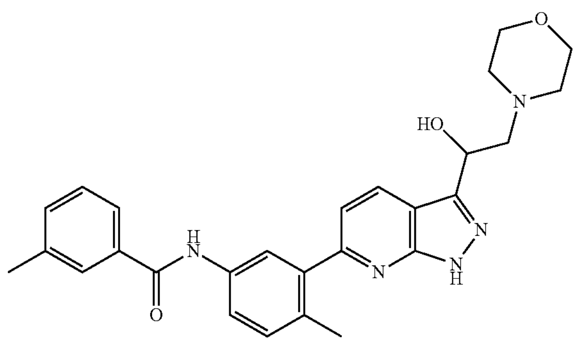 [SMILES: Cc1cccc(C(=O)Nc2ccc(C)c(-c3ccc4c(C(O)CN5CCOCC5)n[nH]c4n3)c2)c1] | N-{3-[3-(1-Hydroxy-2-morpholin-4-yl-ethyl)-1H-pyrazolo[3,4-b]pyridin-6-yl]-4-methyl-phenyl}-3-methyl-benzamide | Gen-75-a I1 | 471 | 472 (M + H) |
| 4 | 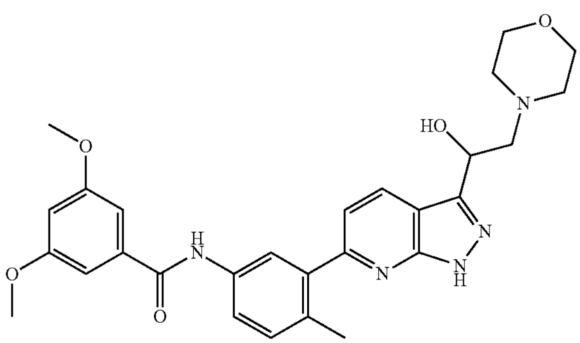 [SMILES: COc1cc(OC)cc(C(=O)Nc2ccc(C)c(-c3ccc4c(C(O)CN5CCOCC5)n[nH]c4n3)c2)c1] | N-{3-[3-(1-Hydroxy-2-morpholin-4-yl-ethyl)-1H-pyrazolo[3,4-b]pyridin-6-yl]-4-methyl-phenyl}-3,5-dimethoxy-benzamide | Gen-64-a I1 | 517 | 518 (M + H) |
| 5 | 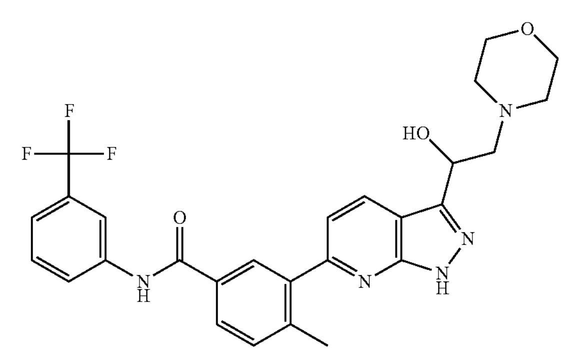 [SMILES: Cc1ccc(C(=O)Nc2cccc(C(F)(F)F)c2)cc1-c1ccc2c(C(O)CN3CCOCC3)n[nH]c2n1] | 3-[3-(1-Hydroxy-2-morpholin-4-yl-ethyl)-1H-pyrazolo[3,4-b]pyridin-6-yl]-4-methyl-N-(3-trifluoromethyl-phenyl)-benzamide | Gen-25-c I1 | 525 | 526 (M + H) |

TABLE III-continued

Illustrative compounds of the invention

| Cpd # | Structure | Name | Mtd (Int) | MW | MS Ms'd |
|---|---|---|---|---|---|
| 6 | 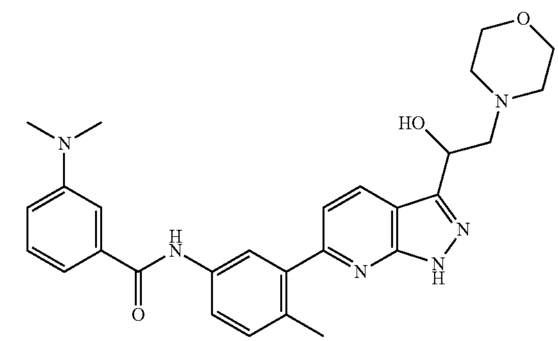 [SMILES: Cc1ccc(NC(=O)c2cccc(N(C)C)c2)cc1-c1ccc2c(C(O)CN3CCOCC3)n[nH]c2n1] | 3-Dimethylamino-N-{3-[3-(1-hydroxy-2-morpholin-4-yl-ethyl)-1H-pyrazolo[3,4-b]pyridin-6-yl]-4-methyl-phenyl}-benzamide | Gen-25-a I1 | 500 | 501 (M + H) |
| 7 | 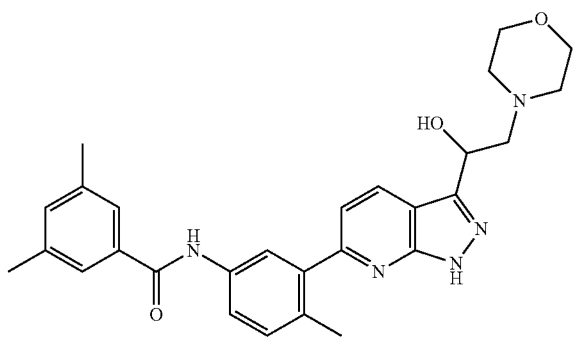 [SMILES: Cc1cc(C)cc(C(=O)Nc2ccc(C)c(-c3ccc4c(C(O)CN5CCOCC5)n[nH]c4n3)c2)c1] | N-{3-[3-(1-Hydroxy-2-morpholin-4-yl-ethyl)-1H-pyrazolo[3,4-b]pyridin-6-yl]-4-methyl-phenyl}-3,5-dimethyl-benzamide | Gen-25-d I1 | 485 | 486 (M + H) |
| 8 | 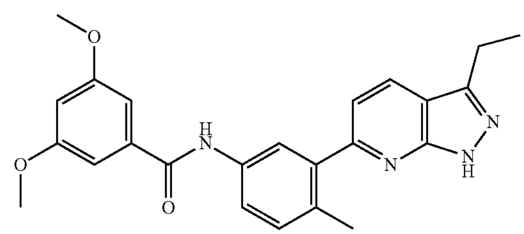 [SMILES: CCc1n[nH]c2nc(-c3cc(NC(=O)c4cc(OC)cc(OC)c4)ccc3C)ccc12] | N-[3-(3-Ethyl-1H-pyrazolo[3,4-b]pyridin-6-yl)-4-methyl-phenyl]-3,5-dimethoxy-benzamide | Gen-28-a See Cpd 8 | 416 | 417 (M + H) |
| 9 | 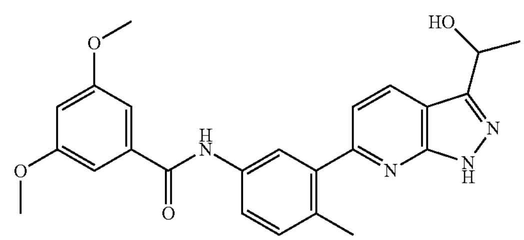 [SMILES: COc1cc(OC)cc(C(=O)Nc2ccc(C)c(-c3ccc4c(C(C)O)n[nH]c4n3)c2)c1] | N-{3-[3-(1-Hydroxy-ethyl)-1H-pyrazolo[3,4-b]pyridin-6-yl]-4-methyl-phenyl}-3,5-dimethoxy-benzamide | Gen-16-a G2 | 432 | 433 (M + H) |
| 10 | 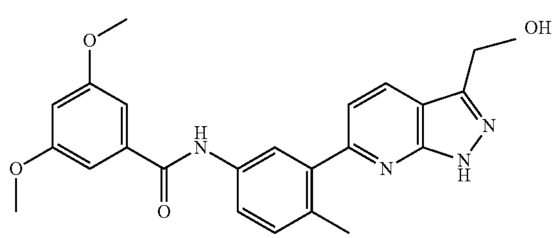 | N-[3-(3-Hydroxymethyl-1H-pyrazolo[3,4-b]pyridin-6-yl)-4-methyl-phenyl]-3,5-dimethoxy-benzamide | Gen-66-a I2 | 418 | 419 (M + H) |

TABLE III-continued

Illustrative compounds of the invention

| Cpd # | Structure | Name | Mtd (Int) | MW | MS Ms'd |
|---|---|---|---|---|---|
| 11 | 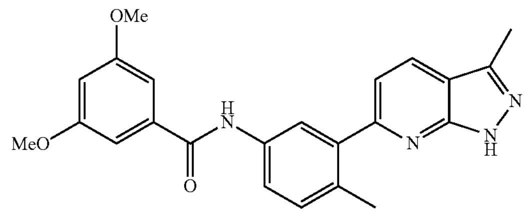 [SMILES: COc1cc(OC)cc(C(=O)Nc2ccc(C)c(-c3ccc4c(C)n[nH]c4n3)c2)c1] | 3,5-Dimethoxy-N-[4-methyl-3-(3-methyl-1H-pyrazolo[3,4-b]pyridin-6-yl)-phenyl]-benzamide | Gen-25-g I2 | 402 | 403 (M + H) |
| 12 | 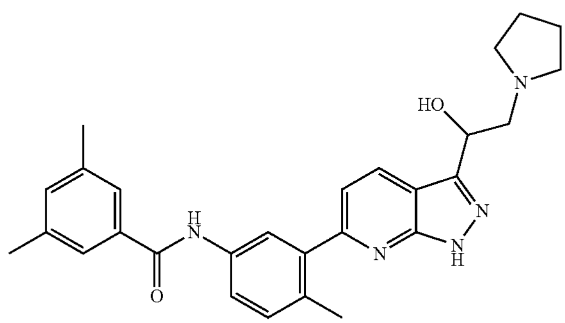 [SMILES: Cc1cc(C)cc(C(=O)Nc2ccc(C)c(-c3ccc4c(C(O)CN5CCCC5)n[nH]c4n3)c2)c1] | N-(3-(3-(1-hydroxy-2-(pyrrolidin-1-yl)ethyl)-1H-pyrazolo[3,4-b]pyridin-6-yl)-4-methylphenyl)-3,5-dimethylbenzamide | Gen-25-h I1 | 469 | 470 M + H |
| 13 | 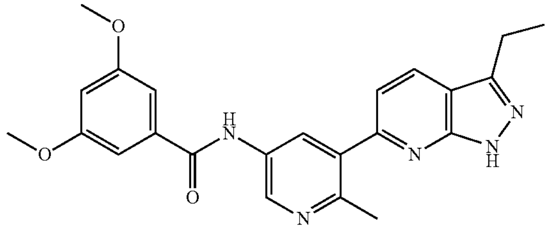 [SMILES: CCc1n[nH]c2nc(-c3cc(NC(=O)c4cc(OC)cc(OC)c4)cnc3C)ccc12] | N-[5-(3-Ethyl-1H-pyrazolo[3,4-b]pyridin-6-yl)-6-methyl-pyridin-3-yl]-3,5-dimethoxy-benzamide | Gen-10-a G1 | 417 | 418 (M + H) |
| 14 | 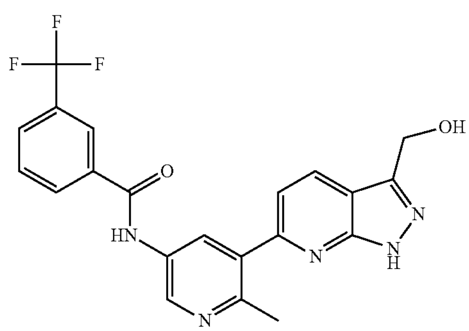 [SMILES: Cc1ncc(NC(=O)c2cccc(C(F)(F)F)c2)cc1-c1ccc2c(CO)n[nH]c2n1] | N-[5-(3-Hydroxymethyl-1H-pyrazolo[3,4-b]pyridin-6-yl)-6-methyl-pyridin-3-yl]-3-trifluoromethyl-benzamide | Gen-77-a I2 | 427 | 428 (M + H) |
| 15 | 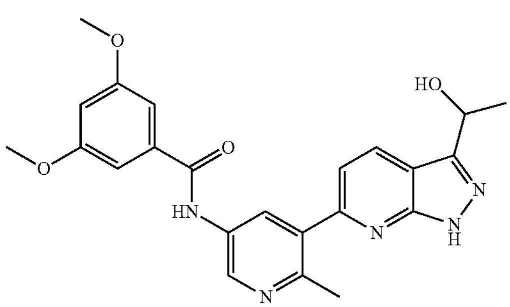 [SMILES: COc1cc(OC)cc(C(=O)Nc2cnc(C)c(-c3ccc4c(C(C)O)n[nH]c4n3)c2)c1] | N-{5-[3-(1-Hydroxy-ethyl)-1H-pyrazolo[3,4-b]pyridin-6-yl]-6-methyl-pyridin-3-yl}-3,5-dimethoxy-benzamide | Gen-79-a I2 | 433 | 434 (M + H) |

TABLE III-continued

Illustrative compounds of the invention

| Cpd # | Structure | Name | Mtd (Int) | MW | MS Ms'd |
|---|---|---|---|---|---|
| 16 | 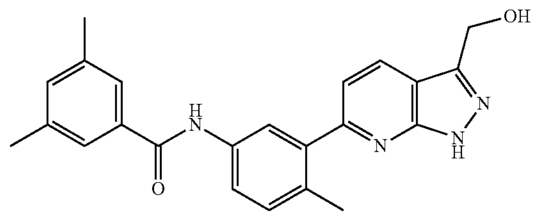 [SMILES: Cc1cc(C)cc(C(=O)Nc2ccc(C)c(-c3ccc4c(CO)n[nH]c4n3)c2)c1] | N-[3-(3-Hydroxymethyl-1H-pyrazolo[3,4-b]pyridin-6-yl)-4-methyl-phenyl]-3,5-dimethyl-benzamide | Gen-28-b I1 | 386 | 387 (M + H) |
| 17 | 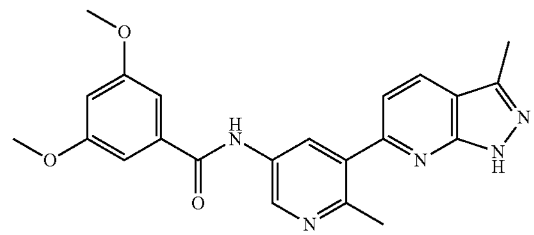 [SMILES: COc1cc(OC)cc(C(=O)Nc2cnc(C)c(-c3ccc4c(C)n[nH]c4n3)c2)c1] | 3,5-Dimethoxy-N-[6-methyl-5-(3-methyl-1H-pyrazolo[3,4-b]pyridin-6-yl)-pyridin-3-yl]-benzamide | Gen-10-b G1 | 403 | 404 (M + H) |
| 18 | 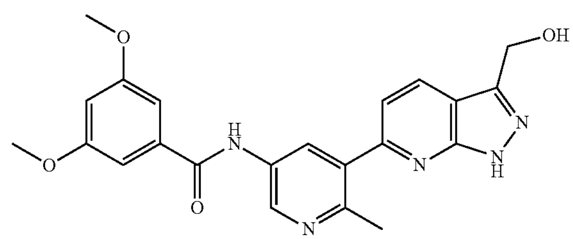 [SMILES: COc1cc(OC)cc(C(=O)Nc2cnc(C)c(-c3ccc4c(CO)n[nH]c4n3)c2)c1] | N-[5-(3-Hydroxymethyl-1H-pyrazolo[3,4-b]pyridin-6-yl)-6-methyl-pyridin-3-yl]-3,5-dimethoxy-benzamide | Gen-80-a I2 | 419 | 420 (M + H) |
| 19 | 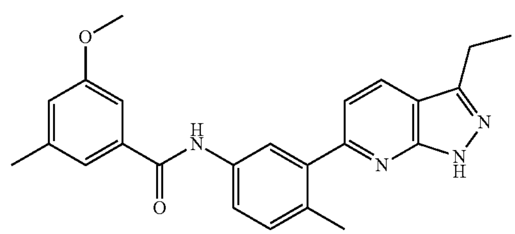 [SMILES: CCc1n[nH]c2nc(-c3cc(NC(=O)c4cc(C)cc(OC)c4)ccc3C)ccc12] | N-[3-(3-Ethyl-1H-pyrazolo[3,4-b]pyridin-6-yl)-4-methyl-phenyl]-3-methoxy-5-methyl-benzamide | Gen-35-a + Gen-41-b B1 | 400 | 401 (M + H) |
| 20 | 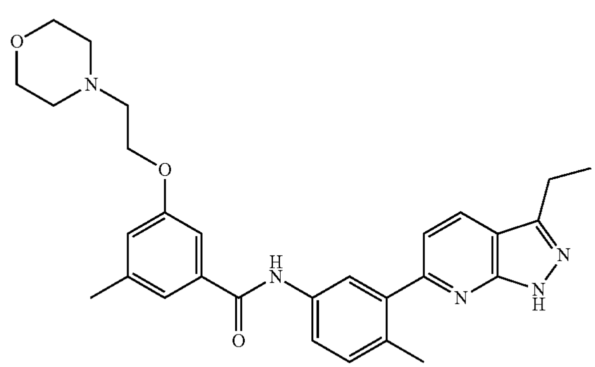 [SMILES: CCc1n[nH]c2nc(-c3cc(NC(=O)c4cc(C)cc(OCCN5CCOCC5)c4)ccc3C)ccc12] | N-[3-(3-Ethyl-1H-pyrazolo[3,4-b]pyridin-6-yl)-4-methyl-phenyl]-3-methyl-5-(2-morpholin-4-yl-ethoxy)-benzamide | Gen-35-a + Gen-63-a B1 | 499 | 500 (M + H) |

TABLE III-continued

Illustrative compounds of the invention

| Cpd # | Structure | Name | Mtd (Int) | MW | MS Ms'd |
|---|---|---|---|---|---|
| 21 | 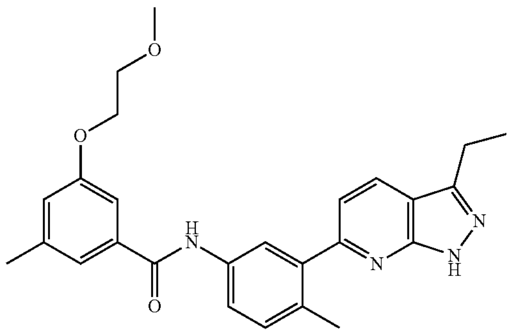 [SMILES: CCc1n[nH]c2nc(-c3cc(NC(=O)c4cc(C)cc(OCCOC)c4)ccc3C)ccc12] | N-[3-(3-Ethyl-1H-pyrazolo[3,4-b]pyridin-6-yl)-4-methyl-phenyl]-3-(2-methoxy-ethoxy)-5-methyl-benzamide | Gen-35-a + Gen-61-a B1 | 444 | 445 (M + H) |
| 22 | 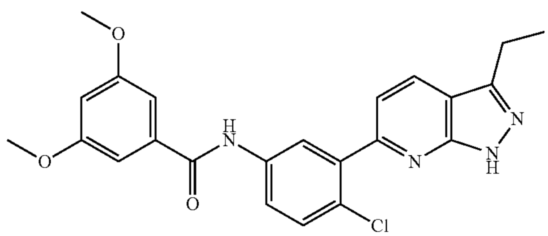 [SMILES: CCc1n[nH]c2nc(-c3cc(NC(=O)c4cc(OC)cc(OC)c4)ccc3Cl)ccc12] | N-[4-Chloro-3-(3-ethyl-1H-pyrazolo[3,4-b]pyridin-6-yl)-phenyl]-3,5-dimethoxy-benzamide | Gen-67-a I1 | 436 | 437 (M + H) |
| 23 | 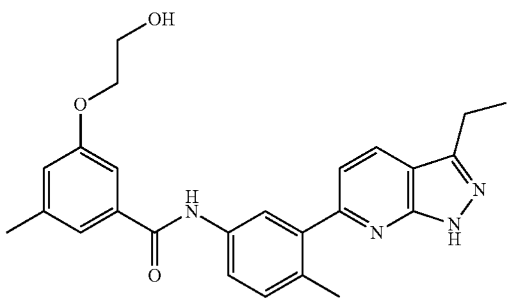 [SMILES: CCc1n[nH]c2nc(-c3cc(NC(=O)c4cc(C)cc(OCCO)c4)ccc3C)ccc12] | N-[3-(3-Ethyl-1H-pyrazolo[3,4-b]pyridin-6-yl)-4-methyl-phenyl]-3-(2-hydroxy-ethoxy)-5-methyl-benzamide | See cpd 23 | 430 | 431 (M + H) |
| 24 | 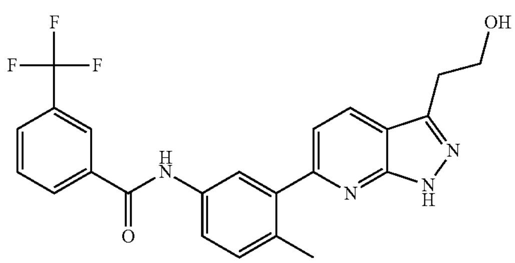 [SMILES: Cc1ccc(NC(=O)c2cccc(C(F)(F)F)c2)cc1-c1ccc2c(CCO)n[nH]c2n1] | N-{3-[3-(2-Hydroxy-ethyl)-1H-pyrazolo[3,4-b]pyridin-6-yl]-4-methyl-phenyl}-3-trifluoromethyl-benzamide | Gen-70-a I1 | 440 | 441 (M + H) |
| 25 | 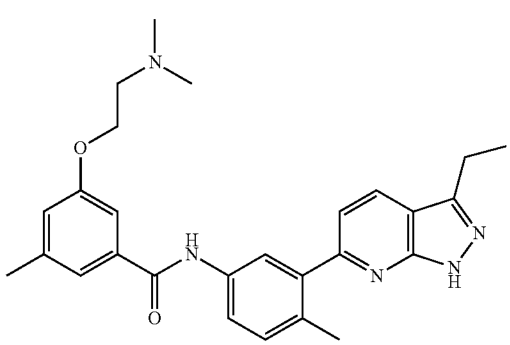 [SMILES: CCc1n[nH]c2nc(-c3cc(NC(=O)c4cc(C)cc(OCCN(C)C)c4)ccc3C)ccc12] | 3-(2-Dimethylamino-ethoxy)-N-[3-(3-ethyl-1H-pyrazolo[3,4-b]pyridin-6-yl)-4-methyl-phenyl]-5-methyl-benzamide | Gen-35-a + Gen-57-a B1 | 457 | 458 (M + H) |

TABLE III-continued

Illustrative compounds of the invention

| Cpd # | Structure | Name | Mtd (Int) | MW | MS Ms'd |
|---|---|---|---|---|---|
| 26 | 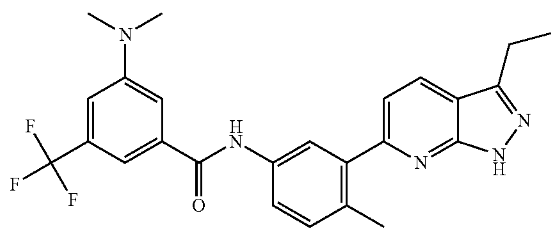 [SMILES: CCc1n[nH]c2nc(-c3cc(NC(=O)c4cc(N(C)C)cc(C(F)(F)F)c4)ccc3C)ccc12] | 3-Dimethylamino-N-[3-(3-ethyl-1H-pyrazolo[3,4-b]pyridin-6-yl)-4-methyl-phenyl]-5-trifluoromethyl-benzamide | Gen-35-a + Gen-69-a B1 | 467 | 468 (M + H) |
| 27 | 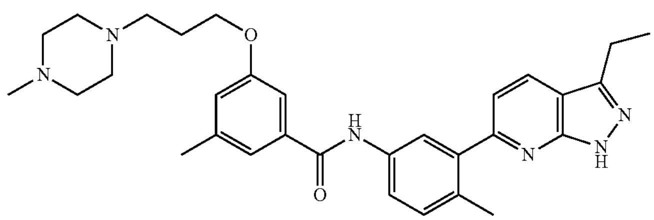 [SMILES: CCc1n[nH]c2nc(-c3cc(NC(=O)c4cc(C)cc(OCCCN5CCN(C)CC5)c4)ccc3C)ccc12] | N-[3-(3-Ethyl-1H-pyrazolo[3,4-b]pyridin-6-yl)-4-methyl-phenyl]-3-methyl-5-[3-(4-methyl-piperazin-1-yl)-propoxy]-benzamide | Gen-35-a + Gen-54-d B1 | 526 | 527 (M + H) |
| 28 | 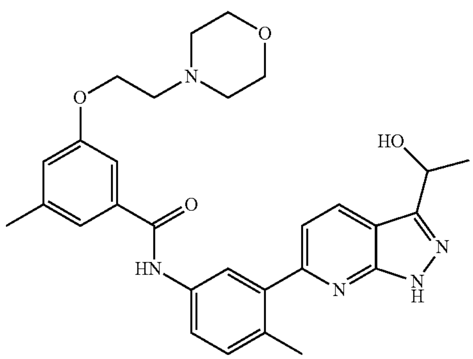 [SMILES: Cc1cc(OCCN2CCOCC2)cc(C(=O)Nc2ccc(C)c(-c3ccc4c(C(C)O)n[nH]c4n3)c2)c1] | N-{3-[3-(1-Hydroxy-ethyl)-1H-pyrazolo[3,4-b]pyridin-6-yl]-4-methyl-phenyl}-3-methyl-5-(2-morpholin-4-yl-ethoxy)-benzamide | Gen-18-b L | 515 | N.A. |
| 29 | 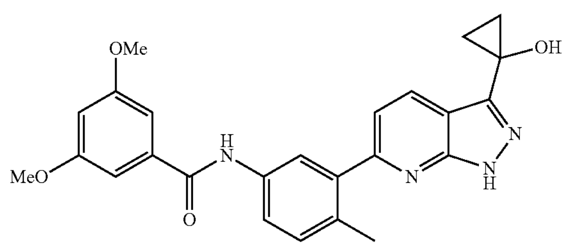 [SMILES: COc1cc(OC)cc(C(=O)Nc2ccc(C)c(-c3ccc4c(C5(O)CC5)n[nH]c4n3)c2)c1] | N-{3-[3-(1-Hydroxy-cyclopropyl)-1H-pyrazolo[3,4-b]pyridin-6-yl]-4-methyl-phenyl}-3,5-dimethoxy-benzamide | Gen-16-d G2 | 444 | 445 (M + H) |
| 30 | 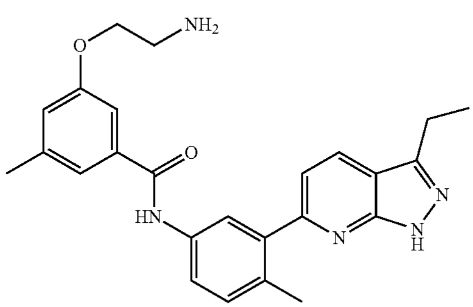 [SMILES: CCc1n[nH]c2nc(-c3cc(NC(=O)c4cc(C)cc(OCCN)c4)ccc3C)ccc12] | 3-(2-Amino-ethoxy)-N-[3-(3-ethyl-1H-pyrazolo[3,4-b]pyridin-6-yl)-4-methyl-phenyl]-5-methyl-benzamide | Gen-55-b G3 | 429 | 430 (M + H) |

TABLE III-continued

Illustrative compounds of the invention

| Cpd # | Structure | Name | Mtd (Int) | MW | MS Ms'd |
|---|---|---|---|---|---|
| 31 | 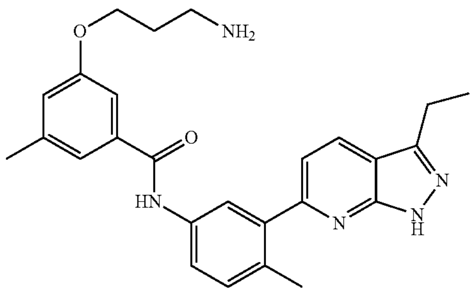 [SMILES: CCc1n[nH]c2nc(-c3cc(NC(=O)c4cc(C)cc(OCCCN)c4)ccc3C)ccc12] | 3-(3-Amino-propoxy)-N-[3-(3-ethyl-1H-pyrazolo[3,4-b]pyridin-6-yl)-4-methyl-phenyl]-5-methyl-benzamide | Gen-55-a G3 | 443 | 444 (M + H) |
| 32 | 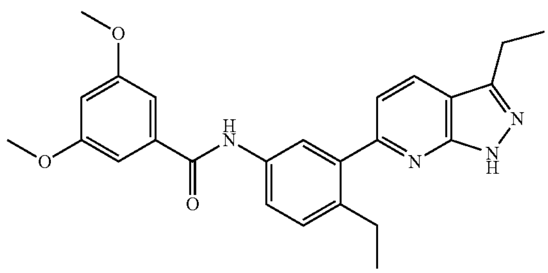 [SMILES: CCc1ccc(NC(=O)c2cc(OC)cc(OC)c2)cc1-c1ccc2c(CC)n[nH]c2n1] | N-[4-Ethyl-3-(3-ethyl-1H-pyrazolo[3,4-b]pyridin-6-yl)-phenyl]-3,5-dimethoxy-benzamide | Gen-67-b I1 | 430 | 431 (M + H) |
| 33 | 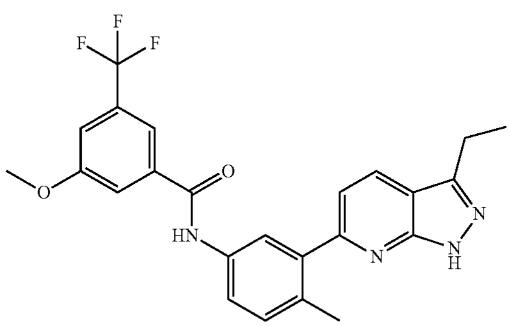 [SMILES: CCc1n[nH]c2nc(-c3cc(NC(=O)c4cc(OC)cc(C(F)(F)F)c4)ccc3C)ccc12] | N-[3-(3-Ethyl-1H-pyrazolo[3,4-b]pyridin-6-yl)-4-methyl-phenyl]-3-methoxy-5-trifluoromethyl-benzamide | Gen-35-a + Gen-50-a K | 454 | 455 (M + H) |
| 34 | 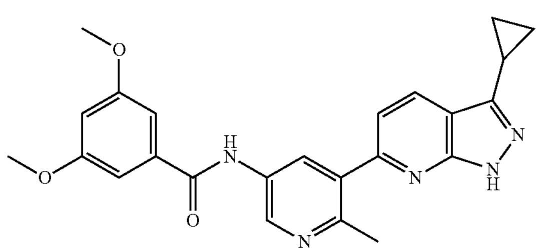 [SMILES: COc1cc(OC)cc(C(=O)Nc2cnc(C)c(-c3ccc4c(C5CC5)n[nH]c4n3)c2)c1] | N-(5-(3-cyclopropyl-1H-pyrazolo[3,4-b]pyridin-6-yl)-6-methylpyridin-3-yl)-3,5-dimethoxybenzamide | Gen-73-a I1 | 429 | 430 (M + H) |
| 35 | 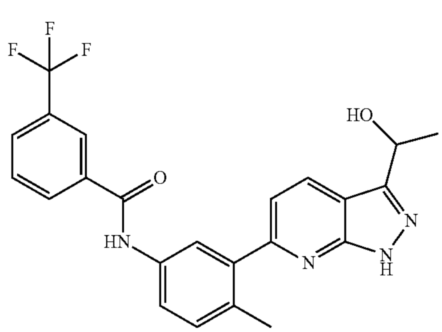 [SMILES: Cc1ccc(NC(=O)c2cccc(C(F)(F)F)c2)cc1-c1ccc2c(C(C)O)n[nH]c2n1] | N-{3-[3-(1-Hydroxy-ethyl)-1H-pyrazolo[3,4-b]pyridin-6-yl]-4-methyl-phenyl}-3-trifluoromethyl-benzamide | Gen-18-a L | 440 | 441 (M + H) |

TABLE III-continued

Illustrative compounds of the invention

| Cpd # | Structure | Name | Mtd (Int) | MW | MS Ms'd |
|---|---|---|---|---|---|
| 36 | 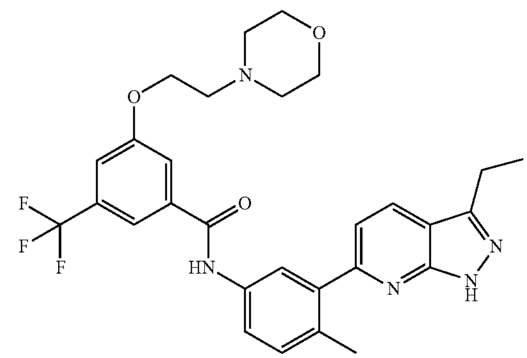 [SMILES: CCc1n[nH]c2nc(-c3cc(NC(=O)c4cc(OCCN5CCOCC5)cc(C(F)(F)F)c4)ccc3C)ccc12] | N-[3-(3-Ethyl-1H-pyrazolo[3,4-b]pyridin-6-yl)-4-methyl-phenyl]-3-(2-morpholin-4-yl-ethoxy)-5-trifluoromethyl-benzamide | Gen-35-a + Gen-49-a K | 553 | 554 (M + H) |
| 37 | 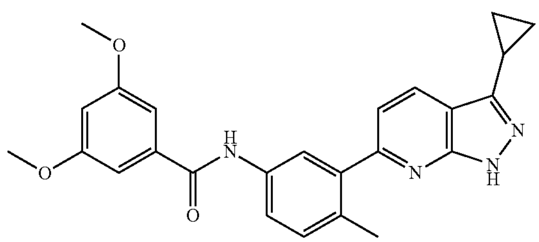 [SMILES: COc1cc(OC)cc(C(=O)Nc2ccc(C)c(-c3ccc4c(C5CC5)n[nH]c4n3)c2)c1] | N-(3-(3-cyclopropyl-1H-pyrazolo[3,4-b]pyridin-6-yl)-4-methylphenyl)-3,5-dimethoxybenzamide | Gen-71-a G1 | 428 | 429 (M + H) |
| 38 | 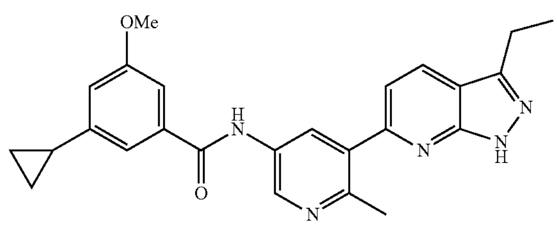 [SMILES: CCc1n[nH]c2nc(-c3cc(NC(=O)c4cc(OC)cc(C5CC5)c4)cnc3C)ccc12] | 3-Cyclopropyl-N-[5-(3-ethyl-1H-pyrazolo[3,4-b]pyridin-6-yl)-6-methyl-pyridin-3-yl]-5-methoxy-benzamide | Gen-13-a + Gen-39-a K | 427 | 428 (M + H) |
| 39 | 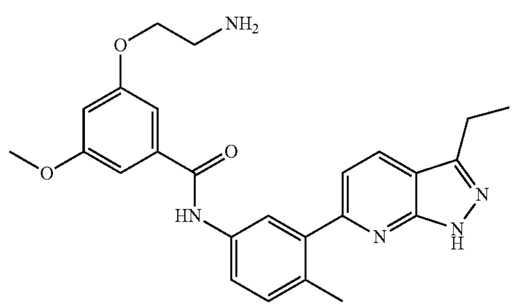 [SMILES: CCc1n[nH]c2nc(-c3cc(NC(=O)c4cc(OC)cc(OCCN)c4)ccc3C)ccc12] | 3-(2-Amino-ethoxy)-N-[3-(3-ethyl-1H-pyrazolo[3,4-b]pyridin-6-yl)-4-methyl-phenyl]-5-methoxy-benzamide | Gen-47-d G3 | 445 | 446 (M + H) |
| 40 | 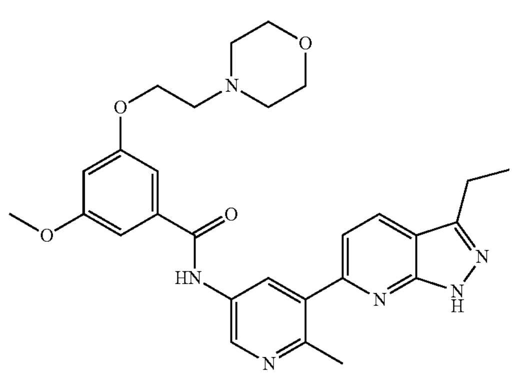 [SMILES: CCc1n[nH]c2nc(-c3cc(NC(=O)c4cc(OC)cc(OCCN5CCOCC5)c4)cnc3C)ccc12] | N-[5-(3-Ethyl-1H-pyrazolo[3,4-b]pyridin-6-yl)-6-methyl-pyridin-3-yl]-3-methoxy-5-(2-morpholin-4-yl-ethoxy)-benzamide | Gen-13-a + Gen-39-c B1 | 516 | 517 (M + H) |

TABLE III-continued

Illustrative compounds of the invention

| Cpd # | Structure | Name | Mtd (Int) | MW | MS Ms'd |
|---|---|---|---|---|---|
| 41 | 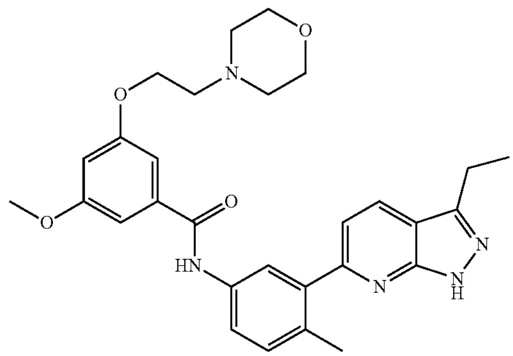 [SMILES: CCc1n[nH]c2nc(-c3cc(NC(=O)c4cc(OC)cc(OCCN5CCOCC5)c4)ccc3C)ccc12] | N-[3-(3-Ethyl-1H-pyrazolo[3,4-b]pyridin-6-yl)-4-methyl-phenyl]-3-methoxy-5-(2-morpholin-4-yl-ethoxy)-benzamide | Gen-35-a + Gen-39-c K | 515 | 516 (M + H) |
| 42 | 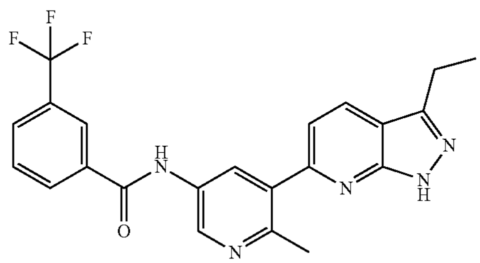 [SMILES: CCc1n[nH]c2nc(-c3cc(NC(=O)c4cccc(C(F)(F)F)c4)cnc3C)ccc12] | N-[5-(3-Ethyl-1H-pyrazolo[3,4-b]pyridin-6-yl)-6-methyl-pyridin-3-yl]-3-trifluoromethyl-benzamide | Gen-13-a + Gen-1-c K | 425 | 426 (M + H) |
| 43 | 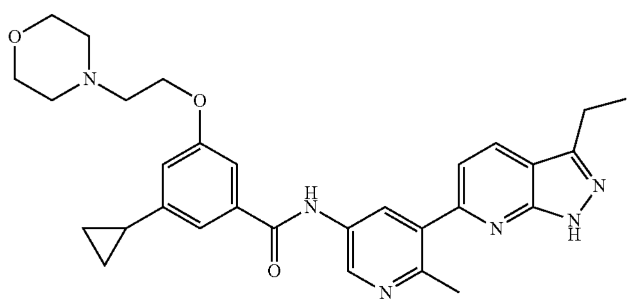 [SMILES: CCc1n[nH]c2nc(-c3cc(NC(=O)c4cc(OCCN5CCOCC5)cc(C5CC5)c4)cnc3C)ccc12] | 3-Cyclopropyl-N-[5-(3-ethyl-1H-pyrazolo[3,4-b]pyridin-6-yl)-6-methyl-pyridin-3-yl]-5-(2-morpholin-4-yl-ethoxy)-benzamide | Gen-13-a + Gen-39-b K | 526 | 527 (M + H) |
| 44 | 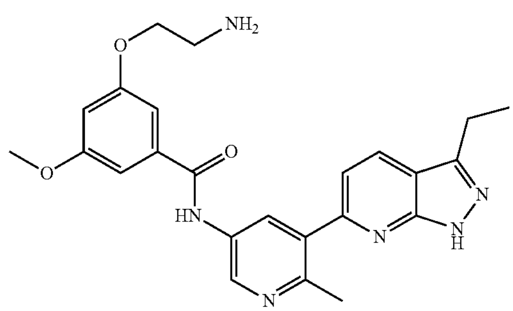 [SMILES: CCc1n[nH]c2nc(-c3cc(NC(=O)c4cc(OC)cc(OCCN)c4)cnc3C)ccc12] | 3-(2-Amino-ethoxy)-N-[5-(3-ethyl-1H-pyrazolo[3,4-b]pyridin-6-yl)-6-methyl-pyridin-3-yl]-5-methoxy-benzamide | Gen-47-c G3 | 446 | 447 (M + H) |
| 45 | 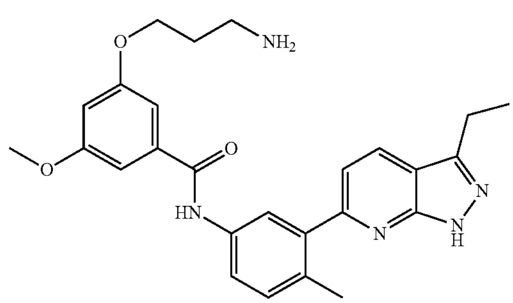 [SMILES: CCc1n[nH]c2nc(-c3cc(NC(=O)c4cc(OC)cc(OCCCN)c4)ccc3C)ccc12] | 3-(3-Amino-propoxy)-N-[3-(3-ethyl-1H-pyrazolo[3,4-b]pyridin-6-yl)-4-methyl-phenyl]-5-methoxy-benzamide | Gen-47-b G3 | 459 | 460 (M + H) |

TABLE III-continued

Illustrative compounds of the invention

| Cpd # | Structure | Name | Mtd (Int) | MW | MS Ms'd |
|---|---|---|---|---|---|
| 46 | 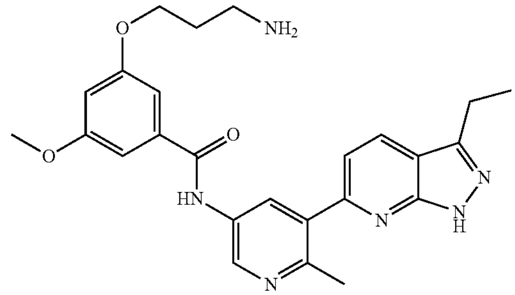 [SMILES: CCc1n[nH]c2nc(-c3cc(NC(=O)c4cc(OC)cc(OCCCN)c4)cnc3C)ccc12] | 3-(3-Amino-propoxy)-N-[5-(3-ethyl-1H-pyrazolo[3,4-b]pyridin-6-yl)-6-methyl-pyridin-3-yl]-5-methoxy-benzamide | Gen-47-a G3 | 460 | 461 (M + H) |
| 47 | 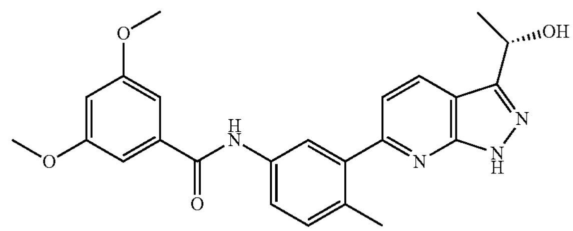 [SMILES: COc1cc(OC)cc(C(=O)Nc2ccc(C)c(-c3ccc4c([C@H](C)O)n[nH]c4n3)c2)c1] | N-{3-[3-((S)-1-Hydroxy-ethyl)-1H-pyrazolo[3,4-b]pyridin-6-yl]-4-methyl-phenyl}-3,5-dimethoxy-benzamide | Gen-16-f G2 | 432 | 433 (M + H) |
| 48 | 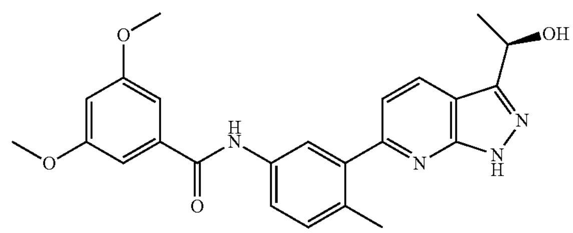 [SMILES: COc1cc(OC)cc(C(=O)Nc2ccc(C)c(-c3ccc4c([C@@H](C)O)n[nH]c4n3)c2)c1] | N-{3-[3-((R)-1-Hydroxy-ethyl)-1H-pyrazolo[3,4-b]pyridin-6-yl]-4-methyl-phenyl}-3,5-dimethoxy-benzamide | Gen-16-e G2 | 432 | 433 (M + H) |
| 49 | 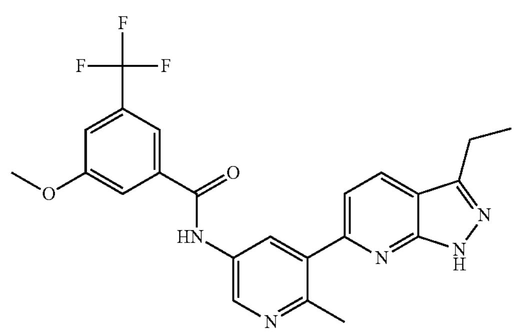 [SMILES: CCc1n[nH]c2nc(-c3cc(NC(=O)c4cc(OC)cc(C(F)(F)F)c4)cnc3C)ccc12] | N-[5-(3-Ethyl-1H-pyrazolo[3,4-b]pyridin-6-yl)-6-methyl-pyridin-3-yl]-3-methoxy-5-trifluoromethyl-benzamide | Gen-13-a + Gen-50-a K | 455 | 456 (M + H) |
| 50 | 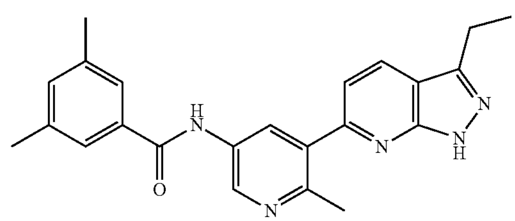 [SMILES: CCc1n[nH]c2nc(-c3cc(NC(=O)c4cc(C)cc(C)c4)cnc3C)ccc12] | N-[5-(3-Ethyl-1H-pyrazolo[3,4-b]pyridin-6-yl)-6-methyl-pyridin-3-yl]-3,5-dimethyl-benzamide | Gen-13-a + Gen-1-b B1 | 385 | 386 (M + H) |
| 51 | 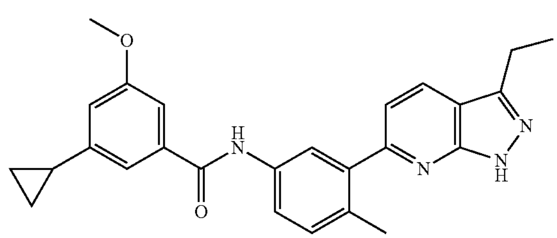 [SMILES: CCc1n[nH]c2nc(-c3cc(NC(=O)c4cc(OC)cc(C5CC5)c4)ccc3C)ccc12] | 3-Cyclopropyl-N-[3-(3-ethyl-1H-pyrazolo[3,4-b]pyridin-6-yl)-4-methyl-phenyl]-5-methoxy-benzamide | Gen-39-a + Gen-35-a K | 426 | 427 (M + H) |

TABLE III-continued

Illustrative compounds of the invention

| Cpd # | Structure | Name | Mtd (Int) | MW | MS Ms'd |
|---|---|---|---|---|---|
| 52 | 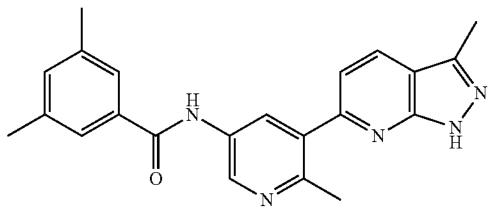 [SMILES: Cc1cc(C)cc(C(=O)Nc2cnc(C)c(-c3ccc4c(C)n[nH]c4n3)c2)c1] | 3,5-Dimethyl-N-[6-methyl-5-(3-methyl-1H-pyrazolo[3,4-b]pyridin-6-yl)-pyridin-3-yl]-benzamide | Gen-10-h G1 | 371 | 372 (M + H) |
| 53 | 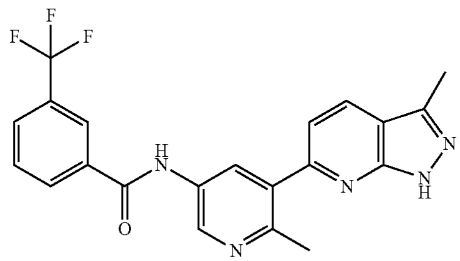 [SMILES: Cc1ncc(NC(=O)c2cccc(C(F)(F)F)c2)cc1-c1ccc2c(C)n[nH]c2n1] | N-[6-Methyl-5-(3-methyl-1H-pyrazolo[3,4-b]pyridin-6-yl)-pyridin-3-yl]-3-trifluoromethyl-benzamide | Gen-10-g G1 | 411 | 412 (M + H) |
| 54 | 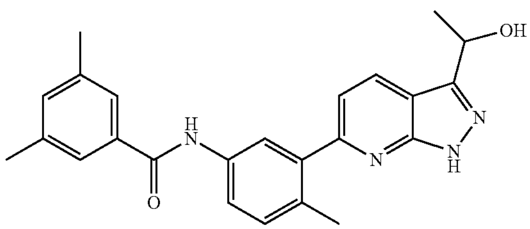 [SMILES: Cc1cc(C)cc(C(=O)Nc2ccc(C)c(-c3ccc4c(C(C)O)n[nH]c4n3)c2)c1] | N-{3-[3-(1-Hydroxy-ethyl)-1H-pyrazolo[3,4-b]pyridin-6-yl]-4-methyl-phenyl}-3,5-dimethyl-benzamide | Gen-28-c I2 | 400 | 401 (M + H) |
| 55 | 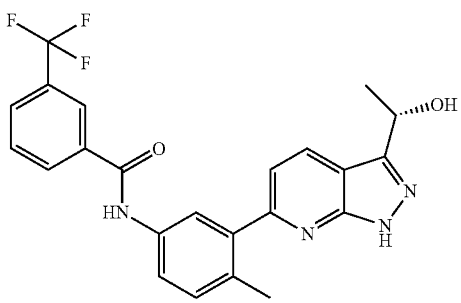 [SMILES: Cc1ccc(NC(=O)c2cccc(C(F)(F)F)c2)cc1-c1ccc2c([C@H](C)O)n[nH]c2n1] | N-{3-[3-((S)-1-Hydroxy-ethyl)-1H-pyrazolo[3,4-b]pyridin-6-yl]-4-methyl-phenyl}-3-trifluoromethyl-benzamide | Gen-16-b See Cpd 55 | 440 | 441 (M + H) |
| 56 | 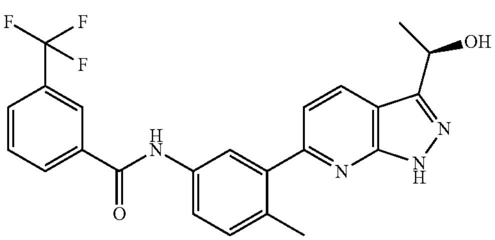 [SMILES: Cc1ccc(NC(=O)c2cccc(C(F)(F)F)c2)cc1-c1ccc2c([C@@H](C)O)n[nH]c2n1] | N-{3-[3-((R)-1-Hydroxy-ethyl)-1H-pyrazolo[3,4-b]pyridin-6-yl]-4-methyl-phenyl}-3-trifluoromethyl-benzamide | Gen-16-c G2 | 440 | 441 (M + H) |

TABLE IV

NMR of illustrative compounds of the invention

| Cpd # | NMR |
|---|---|
| 1 | $^1$H NMR (300 MHz, DMSO-d$_6$): δ ppm 13.41 (s, 1H), 10.55 (s, 1H), 8.38 (1H, d), 8.33 (1H, s), 8.30 (1H, d), 7.99 (1H, d), 7.92-7.91 (1H, m), 7.84-7.78 (2H, m), 7.36 (1H, d), 7.34 (1H, d), 5.40 (1H, t), 4.82 (2H, d), 2.36 (3H, s) |

TABLE IV-continued

NMR of illustrative compounds of the invention

| Cpd # | NMR |
|---|---|
| 2 | $^1$H NMR (400 MHz, CDCl$_3$) δ ppm 12.34 (1 H, s), 8.57 (1 H, s), 8.33 (1 H, d), 8.17 (1H, s), 8.06 (1 H, d), 7.79-7.61 (3 H, m), 7.57 (1 H, t), 7.29-7.25 (1 H, m), 5.18 (1 H, dd), 4.32 (1 H, s), 3.81-3.72 (4 H, m), 3.48 (1 H, q), 2.93 (1 H, m), 2.79-2.67 (3H, m), 2.51-2.46 (2H, m), 2.35 (3H, s). |
| 4 | $^1$H NMR (400 MHz, DMSO-d$_6$): δ ppm 13.11 (1H, s), 9.97 (1H, s), 8.36 (1H, d), 7.85 (1H, s), 7.73-7.71 (1H, m), 7.28-7.23 (2H, m), 7.11-7.10 (2H, m), 6.67 (1H, s), 5.13-5.05 (1H, m), 3.82 (6H, s), 3.67-3.54 (4H, m), 2.85-2.82 (2H, m), 2.56-2.43 (4H, m), 2.30 (3H, s) |
| 5 | $^1$H NMR (400 MHz, DMSO-d$_6$): δ ppm 13.40 (1H, s), 10.55 (1H, s), 8.45 (1H, d), 8.25 (1H, s), 8.12-8.07 (2H, m), 8.00 (1H, d), 7.63-7.59 (1H, m), 7.55 (1H, d), 7.46 (1H, d), 7.41 (1H, d), 5.42-5.41 (1H, m), 5.15-5.13 (1H, m), 3.58-3.56 (4H, m), 2.85-2.81 (2H, m), 2.51-2.46 (4H, m), 2.46 (3H, s) |
| 6 | $^1$H NMR (400 MHz, CDCl$_3$) δ ppm 13.36 (1 H, s), 10.18 (1 H, s), 8.39 (1 H, d), 7.91 (1H, s), 7.77 (1 H, d), 7.33-7.22 (5 H, m), 6.92 (1 H, d), 5.11 (1 H, d), 3.57-3.55 (4 H, m), 2.96 (6 H, s), 2.83-2.79 (2 H, m), 2.60-2.54 (4H, m), 2.33 (3 H, s). |
| 7 | $^1$H NMR (400 MHz, DMSO-d$_6$): δ ppm 13.35 (1H, bs), 10.19 (1H, s), 8.40 (1H, d), 7.91 (1H, s), 7.78-7.76 (1H, m), 7.57 (s, 2H), 7.32-7.29 (2H, m), 7.22 (1H, s), 5.14-5.10 (1H, m), 3.61-3.56 (4H, m), 2.85-2.80 (2H, m), 2.51-2.42 (4H, m), 2.35 (6H, s), 2.33 (3H, s) |
| 8 | $^1$H NMR (400 MHz, CDCl$_3$) δ ppm 13.20 (1 H, s), 10.20 (1 H, s), 8.30 (1H, d), 7.88 (1 H, s), 7.77 (1 H, d), 7.30 (2 H, d), 7.27 (2 H, d), 6.70 (1 H, d), 3.82 (6 H, s ), 2.96 (2 H, q), 2.31 (3 H, s), 1.35 (3 H, t). |
| 9 | $^1$H NMR (300 MHz, DMSO-d$_6$): δ ppm 13.29 (1 H, s), 10.22 (1 H, s), 8.41 (1 H, d), 7.96-7.85 (1 H, m), 7.78 (1 H, dd), 7.41-7.23 (2 H, m), 7.12 (2 H, d), 6.71 (1 H, t), 5.45 (1 H, d), 5.21-5.01 (1 H, m), 3.82 (6 H, s), 2.33 (3 H, s), 1.57 (3 H, d) |
| 10 | $^1$H NMR (400 MHz, DMSO-d$_6$): δ ppm 13.37 (1H, s), 10.21 (1H, s), 8.36 (1H, d), 7.89 (1H, d), 7.77 (1H, d), 7.33-7.31 (2H, m), 7.13-7.12 (2H, m), 6.70 (1H, s), 5.36 (1H, t), 4.81 (2H, s), 3.92 (6H, s), 2.33 (3H, s) |
| 11 | $^1$H NMR (400 MHz, MeOD-d$_4$) δ ppm 8.22 (1H, d), 7.78 (1H, d), 7.67 (1H, dd), 7.29 (1H, d), 7. 27 (1H, d), 7.07 (1H, s), 7.06 (1H, s), 6.66-6.63 (1H, m), 3.81 (6H, s), 2.58 (3H, s), 2.31 (3H, s) |
| 12 | $^1$H NMR (400 MHz, DMSO-d$_6$): δ ppm 13.35 (1H, bs), 10.22 (1H, s), 8.38 (1H, d), 7.91 (1H, s), 7.78-7.76 (1H, m), 7.57 (s, 2H), 7.32-7.29 (2H, m), 7.22 (1H, s), 5.44 (1H, m), 5.03 (1H, m), 2.93 (2H, m), 2.63 (2H, m), 2.35 (6H, s), 2.33 (3H, s), 1.65 (4H, m), |
| 13 | $^1$H NMR (400 MHz, DMSO-d$_6$): δ ppm 10.42 (1 H, s), 8.92 (1 H, d), 8.36 (1 H, d), 8.29 (1 H, d), 7.36 (1 H, d), 7.15 (2 H, d), 6.74 (1 H, app. t), 3.83 (6 H, s), 2.98 (2 H, q), 2.54 (3 H, s), 1.36 (3 H, t) |
| 15 | $^1$H NMR (400 MHz, MeOD-d$_4$) δ ppm 8.94 (1 H, s), 8.57 (1 H, d), 8.40 (1H, s), 7.46 (1 H, d), 7.19 (2H, s), 6.76 (1H, s), 5.32 (1H, q), 3.91 (6H, s ), 2.64 (3H, s), 1.76 (3H, s), 1.36 (1H, t). |
| 16 | $^1$H NMR (400 MHz, MeOD-d$_4$) δ ppm 8.41 (1H, d), 7.81 (1H, d), 7.69 (1H, dd), 7.56-7.53 (2H, m), 7.36 (1H, d), 7.32 (1H, d), 7.22 (1H, s), 4.97 (s, 2H), 2.38 (6H, s), 2.35 (3H, s) |
| 17 | $^1$H NMR (400 MHz, MeOD-d$_4$) δ ppm ppm 8.87 (1 H, d), 8.36-8.30 (2 H, m), 7.39 (1 H, d), 7.13 (2 H, d), 6.70 (1 H, app. t), 3.85 (6 H, s), 2.62 (3 H, s), 2.58 (3 H, s) |
| 18 | $^1$H NMR (400 MHz, DMSO-d$_6$): δ ppm 10.45 (1 H, s), 8.93 (1 H, s), 8.41 (1H, d), 8.30 (1 H, m), 7.41 (1 H, d), 7.15 (2 H, s), 6.74 (1 H, s), 4.81 (2H, s), 3.82 (6 H, s ), 2.54 (3H, s). |
| 19 | $^1$H NMR (400 MHz, MeOD-d$_4$) δ ppm 8.41 (1H, d), 7.81 (1H, d), 7.69 (1H, dd), 7.56-7.53 (2H, m), 7. 36 (1H, d), 7.32 (1H, d), 7.22 (1H, s), 4.97 (s, 2H), 2.38 (6H, s), 2.35 (3H, s) |
| 20 | $^1$H NMR (400 MHz, MeOD-d$_4$) δ ppm 8.28 (1H, d), 7.80 (1H, d), 7.68 (1H, dd), 7.34 (1H, s), 7.32-7.27 (3H, m), 6.96 (1H, s), 4.17 (2H, t), 3.73-3.68 (4H, m), 3.03 (2H, q), 2.80 (2H, t), 2.62-2.56 (4H, m), 2.37 (3H, s), 2.33 (3H, s), 1.42 (3H, t) |
| 21 | $^1$H NMR (300 MHz, MeOD-d$_4$) δ ppm 8.30 (1H, d), 7.80 (1H, d), 7.69 (1H, dd), 7.39-7.27 (4H, m), 6.98 (1H, s), 4.20-4.13 (2H, m), 3.79-3.72 (2H, m), 3.43 (3H, s), 3.04 (2H, q), 2.39 (3H, s), 2.34 (3H, s), 1.43 (3H, t) |
| 22 | $^1$H NMR (400 MHz, MeOD-d$_4$) δ ppm 8.31 (1H, d), 7.98 (1H, d), 7.84 (1H, dd), 7.53 (1H, d), 7.44 (1H, d), 7.11-7.08 (2H, m), 6.70-6.67 (1H, m), 3.84 (3H, s), 3.05 (2H, q), 1.43 (3H, t) |
| 23 | $^1$H NMR (400 MHz, CDCl$_3$) δ ppm 8.53 (1H, s), 8.14 (1H, d), 7.80 (1H, dd), 7.75 (1H, d), 7.34 (1H, d), 7.31 (1H, d), 7.27 (1H, m), 6.91 (1H, s), 4.12 (2H, t), 3.99 (2H, t), 2.99 (2H, q), 2.40 (3H, s), 2.38 (3H, s), 1.42 (3H, t) |
| 24 | $^1$H NMR (400 MHz, CDCl$_3$) δ ppm 8.15 (1H, s), 8.11 (1H, d), 8.06 (1H, d), 7.74-7.67 (2H, m), 7.58-7.51 (2H, m), 7.23 (1H, d), 7.19 (1H, d), 3.94 (2H, t), 3.68 (1H, bs), 3.14 (2H, t), 2.24 (3H, s) |
| 25 | $^1$H NMR (400 MHz, MeOD-d$_4$) δ ppm 8.31 (1H, d), 7.80 (1H, d), 7.69 (1H, dd), 7.36 (1H, s), 7.34-7.29 (3H, m), 6.99 (1H, s), 4.17 (2H, t), 3.04 (2H, q), 2.82 (2H, t), 2.39 (3H, s), 2.37 (6H, s), 2.34 (3H, s), 1.43 (3H, t) |

TABLE IV-continued

NMR of illustrative compounds of the invention

| Cpd # | NMR |
|---|---|
| 26 | $^1$H NMR (400 MHz, DMSO-$d_6$): δ ppm 13.22 (1H, s), 10.37 (1H, s), 8.31 (1H, d), 7.88-7.87 (1H, m), 7.79 (1H, d), 7.51 (1H, s), 7.48 (1H, s), 7.32-7.07 (2H, m), 7.07 (1H, s), 3.04 (6H, s), 2.96 (2H, q), 2.34 (3H, s), 1.35 (3H, t) |
| 27 | $^1$H NMR (400 MHz, MeOD-$d_4$) δ ppm 8.32 (1H, d), 7.81 (1H, d), 7.70 (1H, dd), 7.37-7.31 (3H, m), 7.29 (1H, s), 6.97 (1H, s), 4.09 (2H, t), 3.06 (2H, q), 2.82 (2H, t), 2.77-2.40 (8H, m), 2.40 (3H, s), 2.36 (3H, s), 2.29 (3H, s), 2.05-1.96 (2H, m), 1.44 (3H, t) |
| 28 | $^1$H NMR (400 MHz, CDCl$_3$) δ ppm 8.46 (1H, bs), 8.35 (1H, d), 7.88 (1H, d), 7.71 (1H, d), 7.37-7.27 (4H, m), 6.90 (1H, s), 5.26 (q, 1H), 4.16 (2H, t), 3.77-3.69 (4H, m), 2.81 (2H, t), 2.62-2.54 (4H, m), 2.40 (3H, s), 2.39 (3H, s), 1.63 (3H, d) |
| 29 | $^1$H NMR (300 MHz, DMSO-$d_6$): δ ppm 13.24 (1 H, s), 10.21 (1 H, s), 8.46 (1 H, d), 7.89 (1 H, d), 7.78 (1 H, dd), 7.37-7.23 (2 H, m), 7.12 (2 H, d), 6.71 (1 H, app. t), 6.36 (1 H, s), 3.82 (6 H, s), 2.34 (3 H, s), 1.20-1.10 (4 H, m) |
| 30 | $^1$H NMR (400 MHz, CDCl$_3$) δ ppm 8.44 (1H, bs), 8.15 (1H, d), 7.85 (1H, d), 7.78 (1H, d), 7.36 (1H, d), 7.35 (1H, d), 7.29-7.26 (2H, m), 6.92 (1H, s), 4.06 (2H, t), 3.12 (2H, t), 2.99 (2H, q), 2.43 (3H, s), 2.40 (3H, s), 1.42 (3H, t) |
| 31 | $^1$H NMR (400 MHz, CDCl$_3$) δ ppm 8.56 (1H, bs), 8.14 (1H, d), 7.82 (1H, d), 7.76-7.73 (1H, m), 7.37-7.31 (2H, m), 7.22 (2H, d), 6.86 (1H, s), 4.06 (2H, t), 3.00 (2H, q), 2.89 (2H, t), 2.41 (3H, s), 2.36 (3H, s), 1.94 (2H, qt), 1.42 (3H, t) |
| 32 | $^1$H NMR (400 MHz, CDCl$_3$) δ ppm 11.88 (1H, bs), 8.49 (1H, s), 8.15 (1H, d), 7.95 (1H, dd), 7.71 (1H, d), 7.41 (1H, d), 7.35 (1H, d), 7.06 (1H, s), 7.0 (1H, s), 6.66-6.64 (1H, m), 3.87 (6H, s), 2.96 (2H, q), 2.80 (2H, q), 1.39 (3H, t), 1.16 (3H, t) |
| 33 | $^1$H NMR (400 MHz, CDCl$_3$) δ ppm 8.65 (1H, bs), 8.17 (1H, d), 7.93 (1H, d), 7.79 (1H, d), 7.71 (1H, s), 7.67-7.65 (1H, m), 7.38 (1H, d), 7.37 (1H, d), 7.33-7.31 (1H, m), 3.94 (3H, s), 2.92 (2H, q), 2.45 (3H, s), 1.37 (2H, t) |
| 34 | $^1$H NMR (400 MHz, CDCl$_3$) δ ppm 11.96 (1H, bs), 8.91 (1H, s), 8.56 (1H, s), 8.36 (1H, s), 8.19 (1H, d), 7.36 (1H, d), 7.10-7.04 (2H, m), 6.62 (1H, s), 3.84 (6H, s), 2.67 (3H, s), 2.31-2.22 (1H, m), 1.18-1.12 (2H, m), 1.12-1.04 (2H, m) |
| 35 | $^1$H NMR (300 MHz, MeOD-$d_4$) δ ppm 8.48 (1 H, d), 8.27 (1 H, bs), 8.20 (1 H, bd), 7.89 (1 H, bd), 7.83 (1 H, d), 7.77-7.67 (2 H, m), 7.35 (2 H, d), 5.25 (1 H, q), 2.36 (3 H, s), 1.70 (3 H, d) |
| 36 | $^1$H NMR (300 MHz, MeOD-$d_4$) δ ppm 8.31 (1H, d), 7.84 (1H, s), 7.82 (1H, d), 7.78-7.75 (1H, m), 7.72 (1H, dd), 7.42 (1H, s), 7.34 (1H, d), 7.32 (1H, d), 4.29 (2H, t), 3.74-3.68 (4H, m), 3.05 (2H, q), 2.86 (2H, t), 2.64-2.58 (4H, m), 2.35 (3H, s), 1.43 (3H, t) |
| 37 | $^1$H NMR (300 MHz, CDCl$_3$) δ ppm 8.75 (1H, s), 8.12 (1H, d), 7.95 (1H, dd), 7.77 (1H, d), 7.36 (1H, s), 7.33 (1H, s), 7.10-7.07 (2H, m), 6.64-6.61 (1H, m), 3.84 (6H, s), 2.43 (3H, s), 2.19-2.09 (1H, m), 1.11-1.03 (2H, m), 1.02-0.92 (2H, m) |
| 38 | $^1$H NMR (400 MHz, MeOD-$d_4$) δ ppm 8.93 (1H, d), 8.41 (1H, d), 8.39 (1H, s), 7.47 (1H, d), 7.35-7.33 (1H, m), 7.33-7.31 (1H, m), 6.93-6.91 (1H, m), 3.90 (3H, s), 3.11 (2H, q), 2.63 (3H, s), 2.06-1.99 (1H, m), 1.49 (3H, t), 1.09-1.03 (2H, m), 0.85-0.80 (2H, m) |
| 39 | $^1$H NMR (300 MHz, MeOD-$d_4$) δ ppm 8.33 (1H, d), 7.82 (1H, d), 7.72 (1H, dd), 7.36 (1H, d), 7.35 (1H, d), 7.19-7.14 (2H, m), 6.79-6.75 (1H, m), 4.19 (2H, t), 3.88 (3H, s), 3.80 (2H, t), 3.07 (2H, q), 2.37 (3H, s), 1.45 (3H, t) |
| 41 | $^1$H NMR (300 MHz, CDCl$_3$) δ ppm 11.77 (1H, bs), 8.40 (1H, s), 8.13 (1H, d), 7.84 (1H, dd), 7.73 (1H, d), 7.34 (1H, s), 7.31 (1H, s), 7.05-7.01 (2H, m), 6.64-6.61 (1H, m), 4.18-4.12 (2H, m), 3.83 (3H, s), 3.77-3.71 (4H, m), 2.96 (2H, q), 2.81 (2H, t), 2.66-2.6 (4H, m), 2.40 (3H, s), 1.38 (3H, t) |
| 42 | $^1$H NMR (300 MHz, MeOD-$d_4$) δ ppm 8.92 (1H, d), 8.40 (1H, d), 8.38 (1H, d), 8.33 (1H, s), 8.27 (1H, d), 7.94 (1H, d), 7.80-7.74 (1H, m), 7.41 (1H, d), 3.08 (2H, q), 2.61 (3H, s), 1.46 (3H, t) |
| 43 | $^1$H NMR (400 MHz, MeOD-$d_4$) δ ppm 8.94 (1H, d), 8.41 (1H, d), 8.41 (1H, s), 7.44 (1H, d), 7.38-7.36 (1H, m), 7.35-7.33 (1H, m), 6.95 (1H, m), 4.26 (2H, t), 3.78 (4H, m), 3.12 (2H, q), 2.88 (2H, t), 2.70-2.65 (4H, m), 2.64 (3H, s), 2.06-2.00 (1H, m), 1.50 (3H, t), 1.10-1.05 (2H, m), 0.86-0.81 (2H, m) |
| 44 | $^1$H NMR (300 MHz, MeOD-$d_4$) δ ppm 8.88 (1H, d), 8.36 (1H, d), 8.34 (1H, d), 7.38 (1H, d), 7.18-7.13 (2H, m), 6.77-6.74 (1H, m), 4.09 (2H, t), 3.86 (3H, s), 3.11-3.01 (2H, m), 2.84 (2H, q), 2.58 (3H, s), 1.43 (3H, t) |
| 45 | $^1$H NMR (400 MHz, CDCl$_3$) δ ppm 8.31 (1H, d), 7.81 (1H, d), 7.71 (1H, dd), 7.34 (1H, d), 7.33 (1H, d), 7.11 (2H, d), 6.70 (1H, m), 4.13 (2H, t), 3.86 (3H, s), 3.06 (2H, q), 2.90 (2H, t), 2.36 (3H, s), 1.99 (2H, qt), 1.45 (3H, t) |
| 46 | $^1$H NMR (400 MHz, DMSO-$d_6$): δ ppm 10.53 (1H, bs), 8.96-8.92 (1H, m), 8.35 (1H, d), 8.33-8.29 (1H, m), 7.36 (1H, d), 7.21-7.15 (1H, m), 7.12 (1H, s), 6.80-6.68 (1H, m), 4.13-4.02 (2H, m), 3.81 (3H, s), 2.95 (2H, q), 2.53 (3H, s), 1.88-1.76 (2H, m), 1.35 (2H, t), 0.98 (3H, t) |
| 47 | $^1$H NMR (400 MHz, CDCl$_3$) δ ppm 8.73 (1H, s), 8.32 (1H, d), 7.96 (1H, d), 7.65-7.62 (1H, m), 7.33-7.26 (2H, m), 7.06 (1H, d), 6.63-6.61 (1H, m), 5.22-5.15 (1H, m), 3.84 (6H, s), 2.41 (3H, s), 1.65 (3H, d) |
| 48 | $^1$H NMR (400 MHz, CDCl$_3$) δ ppm 12.86 (1H, bs), 8.72 (1H, s), 8.32 (1H, d), 7.96 (1H, d), 7.66-7.62 (1H, m), 7.34-7.27 (2H, m), 7.06 (1H, d), 6.64-6.62 (1H, m), 5.23-5.15 (1H, m), 3.85 (6H, s), 2.42 (3H, s), 1.70 (2H, s), 1.65 (3H, d) |

TABLE IV-continued

NMR of illustrative compounds of the invention

| Cpd # | NMR |
|---|---|
| 50 | $^1$H NMR (400 MHz, DMSO-$d_6$): δ ppm 10.41 (1 H, bs), 8.92 (1 H, bd), 8.36 (1 H, d), 8.31 (1 H, bd), 7.60 (2 H, s), 7.36 (1 H, d), 7.24 (1 H, s), 2.98 (2 H, q), 2.53 (3 H, s), 2.36 (6 H, s), 1.36 (3 H, t) |
| 51 | $^1$H NMR (300 MHz, DMSO-$d_6$): δ ppm 13.21 (1H, s), 10.18 (1H, s), 8.30 (1H, d), 7.87 (1H, d), 7.77 (1H, dd), 7.33-7.22 (4H, m), 6.86-6.83 (1H, m), 3.81 (3H, s), 2.97 (2H, q), 2.33 (3H, s), 2.03-1.93 (1H, m), 1.35 (3H, t), 1.02-0.94 (2H, m), 0.81-0.74 (2H, m) |
| 52 | $^1$H NMR (300 MHz, DMSO-$d_6$): δ ppm 13.30 (1H, s), 10.40 (1H, s), 8.95-8.88 (1H, m), 8.36-8.25 (2H, m), 7.60 (2H, s), 7.36 (1H, d), 7.24 (1H, s), 3.32 (6H, s), 2.36 (6H, s) |
| 53 | $^1$H NMR (300 MHz, DMSO-$d_6$): δ ppm 13.32 (1H, bs), 10.74 (1H, bs), 8.95 (1H, d), 8.38-8.29 (4H, m), 8.01 (1H, d), 7.82 (1H, d), 7.40 (1H, d), 2.56 (6H, s) |
| 54 | $^1$H NMR (300 MHz, MeOD-$d_4$) δ ppm 8.27 (1H, d), 7.61 (1H, d), 7.49 (1H, dd), 7.34 (2H, s), 7.13 (1H, d), 7.11 (1H, d), 7.02 (1H, s), 5.05 (1H, q), 3.14 (1H, s), 2.18 (6H, s), 2.14 (3H, s), 1.49 (3H, d) |
| 55 | $^1$H NMR (300 MHz, MeOD-$d_4$) δ ppm 8.45 (1 H, d), 8.25 (1 H, bs), 8.18 (1 H, bd), 7.90-7.80 (2 H, m), 7.75-7.63 (2 H, m), 7.31 (2 H, d), 5.26 (1 H, q), 2.33 (3 H, s), 1.69 (3 H, d) |
| 56 | $^1$H NMR (300 MHz, MeOD-$d_4$) δ ppm 8.48 (1 H, d), 8.27 (1 H, bs), 8.21 (1 H, bd), 7.89 (1 H, bd), 7.84 (1 H, d), 7.78-7.67 (2 H, m), 7.35 (2 H, d), 5.25 (1 H, q), 2.36 (3 H, s), 1.70 (3 H, d) |

Compound A was prepared as disclosed in US 2010/0113415

TABLE V

Comparative compounds

| Cpd # | Structure | Name |
|---|---|---|
| A | [structure] | N-(3-(3-amino-4-methyl-1H-pyrazolo[3,4-b]pyridin-6-yl)-4-methylphenyl)-3-(trifluoromethyl)benzamide |

BIOLOGICAL EXAMPLES

Example 4

In Vitro Assays

4.1. EphA2 Assay

Inhibition of EphA2 (UniProt Ref: P29317) by a test compound is determined by a commercially available Reaction Biology proprietary nanoliter radioactive HotSpot$^{SM}$ assay (Reaction Biology, One great valley parkway, Suite 2, Malvern Pa., 19355, USA). The principle of the assay consists of the measurement of incorporated $^{33}$P into poly[Glu:Tyr] (4:1) (0.2 mg/mL) when the substrate is phosphorylated by the enzyme using [$^{33}$P]-γ-ATP and ATP (10 μM).

To determine the IC$_{50}$, a serial dilution of compound is tested starting from 10, or 3 μM (highest dilution) with a 1/3 dilution.

TABLE VI

EphA2 potency for illustrative compounds of the invention

| Cpd # | IC$_{50}$ |
|---|---|
| 1 | **** |
| 2 | ** |
| 2 | ** |
| 4 | * |
| 5 | **** |
| 6 | ** |
| 7 | *** |
| 9 | *** |
| 10 | **** |
| 11 | **** |
| 13 | ** |
| 16 | **** |
| 17 | ** |
| 19 | **** |
| 20 | **** |
| 21 | *** |
| 22 | *** |
| 23 | **** |
| 25 | **** |
| 26 | ** |

TABLE VI-continued

EphA2 potency for illustrative compounds of the invention

| Cpd # | IC$_{50}$ |
|---|---|
| 28 | *** |
| 29 | ** |
| 30 | **** |
| 31 | **** |
| 32 | ** |
| 33 | **** |
| 35 | *** |
| 36 | **** |
| 38 | **** |
| 39 | **** |
| 41 | **** |
| 42 | ** |
| 43 | **** |
| 44 | ** |
| 45 | **** |
| 46 | **** |
| 47 | **** |
| 48 | *** |
| 50 | ** |
| 51 | **** |
| 52 | **** |
| 53 | **** |
| 54 | **** |
| 55 | **** |
| 56 | **** |

\* >100 nM
\*\* >50-100 nM
\*\*\* >25-50 nM
\*\*\*\* 0.01-25 nM

TABLE VII

EphA2 potency for comparative compounds

| Cpd | IC$_{50}$ |
|---|---|
| A | **** |

4.2. EphA4 Assay

Inhibition of EphA4 (UniProt Ref: P54764) by a test compound is determined by a commercially available Reaction Biology proprietary nanoliter radioactive HotSpot$^{SM}$ assay (Reaction Biology, One great valley parkway, Suite 2, Malvern Pa., 19355, USA). The principle of the assay consists of the measurement of incorporated $^{33}$P into poly[Glu:Tyr] (4:1) (0.2 mg/mL) when the substrate is phosphorylated by the enzyme using [$^{33}$P]-γ-ATP and ATP (10 μM).

To determine the IC$_{50}$, a serial dilution of compound is tested starting from 10 or 3 μM (highest dilution) with a 1/3 dilution.

TABLE VIII

EphA4 potency for illustrative compounds of the invention

| Cpd | IC$_{50}$ |
|---|---|
| 2 | **** |
| 9 | ** |
| 29 | * |
| 47 | ** |
| 55 | *** |

\* >100 nM
\*\* >50-100 nM
\*\*\* >25-50 nM
\*\*\*\* 0.01-25 nM

4.3. EphA7 Assay

The principle of the assay consists of the measurement of incorporated $^{33}$P into the substrate poly GT when phosphorylated by the enzyme EphA7 using [$^{33}$P]-γ-ATP and ATP. Unincorporated $^{33}$P is removed by loading the samples on a filter plate (using a harvester, Perkin Elmer) and 6 subsequent washing steps. $^{33}$P incorporated in polyGT is measured on a Topcount after addition of microscint to the filter plates (Perkin Elmer).

Recombinant EphA7 (Carna Cat#08-126, 2 ng per well) was incubated with 0.1 mg/mL Poly(Glu,Tyr)sodium salt (4:1), MW 20 000-50 000 (Sigma catalog number P0275) in kinase reaction buffer (10 mM MOPS pH 7.2, 5 mM DTT, 0.01% Triton-X100, 5 mM MnCl$_2$, 0.5 mM Na$_3$VO$_4$, 5 mM beta-glycerolphosphate), 0.15 μM non-radioactive ATP, 0.125 μCi/25 μl $^{33}$P-gamma-ATP (Perkin Elmer, catalog number NEG602K) final concentrations with or without 5 μL containing test compound or vehicle (DMSO, 1% final concentration), in a total volume of 25 μL, in a polypropylene 96-well plate (Greiner, V-bottom). After 90 min at 30° C., reactions were stopped by adding of 25 μL/well of 150 mM phosphoric acid. All of the terminated kinase reaction was transferred to prewashed (75 mM phosphoric acid) 96 well filter plates (Perkin Elmer catalog number 6005177) using a cell harvester (Perkin Elmer). Plates were washed 6 times with 300 μL per well of a 75 mM phosphoric acid solution and the bottom of the plates was sealed. 40 μL/well of Microscint-20 was added, the top of the plates was sealed and readout was performed using the Topcount (Perkin Elmer). The ability of a test compound to inhibit the kinase activity was determined using counts per minutes (cpm) measured by the Topcount as:

$$\% \text{ inhibition} = \frac{Cpm(cpd) - Cpm(\text{control})}{Cpm(\text{vehicle}) - Cpm(\text{control})} * 100\%$$

Cpm (cpd): cpm determined for sample with test compound present

Cpm (control): cpm determined for sample with positive control inhibitor (10 μM staurosporine)

Cpm (vehicle): cpm determined in the presence of vehicle (1% DMSO)

Dose dilution series were prepared for the compounds enabling the testing of dose-response effects in the EphA7 assay and the calculation of the IC$_{50}$ for each compound. Each compound was routinely tested at concentration of 20 μM followed by a 1/5 serial dilution, 10 points in a final concentration of 1% DMSO. When potency of compound series increased, more dilutions may be prepared and/or the top concentration may be lowered (e.g. 5 μM, 1 μM).

TABLE IX

EphA7 potency for illustrative compounds of the invention

| Cpd | IC$_{50}$ |
|---|---|
| 3 | * |
| 4 | * |
| 5 | *** |
| 6 | * |
| 9 | * |
| 11 | * |
| 13 | * |
| 16 | * |
| 17 | N/A |
| 20 | ** |

TABLE IX-continued

EphA7 potency for illustrative compounds of the invention

| Cpd | IC$_{50}$ |
|---|---|
| 21 | * |
| 28 | * |
| 29 | * |
| 30 | *** |
| 31 | **** |
| 34 | * |
| 35 | * |
| 36 | ** |
| 38 | *** |
| 40 | * |
| 42 | * |
| 43 | **** |
| 45 | *** |
| 46 | ** |
| 49 | * |
| 50 | ** |
| 55 | ** |
| 56 | * |

\* >1000 nM
\*\* >500-1000 nM
\*\*\* >250-500 nM
\*\*\*\* 0.01-250 nM

TABLE X

EphA7 potency for comparative compounds

| Cpd | IC$_{50}$ |
|---|---|
| A | * |

4.4. EphB2 Assay

The principle of the assay consists of the measurement of incorporated $^{33}$P into the substrate poly GT when phosphorylated by the enzyme EphB2 using [$^{33}$P]-γ-ATP and ATP. Unincorporated $^{33}$P is removed by loading the samples on a filter plate (using a harvester, Perkin Elmer) and 6 subsequent washing steps. $^{33}$P incorporated in polyGT is measured on a Topcount after addition of microscint to the filter plates (Perkin Elmer).

Recombinant EphB2 (Carna Cat#08-129, 0.6 ng per well) was incubated with 0.05 mg/mL Poly(Glu,Tyr)sodium salt (4:1), MW 20 000-50 000 (Sigma catalog number P0275) in kinase reaction buffer (10 mM MOPS pH 7.2, 5 mM DTT, 0.01% Triton-X100, 5 mM MnCl$_2$, 0.5 mM Na$_3$VO$_4$, 5 mM beta-glycerolphosphate), 0.5 μM non-radioactive ATP, 0.25 μCi/25 μl $^{33}$P-gamma-ATP (Perkin Elmer, catalog number NEG602K) final concentrations with or without 5 μL containing test compound or vehicle (DMSO, 1% final concentration), in a total volume of 25 μL, in a polypropylene 96-well plate (Greiner, V-bottom). After 45 min at 30° C., reactions were stopped by adding of 25 μL/well of 150 mM phosphoric acid. The experiment was then conducted as described for EphA7. The ability of a test compound to inhibit the kinase activity was determined using counts per minutes (cpm) measured by the Topcount as:

$$\% \text{ inhibition} = \frac{Cpm(cpd) - Cpm(\text{control})}{Cpm(\text{vehicle}) - Cpm(\text{control})} * 100\%$$

Cpm (cpd): cpm determined for sample with test compound present

Cpm (control): cpm determined for sample with positive control inhibitor (10 μM staurosporine)

Cpm (vehicle): cpm determined in the presence of vehicle (1% DMSO)

Dose dilution series were prepared for the compounds enabling the testing of dose-response effects in the EphB2 assay and the calculation of the IC$_{50}$ for each compound. Each compound was routinely tested at concentration of 20 μM followed by a 1/5 serial dilution, 10 points in a final concentration of 1% DMSO. When potency of compound series increased, more dilutions may be prepared and/or the top concentration may be lowered (e.g. 5 μM, 1 μM).

TABLE XI

EphB2 potency for illustrative compounds of the invention

| Cpd | IC$_{50}$ |
|---|---|
| 2 | *** |
| 3 | ** |
| 4 | ** |
| 5 | * |
| 6 | *** |
| 7 | **** |
| 9 | *** |
| 11 | **** |
| 13 | ** |
| 16 | **** |
| 17 | *** |
| 20 | **** |
| 21 | **** |
| 28 | **** |
| 29 | **** |
| 30 | **** |
| 31 | **** |
| 34 | **** |
| 35 | ** |
| 36 | * |
| 38 | * |
| 40 | * |
| 42 | * |
| 45 | **** |
| 46 | *** |
| 49 | * |
| 50 | * |
| 55 | **** |
| 56 | **** |

\* >100 nM
\*\* >50-100 nM
\*\*\* >25-50 nM
\*\*\*\* 0.01-25 nM

TABLE XII

EphB2 potency for comparative compounds

| Cpd | IC$_{50}$ |
|---|---|
| A | **** |

4.5. EphB4 Assay

Inhibition of EphB4 (UniProt Ref: Q541P7) by a test compound is determined by a commercially available Reaction Biology proprietary nanoliter radioactive HotSpot$^{SM}$ assay (Reaction Biology, One great valley parkway, Suite 2, Malvern Pa., 19355, USA). The principle of the assay consists of the measurement of incorporated $^{33}$P into poly[Glu:Tyr] (4:1) (0.2 mg/mL) when the substrate is phosphorylated by the enzyme using [$^{33}$P]-γ-ATP and ATP (10 μM).

To determine the IC$_{50}$, a serial dilution of compound is tested starting from 10 or 3 μM (highest dilution) with a 1/3 dilution.

TABLE XIII

EphB4 potency for illustrative compounds of the invention

| Cpd | IC$_{50}$ |
|---|---|
| 2 | **** |
| 3 | **** |
| 4 | *** |
| 5 | *** |
| 6 | *** |
| 7 | **** |
| 9 | *** |
| 11 | **** |
| 13 | *** |
| 16 | **** |
| 17 | *** |
| 20 | **** |
| 21 | **** |
| 35 | *** |
| 47 | **** |
| 49 | * |
| 50 | **** |
| 55 | **** |

\* >100 nM
\*\* >50-100 nM
\*\*\* >25-50 nM
\*\*\*\* 0.01-25 nM

Example 5

Cellular Assays

5.1. pEPHA2 Inhibition in MDA-MB-231 Cells

5.1.1. Synopsis

MDA-MB-231 is a human triple negative breast cancer cell line with high EphA2 expression level (Zhuang, et al. 2010), therefore, a cellular assay measuring inhibition of EphA2 autophosphorylation by a test compound in MDA-MB-231 cells has been developed.

MDA-MB-231 cells are incubated with different concentrations of the test compound (30 nM-30 μM) for 2 h at 37° C. Phosphorylated EphA2 protein levels are detected by western blotting in cell lysates using the rabbit p-Ser897 EphA2 antibody and normalized for β-actin protein levels. IC$_{50}$ values are derived from quantitating band intensities of the western blots.

5.1.2. Protocol

MDA-MB-231 cells are cultured in Dulbecco's Modified eagle's Medium (DMEM) containing 10% heat inactivated fetal bovine serum (FBS) at 37° C., 5% CO$_2$.

400,000 cells/6-well in a volume of 1800 μL DMEM+10% FBS are seeded and incubated overnight at 37° C., 5% CO$_2$. 200 μL of test compound at 10× concentration is added and plates are incubated for 2 hours at 37° C., 5% CO$_2$. After removal of the medium followed by PBS wash, 80 μL of Lysis Buffer is added to the cells. Cell lysates are collected and 25 μg protein is loaded on a 10% Bis-Tris Gel. After transfer of the proteins to a PVDF membrane, the membranes are incubated for 1 h in 2% milk solution followed by overnight incubation at 4° C. with the rabbit p-Ser897 EphA2 antibody (Cell Signaling, 3 Trask Lane Danvers, Mass. 01923, US, cat n° 6347). After washing the membranes and incubation for 1 h with the secondary antibody (swine anti-rabbit HRP (Dako, Produktionsvej 42, DK-2600 Glostrup, Denmark, Cat n° P039901), at RT) the membranes are developed with the HRP substrate and the bands (band peak values) are quantified with the Kodak Imager. After quantification of the p-Ser897 EphA2 levels, the blots are incubated with the goat Actin antibody (Santa Cruz, 10410 Finnell Street, Dallas, Tex. 75220, U.S.A, Cat n°: sc-1615) to check if there is an equal loading for all samples on the blots.

5.1.3. Analysis

The EC$_{50}$ of the compounds are determined using GraphPad software, based on band peak values of the p-Ser897 EphA2 Western Blot and the Actin Western Blot.

p-Epha2 values are divided by the actin values to normalize for loading. Percentage Inhibition value (PIN) is calculated by dividing the value of the compound condition by the value obtained for the vehicle condition. EC$_{50}$ are calculated with sigmoidal dose with variable slope curve fitting parameter and fix top at 100% and bottom at 0% PIN.

5.2. Anchorage Independent Growth Assay in MDA-MB-231 Cells

5.2.1. Synopsis

EphA2 antisense oligonucleotides inhibits the growth of MDA-MB-231 cells in soft agar (Carles-Kinch, et al. 2002), therefore compounds are assessed for cell growth inhibition in soft agar and also polypropylene anchorage independent growth (AIG) assays. MDA-MB-231 cells are incubated with different concentrations of test compound (10 nM-30 μM) and cell viability is determined 10 days later

5.2.2. Protocol

MDA-MB-231 cells are cultured in Dulbecco's Modified eagle's Medium (DMEM) containing 10% heat inactivated fetal bovine serum (FBS) at 37° C., 5% CO$_2$.

5.2.2.1. Soft Agar Assay

Agar is prepared as a 1.2% (w/vol in H$_2$O) solution and autoclaved in order to melt it into solution and for sterilization. The agar was heated in microwave until completely dissolved and cooled to 37° C. in a water bath. Soft agar medium is prepared by diluting the 1.2% agar solution ½ in DMEM+10% FBS+1×P/S. Coat 96 well plates (TC, transparent, polystyrene) with 50 μL soft agar medium and the plate is transferred to 4° C. for 30 min to allow the base agar layer to solidify. MDA-MB-231 cells are harvested and resuspended as 4000 MDA-MB-231 cells into each aliquot of 25 μL culture medium, and kept at 37° C. 25 μL cell suspension and 50 μL soft agar medium are mixed and immediately transferred to each well of the 96-well flat-bottom microplate already containing the solidified base agar layer. The plate is placed at 4° C. for 15 minutes to allow the cell agar layer to solidify. To each well are added 90 μL of growth medium, and 10 μL of compound at a concentration 22.5 fold higher than final (total volume in each well is 225 μL). Finally, the plate is incubated at 37° C., 5% CO$_2$ for 10 days.

40 μL Alamar blue reagent (1:2 diluted in medium) is added to each well and incubated for 5 h at 37° C. 80 μL is then transferred to a black 96-w plate and the fluoresence is measured at exc530_em590 with Envision.

5.2.2.2. PP Assay

In a black polypropylene 96-well plates is dispense 15 μL of compound at a concentration 10 fold higher than final or of vehicle at a concentration 10 fold higher than final (total volume in each well is 150 μL). 2000 MDA-MB-231 cells in 135 μL (in complete growth medium) are added to the plates, and the plate is incubated for 10 days at 37° C., 5% $CO_2$. 15 μL Alamar blue reagent to each well is added, and the plate is incubated for 5 h at 37° C. The fluoresence is measured at exc530_em590 with an Envision.

5.2.3. Calculations and Statistics

The $EC_{50}$ values of test compounds are calculated using a Graphpad regression based on percentage inhibition values, calculated with vehicle (0% PIN) and 1 μM staurosporin (100% PIN).

Example 6

Pharmacokinetics

6.1. Mice

6.1.1. Animals

This study was performed with 42 naïve male CD1 mice (18-20 g, 4-5 weeks old). Mice are obtained from Janvier, Le Genest St Isle, France.

A controlled environment was maintained in the room with optimal conditions of approximately 15 air changes per hour, a temperature of 22±2 C, a relative humidity of 30-70% and a 12 hour light/12 hour dark cycle (nightlight during the night period).

Pelleted diet for rodents (UAR A04C-10) was used and was provided ad libitum. Before p.o. dosing, the animals are deprived of food for at least 12 hours before compound administration and 4 hours after administration. All animals had free access to tap water.

6.1.2. Protocol

Mice (n=3/sampling time) are dosed intravenously with Compound 55 via a bolus in the tail vein with a dose level of 1 mg/kg, and a second group of mice is dosed orally as a single oral gavage with a dose level of 5 mg/kg. The i.v. bolus administration is given with a dose volume of 5 mL/kg and the oral administration is given with a dose volume of 10 mL/kg. Actual dose volumes are based on the mean of 10 body weights.

The vehicle used to formulate compounds for oral administration is methylcellulose in water (0.5% in water)

From all animals approximately 500 μL blood samples are collected by intra-cardiac puncture under gaseous anesthesia and placed into tubes containing Li-heparin as anticoagulant. Blood samples are collected at various time points (i.v.: 0.05, 0.25, 0.5, 1, 3, 5 and 8 hours after dosing; p.o.: 0.25, 0.5, 1, 3, 5, 8 and 24 hours after dosing). Each mouse is sampled once and euthanized.

Blood is kept on ice. Within 1 hour after sampling, blood is centrifuged at 5,000 rpm for 10 min at 4° C. Immediately after centrifugation, the resulting plasma samples are collected into polypropylene tubes and are kept frozen at −20° C. pending bioanalysis.

6.2. Rats

6.2.1. Animals

This study is performed with 6 naïve male Sprague Dawley rats (180-200 g, 6-8 weeks old). Rats are obtained from Janvier, Le Genest St Isle, France.

A controlled environment is maintained in the room with optimal conditions of approximately 15 air changes per hour, a temperature of 22±2 C, a relative humidity of 30-70% and a 12 hour light/dark cycle Pelleted diet for rodents (UAR A04C-10) is used and is provided ad libitum. Before p.o. dosing, the animals are deprived of food for at least 12 hours before compound administration and 4 hours after administration. All animals had free access to tap water.

6.2.2. Protocol

Two days before the dosing day, the implantation of a catheter in the jugular vein is done under gaseous anaesthesia with isoflurane.

Rats are dosed intravenously with test compound via a bolus in the tail vein with a dose level of 1 mg/kg.

Three additional rats are dosed orally as a single gavage of compound formulated in hydroxy-propyl-β-cyclodextrin (HPβCD) 10% w/v in water with a dose level of 5 mg/kg or 30 mg/kg.

The i.v. bolus and the oral administration are given a dose volume of 5 mL/kg.

From all animals approximately 200 μL blood samples are collected via the catheter and placed into tubes containing Li-heparin as anticoagulant. Blood samples are collected at the various time points (i.v.: 0.05, 0.25, 0.5, 1, 3, 5, 8 and 24 hours after dosing; p.o.: 0.25, 0.5, 1, 3, 5, 8 and 24 hours after dosing).

Blood is kept on ice. Within 1 hour after sampling, blood is centrifuged at 5,000 rpm for 10 min at 4° C. Immediately after centrifugation, the resulting plasma samples are collected into polypropylene tubes and are kept frozen at −20° C. pending bioanalysis.

6.3. Analysis

Plasma samples are assayed by LC-MS/MS. Plasma proteins are precipitated with an excess of methanol containing the internal standard and the corresponding supernatant is injected on a C18 column. Analytes are eluted out the HPLC system by increasing the percentage of the organic mobile phase. An API4000 mass spectrometer (AB Sciex™) is used for the detection and quantification.

6.4. Calculations and Statistics

Pharmacokinetic parameters are calculated by non-compartmental analysis using WinNonlin® software (Pharsight, version 5.2).

6.5. Results

When subjected to this protocol, the following exposure values after oral administration are measured:

TABLE XIV

Exposure (AUC) in rats for illustrative compounds of the invention

| Cpd | Dose (mg/kg, po) | AUC (ng · h/mL) |
|---|---|---|
| 2 | 5 | 852, 659 |
| 3 | 5 | 214, 159 |
| 4 | 5* | 407 |
| 6 | 5 | 1787 |
| 8 | 5 | 2005 |
| 9 | 5 | 3265 |

TABLE XIV-continued

Exposure (AUC) in rats for illustrative compounds of the invention

| Cpd | Dose (mg/kg, po) | AUC (ng · h/mL) |
|---|---|---|
| 10 | 5 | 274 |
| 13 | 5 | 1418 |
| 17 | 5 | 1230 |
| 29 | 5 | 5837 |
| 35 | 5 | 3573 |
| 50 | 5 | 1266 |
| 55 | 3 | 1060 |
|  | 5 | 965 |
|  | 30 | 13633 |

*: Cpd 4 was formulated in methylcellulose 5% in water

TABLE XV

Exposure for comparative compounds

| Cpd | Dose (mg/kg, po) | AUC (ng · h/mL) |
|---|---|---|
| A | 5 | 273 |

TABLE XVI

Exposure (AUC) in mouse for illustrative compounds of the invention

| Cpd | Dose (mg/kg, po) | AUC (ng · h/mL) |
|---|---|---|
| 47 | 30 | 39029 |
| 55 | 5 | 851 |
|  | 30 | 31636 |

TABLE XVII

Exposure (AUC) in mouse for comparative compounds

| Cpd | Dose (mg/kg, po) | AUC (ng · h/mL) |
|---|---|---|
| A | 30 | 1130 |

Example 7

In Vivo Assays

7.1. Mouse Xenograft Model of Human Triple Negative Breast Cancer (MDA-MB-231)

7.1.1. Animals

Animals (Female BALB/c Mice, Harlan, 51930, 18-20 g) are provided with filtered tap water and standard chow ad libitum and maintained at 22±2° C. in 55±10% humidity on a 12 h light/dark cycle.

7.1.2. Compounds Preparation

Paclitaxel used as a positive control is formulated by 1/3 dilution of commercial solution (Fresenius kabi, 871WF014/4) in saline.

The test compounds for po administration are formulated in 0.5% methylcellulose (VWR, ref AX021233).

7.1.3. Cell Line

MDA-MB-231 cell line is obtained from the ATCC collection (ref HTB-26). The cells are then cultured in RPMI 1640 medium supplemented with 10% (v/v) penicillin/Streptomycin (Gibco 15140-148) and 1% (v/v) L-Glutamine 200 mM (Gibco 25030-024) at 37° C. in a 5% $CO_2$ incubator.

7.1.4. Tumor implantation 5 million MDA-MB-231 cells/mice in 0.1 mL of 50% Matrigel (BD biosciences, LDEV free 256235)+50% D-PBS 1× (Gibco 14190-086) are injected by subcutaneous route on the upper back of 120 mice. Prior to implantation, mice are anesthetized by intra-peritoneal injection with a 0.1 mL/10 g dose of anaesthetic solution (18 mL NaCl, 0.9%+0.5 mL xylazine, +1.5 mL ketamine. After implantation, tumours are regularly measured with a calliper, and mice with a mean tumour volume of about 200 mm$^3$ are randomized into groups of 10 individuals, and each group is dosed either with vehicle (p.o.), paclitaxel as control (3×/week, 20 mg/kg i.p.), or a test compound at doses of 3, 10, 30 or 100 mg/kg (p.o., QD, in 10 mL/kg administration volume)

Body weight, and tumor growth is recorded twice a week during the course of treatment.

After 26 days the treatment is stopped, in each group half of the mice are euthanized for tissue collection, and the other half is kept for a further 7 days, during which period body weight and tumour sized are measured.

In sacrificed mice, blood and tumours are collected, analysed, and the effect of the test compounds is compared with controls (vehicle and paclitaxel).

7.1.5. Results

7.1.5.1. Tumorous Growth Inhibition after 26 Days Treatment

The values were obtained using the following calculations Relative Tumor Volume (RTV):

$$RTV = \frac{\text{Tumour volume day 26}}{\text{Tumour volume day 0}}$$

Tumour Vs Control (T/C)

$$T/C = \frac{(1 - RTV \text{ test compound})}{(1 - RTV \text{ control})} * 100$$

Tumor Growth Inhibition (TGI)

$$TGI = 1 - T/C$$

TABLE XVIII

Tumorous growth inhibition results at day 26

| Cpds | Dose (mg/kg) | Regimen | RTV | T/C | TGI |
|---|---|---|---|---|---|
| Control | — | — | 5.38 | 100.00% | 0.00% |
| Paclitaxel | 20 | ip, 3x/ week | 2.06 | 24.31% | 75.69% |
| 55 | 30 | p.o., qd | 1.01 | 0.14% | 99.86% |
| A | 30 | p.o., qd | 3.40 | 54.89% | 45.11% |
|  | 100 | p.o., qd | 3.09 | 47.80% | 52.20% |
|  | 300 | p.o., qd | 4.74 | 85.40% | 14.60% |

As shown in the Table above, and FIG. 1, Compound 55 administered at 30 mg/kg leads to complete block of tumour growth (statistically significant), whereas the comparison compound A dosed at 30, 100 or 300 mg/kg shows a plateau of its anti-tumour effect and is not able to achieve the same effect on inhibition of tumour growth.

7.1.5.2. Exposure at Day 7

During the experiment, the plasma exposure is measured at day 7, as shown in the Table below. The compound of the invention shows a >24 fold higher exposure than the comparison compound A at 30 mg/kg (p.o.). Even at a 10 fold higher dosing (300 mg/kg, p.o.), Comparative Compound A remains 3.9 fold less exposed than Compound 55.

TABLE XIX

Plasma exposure determined at day 7

| Cpd # | Dose (mg/ kg p.o.) | AUC (ng · hr/mL) |
|---|---|---|
| 55 | 30 | 30953 |
| A | 30 | 1285 |
|  | 100 | 4236 |
|  | 300 | 7923 |

7.1.6. Conclusion

The data reported show that Compound 55 surprisingly shows higher in vivo activity in contrast with close analogues of the prior art and blocks tumorous growth at 30 mg/kg, p.o.

Moreover Compound 55 shows an exposure that is higher than that achieved with comparative Compound A, even if Compound A is administered at a 10 fold higher dose.

7.2. Oral Glucose Tolerance Test (OGTT)

The oral glucose tolerance test can be used to measure the effect of compounds on the rate of glucose absorption and can therefore be a measure of insulin secretion Animals (Sprague-Dawley rats, male, 250 g, n=12 per group) are overnight fasted. Vehicle, Metformin (positive control, 250 mg/kg po) and compound treated rats receive a glucose load (2 g/kg, po). Blood glucose values are measured with a hand glucometer (One Touch Ultra 2®, Lifescan), just before (t=0 min) and 15, 30, 60, 90, 120 and 180 min after the glucose loading, on a drop of blood obtained by pricking rat tail vein.

7.3. In Vivo Efficacy in the Rat MNX Model

7.3.1. Pharmacology Procedure

In vivo efficacy was studied in a female Lewis meniscectomised rat (MNX) model. The MNX rat model is a well-validated disease model of osteoarthritis (Janusz et al., 2002; Pritzker et al., 2006; Bendele et al., 2001).

7.3.2. Surgery and Dosing

Osteoarthritis is induced by meniscectomy at day 0 (D0) in the right leg of each rat by a transection of the medial collateral ligament and 4 mm of ligament are removed. Internal part of the meniscus is transected vertically into two flaps which are pushed to the front and the back of the synovial cavity. Sham animals undergo only anaesthesia, skin and muscle incision then suture. On day 1, rats are randomly assigned to a treatment group (n=20 per group) according to their body weight, in order to have a homogenous distribution. From D2 to D21, rats are dosed per os (po) once daily (qd) or twice a day (bid) with compounds formulated in methylcellulose (MC) 0.5% or in HPβCD 10% pH3.0.

7.3.3. Steady-State PK Determination (ssPK)

After at least 7 days of treatment, blood is sampled at 4 time points post administration: 0, 1, 3 and 6 h (and assuming 24 h is equal to the pre-dose sample), in order to determine steady-state plasma exposure.

7.3.4. Histology

At sacrifice, the right tibia of each rat is collected and processed for histological analysis. After 48 h of fixation in 4% formaldehyde, tibias are decalcified in Osteosoft for 7 days, and cut into 2 half parts prior to embedding face to face in paraffin. Five series of sections are cut at 200 μm intervals, covering about 1.5 mm of the middle part of the bone. One series of slides is stained with Safranin O and light green for morphological evaluation and OARSI scoring. The other series of slides are mounted with DAPI for chondrocyte density measurement.

The extent of cartilage injury reflecting osteoarthritis in the tibial plateau is evaluated and scored using the OARSI method based on the grading and the staging of cartilage lesion (Pritzker et al., 2006). The OARSI scoring is assessed in a blinded manner by two different readers. For each tibia, one score is attributed as the median of the OARSI score of the 5 sections.

OARSI score=grade×stage (1 to 24)

Grade=lesion depth into cartilage area, providing information on arthritis severity.

Stage=lesion extent over cartilage surface, providing information on arthritis extent.

For statistical analysis, medians of groups are compared with a stratified Kruskal-Wallis test followed by Dunnett multiple comparison post hoc test.

Significance levels: *$p<0.05$; $p<0.01$; *$p<0.001$ versus MNX-vehicle. Statistical analyses are done on all groups of the studies

TABLE XX

MNX study results for compounds of the invention

| Cpd # | Dose regimen (mg/kg) | OARSI score |
|---|---|---|
| 2 | 20 | −17%, p < 0.05 |
| 6 | 30 | ns |
| 9 | 30 | ns |
| 13 | 30 | ns |
| 29 | 15 | ns |
| 55 | 30 | −23%, p < 0.05 |

7.4. Anti-Inflammatory Determination

It will be appreciated by the man skilled in the art that many assays have been developed, and are well established, which can be used to measure anti-inflammatory activity (Brand et al., 2007; Miescher et al., 1989).

7.5. Clonogenic Assay

This assay evaluates the ability of a test compound to inhibit anchorage-independent growth and ex vivo colony formation of tumor cells in semi-solid medium. To this end, a test compound is evaluated at concentrations ranging from 0.001 μM to 30 μM in half-log increments in 104 tumor xenograft-derived cell suspensions of different histotypes as follows anal cancer (1), bladder (6), central nervous system (1), colon (13), Asian gastric (8), Caucasian gastric (4), head and neck (2), liver (1), NSC lung (adeno 14, epidermoid 2, large cell 4), breast (6), ovarian (1), pancreatic (10), prostate (3), renal (10), uterine body cancer (1), as well as melanoma (10), pleuramesothelioma (3) soft tissue sarcoma (3), and osteo sarcoma (1).

7.5.1. Cultivation of Cell Lines

Patient-derived tumor cell lines were routinely passaged once or twice weekly. All cells were grown at 37° C. in a humidified atmosphere with 5% $CO_2$ in RPMI 1640 medium supplemented with 10% (v/v) fetal calf serum and 0.01% (w/v) gentamicin. The percentage of viable cells was determined in a Neubauer-hemocytometer using trypan blue exclusion.

7.5.2. Preparation of Single Cell Suspensions from Human Tumor Xenografts

Solid human tumor xenografts growing subcutaneously in serial passages in thymus-aplastic nude mice (NMRI nu/nu strain) were removed under sterile conditions. The MDA-MB-231 xenograft was removed under sterile conditions, put into pre-cooled Oncostore® transport medium (Oncoscience AG), and was immediately shipped on cool packs to run the experiment. All xenograft materials were mechanically disaggregated and subsequently incubated with an enzyme cocktail consisting of collagenase type IV (41 U/mL), DNase I (125 U/mL), hyaluronidase (100 U/mL) and dispase II (1.0 U/mL) in RPMI 1640 medium at 37° C. for 45 minutes. Cells were passed through sieves of 100 μm and 40 μm mesh size (Cell Strainer, BD Falcon™) and washed twice with RPMI 1640 medium. The percentage of viable cells was determined in a Neubauer-hemocytometer using trypan blue exclusion. Aliquots of the cells were frozen down, and stored in liquid nitrogen. On each day of an experiment, a frozen aliquot of tumor cells was thawed and used for preparation of assay plates.

7.5.3. Clonogenic Assay Procedure

The clonogenic assay was performed in a 96 well plate format according to a modified two-layer soft agar assay. For each test, the tumor material was prepared as described above and assay plates were prepared as follows: each test well contained three layers of equal volume, 2 layers of semi-solid medium (bottom and top layer), and one layer of medium supernatant, with or without test compound. The bottom layer consisted of 0.05 mL/well cell culture medium (IMDM or RPMI 1640 with or w/o pyruvate, supplemented with 20% (v/v) fetal calf serum, 0.01% (w/v) gentamicin and 0.75% (w/v) agar). $1.5 \cdot 10^3$ to $1 \cdot 10^4$ cells were added to 0.05 mL of the same culture medium supplemented with 0.4% (w/v) agar and plated in onto the bottom layer. The test compounds were added after serial dilution in DMSO and transfer in cell culture medium, and left on the cells for the duration of the experiment (continuous exposure, 0.05 mL drug overlay). Every plate included six untreated control wells and drug-treated groups in duplicate at 10 concentrations. Cultures were incubated at 37° C. and 7.5% $CO_2$ in a humidified atmosphere for 8 to 13 days and monitored closely for colony growth using an inverted microscope. Within this period, ex vivo tumor growth led to the formation of colonies with a diameter of >50 μm. At the time of maximum colony formation, counts were performed with an automatic image analysis system (BIOREADER 5000-Wα, Biosys GmbH). 48 hours prior to evaluation, vital colonies were stained with a sterile aqueous solution of 2-(4-iodophenyl)-3-(4-nitrophenyl)-5-phenyltetrazolium chloride (1 mg/mL, 100 μL/well).

7.5.4. Data Evaluation

An assay was considered fully evaluable if the following quality control criteria were fulfilled:
mean number of colonies in the control wells >50 colonies with a colony diameter of >50 μm
Z'-factor calculated within the assay plate ≥0.5
coefficient of variation in the growth control wells ≤30%
the positive reference compound sunitinib at a concentration of 100 μM must cause a reduction of signal to <30% of the growth control Drug effects were expressed in terms of the percentage of colony formation, obtained by comparison of the mean signal in the treated wells with the mean signal of the untreated controls (expressed by the test-versus-control value, T/C-value [%]):

$$\frac{T}{C}[\%] = \frac{\text{mean signal}_{treated\ group}}{\text{mean signal}_{control\ group}} * 100$$

Sigmoidal concentration-response curves were fitted to the data points obtained for each tumor model using 4 parameter non-linear curve fit (Oncotest Warehouse Software). $IC_{50}$ values are reported as relative and absolute $IC_{50}$ values. The relative $IC_{50}$ value is the concentration of test compound that gives a response (inhibition of colony formation) half way between the top and bottom plateau of the sigmoidal concentration-response curve (inflection point of the curve). The absolute $IC_{50}$ value is determined as the concentration at the intersection of the concentration effect curve with T/C=50%.

The overall potency of a compound was expressed by the geometric mean $IC_{50}$ value of all individual $IC_{50}$ values. If an $IC_{50}$ value could not be determined within the examined dose range (because a compound was either too active or lacked activity), the lowest or highest concentration studied was used for calculation of the geometric mean value.

7.5.5. Results

When subjected to this assay, and based on relative $IC_{50}$ values, sensitive tumor models were found in particular within melanoma, prostate, renal cancer, sarcoma, uterine, lung, colon, gastric, liver, breast, and ovarian cancer.

GENERAL CONCLUSIONS

The data provided in the present application demonstrate that the compounds according to Formula I surprisingly exhibit an improved exposure as compared to structurally similar compounds described in the prior art. A higher exposure may result in lower dosage of the compound, and in turn a lower dosage level may reduce drug-drug interactions, side effects, and/or toxicity of the compound.

In addition, the compounds of the invention surprisingly also show higher in vivo activity compared to a close analogue from the prior art and specifically may be useful to reduce and/or block tumorous growth. This improved exposure and in vivo activity could not have been predicted by a person of skill in the art.

FINAL REMARKS

It will be appreciated by those skilled in the art that the foregoing descriptions are exemplary and explanatory in nature, and intended to illustrate the invention and its preferred embodiments. Through routine experimentation, an artisan will recognize apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of compound of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

REFERENCES

Bolen, S., Feldman, L., Vassy, J., Wilson, L., Yeh, H.-C., Marinopoulos, S., Wiley, C., Selvin, E., Wilson, R., Bass, E. B., et al. (2007). Systematic review: comparative effectiveness and safety of oral medications for type 2 diabetes mellitus. Ann. Intern. Med. 147, 386-399.

Brand, D. D., Latham, K. A., and Rosloniec, E. F. (2007). Collagen-induced arthritis. Nat. Protoc. 2, 1269-1275.

Brantley-Sieders, D. M., Jiang, A., Sarma, K., Badu-Nkansah, A., Walter, D. L., Shyr, Y., and Chen, J. (2011). Eph/ephrin profiling in human breast cancer reveals significant associations between expression level and clinical outcome. PloS One 6, e24426.

Bundgaard, H. (1985). Design of prodrugs (Elsevier).

Carles-Kinch, K., Kilpatrick, K. E., Stewart, J. C., and Kinch, M. S. (2002). Antibody Targeting of the EphA2 Tyrosine Kinase Inhibits Malignant Cell Behavior. Cancer Res. 62, 2840-2847.

Ivanov, A. I., Steiner, A. A., Scheck, A. C., and Romanovsky, A. A. (2005). Expression of Eph receptors and their ligands, ephrins, during lipopolysaccharide fever in rats. Physiol. Genomics 21, 152-160.

Jensen, K. L., Dickmeiss, G., Donslund, B. S., Poulsen, P. H., and Jorgensen, K. A. (2011). Asymmetric Organocatalytic Synthesis of Complex Cyclopenta[b]quinoline Derivatives. Org. Lett. 13, 3678-3681.

Kitamura, T., Kabuyama, Y., Kamataki, A., Homma, M. K., Kobayashi, H., Aota, S., Kikuchi, S., and Homma, Y. (2008). Enhancement of lymphocyte migration and cytokine production by ephrinB1 system in rheumatoid arthritis. Am. J. Physiol.—Cell Physiol. 294, C189-C196.

Konstantinova, I., Nikolova, G., Ohara-Imaizumi, M., Meda, P., Kuc era, T., Zarbalis, K., Wurst, W., Nagamatsu, S., and Lammert, E. (2007). EphA-Ephrin-A-Mediated β Cell Communication Regulates Insulin Secretion from Pancreatic Islets. Cell 129, 359-370.

Kwan Tat, S., Pelletier, J.-P., Amiable, N., Boileau, C., Lajeunesse, D., Duval, N., and Martel-Pelletier, J. (2008). Activation of the receptor EphB4 by its specific ligand ephrin B2 in human osteoarthritic subchondral bone osteoblasts. Arthritis Rheum. 58, 3820-3830.

Miescher, G. C., Schreyer, M., and MacDonald, H. R. (1989). Production and characterization of a rat monoclonal antibody against the murine CD3 molecular complex. Immunol Lett. 23, 113-118.

Murai, K. K., and Pasquale, E. B. (2003). 'Eph'ective signaling: forward, reverse and crosstalk. J. Cell Sci. 116, 2823-2832.

Pasquale, E. B. (2008). Eph-Ephrin Bidirectional Signaling in Physiology and Disease. Cell 133, 38-52.

Pritzker, K. P. H., Gay, S., Jimenez, S. A., Ostergaard, K., Pelletier, J.-P., Revell, P. A., Salter, D., and van den Berg, W. B. (2006). Osteoarthritis cartilage histopathology: grading and staging. Osteoarthritis Cartilage 14, 13-29.

Rajapakse, H. a, Moore, K. P., Nantermet, P. G., Sanders, J. M., Parmentier-Batteur, S., and Mark, R. J. (2010). Epha4 Rtk Inhibitors for Treatment of Neurological and Neurodegenerative Disorders and Cancer.

Remington, J. P. (1985). Pharmaceutical Preparations and Their Manufacture. In Remington's Pharmaceutical Sciences, A. R. Gennaro, ed. (Easton, Pa. 18042: Mack Pub. Co.),.

Tandon, M., Vemula, S. V., and Mittal, S. K. (2011). Emerging strategies for EphA2 receptor targeting for cancer therapeutics. Expert Opin. Ther. Targets 15, 31-51.

Wuts, P. G. M., and Greene, T. W. (2012). Greene's Protective Groups in Organic Synthesis (Wiley-Interscience).

Xi, H.-Q., Wu, X.-S., Wei, B., and Chen, L. (2012). Eph receptors and ephrins as targets for cancer therapy. J. Cell. Mol. Med. 16, 2894-2909.

Zamora, D. O., Babra, B., Pan, Y., Planck, S. R., and Rosenbaum, J. T. (2006). Human leukocytes express ephrinB2 which activates microvascular endothelial cells. Cell. Immunol. 242, 99-109.

Zhao, C., Irie, N., Takada, Y., Shimoda, K., Miyamoto, T., Nishiwaki, T., Suda, T., and Matsuo, K. (2006). Bidirectional ephrinB2-EphB4 signaling controls bone homeostasis. Cell Metab. 4, 111-121.

Zhuang, G., Brantley-Sieders, D. M., Vaught, D., Yu, J., Xie, L., Wells, S., Jackson, D., Muroaka-Cook, R., Arteaga, C., and Chen, J. (2010). Elevation of receptor tyrosine kinase EphA2 mediates resistance to trastuzumab therapy. Cancer Res. 70.

The invention claimed is:

1. A compound according to Formula I:

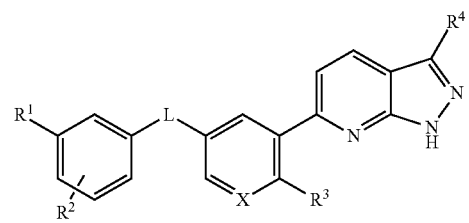

wherein
 X is N, or CH;
 L is —NH(C=O)—, or —C(=O)NH—;
 $R^1$ is
  —CN,
  halo,
  $C_{1-4}$ alkyl optionally substituted with one or more independently selected $R^{6a}$ groups, $C_{1-4}$ alkoxy optionally substituted with one or more independently selected $R^{6b}$ groups,
$C_{3-4}$ cycloalkyl,
phenyl,
—$SO_2C_{1-4}$ alkyl, or
—$NR^{7a}R^{7b}$;

$R^2$ is H, cyclopropyl, $C_{1-4}$ alkyl (optionally substituted with one or more halo), or $C_{1-4}$ alkoxy;

$R^3$ is —$CH_3$, —$CH_2CH_3$, or Cl;

$R^4$ is
$C_{1-2}$ alkyl optionally substituted with one OH,
$C_{1-2}$ alkyl substituted with one OH and one 5-6 membered heterocycloalkyl comprising one or two heteroatoms independently selected from N, O, and S,
$C_{3-6}$ cycloalkyl optionally substituted with one OH;

each $R^{6a}$ is
OH,
halo, or
$C_{1-4}$ alkoxy each $R^{6b}$ is
OH,
halo,
$C_{1-4}$ alkoxy,
—$NR^{8a}R^{8b}$, or
5-6 membered heterocycloalkyl comprising one or two heteroatoms independently selected from N, O, and S, optionally substituted with one $C_{1-4}$ alkyl;

each $R^{7a}$, $R^{7b}$ is independently selected from H, and $C_{1-4}$ alkyl; and each $R^{8a}$ or $R^{8b}$ is independently selected from H, and $C_{1-4}$ alkyl;

or a pharmaceutically acceptable salt thereof.

2. The compound or pharmaceutically acceptable salt thereof, according to claim 1, wherein the compound is according to Formula II:

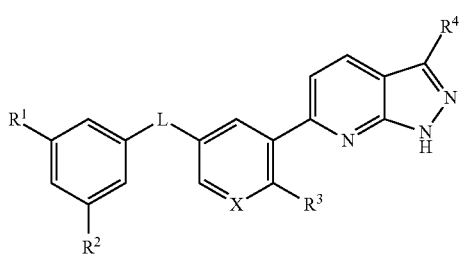

II wherein $R^1$, $R^2$, $R^3$, $R^4$ and L are as defined in claim 1.

3. The compound or pharmaceutically acceptable salt thereof, according to claim 1, wherein $R^1$ is —$CH_3$, or —$CH_2CH_3$, each of which is substituted with one or more independently selected OH, F, Cl, —$OCH_3$, or —$OCH_2CH_3$.

4. The compound or pharmaceutically acceptable salt thereof, according to claim 1, wherein $R^1$ is
—$OCH_3$, or —$OCH_2CH_3$.

5. The compound or pharmaceutically acceptable salt thereof, according to claim 1, wherein $R^2$ is —$CH_3$, —$CH_2CH_3$, —$OCH_3$, or —$OCH_2CH_3$.

6. The compound or pharmaceutically acceptable salt thereof, according to claim 1, wherein the compound is according to Formula IIIa:

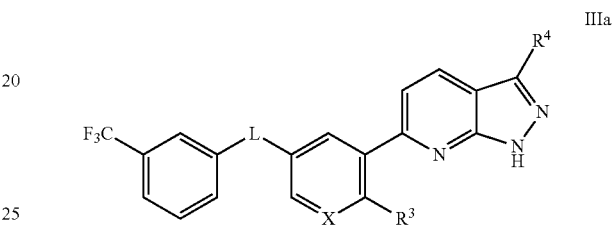

IIIa wherein X, L, $R^3$, and $R^4$ are as defined in claim 1.

7. The compound or pharmaceutically acceptable salt thereof, according to claim 1, wherein L is —NH(C=O)—.

8. The compound or pharmaceutically acceptable salt thereof, according to claim 1, wherein L is —C(=O)NH—.

9. The compound or pharmaceutically acceptable salt thereof, according to claim 1, wherein $R^4$ is $C_{1-2}$ alkyl substituted with one OH.

10. The compound or pharmaceutically acceptable salt thereof, according to claim 1, wherein X is CH.

11. The compound or pharmaceutically acceptable salt thereof, according to claim 1, wherein X is N.

12. A pharmaceutical composition comprising a pharmaceutically acceptable carrier and a pharmaceutically effective amount of the compound according to claim 1.

13. The pharmaceutical composition according to claim 12 comprising a further therapeutic agent.

* * * * *